United States Patent
Samajdar et al.

(10) Patent No.: US 11,186,576 B2
(45) Date of Patent: Nov. 30, 2021

(54) PYRAZOLO[1,5-A][1,3,5]TRIAZINE AND PYRAZOLO[1,5-A]PYRIMIDINE DERIVATIVES AS CDK INHIBITORS

(71) Applicant: Aurigene Discovery Technologies Limited, Bangalore (IN)

(72) Inventors: Susanta Samajdar, Bangalore (IN); Ramulu Poddutoori, Karimnagar (IN); Subhendu Mukherjee, Hooghly (IN); Rajeev Goswami, Deharadun (IN)

(73) Assignee: Aurigene Discovery Technologies Limited, Bangalore (IN)

( * ) Notice: Subject to any disclaimer, the term of this patent is extended or adjusted under 35 U.S.C. 154(b) by 0 days.

(21) Appl. No.: 15/557,028

(22) PCT Filed: Mar. 8, 2016

(86) PCT No.: PCT/IB2016/051302
§ 371 (c)(1),
(2) Date: Sep. 8, 2017

(87) PCT Pub. No.: WO2016/142855
PCT Pub. Date: Sep. 15, 2016

(65) Prior Publication Data
US 2018/0057497 A1  Mar. 1, 2018
US 2018/0258092 A9  Sep. 13, 2018

(30) Foreign Application Priority Data
Mar. 9, 2015  (IN) .......................... 1128/CHE/2015

(51) Int. Cl.
C07D 487/04  (2006.01)
A61K 45/06  (2006.01)
A61K 31/53  (2006.01)

(52) U.S. Cl.
CPC ............ *C07D 487/04* (2013.01); *A61K 31/53* (2013.01); *A61K 45/06* (2013.01)

(58) Field of Classification Search
CPC .................................................... C07D 487/04
See application file for complete search history.

(56) References Cited

U.S. PATENT DOCUMENTS

| | | |
|---|---|---|
| 6,194,410 B1 | 2/2001 | Bos et al. |
| 9,096,608 B2 | 8/2015 | Eickhoff et al. |
| 9,567,345 B2 | 2/2017 | Eickhoff et al. |
| 10,112,927 B2 | 10/2018 | Gray et al. |
| 2012/0184557 A1 | 7/2012 | Meijer et al. |

FOREIGN PATENT DOCUMENTS

| | | |
|---|---|---|
| EP | 2634190 A1 | 9/2013 |
| WO | 2001012189 A1 | 2/2001 |
| WO | 2006070195 A1 | 7/2006 |
| WO | 2006070198 A1 | 7/2006 |
| WO | 2008036277 A1 | 3/2008 |

(Continued)

OTHER PUBLICATIONS

Navigatingcancer.com. "List of Cancer Chemotherapy Drugs." (2013). Accessed Nov. 26, 2013. Available from: < https://www.navigatingcancer.com/library/all/chemotherapy_drugs >. (Year: 2013).*

(Continued)

*Primary Examiner* — John S Kenyon
(74) *Attorney, Agent, or Firm* — Honigman LLP; Heidi M. Berven; Andrew S. Chipouras

(57) ABSTRACT

The present invention provides substituted pyrazolo[1,5-a][1,3,5]triazine and pyrazolo[1,5-a]pyrimidine derivatives of formula (I), which are therapeutically useful, particularly as selective transcriptional CDK inhibitors including CDK7, CDK9, CDK12, CDK13 and CDK18, more particularly transcriptional CDK7 inhibitors

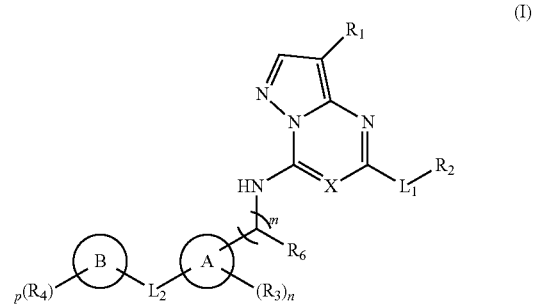

wherein X, ring A, ring B, $L_1$, $L_2$, $R_1$, $R_2$, $R_3$, $R_4$, $R_6$, m, n and p have the meanings given in the specification and pharmaceutically acceptable salts thereof that are useful in the treatment and prevention of diseases or disorder associated with selective transcriptional CDKs in a mammal. The present invention also provides preparation of the compounds and pharmaceutical formulations comprising at least one of the substituted pyrazolo[1,5-*a*][1,3,5]triazine and pyrazolo[1,5-*a*]pyrimidine derivatives of formula (I) or a pharmaceutically acceptable salt thereof or a stereoisomer thereof.

22 Claims, 1 Drawing Sheet

(56) References Cited

FOREIGN PATENT DOCUMENTS

| WO | 2008151304 A1 | 12/2008 | |
|---|---|---|---|
| WO | 2013128028 A1 | 9/2013 | |
| WO | 2013128029 A1 | 9/2013 | |
| WO | WO-2013128028 A1 * | 9/2013 | ........... C07D 487/04 |
| WO | 2014063068 A1 | 4/2014 | |
| WO | 2015154022 A1 | 10/2015 | |
| WO | WO-2015154022 A1 * | 10/2015 | ............. A61K 31/53 |
| WO | 2016160617 A2 | 10/2016 | |
| WO | WO-2016160617 A2 * | 10/2016 | .............. A61P 43/00 |

OTHER PUBLICATIONS

Extended European Search Report issued by the European Patent Office for European Application No. 16761176.3 dated Jul. 19, 2018.

International Preliminary Report on Patentability issued by the International Bureau of WIPO for International Application PCT/IB2016/051302 dated Sep. 21, 2017.

Shiota et al., Synthesis and structure-activity relationship of a new series of potent angiotensin II receptor antagonists: pyrazolo[1,5-a]pyrimidine derivatives. Chemical & Pharmaceutical Bulletin, vol. 47, No. 7, (1999), pp. 928-938.

\* cited by examiner

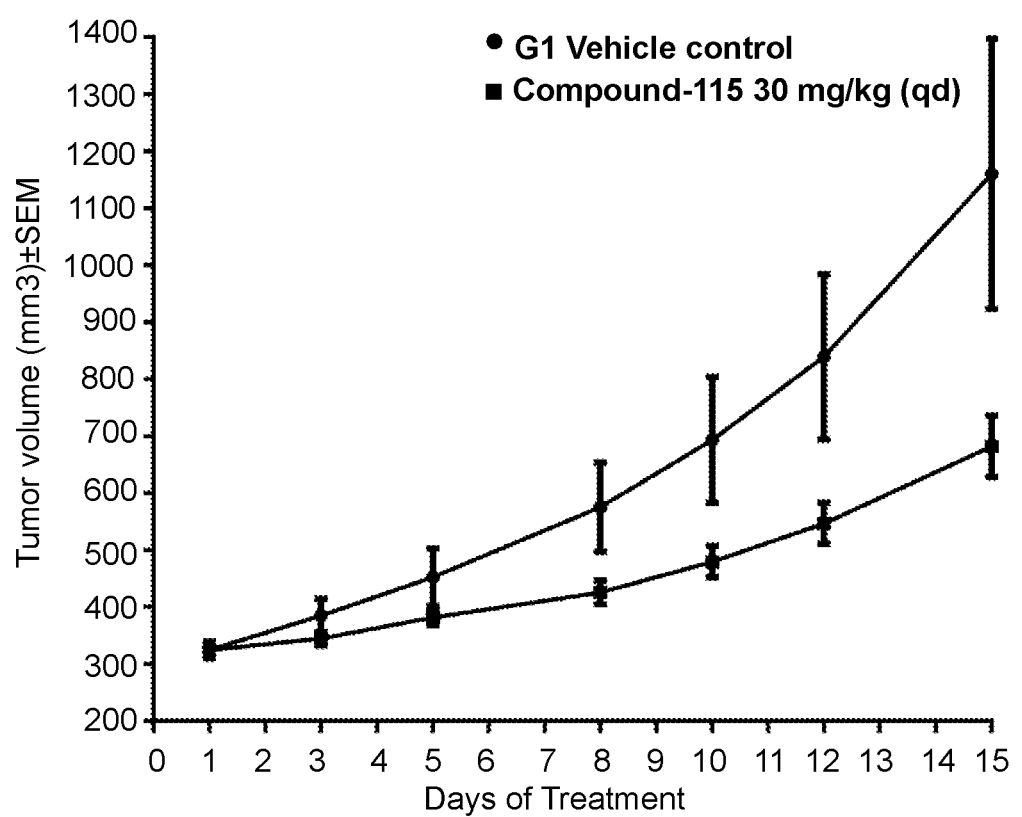

PYRAZOLO[1,5-A][1,3,5]TRIAZINE AND PYRAZOLO[1,5-A]PYRIMIDINE DERIVATIVES AS CDK INHIBITORS

CROSS-REFERENCE TO RELATED APPLICATIONS

This application is a national stage application under 35 U.S.C. § 371 of pending international application PCT/162013/055388, filed Mar. 8, 2016, which claims the benefit of Indian provisional application number 1128/CHE/2015 filed on Mar. 9, 2015, which is hereby incorporated by reference.

FIELD OF THE INVENTION

This invention pertains to compounds which inhibit the activity of selective transcriptional cyclin dependent kinases (CDKs) including CDK7, CDK9, CDK12, CDK13 and CDK18, more particularly transcriptional cyclin dependent kinase-7 (CDK7). The invention also provides pharmaceutically acceptable compositions comprising compounds of the present invention and methods of using said compositions in the treatment of diseases or disorder associated with selective transcriptional CDKs.

BACKGROUND OF THE INVENTION

One of the most important and fundamental processes in biology is the division of cells mediated by the cell cycle. This process ensures the controlled production of subsequent generations of cells with defined biological function. It is a highly regulated phenomenon and responds to a complex set of cellular signals both within the cell and from external sources. A complex network of tumor promoting and suppressing gene products are key components of this cellular signalling process. Over-expression of tumor-promoting components or the subsequent loss of the tumor-suppressing products will lead to unregulated cellular proliferation and the generation of tumors (Pardee, *Science* 246:603-608, 1989).

Kinases are important cellular enzymes that perform essential cellular functions such as regulating cell division and proliferation, and also appear to play a decisive role in many disease states that are characterized by uncontrolled proliferation and differentiation of cells. These disease states encompass a variety of cell types and maladies such as cancer, atherosclerosis, restenosis and other proliferative disorders (Kris M G et al.; "*Efficacy of gefitinib, an inhibitor of the epidermal growth factor receptor tyrosine kinase, in symptomatic patients with non-small cell lung cancer: a randomized trial*". *JAMA* 290 (16): 2149-58, October 2003).

Cyclin-dependent kinases (CDKs) are relatively small proteins, with molecular weights ranging from 34 to 40 kDa, and contain little more than the kinase domain. CDK binds a regulatory protein called a cyclin. Without cyclin, CDK has little kinase activity; only the cyclin-CDK complex is an active kinase. CDKs phosphorylate their substrates on serines and threonines, so they are serine-threonine kinases (Morgan, David O., *The Cell Cycle: Principles of Control*. London: New Science Press, 1st edition, (2007)).

The members of the cyclin-dependent kinase (CDK) family play critical regulatory roles in cell proliferation. There are currently 20 known mammalian CDKs. While CDK7-13 and 18 have been linked to transcription, only CDK1, 2, 4 and 6 show demonstrable association with the cell cycle. Unique among the mammalian CDKs, CDK7 has consolidated kinase activities, regulating both the cell cycle and transcription. In the cytosol, CDK7 exists as a heterotrimeric complex and is believed to function as a CDK1/2-activating kinase (CAK), whereby phosphorylation of conserved residues in CDK1/2 by CDK7 is required for full catalytic CDK activity and cell cycle progression (Desai et al., *Mol. Cell Biol.* 15, 345-350 (1995)).

CDK7, which complexes with cyclin H and MAT1, phosphorylates the cell cycle CDKs in the activation of T-loop, to promote their activities (see, e.g., Fisher et al., 1994). As such, it has been proposed that inhibiting CDK7 would provide a potent means of inhibiting cell cycle progression, which may be especially relevant given that there is compelling evidence from gene knockout studies in mice for lack of an absolute requirement for CDK2, CDK4 and CDK6 for the cell cycle, at least in most cell types (see, e.g., Malumbres et al., 2009), whilst different tumors appear to require some, but be independent of other interphase CDKs (CDK2, CDK4, CDK6). Recent genetic and biochemical studies have confirmed the importance of CDK7 for cell cycle progression (see, e.g., Larochelle et al., 2007; Ganuza et al., 2012).

Cyclin-dependent kinase 7 (CDK7) activates cell cycle CDKs and is a member of the general Transcription factor II Human (TFIIH). CDK7 also plays a role in transcription and possibly in DNA repair. The trimeric Cak complex CDK7/CyclinH/MAT1 is also a component of TFIIH, the general transcription/DNA repair factor IIH (reviewed in Morgan, D. O., *Annu Rev Cell Dev Biol* 13, 261-91, (1997)). As a TFIIH subunit, CDK7 phosphorylates the CTD (Carboxy-Terminal-Domain) of the largest subunit of RNA polymerase II (pol II). The CTD of mammalian pol II consists of 52 heptad repeats with the consensus sequence $^1$YSPTSPS$^7$ and the phosphorylation status of the Ser residues at positions 2 and 5 has been shown to be important in the activation of RNAP-II indicating that it is likely to have a crucial role in the function of the CTD. CDK7, which primarily phosphorylates Ser-5 (PS5) of RNAP-II at the promoter as part of transcriptional initiation (Gomes et al., 2006), incontrast with CDK9, which phosphorylates both Ser-2 and Ser-5 of the CTD heptad (Pinhero et al., 2004).

In addition to CDK7, other CDKs have been reported to phosphorylate and regulate RNA pol (II) CTD. The other CDKs include, Cdk9/Cyclin T1 or T2 that constitute the active form of the positive transcription elongation factor (P-TEFb) (Peterlin and Price, 2006) and Cdk12/Cyclin K and Cdk13/Cyclin K as the latest members of RNAPII CTD kinases (Bartkowiak et al., 2010; Blazek et al., 2011).

Disruption of RNAP II CTD phosphorylation has been shown to preferentially effect proteins with short half-lives, including those of the anti-apoptotic BCL-2 family. (Konig et al., "The novel cyclin-dependent kinase inhibitor flavopiridol downregulates Bcl-2 and induces growth arrest and apoptosis in chronic B-cell leukemia lines." (*Blood* 1, 4307-4312 (1997); Gojo et al) The transcriptional non-selective cyclin-dependent kinase inhibitor flavopiridol induces apoptosis in multiple myeloma cells through transcriptional repression and down-regulation of Mcl-1; (Clin. Cancer Res. 8, 3527-3538 (2002)).

This suggests that the CDK7 enzyme complexes are involved in multiple functions in the cell: cell cycle control, transcription regulation and DNA repair. It is surprising to find one kinase involved in such diverse cellular processes, some of which are even mutually exclusive. It also is puzzling that multiple attempts to find cell cycle dependent changes in CDK7 kinase activity remained unsuccessful. This is unexpected since activity and phosphorylation state of its substrate, CDC2, fluctuate during the cell cycle (Larochelle, S. et al. *Genes Dev* 12,370-81, (1998)). Indeed, flavopiridol, a non-selective pan-CDK inhibitor that targets CTD kinases, has demonstrated efficacy for the treatment of chronic lymphocytic leukemia (CLL), but suffers from a poor toxicity profile (Lin et al., "Phase II study of flavopiridol in relapsed chronic lymphocytic leukemia demonstrating high response rates in genetically high-risk disease." *J. Clin. Oncol.* 27, 6012-6018 (2009); Christian et al., "Flavopiridol in chronic lymphocytic leukemia: a concise review." *Clin. Lymphoma Myeloma* 9 Suppl. 3, S179-S185 (2009)).

In-vitro studies revealed substrate preferences for the different CDK7 complexes, indicating that CDK7 may form different complexes with different substrate specificity and presumably different in-vivo functions (Frit, P. et al., *Biochimie* 81, 27-38, (1999); Schutz, P. et al. *Cell* 102, 599-607, (2000)).

Various CDK inhibitors have been reported in the literature including WO2006052936 A2, WO2007038314A2, WO2008119792A1, WO2013169401A1, US20020091263A1, WO2008151304A1, WO2010103486A1, WO2010003133A2, WO2005026129A1, WO2012045195A1, WO2007038314A2 etc.

There is a need for new compounds, formulations, treatments and therapies to treat diseases and/or disorders associated with selective transcriptional CDKs including CDK7, CDK9, CDK12, CDK13 and CDK18; more particularly CDK7. It is, therefore, an object of this invention to provide compounds useful in the treatment and/or prevention or amelioration of such diseases and/or disorders.

BRIEF DESCRIPTION OF ACCOMPANYING DRAWINGS

FIG. 1: In vivo antitumor activity of CDK7 inhibitor in the MV4-11 AML xenograft model in athymic nude mice.

SUMMARY OF THE INVENTION

Provided herein are pyrazolo[1,5-a][1,3,5]triazine and pyrazolo[1,5-a]pyrimidine derivatives and pharmaceutical compositions thereof, which are useful as selective transcriptional CDK inhibitors.

In one aspect of the present invention, it comprises compounds of formula (I):

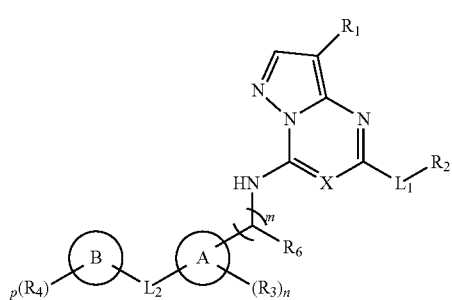

or a pharmaceutically acceptable salt or a stereoisomer thereof;
wherein,
X is CH or N;
Ring A is monocyclic or bicyclic aryl, heteroaryl or heterocycloalkyl;

Ring B is cycloalkyl, heterocycloalkyl, aryl, heteroaryl or absent;

$R_1$ is hydrogen, alkyl or cycloalkyl;

$R_2$ is an optionally substituted alkyl, cycloalkyl or heterocycloalkyl; wherein the optional substituents are amino, halo, hydroxy, alkyl, alkoxy, alkoxyalkoxy, alkylamino, cyano, nitro or haloalkyl;

$R_3$ at each occurrence independently is halo, alkyl, hydroxy, alkoxy, amino, alkylamino, cyano, nitro or haloalkyl;

$R_4$ at each occurrence independently is halo, alkyl, hydroxy, alkoxy, —(NH)$_q$—S(O)$_2$—CH=CH$_2$, —(NH)$_q$—CH$_2$—CH=CH—C(O)—NR$_a$R$_b$,

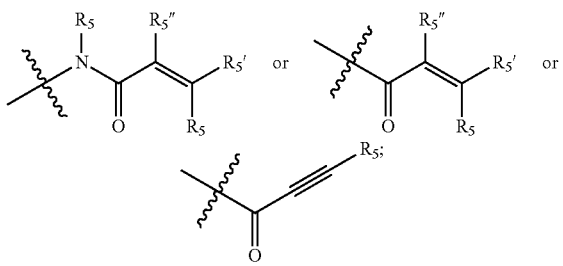

wherein $R_5$ and $R_5''$ at each occurrence independently are hydrogen or alkyl; $R_5'$ is hydrogen, halo, alkyl, alkoxyalkyl or —CH$_2$—NR$_a$R$_b$;

$R_6$ is hydrogen or alkyl;

$R_a$ and $R_b$ are independently hydrogen or alkyl; or $R_a$ and $R_b$ along with the nitrogen atom to which they are attached form an optionally substituted heterocyclic ring having 0-2 additional heteroatoms selected from O, S and N; wherein the optional substituent is one or more alkyl or halo;

$L_1$ is —O—, —S—, —NH— or absent;

$L_2$ is absent or optionally substituted $C_1$-$C_6$ alkylene, wherein one or more methylene units of the alkylene is optionally and independently replaced with —C(O)—, —O—, —N(R$_7$)— or cycloalkylene; wherein $R_7$ is hydrogen or alkyl;

m is 0 to 1;
n is 0, 1 or 2;
p is 1, 2 or 3; and
q is 0 to 1.

In another aspect, the present invention provides a pharmaceutical composition comprising the compound of formula (I) and at least one pharmaceutically acceptable excipient (such as a pharmaceutically acceptable carrier or diluent).

In yet another aspect, the present invention relates to the preparation of compounds of formula (I).

In yet another aspect of the present invention, provided herein are pyrazolo[1,5-a][1,3,5]triazine and pyrazolo[1,5-a]pyrimidine derivatives of formula (I), which are useful for medical use. In particular for the treatment or prevention of diseases and/or disorders where selective transcriptional CDK inhibition is desired.

DETAILED DESCRIPTION OF THE INVENTION

Unless defined otherwise, all technical and scientific terms used herein have the same meaning as is commonly understood by one of skill in art to which the subject matter herein belongs. As used in the specification and the appended claims, unless specified to the contrary, the following terms have the meaning indicated in order to facilitate the understanding of the present invention.

As used herein, the term "optionally substituted" or "suitable groups" refers to replacement of one or more hydrogen radicals in a given structure with a radical of a specified substituent including, but not limited to: halo, alkyl, alkenyl, alkynyl, aryl, heterocyclyl, thiol, alkylthio, arylthio, alkylthioalkyl, arylthioalkyl, alkylsulfonyl, alkylsulfonylalkyl, arylsulfonylalkyl, alkoxy, aryloxy, aralkoxy, aminocarbonyl, alkylaminocarbonyl, arylaminocarbonyl, alkoxycarbonyl, aryloxycarbonyl, haloalkyl, amino, cyano, nitro, alkylamino, arylamino, alkylaminoalkyl, arylaminoalkyl, aminoalkylamino, hydroxy, alkoxyalkyl, carboxyalkyl, alkoxycarbonylalkyl, aminocarbonylalkyl, acyl, aralkoxycarbonyl, carboxylic acid, sulfonic acid, sulfonyl, phosphonic acid, aryl, heteroaryl and heterocyclic. It is understood that the substituent may be further substituted.

As used herein, unless otherwise defined the term "alkyl" alone or in combination with other term(s) means saturated aliphatic hydrocarbon chains, including $C_1$-$C_{10}$ straight or $C_1$-$C_{10}$ branched alkyl groups. Examples of "alkyl" include but are not limited to methyl, ethyl, propyl, isopropyl, butyl, isobutyl, sec-butyl, tert-butyl, isopentyl or neopentyl and the like.

As used herein, the term "halo" or "halogen" alone or in combination with other term(s) means fluorine, chlorine, bromine or iodine.

The term "hydroxy" or "hydroxyl" refers to —OH group.

The term "amino" refers to —$NH_2$ group.

As used herein, the term "alkoxy" or "alkoxyl" refers to the group alkyl-O— or —O-alkyl, where alkyl groups are as defined above. Exemplary $C_1$-$C_{10}$ alkyl group containing alkoxy groups include but are not limited to methoxy, ethoxy, n-propoxy, n-butoxy, t-butoxy and the like. An alkoxy group can be unsubstituted or substituted with one or more suitable groups.

As used herein, the term "alkoxylalkoxy" refers to the group alkyl-O-alkoxy- or -alkoxy-O-alkyl, where alkoxy groups are defined above. Exemplary alkoxylalkoxy groups include but are not limited to methoxyethoxy, ethoxyethoxy, methoxypropoxy, ethoxymethoxy, ethoxypropoxy, propoxymethoxy, propoxyethoxy and the like.

As used herein, the term "cycloalkyl" alone or in combination with other term(s) means —$C_3$-$C_{10}$ saturated cyclic hydrocarbon ring. A cycloalkyl may be a single ring, which typically contains from 3 to 7 carbon ring atoms. Examples of single-ring cycloalkyls include but are not limited to cyclopropyl, cyclobutyl, cyclopentyl, cyclohexyl, cycloheptyl and the like. A cycloalkyl may alternatively be polycyclic or contain more than one ring. Examples of polycyclic cycloalkyls include bridged, fused and spirocyclic carbocyclyls and the like.

As used herein, the term "aryl" is optionally substituted monocyclic, bicyclic or polycyclic aromatic hydrocarbon ring system of about 6 to 14 carbon atoms. Examples of a $C_6$-$C_{14}$ aryl group include, but are not limited to phenyl, naphthyl, biphenyl, anthryl, tetrahydronaphthyl, fluorenyl, indanyl, biphenylenyl and acenaphthyl. Aryl group can be unsubstituted or substituted with one or more suitable groups.

The term "heterocycloalkyl" refers to a non-aromatic, saturated or partially saturated, monocyclic or polycyclic ring system of 3 to 15 members having at least one heteroatom or heterogroup selected from O, N, S, S(O), S(O)$_2$, NH or C(O) with the remaining ring atoms being independently selected from the group consisting of carbon, oxygen, nitrogen and sulfur. Examples of "Heterocycloalkyl" include, but are not limited to azetidinyl, oxetanyl, imidazolidinyl, pyrrolidinyl, oxazolidinyl, thiazolidinyl, pyrazolidinyl, tetrahydrofuranyl, piperidinyl, piperazinyl, tetrahydropyranyl, morpholinyl, oxapiperazinyl, oxapiperidinyl, tetrahydrofuryl, tetrahydropyranyl, tetrahydrothiophenyl, dihydropyranyl, indolinyl, indolinylmethyl, azepanyl and their N-oxides thereof. Attachment of a heterocycloalkyl substituent can occur via either a carbon atom or a heteroatom. A heterocycloalkyl group can be optionally substituted with one or more suitable groups by one or more aforesaid groups.

As used herein, the term "heteroaryl" alone or in combination with other term(s) means a completely unsaturated ring system containing a total of 5 to 14 ring atoms. At least one of the ring atoms is a heteroatom (i.e., oxygen, nitrogen or sulfur), with the remaining ring atoms/groups being independently selected from the group consisting of carbon, oxygen, nitrogen or sulfur. A heteroaryl may be a single-ring (monocyclic), bicyclic or polycyclic ring system. Examples of "heteroaryl" include but are not limited to pyridyl, pyridine-1-oxide, indolyl, benzimidazolyl, benzothiazolyl and the like. The term heteroaryl includes their N-oxides thereof.

The term "heteroatom" as used herein designates a sulfur, nitrogen or oxygen atom.

As used herein, the term "compound(s)" comprises the compounds disclosed in the present invention.

As used herein, the term "comprise" or "comprising" is generally used in the sense of include, that is to say permitting the presence of one or more features or components.

As used herein, the term "or" means "and/or" unless stated otherwise.

As used herein, the term "including" as well as other forms, such as "include", "includes" and "included" is not limiting.

As used herein, the term "composition" is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

As used herein, the term "treat", "treating" and "treatment" refer to a method of alleviating or abrogating a disease and/or its attendant symptoms.

As used herein, the term "prevent", "preventing" and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring a disease.

As used herein, the term "subject" to which administration is contemplated includes, but are not limited to humans and/or non-human animals; for example, mammals and birds. In certain embodiments the animal is mammal. A non-human animal may be transgenic animal.

As used herein, the term "administer", "administering" or "administration" refers to implanting, absorbing, ingesting, injecting, inhaling or otherwise introducing a compound of formula (I) or a pharmaceutical composition thereof.

As used herein, the term "therapeutically effective amount" refers to that amount of the compound being administered sufficient to prevent development of or alleviate to some extent one or more of the symptoms of the condition or disorder being treated.

"Pharmaceutically acceptable" means that, which is useful in preparing a pharmaceutical composition that is generally safe, non-toxic and neither biologically nor otherwise undesirable and includes that which is acceptable for veterinary as well as human pharmaceutical use.

The term "stereoisomers" or "isomers" refers to any enantiomers, diastereoisomers or geometrical isomers of the compounds of formula (I), (IA), (IB), (IC), (ID), (IE) and (IF); wherever they are chiral or when they bear one or more double bonds. When the compounds of the formula (I), (IA), (IB), (IC), (ID), (IE) and (IF); and related formulae are chiral, they can exist in racemic or in optically active form. It should be understood that the invention encompasses all stereochemical isomeric forms, including diastereomeric, enantiomeric and epimeric forms, as well as d-isomers and l-isomers and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns or any other appropriate method known in the art. Starting compounds of particular stereochemistry are either commercially available or can be made and resolved by techniques known in the art. Additionally, the compounds of the present invention may exist as geometric isomers. The present invention includes all cis, trans, syn, anti, entgegen (E) and zusammen (Z) isomers as well as the appropriate mixtures thereof.

As used herein the term "CDK" refers to a cyclin-dependent kinase. A CDK binds a cyclin (e.g., Cyclin H), which is a regulatory protein. CDKs phosphorylate their substrates at serines and threonines. CDKs include CDK1, CDK2, CDK2, CDK4, CDK5, CDK7, CDK8, CDK9, CDK10, CDK11, CDK12, CDK13, CDK14, CDK16, CDK18 and CDK20. CDK7 is a CDK wherein the substrate is Cyclin H, MAT1 (e.g., MNAT1) or Cyclin H and MAT1 complex. The term CDK inhibitor refers to selective transcriptional CDK inhibitor.

The present invention provides substituted pyrazolo[1,5-a][1,3,5]triazine and pyrazolo[1,5-a]pyrimidine derivatives of formula (I), which are useful for the inhibition of selective transcriptional CDKs, particularly selective transcriptional CDK7, CDK9, CDK 12, CDK13 or CDK18, more particularly selective transcriptional CDK7.

The present invention further provides pharmaceutical compositions comprising the said substituted pyrazolo[1,5-a][1,3,5]triazine and pyrazolo[1,5-a]pyrimidine compounds and their derivatives as therapeutic agents.

According to first embodiment, the present invention provides compounds of formula (I)

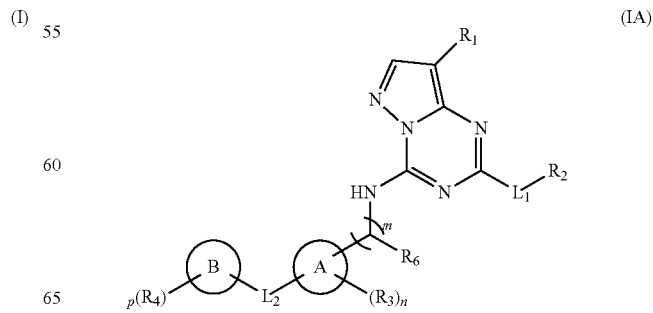

(I)

or a pharmaceutically acceptable salt or a stereoisomer thereof;

wherein,

X is CH or N;

Ring A is monocyclic or bicyclic aryl, heteroaryl or heterocycloalkyl;

Ring B is cycloalkyl, heterocycloalkyl, aryl, heteroaryl or absent;

$R_1$ is hydrogen, alkyl or cycloalkyl;

$R_2$ is an optionally substituted alkyl, cycloalkyl or heterocycloalkyl; wherein the optional substituents are amino, halo, hydroxy, alkyl, alkoxy, alkoxyalkoxy, alkylamino, cyano, nitro or haloalkyl;

$R_3$ at each occurrence independently is halo, alkyl, hydroxy, alkoxy, amino, alkylamino, cyano, nitro or haloalkyl;

$R_4$ at each occurrence independently is halo, alkyl, hydroxy, alkoxy, $-(NH)_q-SO_2-CH=CH_2$, $-(NH)_q-CH_2CH=CH-C(O)-NR_aR_b$,

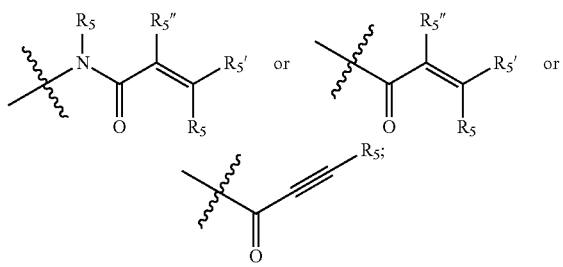

wherein $R_5$ and $R_5''$ at each occurrence independently are hydrogen or alkyl; $R_5'$ is hydrogen, halo, alkyl, alkoxyalkyl or $-CH_2-NR_aR_b$;

$R_6$ is hydrogen or alkyl;

$R_a$ and $R_b$ are independently hydrogen or alkyl; or $R_a$ and $R_b$ along with the nitrogen atom to which they are attached form an optionally substituted heterocyclic ring having 0-2 additional heteroatoms selected from O, S and N; wherein the optional substituent is one or more alkyl or halo;

$L_1$ is $-O-$, $-S-$, $-NH-$ or absent;

$L_2$ is absent or optionally substituted $C_1-C_6$ alkylene, wherein one or more methylene units of the alkylene is optionally and independently replaced with $-C(O)-$, $-O-$, $-N(R_7)-$ or cycloalkylene; wherein $R_7$ is hydrogen or alkyl;

m is 0 to 1;

n is 0, 1 or 2;

p is 1, 2 or 3; and q is 0 to 1.

In another embodiment of the present invention, the compound of formula (I) is a compound of formula (IA):

(IA)

or a pharmaceutically acceptable salt thereof or a stereoisomer thereof, wherein, ring A, ring B, $L_1$, $L_2$, $R_1$, $R_2$, $R_3$, $R_4$, $R_6$, m, n and p are same as defined in formula (I).

In yet another embodiment of the present invention, the compound of formula (I) is a compound of formula (IB):

(IB)

or a pharmaceutically acceptable salt thereof or a stereoisomer thereof;

wherein,

X, ring B, $L_1$, $L_2$, $R_1$, $R_2$, $R_3$, $R_4$, $R_6$, m, n and p are same as defined in formula (I).

In yet another embodiment of the present invention, the compound of formula (I) is a compound of formula (IC):

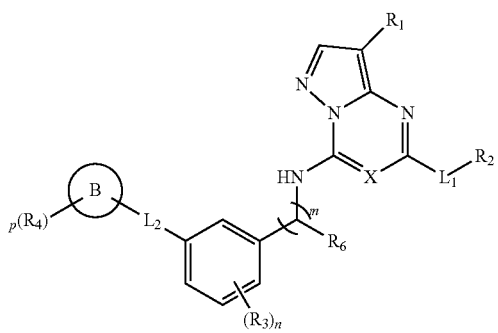

(IC)

or a pharmaceutically acceptable salt thereof or a stereoisomer thereof;

wherein, $R_2$ is optionally substituted cycloalkyl or optionally substituted heterocycloalkyl;

X, ring A, ring B, $L_2$, $R_1$, $R_3$, $R_4$, $R_6$, m, n and p are same as defined in formula (I).

In another embodiment of the present invention, the compound of formula (I) is a compound of formula (ID):

(ID)

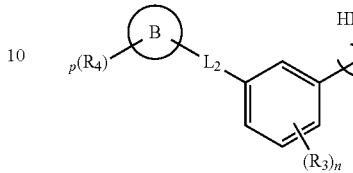

or a pharmaceutically acceptable salt thereof or a stereoisomer thereof;

wherein, $R_2$ is optionally substituted cycloalkyl or optionally substituted heterocycloalkyl;

X, ring B, $L_2$, $R_1$, $R_3$, $R_4$, $R_6$, m, n and p are same as defined in formula (I).

In another embodiment of the present invention, the compound of formula (I) is a compound of formula (IE):

(IE)

or a pharmaceutically acceptable salt thereof or a stereoisomer thereof;

wherein,

X, ring B, $L_2$, $R_1$, $R_3$, $R_4$, $R_6$, m, n and p are same as defined in formula (I).

In another embodiment of the present invention, the compound of formula (I) is a compound of formula (IF):

(IF)

or a pharmaceutically acceptable salt thereof or a stereoisomer thereof;
wherein,
X, $L_1$, $R_1$, $R_2$, $R_3$, $R_4$, $R_6$, m, n and p are same as defined in formula (I).

According to one embodiment, the present invention provides compounds of formula (I) and (IA); wherein, ring A is aryl; and ring B, X, $L_1$, $L_2$, $R_1$, $R_2$, $R_3$, $R_4$, $R_6$, m, n and p are same as defined in formula (I).

According to another embodiment the present invention provides compounds of formula (I) and (IA); wherein ring A is monocyclic or bicyclic heteroaryl or heterocycloalkyl and their N-oxides thereof; and ring B, X, $L_1$, $L_2$, $R_1$, $R_2$, $R_3$, $R_4$, $R_6$, m, n and p are same as defined in formula (I).

According to yet another embodiment the present invention provides compounds of formula (I), (IB), (IC), (ID), (IE) and (IF); wherein X is N.

According to yet another embodiment the present invention provides compounds of formula (I), (IA), (IB), (IC), (ID) and (IE); wherein, $L_2$ is absent or selected from —NHC(O)—, —C(O)NH—, —OC(O)—,

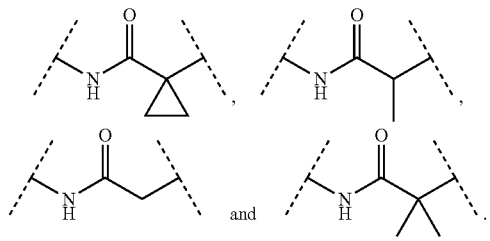

According to yet another embodiment the present invention provides compounds of formula (I), (IA), (IB), (IC), (ID) and (IE); wherein ring B is absent or selected from phenyl, cyclohexyl, piperidinyl, pyrrolidinyl, azitidinyl, 1-methyl-1H-pyrazole, piperazinyl and morpholinyl.

The embodiments below are illustrative of the present invention and are not intended to limit the claims to the specific embodiments exemplified.

According to certain embodiments of the present invention, specifically provided are compounds of formula (I), (IA), (IB), (IC), (ID), (IE) and (IF); wherein, $R_1$ is hydrogen, alkyl or cycloalkyl; preferably the said alkyl is ethyl or isopropyl and the said cycloalkyl is cyclopropyl.

According to certain embodiments of the present invention, specifically provided are compounds of formula (I), (IA), (IB) (IC), (ID), (IE) and (IF); wherein, $R_2$ is optionally substituted cycloalkyl or heterocycloalkyl; preferably optionally substituted cycloalkyl is

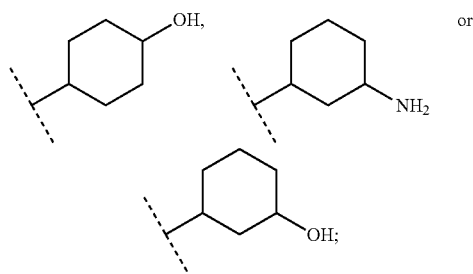

and in particular optionally substituted heterocycloalkyl is

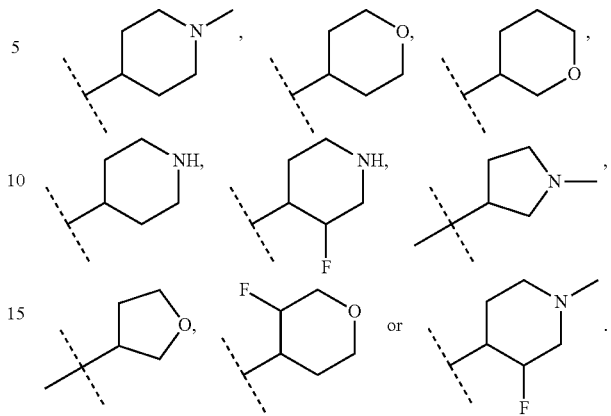

According to certain embodiments of the present invention, specifically provided are compounds of formula (I), (IA), (IB), (IC), (ID), (IE) and (IF); wherein, $R_2$ is alkyl optionally substituted with amino, alkoxy or alkoxylalkoxy; preferably $R_2$ is methyl, aminobutyl, methoxyethyl, isobutanyl and methoxyethoxyethyl.

According to certain embodiments of the present invention, specifically provided are compounds of formula (I), (IA), (IB), (IC), (ID), (IE) and (IF); wherein, $R_6$ is hydrogen or alkyl; preferably the said alkyl is methyl.

According to certain embodiments of the present invention, specifically provided are compounds of formula (I), (IA) and (IC); wherein, ring A is phenyl, piperidinyl, pyridyl and pyridine-N-oxide.

According to certain embodiments of the present invention, specifically provided are compounds of formula (I), (IA), (IB), (IC), (ID), (IE) and (IF); wherein, $R_3$ is halo or alkyl; preferably the said halo is fluoro and the said alkyl is methyl or ethyl.

According to certain embodiments of the present invention, specifically provided are compounds of formula (I), (IA), (IB), (IC), (ID), (IE) and (IF); wherein, $R_4$ is —$(NH)_q$—$S(O)_2$—CH=$CH_2$, —$(NH)_q$—$CH_2$—CH=CH—C(O)—$NR_aR_b$,

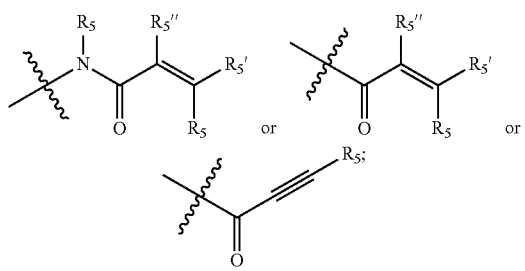

and $R_5$, $R_5'$, $R_5''$, $R_a$, $R_b$ and q are same as defined in formula (I).

According to the preceding embodiment, specifically provided are compounds of formula (I), (IA), (IB), (IC), (ID), (IE) and (IF); wherein, $R_4$ is

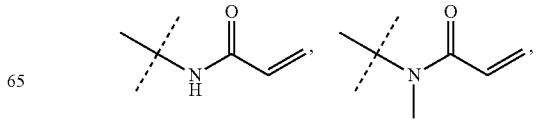

-continued

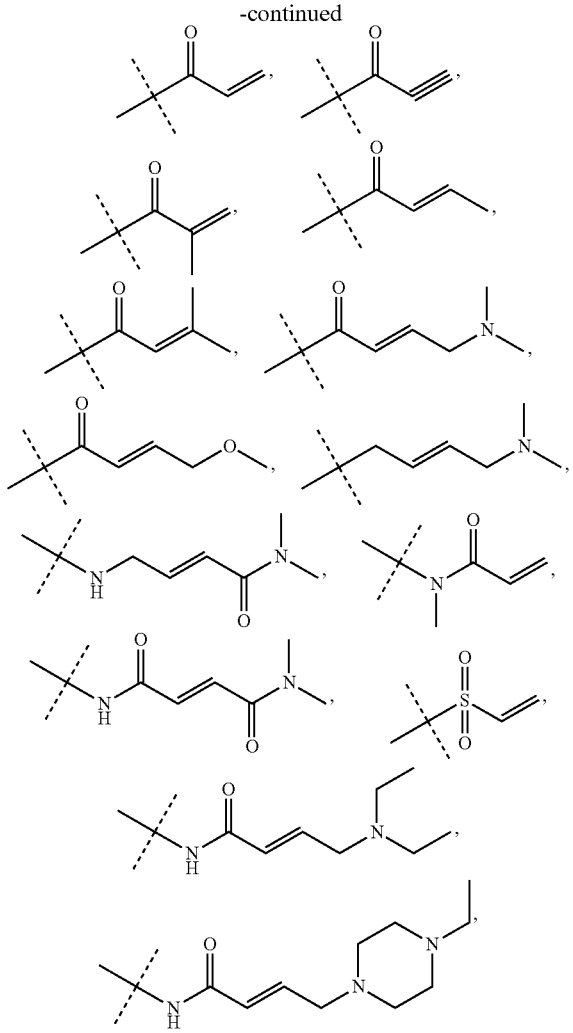

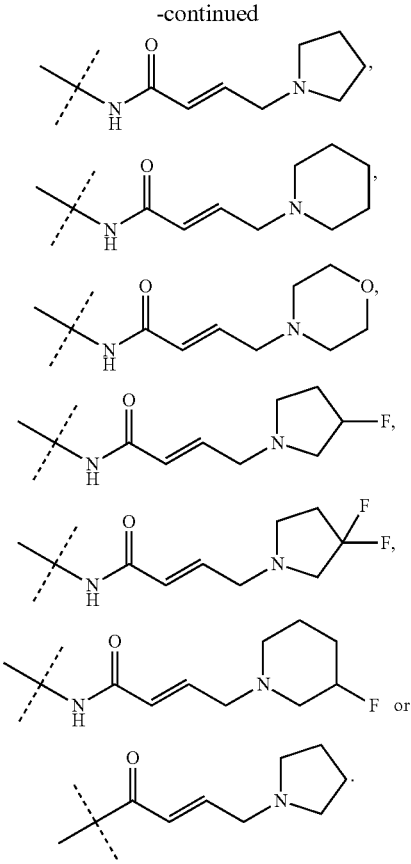

According to certain embodiments, the present invention provides compounds of the formula (I) in which 'm' and 'n' are independently 0 or 1; and 'p' is 1.

According to certain embodiments, the present invention provides a compound selected from the group consisting of:

| Compound No: | IUPAC name |
|---|---|
| 1. | 1-acryloyl-N-(3-(((8-isopropyl-2-((tetrahydro-2H-pyran-4-yl)amino)pyrazolo[1,5-a][1,3,5]triazin-4-yl)amino)methyl)phenyl)piperidine-3-carboxamide; |
| 2. | 1-acryloyl-N-(3-(((8-isopropyl-2-((tetrahydro-2H-pyran-4-yl)amino)pyrazolo[1,5-a][1,3,5]triazin-4-yl)amino)methyl)phenyl)azetidine-2-carboxamide; |
| 3. | 1-acryloyl-N-(3-(((8-isopropyl-2-((tetrahydro-2H-pyran-4-yl)amino)pyrazolo[1,5-a][1,3,5]triazin-4-yl)amino)methyl)phenyl)pyrrolidine-2-carboxamide; |
| 4. | 1-acryloyl-N-(3-(((8-isopropyl-2-((tetrahydro-2H-pyran-4-yl)amino)pyrazolo[1,5-a][1,3,5]triazin-4-yl)amino)methyl)phenyl)pyrrolidine-3-carboxamide; |
| 5. | Isomer-1: 1-acryloyl-N-(3-(((8-isopropyl-2-((tetrahydro-2H-pyran-4-yl)amino) pyrazolo[1,5-a][1,3,5]triazin-4-yl)amino)methyl)phenyl)pyrrolidine-3-carboxamide; |
| 6. | Isomer-2: 1-acryloyl-N-(3-(((8-isopropyl-2-((tetrahydro-2H-pyran-4-yl)amino) pyrazolo[1,5-a][1,3,5]triazin-4-yl)amino)methyl)phenyl)pyrrolidine-3-carboxamide; |
| 7. | (1,4-cis)-4-acrylamido-N-(3-(((8-isopropyl-2-((tetrahydro-2H-pyran-4-yl)amino)pyrazolo[1,5-a][1,3,5]triazin-4-yl)amino)methyl)phenyl)cyclohexane-1-carboxamide; |
| 8. | 1-acryloyl-N-(3-(((8-isopropyl-2-((1-methylpiperidin-4-yl)amino)pyrazolo[1,5-a][1,3,5]triazin-4-yl)amino)methyl)phenyl)piperidine-3-carboxamide; |
| 9. | (1,4-cis)-4-acrylamido-N-(3-(((2-(((1r,4r)-4-hydroxycyclohexyl)amino)-8-isopropylpyrazolo[1,5-a][1,3,5]triazin-4-yl)amino)methyl)phenyl)cyclohexane-1-carboxamide; |
| 10. | Isomer-1: 4-acrylamido-N-(3-(((2-((3-hydroxycyclohexyl)amino)-8-isopropyl pyrazolo[1,5-a][1,3,5]triazin-4-yl)amino)methyl)phenyl)cyclohexane-1-carboxamide; |

-continued

| Compound No: | IUPAC name |
| --- | --- |
| 11. | Isomer-2: 4-acrylamido-N-(3-(((2-((3-hydroxycyclohexyl)amino)-8-isopropyl pyrazolo[1,5-a][1,3,5]triazin-4-yl)amino)methyl)phenyl)cyclohexane-1-carboxamide; |
| 12. | Isomer-1: 1-acryloyl-N-(3-(((2-((3-hydroxycyclohexyl)amino)-8-isopropyl pyrazolo[1,5-a][1,3,5]triazin-4-yl)amino)methyl)phenyl)pyrrolidine-3-carboxamide; |
| 13. | Isomer-2: 1-acryloyl-N-(3-(((2-((3-hydroxycyclohexyl)amino)-8-isopropyl pyrazolo[1,5-a][1,3,5]triazin-4-yl)amino)methyl)phenyl)pyrrolidine-3-carboxamide; |
| 14. | 1-acryloyl-N-(3-(((2-(((3S,4S)-3-fluoropiperidin-4-yl)amino)-8-isopropyl pyrazolo[1,5-a][1,3,5]triazin-4-yl)amino)methyl)phenyl)pyrrolidine-3-carboxamide; |
| 15. | 1-acryloyl-N-(3-(((2-((3-aminocyclohexyl)amino)-8-isopropylpyrazolo[1,5-a][1,3,5]triazin-4-yl)amino)methyl)phenyl)pyrrolidine-3-carboxamide; |
| 16. | 1-acryloyl-N-(3-(((8-isopropyl-2-((tetrahydro-2H-pyran-3-yl)amino)pyrazolo[1,5-a][1,3,5]triazin-4-yl)amino)methyl)phenyl)piperidine-2-carboxamide; |
| 17. | N-(3-(((8-isopropyl-2-((tetrahydro-2H-pyran-4-yl)amino)pyrazolo[1,5-a][1,3,5]triazin-4-yl)amino)methyl) phenyl)-1-(3-methylbut-2-enoyl)azetidine-2-carboxamide; |
| 18. | 1-acryloyl-N-(3-(((8-isopropyl-2-((tetrahydro-2H-pyran-4-yl)amino)pyrazolo[1,5-a][1,3,5]triazin-4-yl)amino)methyl)phenyl)azetidine-3-carboxamide; |
| 19. | (R)-1-acryloyl-N-(3-(((8-isopropyl-2-((tetrahydro-2H-pyran-4-yl)amino)pyrazolo[1,5-a][1,3,5]triazin-4-yl)amino)methyl)phenyl)azetidine-2-carboxamide; |
| 20. | (S)-1-acryloyl-N-(3-(((8-isopropyl-2-((tetrahydro-2H-pyran-4-yl)amino)pyrazolo[1,5-a][1,3,5]triazin-4-yl)amino)methyl)phenyl)azetidine-2-carboxamide; |
| 21. | 1-acryloyl-N-(3-(((8-isopropyl-2-((tetrahydro-2H-pyran-4-yl)amino)pyrazolo[1,5-a][1,3,5]triazin-4-yl)amino)methyl)phenyl)piperidine-2-carboxamide; |
| 22. | 3-acrylamido-N-(3-(((8-isopropyl-2-((tetrahydro-2H-pyran-4-yl)amino)pyrazolo[1,5-a][1,3,5]triazin-4-yl)amino)methyl)phenyl)cyclohexane-1-carboxamide; |
| 23. | 4-acryloyl-N-(3-(((8-isopropyl-2-((tetrahydro-2H-pyran-4-yl)amino)pyrazolo[1,5-a][1,3,5]triazin-4-yl)amino)methyl)phenyl)morpholine-2-carboxamide; |
| 24. | 4-acryloyl-N-(3-(((8-isopropyl-2-((tetrahydro-2H-pyran-4-yl)amino)pyrazolo[1,5-a][1,3,5]triazin-4-yl)amino)methyl)phenyl)morpholine-3-carboxamide; |
| 25. | N-(3-(((8-isopropyl-2-((tetrahydro-2H-pyran-4-yl)amino)pyrazolo[1,5-a][1,3,5]triazin-4-yl)amino)methyl)phenyl)-4-propioloylmorpholine-3-carboxamide; |
| 26. | 4-acryloyl-N-(4-ethyl-3-(((8-isopropyl-2-((tetrahydro-2H-pyran-4-yl)amino) pyrazolo[1,5-a][1,3,5]triazin-4-yl)amino)methyl)phenyl)morpholine-3-carboxamide; |
| 27. | 1-acryloyl-N-(3-(((8-isopropyl-2-((tetrahydro-2H-pyran-4-yl)amino)pyrazolo[1,5-a][1,3,5]triazin-4-yl)amino)methyl)-4-methylphenyl)azetidine-2-carboxamide; |
| 28. | 1-acryloyl-N-(5-(((8-isopropyl-2-((tetrahydro-2H-pyran-4-yl)amino)pyrazolo[1,5-a][1,3,5]triazin-4-yl)amino)methyl)-2-methylphenyl)azetidine-2-carboxamide; |
| 29. | 1-acryloyl-N-(4-fluoro-3-(((8-isopropyl-2-((tetrahydro-2H-pyran-4-yl)amino) pyrazolo[1,5-a][1,3,5]triazin-4-yl)amino)methyl)phenyl)azetidine-2-carboxamide; |
| 30. | 1-acryloyl-N-(2-fluoro-3-(((8-isopropyl-2-((tetrahydro-2H-pyran-4-yl)amino) pyrazolo[1,5-a][1,3,5]triazin-4-yl)amino)methyl)phenyl)azetidine-2-carboxamide; |
| 31. | 1-acryloyl-N-(3-fluoro-5-(((8-isopropyl-2-((tetrahydro-2H-pyran-4-yl)amino) pyrazolo[1,5-a][1,3,5]triazin-4-yl)amino)methyl)phenyl)azetidine-2-carboxamide; |
| 32. | 1-acryloyl-N-(4-fluoro-3-(((8-isopropyl-2-((tetrahydro-2H-pyran-4-yl)amino) pyrazolo[1,5-a][1,3,5]triazin-4-yl)amino)methyl)phenyl)pyrrolidine-3-carboxamide; |
| 33. | 1-acryloyl-N-(3-fluoro-5-(((8-isopropyl-2-((tetrahydro-2H-pyran-4-yl)amino) pyrazolo[1,5-a][1,3,5]triazin-4-yl)amino)methyl)phenyl)pyrrolidine-3-carboxamide; |
| 34. | 1-acryloyl-N-(3-(((8-isopropyl-2-((tetrahydro-2H-pyran-4-yl)amino)pyrazolo[1,5-a][1,3,5]triazin-4-yl)amino)methyl)-4-methylphenyl)piperidine-2-carboxamide; |
| 35. | 1-acryloyl-N-(2-fluoro-3-(((8-isopropyl-2-((tetrahydro-2H-pyran-4-yl)amino) pyrazolo[1,5-a][1,3,5]triazin-4-yl)amino)methyl)phenyl)piperidine-2-carboxamide; |
| 36. | 1-acryloyl-N-(3-fluoro-5-(((8-isopropyl-2-((tetrahydro-2H-pyran-4-yl)amino) pyrazolo[1,5-a][1,3,5]triazin-4-yl)amino)methyl)phenyl)piperidine-2-carboxamide; |
| 37. | 1-acryloyl-N-(4-fluoro-3-(((8-isopropyl-2-((tetrahydro-2H-pyran-4-yl)amino) pyrazolo[1,5-a][1,3,5]triazin-4-yl)amino)methyl)phenyl)piperidine-2-carboxamide; |
| 38. | (1,4-cis)-4-acrylamido-N-(2-fluoro-3-(((8-isopropyl-2-((tetrahydro-2H-pyran-4-yl)amino)pyrazolo[1,5-a][1,3,5]triazin-4-yl)amino)methyl)phenyl)cyclohexane-1-carboxamide; |
| 39. | (1,4-cis)-4-acrylamido-N-(4-fluoro-3-(((8-isopropyl-2-((tetrahydro-2H-pyran-4-yl)amino)pyrazolo[1,5-a][1,3,5]triazin-4-yl)amino)methyl)phenyl)cyclohexane-1-carboxamide; |

-continued

| Compound No: | IUPAC name |
|---|---|
| 40. | 4-acryloyl-N-(5-(((8-isopropyl-2-((tetrahydro-2H-pyran-4-yl)amino)pyrazolo[1,5-a][1,3,5]triazin-4-yl)amino)methyl)pyridin-3-yl)morpholine-3-carboxamide; |
| 40A. | 3-acrylamido-N-(3-(((8-isopropyl-2-((tetrahydro-2H-pyran-4-yl)amino)pyrazolo[1,5-a][1,3,5]triazin-4-yl)amino)methyl)phenyl)-4-methylbenzamide; |
| 40B. | 5-acrylamido-N-(3-(((8-isopropyl-2-((tetrahydro-2H-pyran-4-yl)amino)pyrazolo[1,5-a][1,3,5]triazin-4-yl)amino)methyl)phenyl)-2-methylbenzamide; |
| 40C. | 1-acryloyl-N-(3-(((8-isopropyl-2-((tetrahydro-2H-pyran-4-yl)amino)pyrazolo[1,5-a][1,3,5]triazin-4-yl)amino)methyl)phenyl)-6-methylpiperidine-2-carboxamide; |
| 40D. | 1-acryloyl-N-(3-(((8-isopropyl-2-(((S)-tetrahydro-2H-pyran-3-yl)amino)pyrazolo[1,5-a][1,3,5]triazin-4-yl)amino)methyl)phenyl)piperidine-2-carboxamide; |
| 40E. | 1-acryloyl-N-(3-(((8-isopropyl-2-(((R)-tetrahydro-2H-pyran-3-yl)amino)pyrazolo[1,5-a][1,3,5]triazin-4-yl)amino)methyl)phenyl)piperidine-2-carboxamide; |
| 41. | (S)-N-(1-acryloylpiperidin-3-yl)-3-(((8-isopropyl-2-((tetrahydro-2H-pyran-4-yl)amino)pyrazolo[1,5-a][1,3,5]triazin-4-yl)amino)methyl)benzamide; |
| 42. | 1-acryloyl-N-(4-fluoro-3-(((8-isopropyl-2-((tetrahydro-2H-pyran-4-yl)amino)pyrazolo[1,5-a][1,3,5]triazin-4-yl)amino)methyl)phenyl)azetidine-2-carboxamide; |
| 43. | 1-acryloyl-N-(2-fluoro-5-(((8-isopropyl-2-((tetrahydro-2H-pyran-4-yl)amino)pyrazolo[1,5-a][1,3,5]triazin-4-yl)amino)methyl)phenyl)pyrrolidine-3-carboxamide; |
| 44. | 1-acryloyl-N-(2-fluoro-5-(((8-isopropyl-2-((tetrahydro-2H-pyran-4-yl)amino)pyrazolo[1,5-a][1,3,5]triazin-4-yl)amino)methyl)phenyl)piperidine-2-carboxamide; |
| 45. | 1-acryloyl-N-(3-(1-((8-isopropyl-2-((tetrahydro-2H-pyran-4-yl)amino)pyrazolo[1,5-a][1,3,5]triazin-4-yl)amino)ethyl)phenyl)piperidine-3-carboxamide; |
| 46. | 3-(((8-isopropyl-2-((tetrahydro-2H-pyran-4-yl)amino)pyrazolo[1,5-a][1,3,5]triazin-4-yl)amino)methyl)phenyl 4-acryloylpiperazine-1-carboxylate; |
| 47. | 3-acrylamido-N-(3-(((8-isopropyl-2-((tetrahydro-2H-pyran-4-yl)amino)pyrazolo[1,5-a][1,3,5]triazin-4-yl)amino)methyl)phenyl)benzamide; |
| 48. | 2-acrylamido-N-(3-(((8-isopropyl-2-((tetrahydro-2H-pyran-4-yl)amino)pyrazolo[1,5-a][1,3,5]triazin-4-yl)amino)methyl)phenyl)benzamide; |
| 48A. | 3-acrylamido-N-(3-(((8-isopropyl-2-((tetrahydro-2H-pyran-4-yl)amino)pyrazolo[1,5-a][1,3,5]triazin-4-yl)amino)methyl)phenyl)-2-methylbenzamide; |
| 49. | (E)-4-((3-(((8-isopropyl-2-((tetrahydro-2H-pyran-4-yl)amino)pyrazolo[1,5-a][1,3,5]triazin-4-yl)amino)methyl)phenyl)amino)-N,N-dimethylbut-2-enamide; |
| 50. | (E)-4-(diethylamino)-N-(3-(((8-isopropyl-2-((tetrahydro-2H-pyran-4-yl)amino)pyrazolo[1,5-a][1,3,5]triazin-4-yl)amino)methyl)phenyl)but-2-enamide; |
| 51. | (E)-N-(3-(((8-isopropyl-2-((tetrahydro-2H-pyran-4-yl)amino)pyrazolo[1,5-a][1,3,5]triazin-4-yl)amino)methyl)phenyl)-4-morpholinobut-2-enamide; |
| 52. | (E)-4-(4-ethylpiperazin-1-yl)-N-(3-(((8-isopropyl-2-((tetrahydro-2H-pyran-4-yl)amino)pyrazolo[1,5-a][1,3,5]triazin-4-yl)amino)methyl)phenyl)but-2-enamide; |
| 53. | (E)-4-(dimethylamino)-N-(3-(((8-isopropyl-2-((tetrahydro-2H-pyran-4-yl)amino)pyrazolo[1,5-a][1,3,5]triazin-4-yl)amino)methyl)phenyl)but-2-enamide; |
| 54. | (E)-N-(3-(((8-isopropyl-2-((tetrahydro-2H-pyran-4-yl)amino)pyrazolo[1,5-a][1,3,5]triazin-4-yl)amino)methyl)phenyl)-4-(pyrrolidin-1-yl)but-2-enamide; |
| 55. | (E)-N-(3-(((8-isopropyl-2-((tetrahydro-2H-pyran-4-yl)amino)pyrazolo[1,5-a][1,3,5]triazin-4-yl)amino)methyl)phenyl)-4-(piperidin-1-yl)but-2-enamide; |
| 56. | (E)-4-(3-fluoropyrrolidin-1-yl)-N-(3-(((8-isopropyl-2-((tetrahydro-2H-pyran-4-yl)amino)pyrazolo[1,5-a][1,3,5]triazin-4-yl)amino)methyl)phenyl)but-2-enamide; |
| 57. | (E)-4-(3,3-difluoropyrrolidin-1-yl)-N-(3-(((8-isopropyl-2-((tetrahydro-2H-pyran-4-yl)amino)pyrazolo[1,5-a][1,3,5]triazin-4-yl)amino)methyl)phenyl)but-2-enamide; |
| 58. | (E)-4-(3-fluoropiperidin-1-yl)-N-(3-(((8-isopropyl-2-((tetrahydro-2H-pyran-4-yl)amino)pyrazolo[1,5-a][1,3,5]triazin-4-yl)amino)methyl)phenyl)but-2-enamide; |
| 59. | (E)-4-(dimethylamino)-N-(3-fluoro-5-(((8-isopropyl-2-((tetrahydro-2H-pyran-4-yl)amino)pyrazolo[1,5-a][1,3,5]triazin-4-yl)amino)methyl)phenyl)but-2-enamide; |
| 60. | (E)-4-(dimethylamino)-N-(2-fluoro-3-(((8-isopropyl-2-((tetrahydro-2H-pyran-4-yl)amino)pyrazolo[1,5-a][1,3,5]triazin-4-yl)amino)methyl)phenyl)but-2-enamide; |
| 61. | (E)-N-(3-fluoro-5-(((8-isopropyl-2-((tetrahydro-2H-pyran-4-yl)amino)pyrazolo[1,5-a][1,3,5]triazin-4-yl)amino)methyl)phenyl)-4-morpholinobut-2-enamide; |
| 62. | (E)-4-(dimethylamino)-N-(2-(((8-isopropyl-2-((tetrahydro-2H-pyran-4-yl)amino)pyrazolo[1,5-a][1,3,5]triazin-4-yl)amino)methyl)phenyl)but-2-enamide; |
| 63. | (E)-N-(4-(((8-isopropyl-2-((tetrahydro-2H-pyran-4-yl)amino)pyrazolo[1,5-a][1,3,5]triazin-4-yl)amino)methyl)phenyl)-4-(pyrrolidin-1-yl)but-2-enamide; |
| 64. | (E)-1-(4-(dimethylamino)but-2-enoyl)-N-(2-fluoro-5-(((8-isopropyl-2-((tetrahydro-2H-pyran-4-yl)amino)pyrazolo[1,5-a][1,3,5]triazin-4-yl)amino)methyl)phenyl)pyrrolidine-3-carboxamide; |
| 65. | (E)-1-(but-2-enoyl)-N-(3-(((8-isopropyl-2-((tetrahydro-2H-pyran-4-yl)amino)pyrazolo[1,5-a][1,3,5]triazin-4-yl)amino)methyl)phenyl)azetidine-2-carboxamide; |
| 66. | N-(3-(((8-isopropyl-2-((tetrahydro-2H-pyran-4-yl)amino)pyrazolo[1,5-a][1,3,5]triazin-4-yl)amino)methyl)phenyl)-1-propioloylazetidine-2-carboxamide; |

-continued

| Compound No: | IUPAC name |
|---|---|
| 67. | N-(3-(((8-isopropyl-2-((tetrahydro-2H-pyran-4-yl)amino)pyrazolo[1,5-a][1,3,5]triazin-4-yl)amino)methyl)phenyl)-1-methacryloylazetidine-2-carboxamide; |
| 68. | (E)-N-(3-(((8-isopropyl-2-((tetrahydro-2H-pyran-4-yl)amino)pyrazolo[1,5-a][1,3,5]triazin-4-yl)amino)methyl)phenyl)-1-(4-methoxybut-2-enoyl)pyrrolidine-3-carboxamide; |
| 69. | (E)-1-(4-(dimethylamino)but-2-enoyl)-N-(3-(((8-isopropyl-2-((tetrahydro-2H-pyran-4-yl)amino)pyrazolo[1,5-a][1,3,5]triazin-4-yl)amino)methyl)phenyl)pyrrolidine-3-carboxamide; |
| 70. | (E)-1-(4-(dimethylamino)but-2-enoyl)-N-(4-fluoro-3-(((8-isopropyl-2-((tetrahydro-2H-pyran-4-yl)amino)pyrazolo[1,5-a][1,3,5]triazin-4-yl)amino)methyl)phenyl)pyrrolidine-3-carboxamide; |
| 71. | (E)-1-(4-(dimethylamino)but-2-enoyl)-N-(3-fluoro-5-(((8-isopropyl-2-((tetrahydro-2H-pyran-4-yl)amino)pyrazolo[1,5-a][1,3,5]triazin-4-yl)amino)methyl)phenyl)pyrrolidine-3-carboxamide; |
| 72. | (E)-1-(4-(dimethylamino)but-2-enoyl)-N-(3-(1-((8-isopropyl-2-((tetrahydro-2H-pyran-4-yl)amino)pyrazolo[1,5-a][1,3,5]triazin-4-yl)amino)ethyl)phenyl)piperidine-3-carboxamide; |
| 73. | (E)-4-(4-(dimethylamino)but-2-enoyl)-N-(3-(((8-isopropyl-2-((tetrahydro-2H-pyran-4-yl)amino)pyrazolo[1,5-a][1,3,5]triazin-4-yl)amino)methyl)phenyl)morpholine-3-carboxamide; |
| 74. | (E)-1-(4-(dimethylamino)but-2-enoyl)-N-(3-(((8-isopropyl-2-((tetrahydro-2H-pyran-4-yl)amino)pyrazolo[1,5-a][1,3,5]triazin-4-yl)amino)methyl)phenyl)piperidine-2-carboxamide; |
| 75. | 3-(((8-isopropyl-2-((tetrahydro-2H-pyran-4-yl)amino)pyrazolo[1,5-a][1,3,5]triazin-4-yl)amino)methyl)phenyl(E)-4-(4-(dimethylamino)but-2-enoyl)piperazine-1-carboxylate; |
| 76. | (E)-1-(4-(dimethylamino)-4-oxobut-2-en-1-yl)-N-(3-(((8-isopropyl-2-((tetrahydro-2H-pyran-4-yl)amino)pyrazolo[1,5-a][1,3,5]triazin-4-yl)amino)methyl)phenyl)azetidine-2-carboxamide; |
| 77. | (E)-N-(3-(((8-isopropyl-2-((tetrahydro-2H-pyran-4-yl)amino)pyrazolo[1,5-a][1,3,5]triazin-4-yl)amino)methyl)phenyl)-1-(4-(pyrrolidin-1-yl)but-2-enoyl)piperidine-2-carboxamide; |
| 78. | N-(3-(((8-isopropyl-2-((tetrahydro-2H-pyran-4-yl)amino)pyrazolo[1,5-a][1,3,5]triazin-4-yl)amino)methyl)phenyl)-1-(vinylsulfonyl)piperidine-2-carboxamide; |
| 79. | N-(2-((3-(((8-isopropyl-2-((tetrahydro-2H-pyran-4-yl)amino)pyrazolo[1,5-a][1,3,5]triazin-4-yl)amino)methyl)phenyl)amino)-2-oxoethyl)acrylamide; |
| 80. | N-(1-((3-(((8-isopropyl-2-((tetrahydro-2H-pyran-4-yl)amino)pyrazolo[1,5-a][1,3,5]triazin-4-yl)amino)methyl)phenyl)amino)-1-oxopropan-2-yl)acrylamide; |
| 81. | N-(2-((3-(((8-isopropyl-2-((tetrahydro-2H-pyran-4-yl)amino)pyrazolo[1,5-a][1,3,5]triazin-4-yl)amino)methyl)phenyl)amino)-2-oxoethyl)-N-methyl acrylamide; |
| 82. | N-(1-((3-(((8-isopropyl-2-((tetrahydro-2H-pyran-4-yl)amino)pyrazolo[1,5-a][1,3,5]triazin-4-yl)amino)methyl)phenyl)amino)-2-methyl-1-oxopropan-2-yl)acrylamide; |
| 83. | 1-acrylamido-N-(3-(((8-isopropyl-2-((tetrahydro-2H-pyran-4-yl)amino)pyrazolo[1,5-a][1,3,5]triazin-4-yl)amino)methyl)phenyl)cyclopropane-1-carboxamide; |
| 84. | N-(3-(((8-isopropyl-2-((tetrahydro-2H-pyran-4-yl)amino)pyrazolo[1,5-a][1,3,5]triazin-4-yl)amino)methyl)phenyl)-1-(N-methylacrylamido)cyclopropane-1-carboxamide; |
| 85. | 4-acrylamido-N-(3-(((8-isopropyl-2-((tetrahydro-2H-pyran-4-yl)amino)pyrazolo[1,5-a][1,3,5]triazin-4-yl)amino)methyl)phenyl)-1-methyl-1H-pyrazole-3-carboxamide; |
| 86. | 1-acryloyl-N-(3-((8-isopropyl-2-((tetrahydro-2H-pyran-4-yl)amino)pyrazolo[1,5-a][1,3,5]triazin-4-yl)amino)phenyl)azetidine-2-carboxamide; |
| 87. | (1,4-cis)-4-acrylamido-N-(3-((8-isopropyl-2-((tetrahydro-2H-pyran-4-yl)amino)pyrazolo[1,5-a][1,3,5]triazin-4-yl)amino)phenyl)cyclohexane-1-carboxamide; |
| 88. | 1-acryloyl-N-(3-(((8-ethyl-2-((1-methylpiperidin-4-yl)oxy)pyrazolo[1,5-a][1,3,5]triazin-4-yl)amino)methyl)phenyl)piperidine-4-carboxamide; |
| 89. | 1-acryloyl-N-(3-(((2-((1-methylpiperidin-4-yl)oxy)pyrazolo[1,5-a][1,3,5]triazin-4-yl)amino)methyl)phenyl)piperidine-3-carboxamide; |
| 90. | (1,4-cis)-4-acrylamido-N-(3-(((8-ethyl-2-((1-methylpiperidin-4-yl)oxy)pyrazolo[1,5-a][1,3,5]triazin-4-yl)amino)methyl)phenyl)cyclohexane-1-carboxamide; |
| 91. | (1,4-trans)-4-acrylamido-N-(3-(((8-isoproprayl-2-((1-methylpiperidin-4-yl)oxy)pyrazolo[1,5-a][1,3,5]triazin-4-yl)amino)methyl)phenyl)cyclohexane-1-carboxamide; |
| 92. | Isomer-1: 4-acrylamido-N-(3-(((2-((3-fluoro-1-methylpiperidin-4-yl)amino)-8-isopropylpyrazolo[1,5-a][1,3,5]triazin-4-yl)amino)methyl)phenyl)cyclohexane-1-carboxamide; |
| 93. | Isomer-2: 4-acrylamido-N-(3-(((2-((3-fluoro-1-methylpiperidin-4-yl)amino)-8-isopropylpyrazolo[1,5-a][1,3,5]triazin-4-yl)amino)methyl)phenyl)cyclohexane-1-carboxamide; |
| 94. | 1-acryloyl-N-(3-(((8-isopropyl-2-((1-methylpiperidin-4-yl)oxy)pyrazolo[1,5-a][1,3,5]triazin-4-yl)amino)methyl)phenyl)azetidine-2-carboxamide; |

-continued

| Compound No: | IUPAC name |
|---|---|
| 95. | 1-acryloyl-N-(3-(((8-isopropyl-2-((tetrahydro-2H-pyran-4-yl)oxy)pyrazolo[1,5-a][1,3,5]triazin-4-yl)amino)methyl)phenyl)pyrrolidine-3-carboxamide; |
| 96. | 1-acryloyl-N-(3-(((8-isopropyl-2-((tetrahydro-2H-pyran-4-yl)oxy)pyrazolo[1,5-a][1,3,5]triazin-4-yl)amino)methyl)phenyl)piperidine-3-carboxamide; |
| 97. | (1,4-cis)-4-acrylamido-N-(3-(((8-isopropyl-2-((tetrahydro-2H-pyran-4-yl)oxy)pyrazolo[1,5-a][1,3,5]triazin-4-yl)amino)methyl)phenyl)cyclohexane-1-carboxamide; |
| 98. | Isomer-1: 4-acrylamido-N-(3-(((2-((3-fluorotetrahydro-2H-pyran-4-yl)oxy)-8-isopropylpyrazolo[1,5-a][1,3,5]triazin-4-yl)amino)methyl)phenyl)cyclohexane-1-carboxamide; |
| 99. | Isomer-2: 4-acrylamido-N-(3-(((2-((3-fluorotetrahydro-2H-pyran-4-yl)oxy)-8-isopropylpyrazolo[1,5-a][1,3,5]triazin-4-yl)amino)methyl)phenyl)cyclohexane-1-carboxamide; |
| 100. | (1,4-cis)-4-acrylamido-N-(3-(((8-isopropyl-2-((tetrahydrofuran-3-yl)oxy)pyrazolo[1,5-a][1,3,5]triazin-4-yl)amino)methyl)phenyl)cyclohexane-1-carboxamide; |
| 101. | (1,4-cis)-4-acrylamido-N-(3-(((8-isopropyl-2-((1-methylpyrrolidin-3-yl)oxy)pyrazolo[1,5-a][1,3,5]triazin-4-yl)amino)methyl)phenyl)cyclohexane-1-carboxamide; |
| 102. | 1-acryloyl-N-(3-(((2-isobutoxy-8-isopropylpyrazolo[1,5-a][1,3,5]triazin-4-yl)amino)methyl)phenyl)pyrrolidine-3-carboxamide; |
| 103. | 1-acryloyl-N-(3-(((8-isopropyl-2-(2-methoxyethoxy)pyrazolo[1,5-a][1,3,5]triazin-4-yl)amino)methyl)phenyl)pyrrolidine-3-carboxamide; |
| 104. | 1-acryloyl-N-(3-(((8-isopropyl-2-(2-(2-methoxyethoxy)ethoxy)pyrazolo[1,5-a][1,3,5]triazin-4-yl)amino)methyl)phenyl)pyrrolidine-3-carboxamide; |
| 105. | (1,4-cis)-4-acrylamido-N-(3-(((8-cyclopropyl-2-((1-methylpiperidin-4-yl)oxy)pyrazolo[1,5-a][1,3,5]triazin-4-yl)amino)methyl)phenyl)cyclohexane-1-carboxamide; |
| 106. | (1,4-cis)-4-acrylamido-N-(3-(((8-isopropyl-2-((tetrahydro-2H-pyran-4-yl)amino)pyrazolo[1,5-a][1,3,5]triazin-4-yl)amino)methyl)phenyl)cyclohexane-1-carboxamide; |
| 107. | 1-acryloyl-N-(3-(((2-(4-aminobutoxy)-8-isopropylpyrazolo[1,5-a][1,3,5]triazin-4-yl)amino)methyl)phenyl)piperidine-4-carboxamide; |
| 108. | 1-acryloyl-N-(3-(((8-isopropyl-2-((1-methylpiperidin-4-yl)oxy)pyrazolo[1,5-a][1,3,5]triazin-4-yl)amino)methyl)phenyl)pyrrolidine-3-carboxamide; |
| 109. | Isomer-1: 1-acryloyl-N-(3-(((8-isopropyl-2-((1-methylpiperidin-4-yl)oxy)pyrazolo[1,5-a][1,3,5]triazin-4-yl)amino)methyl)phenyl)pyrrolidine-3-carboxamide; |
| 110. | Isomer-2: 1-acryloyl-N-(3-(((8-isopropyl-2-((1-methylpiperidin-4-yl)oxy)pyrazolo[1,5-a][1,3,5]triazin-4-yl)amino)methyl)phenyl)pyrrolidine-3-carboxamide; |
| 111. | 1-acryloyl-N-(3-(((8-isopropyl-2-((1-methylpiperidin-4-yl)oxy)pyrazolo[1,5-a][1,3,5]triazin-4-yl)amino)methyl)phenyl)piperidine-4-carboxamide; |
| 112. | 4-acryloyl-N-(3-(((8-isopropyl-2-((1-methylpiperidin-4-yl)oxy)pyrazolo[1,5-a][1,3,5]triazin-4-yl)amino)methyl)phenyl)morpholine-2-carboxamide; |
| 113. | 4-acryloyl-N-(3-(((8-isopropyl-2-((1-methylpiperidin-4-yl)oxy)pyrazolo[1,5-a][1,3,5]triazin-4-yl)amino)methyl)phenyl)morpholine-3-carboxamide; |
| 114. | 3-acrylamido-N-(3-(((8-isopropyl-2-((1-methylpiperidin-4-yl)oxy)pyrazolo[1,5-a][1,3,5]triazin-4-yl)amino)methyl)phenyl)cyclohexane-1-carboxamide; |
| 115. | (1,4-cis)-4-acrylamido-N-(3-(((8-isopropyl-2-((1-methylpiperidin-4-yl)oxy)pyrazolo[1,5-a][1,3,5]triazin-4-yl)amino)methyl)phenyl)cyclohexane-1-carboxamide; |
| 116. | 1-acryloyl-N-(3-(((8-isopropyl-2-((1-methylpiperidin-4-yl)oxy)pyrazolo[1,5-a][1,3,5]triazin-4-yl)amino)methyl)phenyl)piperidine-3-carboxamide; |
| 117. | 1-acryloyl-N-(2-fluoro-5-(((8-isopropyl-2-((1-methylpiperidin-4-yl)oxy)pyrazolo[1,5-a][1,3,5]triazin-4-yl)amino)methyl)phenyl)piperidine-3-carboxamide; |
| 118. | (1,4-cis)-4-acrylamido-N-(2-fluoro-5-(((8-isopropyl-2-((1-methylpiperidin-4-yl)oxy)pyrazolo[1,5-a][1,3,5]triazin-4-yl)amino)methyl)phenyl)cyclohexane-1-carboxamide; |
| 119. | 1-acryloyl-N-(3-(1-((8-isopropyl-2-((1-methylpiperidin-4-yl)oxy)pyrazolo[1,5-a][1,3,5]triazin-4-yl)amino)ethyl)phenyl)piperidine-3-carboxamide; |
| 120. | 2-(1-acryloylpiperidine-3-carboxamido)-5-(((8-isopropyl-2-((1-methylpiperidin-4-yl)oxy)pyrazolo[1,5-a][1,3,5]triazin-4-yl)amino)methyl)pyridine 1-oxide; |
| 121. | 3-(((8-isopropyl-2-((1-methylpiperidin-4-yl)oxy)pyrazolo[1,5-a][1,3,5]triazin-4-yl)amino)methyl)phenyl 4-acryloylpiperazine-1-carboxylate; |
| 122. | (E)-1-(4-(dimethylamino)but-2-enoyl)-N-(3-(((8-isopropyl-2-((1-methylpiperidin-4-yl)oxy)pyrazolo[1,5-a][1,3,5]triazin-4-yl)amino)methyl)phenyl)piperidine-3-carboxamide; |
| 123. | (E)-1-(4-(dimethylamino)but-2-enoyl)-N-(2-fluoro-5-(((8-isopropyl-2-((1-methylpiperidin-4-yl)oxy)pyrazolo[1,5-a][1,3,5]triazin-4-yl)amino)methyl)phenyl)piperidine-3-carboxamide; |
| 124. | (1,4-cis)-4-((E)-4-(dimethylamino)but-2-enamido)-N-(2-fluoro-5-(((8-isopropyl-2-((1-methylpiperidin-4-yl)oxy)pyrazolo[1,5-a][1,3,5]triazin-4-yl)amino)methyl)phenyl)cyclohexane-1-carboxamide; |
| 125. | 4-acrylamido-N-(3-(((8-isopropyl-2-((1-methylpiperidin-4-yl)oxy)pyrazolo[1,5-a][1,3,5]triazin-4-yl)amino)phenyl)benzamide; |

| Compound No: | IUPAC name |
| --- | --- |
| 126. | (1,4-cis)-4-acrylamido-N-(3-((8-isopropyl-2-((1-methylpiperidin-4-yl)oxy) pyrazolo[1,5-a][1,3,5]triazin-4-yl)amino)phenyl)cyclohexane-1-carboxamide; |
| 127. | 1-acryloyl-N-(3-((8-isopropyl-2-((1-methylpiperidin-4-yl)oxy)pyrazolo[1,5-a][1,3,5]triazin-4-yl)amino)phenyl)piperidine-4-carboxamide; |
| 128. | N-(1-acryloylpiperidin-4-yl)-3-((8-isopropyl-2-((1-methylpiperidin-4-yl)oxy)pyrazolo[1,5-a][1,3,5]triazin-4-yl)amino)benzamide; |
| 129. | N-(1-acryloylpiperidin-3-yl)-3-((8-isopropyl-2-((1-methylpiperidin-4-yl)oxy) pyrazolo[1,5-a][1,3,5]triazin-4-yl)amino)benzamide; |
| 130. | (E)-4-(4-(dimethylamino)but-2-enamido)-N-(3-((8-isopropyl-2-((1-methyl piperidin-4-yl)oxy)pyrazolo[1,5-a][1,3,5]triazin-4-yl)amino)phenyl)benzamide; |
| 131. | (1,4-cis)-4-((E)-4-(dimethylamino)but-2-enamido)-N-(3-((8-isopropyl-2-((1-methylpiperidin-4-yl)oxy)pyrazolo[1,5-a][1,3,5]triazin-4-yl)amino)phenyl) cyclohexane-1-carboxamide; |
| 132. | (1,4-Trans)-4-((E)-4-(dimethylamino)but-2-enamido)-N-(3-((8-isopropyl-2-((1-methylpiperidin-4-yl)oxy)pyrazolo[1,5-a][1,3,5]triazin-4-yl)amino)phenyl) cyclohexane-1-carboxamide; |
| 133. | (E)-N-(1-(4-(dimethylamino)but-2-enoyl)piperidin-3-yl)-3-((8-isopropyl-2-((1-methylpiperidin-4-yl)oxy)pyrazolo[1,5-a][1,3,5]triazin-4-yl)amino)benzamide; |
| 134. | (E)-N-(1-(4-(dimethylamino)but-2-enoyl)piperidin-4-yl)-3-((8-isopropyl-2-((1-methylpiperidin-4-yl)oxy)pyrazolo[1,5-a][1,3,5]triazin-4-yl)amino)benzamide; |
| 135. | (1,4-cis)-4-(((E)-4-(dimethylamino)-4-oxobut-2-en-1-yl)amino)-N-(3-(((8-isopropyl-2-((1-methylpiperidin-4-yl)oxy)pyrazolo[1,5-a][1,3,5]triazin-4-yl)amino)methyl)phenyl)cyclohexane-1-carboxamide; |
| 136. | 1-acryloyl-N-(3-(((8-isopropyl-2-methoxypyrazolo[1,5-a][1,3,5]triazin-4-yl) amino)methyl)phenyl)piperidine-4-carboxamide; |
| 137. | (E)-4-(dimethylamino)-1-(4-(2-(((8-isopropyl-2-((tetrahydro-2H-pyran-4-yl) amino)pyrazolo[1,5-a][1,3,5]triazin-4-yl)amino)methyl)phenyl)piperazin-1-yl)but-2-en-1-one; |
| 138. | (E)-1-(4-(((8-isopropyl-2-((tetrahydro-2H-pyran-4-yl)amino)pyrazolo[1,5-a] [1,3,5]triazin-4-yl)amino)methyl)piperidin-1-yl)-4-(pyrrolidin-1-yl)but-2-en-1-one; and |
| 139. | 1-acryloyl-N-(3-(((3-isopropyl-5-((tetrahydro-2H-pyran-4-yl)amino)pyrazolo[1,5-a]pyrimidin-7-yl)amino)methyl)phenyl)azetidine-2-carboxamide, | or a pharmaceutically acceptable salt thereof or a stereoisomer thereof.

In certain embodiments, the present invention provides a pharmaceutical composition comprising a compound of formula (I), (IA), (IB), (IC), (ID), (IE) and (IF) or a pharmaceutically acceptable salt thereof or a stereoisomer thereof as described herein and at least one pharmaceutically acceptable excipient (such as a pharmaceutically acceptable carrier or diluent). Preferably, the pharmaceutical composition comprises a therapeutically effective amount of at least one compound described herein. The compounds described in the present patent application may be associated with a pharmaceutically acceptable excipient (such as a carrier or a diluent) or be diluted by a carrier or enclosed within a carrier which can be in the form of a capsule, sachet, paper or other container.

In yet another embodiment, the compounds of the present invention are thought to be kinase inhibitors. In certain embodiments, the compounds of the present invention are CDK inhibitors. In certain embodiments, the compounds of the present invention are CDK7 inhibitors. In certain embodiments, the compounds of the present invention are selective CDK inhibitors (e.g., being more active in inhibiting a CDK than a non-CDK kinase). In certain embodiments, the compounds of the present invention are selective CDK7 inhibitors (e.g., being more active in inhibiting CDK7 than a non-CDK7 kinase). In certain embodiments, the compounds of the present invention are selective CDK9 inhibitors. In certain embodiments, the compounds of the present invention are selective CDK12 inhibitors. In certain embodiments, the compounds of the present invention are selective CDK 13 inhibitors. In certain embodiments, the compounds of the present invention are selective CDK18 inhibitors.

In another embodiment, the present invention provides pharmaceutical composition for use in treating and/or preventing a disease and/or disorder associated with selective transcriptional CDKs.

In another embodiment, the present invention provides pharmaceutical composition for use in treating a subject suffering from a disease or condition associated with aberrant activity of selective transcriptional CDKs.

In another embodiment, the present invention provides pharmaceutical composition comprising the compound of formula (I), (IA), (IB), (IC), (ID), (IE) and (IF) for use in treating and/or preventing a disease and/or disorder associated with s selective transcriptional CDK inhibitors, in particularly selective transcriptional inhibitor is CDK7, CDK9, CDK12, CDK13 or CDK18; more particularly CDK7.

In another embodiment, the present invention provides pharmaceutical composition comprising the compound of formula (I), (IA), (IB), (IC), (ID), (IE) and (IF) for use in treating a subject suffering from a disease or condition associated with aberrant activity of selective transcriptional CDK inhibitors, in particularly selective transcriptional inhibitor is CDK7, CDK9, CDK12, CDK13 or CDK18; more particularly CDK7.

In yet another embodiment, the present invention provides a method of treating disorders or diseases or condition mediated by CDK in a subject comprising administering a therapeutically effective amount of a compound of the present invention, in particularly CDK is CDK7, CDK9, CDK12, CDK13 or CDK18, more particularly selective transcriptional CDK7.

In yet another embodiment, the present invention provides a method of inhibiting selective transcriptional CDK inhibitors, in particularly selective transcriptional inhibitor is CDK7, CDK9, CDK12, CDK13 or CDK18; more particularly CDK7, in a subject in need thereof by administering to the subject one or more compounds described herein in the amount effective to cause inhibition of such receptor.

In another aspect of the present invention relates to methods of inhibiting the activity of a kinase in a biological sample or subject. In certain embodiments, the kinase is selective transcriptional CDK. In certain embodiments, the kinase is selective transcriptional CDK7. In other embodiments, the kinase is selective transcriptional CDK9, CDK12, CDK13 or CDK18.

In other embodiments, the activity of the kinase is aberrant activity of the kinase. In other embodiments, the inhibition of the activity of the kinase is irreversible. In other embodiments, the inhibition of the activity of the kinase is reversible. In other embodiments, the methods of inhibiting the activity of the kinase include attaching a compound of formula (I) to the kinase.

In yet another embodiment, the compounds of present invention are selective transcriptional CDK inhibitors, which are key regulators of the cell cycle.

In yet another embodiment, the compounds of present invention are selective inhibitors of transcriptional CDKs, which are key regulators of the cell cycle, inhibits both cell cycle progression and transcription.

In yet another embodiment, the compounds of present invention are selective transcriptional CDK inhibitors, which are key regulators of the cell cycle, inhibits both cell cycle progression and transcription; wherein the selective transcriptional CDK inhibitor is CDK7, CDK9, CDK12, CDK13 or CDK18.

In yet another embodiment, the compounds of present invention are selective transcriptional CDK inhibitors, which are key regulators of the cell cycle, inhibits both cell cycle progression and transcription; wherein the selective transcriptional CDK inhibitor is CDK7.

In yet another embodiment, the compounds of present invention also inhibits the phosphorylation of ser5 of RNA Polymerase II CTD, consistent with mechanism-based inhibition of CDK7.

In yet another embodiment, the compounds of present invention also inhibits the phosphorylation of ser2 and/or ser7 of RNA Polymerase II CTD, consistent with mechanism-based inhibition of transcriptional CDKs.

In yet another embodiment, the compounds of present invention (selective translational CDK inhibitors) when administered in vivo apoptotic response indicated by PARP cleavage.

In yet another embodiment, the compounds of present invention (selective translational CDK inhibitors) after invivo administration may show pro-apoptotic effects the down-regulation of short half-life survival proteins like Mcl-I.

The compounds of the invention are typically administered in the form of a pharmaceutical composition. Such compositions can be prepared using procedures well known in the pharmaceutical art and comprise at least one compound of the present invention. The pharmaceutical composition of the present invention comprises one or more compounds described herein and one or more pharmaceutically acceptable excipients. Typically, the pharmaceutically acceptable excipients are approved by regulatory authorities or are generally regarded as safe for human or animal use. The pharmaceutically acceptable excipients include, but are not limited to, carriers, diluents, glidants and lubricants, preservatives, buffering agents, chelating agents, polymers, gelling agents, viscosifying agents, solvents and the like.

The pharmaceutical composition can be administered by oral, parenteral or inhalation routes. Examples of the parenteral administration include administration by injection, percutaneous, transmucosal, transnasal and transpulmonary administrations.

Examples of suitable carriers include, but are not limited to, water, salt solutions, alcohols, polyethylene glycols, peanut oil, olive oil, gelatin, lactose, terra alba, sucrose, dextrin, magnesium carbonate, sugar, amylose, magnesium stearate, talc, gelatin, agar, pectin, acacia, stearic acid, lower alkyl ethers of cellulose, silicic acid, fatty acids, fatty acid amines, fatty acid monoglycerides and diglycerides, fatty acid esters and polyoxyethylene.

The pharmaceutical composition may also include one or more pharmaceutically acceptable auxiliary agents, wetting agents, suspending agents, preserving agents, buffers, sweetening agents, flavouring agents, colorants or any combination of the foregoing.

The pharmaceutical compositions may be in conventional forms, for example, tablets, capsules, solutions, suspensions, injectables or products for topical application. Further, the pharmaceutical composition of the present invention may be formulated so as to provide desired release profile.

Administration of the compounds of the invention, in pure form or in an appropriate pharmaceutical composition, can be carried out using any of the accepted routes of administration of pharmaceutical compositions. The route of administration may be any route which effectively transports the active compound of the patent application to the appropriate or desired site of action. Suitable routes of administration include, but are not limited to, oral, nasal, buccal, dermal, intradermal, transdermal, parenteral, rectal, subcutaneous, intravenous, intraurethral, intramuscular or topical.

Solid oral formulations include, but are not limited to, tablets, capsules (soft or hard gelatin), dragees (containing the active ingredient in powder or pellet form), troches and lozenges.

Liquid formulations include, but are not limited to, syrups, emulsions and sterile injectable liquids, such as suspensions or solutions.

Topical dosage forms of the compounds include ointments, pastes, creams, lotions, powders, solutions, eye or ear drops, impregnated dressings and may contain appropriate conventional additives such as preservatives, solvents to assist drug penetration.

The pharmaceutical compositions of the present patent application may be prepared by conventional techniques known in literature.

Suitable doses of the compounds for use in treating the diseases or disorders described herein can be determined by those skilled in the relevant art. Therapeutic doses are generally identified through a dose ranging study in humans based on preliminary evidence derived from the animal studies. Doses must be sufficient to result in a desired therapeutic benefit without causing unwanted side effects. Mode of administration, dosage forms and suitable pharmaceutical excipients can also be well used and adjusted by those skilled in the art. All changes and modifications are envisioned within the scope of the present patent application.

In one embodiment the compounds as disclosed in the present invention are formulated for pharmaceutical administration.

Yet another embodiment of the present invention provides use of the compounds as disclosed in the present invention in the treatment and prevention of diseases or disorder associated with selective transcriptional CDK inhibitors, in particularly selective transcriptional CDK inhibitor is CDK7, CDK9, CDK12, CDK13 or CDK18; more particularly CDK7.

Yet another embodiment of the present invention provides use of the compound or a pharmaceutically acceptable salt thereof, in treating and/or preventing a disease for which the symptoms thereof are treated, improved, diminished and/or prevented by inhibition of selective transcriptional CDK inhibitors, in particularly selective transcriptional inhibitor is CDK7, CDK9, CDK12, CDK13 or CDK18; more particularly CDK7.

According to yet another embodiment, the selective transcriptional CDK's mediated disorder or disease or condition is proliferative diseases or disorder or condition.

According to aforesaid embodiment, the proliferative diseases or disorders or conditions are selected from but are not limited to the group consisting of a cancer, an inflammatory disorder, an auto-inflammatory disorder or an infectious disease.

In other embodiments, the proliferative disease to be treated or prevented using the compounds of formula (I) will typically be associated with aberrant activity of CDKs, more particularly with CDK7, CDK9, CDK12, CDK13 or 18. Aberrant activity of CDK7, CDK9, CDK12, CDK13 or CDK18 may be an elevated and/or an inappropriate (e.g., abnormal) activity of CDK7, CDK9, CDK12, CDK13 or CDK18. In certain embodiments, CDK7, CDK9, CDK12, CDK13 or CDK18 are not overexpressed, and the activity of CDK7, CDK9, CDK12, CDK13 or CDK18 are elevated and/or inappropriate. In certain other embodiments, CDK7, CDK9, CDK12, CDK13 or CDK18 are overexpressed, and the activity of CDK7, CDK9, CDK12, CDK13 or CDK18 are elevated and/or inappropriate. The compounds of formula (I), and pharmaceutically acceptable salts or stereoisomers, and compositions thereof, may inhibit the activity of CDK7, CDK9, CDK12, CDK13 or CDK18 are been useful in treating and/or preventing proliferative diseases.

According to yet another embodiment, the compounds of the present invention are expected to be useful in the therapy of proliferative diseases such as viral diseases, fungal diseases, neurological/neurodegenerative disorders, autoimmune, inflammation, arthritis, anti-proliferative (e.g., ocular retinopathy), neuronal, alopecia and cardiovascular diseases.

According to yet another embodiment, the compounds of the present invention are useful in the treatment of a variety of cancers, including but not limited to carcinoma, including that of the breast, liver, lung, colon, kidney, bladder, including small cell lung cancer, non-small cell lung cancer, head and neck, thyroid, esophagus, stomach, pancreas, ovary, gall bladder, cervix, prostate and skin, including squamous cell carcinoma; hematopoietic tumors of lymphoid lineage, including leukemia, acute lymphoblastic leukemia, acute lymphocytic leukemia, Hodgkins lymphoma, non-Hodgkins lymphoma, B-cell lymphoma, T-cell lymphoma, hairy cell lymphoma, myeloma, mantle cell lymphoma and Burkett's lymphoma; hematopoietic tumors of myeloid lineage, including acute and chronic myelogenous leukemias, myelodysplastic syndrome and promyelocytic leukemia; tumors of masenchymal origin, including fibrosarcoma and rhabdomyosarcoma; tumors of the central and peripheral nervous system, including astrocytoma, neuroblastoma, glioma and schwannomas; and other tumors, including seminoma, melanoma, osteosarcoma, teratocarcinoma, keratoctanthoma, xenoderoma pigmentosum, thyroid follicular cancer and Kaposi's sarcoma.

According to yet another embodiment, the subject is a mammal including human.

According to yet another embodiment the present invention provides compounds for use as a medicament.

According to yet another embodiment the invention provides the use of the compounds of the present invention in the manufacture of a medicament.

According to yet another embodiment the invention provides the use of the compounds of the present invention in the manufacture of a medicament for the treatment of diseases and/or disorder associated with selective transcriptional CDK inhibition.

According to yet another embodiment the present invention provides compounds for use as a medicament for the treatment of diseases and/or disorder associated with selective transcriptional CDK inhibition.

According to yet another embodiment the present invention comprises an additional step of administering to the subject in need thereof one or more additional chemotherapeutic agents independently selected from anti-proliferative agents, anti-cancer agents, immunosuppressant agents and pain-relieving agents.

The method(s) of treatment of the present invention comprises administering a safe and effective amount of a compound according to formula (I) or a pharmaceutically acceptable salt thereof to a patient (particularly a human) in need thereof.

Compounds of the invention are indicated both in the therapeutic and/or prophylactic treatment of the abovementioned conditions. For the above-mentioned therapeutic uses the dosage administered will, of course, vary with the compound employed, the mode of administration, the treatment desired and the disorder or disease indicated.

The compounds of the present invention may be used as single drug or as a pharmaceutical composition in which the compound is mixed with various pharmacologically acceptable materials.

According to one embodiment, the compounds of the present invention can also contain unnatural proportions of atomic isotopes at one or more of the atoms that constitute such compounds. For example, the present invention also embraces isotopically-labeled variants of the present invention which are identical to those recited herein, but for the fact that one or more atoms of the compound are replaced by an atom having the atomic mass or mass number different from the predominant atomic mass or mass number usually found in nature for the atom. All isotopes of any particular atom or element as specified are contemplated within the scope of the compounds of the invention and their uses. Exemplary isotopes that can be incorporated in to compounds of the invention include isotopes of hydrogen, carbon, nitrogen, oxygen, phosphorous, sulfur, fluorine, chlorine and iodine, such as $^{2}H$ ("D"), $^{3}H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$ and $^{125}I$. Isotopically labeled compounds of the present invention can generally be prepared by following procedures analogous to those disclosed in the schemes and/or in the examples herein below, by substituting an isotopically labeled reagent for a non-isotopically labeled reagent.

General Procedures:

Compounds of the present invention may be prepared by synthetic chemical processes, examples of which are shown herein. It is meant to be understood that the order of the steps in the processes may be varied, that reagents, solvents and reaction conditions may be substituted for those specifically mentioned and that vulnerable moieties may be protected and deprotected, as necessary.

A general approach for the synthesis of compounds of general formula (I) is depicted in below schemes. As used herein the below schemes the terms '$R_1$', '$R_2$', '$R_3$', '$R_4$', '$R_6$', 'A', 'B', '$L_1$', '$L_2$', 'm' 'n' and 'p' are same as described in compound of formula (I).

General synthesis for the preparation of key intermediates (formula 1.5) and (formula 3.4) were described in the given scheme-a and scheme-b respectively:

Route-a:

The compound of formula-1.0 can be treated with formula-1.1 in presence of suitable base such as DIPEA, TEA and the like, in presence of suitable polar solvents such as ACN, 1,4-dioxane, DMSO, DCE and the like at a temperature of about 20° C. to 35° C. for about 2 to 24 h to provide the compounds of formula-1.2. Compounds of formula-1.2 can be further treated with mCPBA in presence of suitable solvents such as DCM, CHCl$_3$, DCE and the like at a temperature of about 0° C. to 35° C. for about 2 to 24 h to provide the compounds of formula-1.3. The compounds of

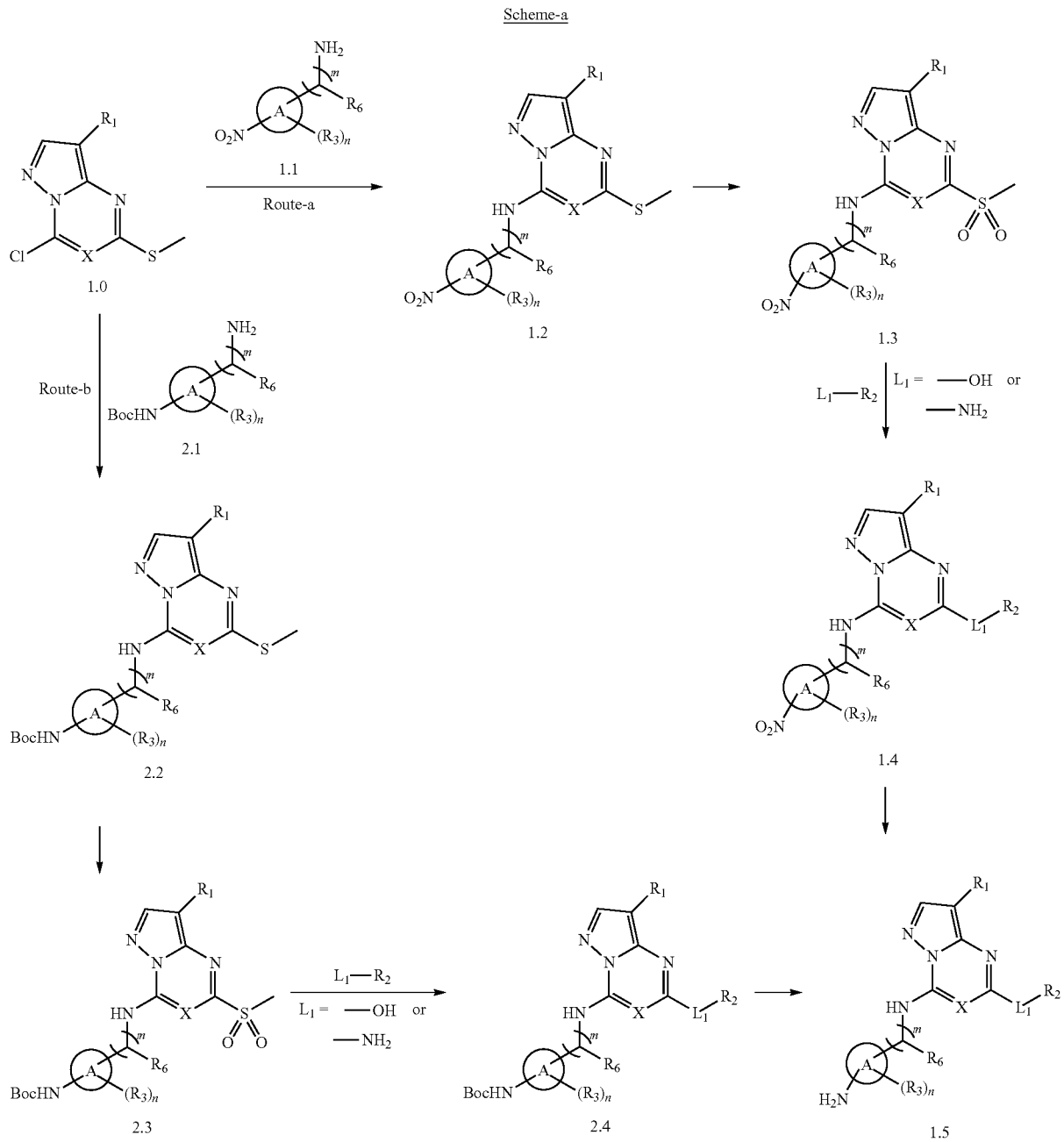

Scheme-a

The general procedure for the preparation of key intermediate (1.5) was synthesized in two routes by using compound of formula-1.0 as starting material.

formula 1.4 (wherein $L_1$=NH) can be synthesized by treating compounds of formula 1.3 with appropriate amine with or without solvent (solvents such as NMP and the like) at a temperature of about 100° C. to 150° C. for about 1 to 24 h. Alternatively, the compounds of formula 1.4 (wherein $L_1$=O) can be synthesized by treating compounds of formula 1.3 with appropriate alcohol in the presence of suitable base such as NaH, LiH, KH, $K_2CO_3$ or $Cs_2CO_3$ and the like in suitable solvents such as THF, DMSO, DMF, 1,4-dioxane or diethyl ether and the like, at a temperature of about −30° C. to 100° C. for about 1-24 h. Compounds of formula-1.4 undergoes reduction of nitro group in presence of suitable reagents like zinc dust/$NH_4Cl$ or Fe/$NH_4Cl$ or Zn/aq.$NH_4Cl$ with appropriate combinational ratios of solvents such as THF:MeOH:Water, THF:EtOH:water, methanol:water, ethanol:water, methanol or ethanol and the like at a temperature of about 20° C. to 120° C. for about 1-24 h to provide the compounds of formula 1.5.

Route-b:

The compound of formula 1.5 can be prepared by using compound of formula-1.0, on reacting with the compound of formula 2.1 and proceeded till the formation of compound of formula 2.4 by using the procedure similar to the preparation of compound of formula 1.4 as depicted in route-a. The resultant compound of formula 2.4 is further undergoes deprotection of Boc in presence of suitable reagents such as TFA and the like, in presence of suitable solvent such as DCM, chloroform, THF or 1,4-dioxane and the like, at a temperature of about 20° C. to 35° C. for about 2 to 24 h to provide the compounds of formula-1.5.

The general procedure for the preparation of key intermediate (3.4) was synthesized according to scheme-b:

Scheme-b

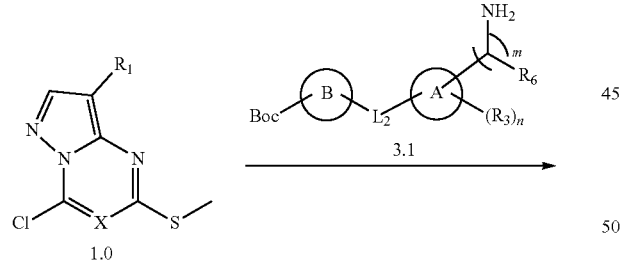

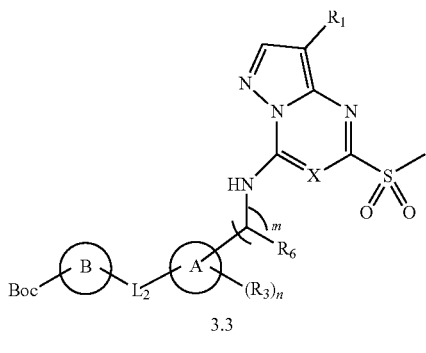

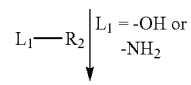

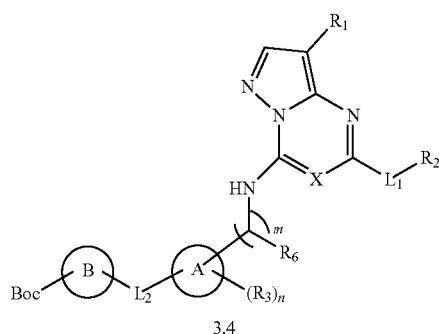

The compounds of general formula-3.4 can be prepared by using compound of formula 1.0 and reacting with compound of formula 3.1 and further proceeded to the formation of compound of formula 3.4 according to the procedure depicted in route-b of scheme-a.

General Scheme for the Preparation of Compound of Formula (I):

The compound according to general formula (I) was prepared according to the procedure depicted in route-a and route-b of scheme-I and scheme-II by using compound of formula-1.5 as starting material.

Scheme-I

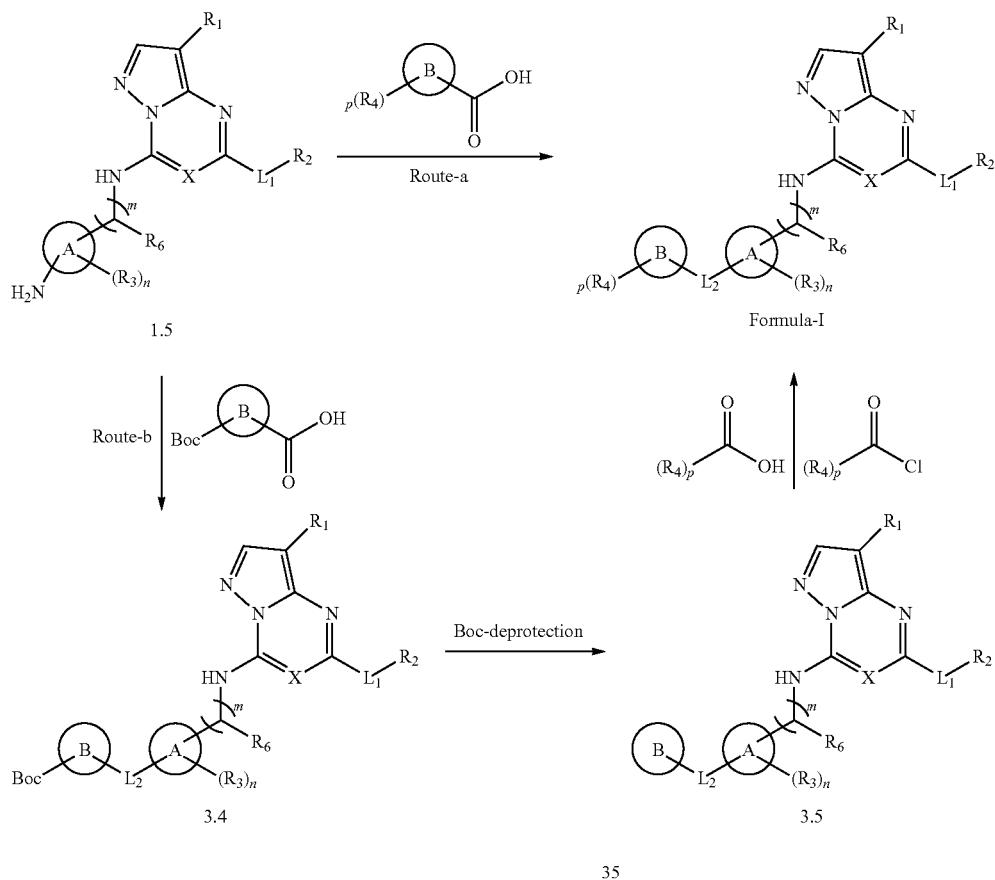

Route-a:
The compound of formula (I) can be synthesized by treating compound of formula-1.5 with appropriate acid in the presence of suitable reagents such as HATU, EDC.HCl—HOBt and the like, in the presence of suitable base such as DIPEA or TEA and the like, in a suitable solvent such as DMF, THF, DMSO or DCM and the like at a temperature of about 20° C. to 35° C. for about 1-24 h.

Route-b:
The compound of formula 3.4 was prepared according to the procedure depicted in route-a of scheme-I. The resulting compound of formula-3.4 undergoes deprotection of Boc in presence of suitable reagent TFA and the like, in presence of suitable solvent such as DCM, chloroform, THF or 1,4-dioxane and the like, at a temperature of about 20° C. to 35° C. for about 2 to 24 h to provide the compounds of formula-3.5. The compound of formula-3.5 can be treated with appropriate acid chloride in presence of suitable base TEA or DIPEA and the like, in presence of suitable solvent such as DCM, chloroform, THF or 1,4-dioxane and the like, at a temperature of about 20° C. to 35° C. for about 2 to 24 h to provide the compounds of formula-I.

Alternatively, the compound of formula-I can be synthesized by treating formula-3.5 with appropriate acid in the presence of suitable reagents such as HATU, EDC.HCl—HOBt and the like, in the presence of suitable base such as DIPEA or TEA and the like, in a suitable solvent such as DMF, THF, DMSO or DCM and the like at a temperature of about 20° C. to 35° C. for about 1-24 h.

Alternatively, the compound of formula (IF) of compound of formula (I), wherein ring B is absent was prepared according to the procedure depicted in scheme-II by using compound of formula-1.5 as starting material.

Scheme-II

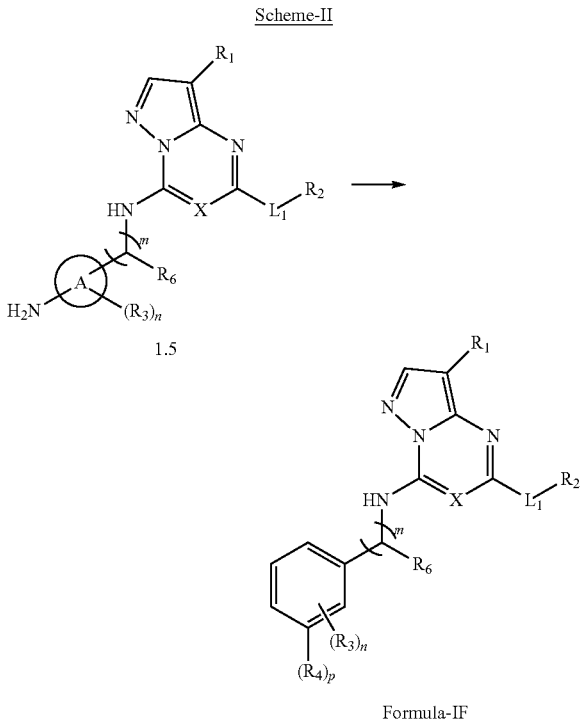

The compounds of formula-IF of formula (I) can be prepared by treating compound of formula-1.5 with respective acid chloride (prepared from respective haloalkenoic acid in presence of suitable reagents such as oxalyl chloride in a suitable solvent such as DMF or THF and the like) in presence of base such as DIPEA or TEA in presence of suitable solvent such as DCM, chloroform, THF or 1,4-dioxane and the like, at a temperature of about 20° C. to 35° C. for about 2 to 24 h. The obtained compound can be treated with various types of amines in presence of base such as $K_2CO_3$, $Na_2CO_3$ and the like in a suitable solvent such as ACN, THF, DMF, DMSO and the like, at a temperature of about 20° C. to 100° C. for about 2 to 24 h.

Abbreviations:

The following abbreviations refer respectively to the definitions herein: LDA (Lithium diisopropylamide); $K_2CO_3$ (Potassium carbonate); $PdCl_2(dppf)_2$-DCM (1,1'-Bis (diphenylphosphino)ferrocene]dichloropalladium(II); dichloromethane complex), DHP (3,4-Dihydro-2H-Pyran); PTSA (p-Toluenesulfonic acid); EDCI (1-Ethyl-3-(3-dimethylaminopropyl)carbodiimide; Dikis (Bis(triphenylphosphine)palladium(II) dichloride); $NH_3$ solution (Ammonia solution); Prep Column (Preparative column); Prep TLC (Preparative Thin layer Chromatography); rt (Retention time); RT (Room temperature); DMF (Dimethylformamide); h (hour); LC-MS (Liquid chromatography mass spectroscopy); NaOH (Sodium hydroxide); $Na_2SO_4$ (Sodium sulphate); ACN/$CH_3CN$ (Acetonitrile); HCl (Hydrochloric acid); THF (tetrahydrofuran); DCM (Dichloromethane); TFA (Trifluoroacetic acid); TLC (Thin layer chromatography); DIPEA (Diisopropyl Ethyl amine); DMSO-$d_6$ (Dimethyl sulfoxide-d); HATU (1-[Bis(dimethylamino)methylene]-1H-1,2,3-triazolo[4,5-b]pyridinium 3-oxid-hexafluorophosphate); $Boc_2O$ (Ditert-butyl dicarbonate); HPLC (High pressure liquid chromatography); $NaHCO_3$ (Sodium bicarbonate); NaH (Sodium hydride); SEM Chloride (2-(Trimethylsilyl)ethoxy methylchloride); $Cs_2CO_3$ (Cesium carbonate); BINAP (2,2'-Bis(diphenylphosphino)-1,1'-binaphthyl); $Pd_2(dba)_3$ (Tris(dibenzylideneacetone)dipalladium(0)); TEA (triethyl amine), TPP (Triphenyl phosphine), DIAD (Diisopropylazodicarboxylate), LiBH4 (Lithium borohydride), TMSCl (Chlorotrimethylsilane).

EXAMPLES

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

The MS data provided in the examples described below were obtained as follows:

Mass spectrum: LC/MS Agilent 6120 Quadrapole LC/MS.

The NMR data provided in the examples described below were obtained as follows:

$^1$H-NMR: Varian 400 MHz.

The microwave chemistry was performed on a CEM Explorer.

Synthesis of Intermediates:

The procedure for the compounds of formula (I) are detailed herein below stepwise including the general synthesis of various intermediates involved in process of manufacture of the compounds according to the present invention.

Intermediate-1: Synthesis of 4-chloro-2-(methylthio)pyrazolo[1,5-a][1,3,5]triazine

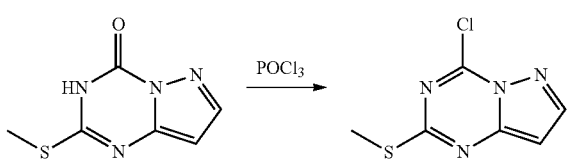

This intermediate was prepared from the procedure depicted in US2008/045536 by using 2-(methylthio)pyrazolo[1,5-a][1,3,5]triazin-4(3H)-one (prepared according to US2006/106019) as starting material; LCMS: m/z=200.9 $(M+H)^+$.

Intermediate-2: Synthesis of 4-chloro-8-ethyl-2-(methylthio)pyrazolo[1,5-a][1,3,5]triazine Step-1: Synthesis of 2-formylbutanenitrile

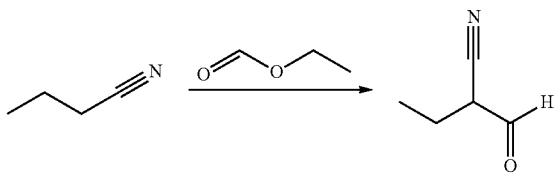

LDA 2.0M solution in THF (55 mL) was added to a stirred solution of butyronitrile (7.5 g, 108.6 mmol) in dry THF (50 mL) at −78° C. The resulting reaction mixture was stirred at −78° C. for 15 min. Ethylformate (8.03 g, 108.6 mmol) was added at −78° C. and then allowed to stir the reaction mixture for overnight. After completion of the reaction, the reaction mixture was quenched with ice water, adjusted to pH 4 by using 2NHCl and extracted with ethyl acetate (2×100 mL). The combined organic phase was washed with brine, dried over $Na_2SO_4$, filtered and concentrated to afford the title compound (5.6 g crude). The obtained product was taken for next step without purification.

Step-2: Synthesis of 4-ethyl-1H-pyrazol-5-amine

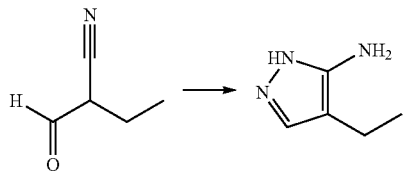

Hydrazine hydrate (5.6 mL) was added to a solution of 2-formylbutanenitrile (5.6 g, 57.73 mmol) in ethanol (112 mL) at room temperature followed by acetic acid (0.5 mL). Then the reaction mixture was heated at 90° C. for 6 h. After completion of the reaction, cooled to room temperature and quenched with ice-water, adjusted the pH 9 by using $K_2CO_3$ and the reaction mixture was extracted with ethyl acetate (2×25 mL). The combined organic phase was washed with brine, dried over Na$_2$SO$_4$, filtered and concentrated to afford the title compound (5.6 g crude) taken for next step without purification; LCMS: m/z=120.3 (M+H)$^+$.

Step-3: Synthesis of 8-ethyl-2-thioxo-2,3-dihydro-pyrazolo[1,5-a][1,3,5]triazin-4(1H)-one

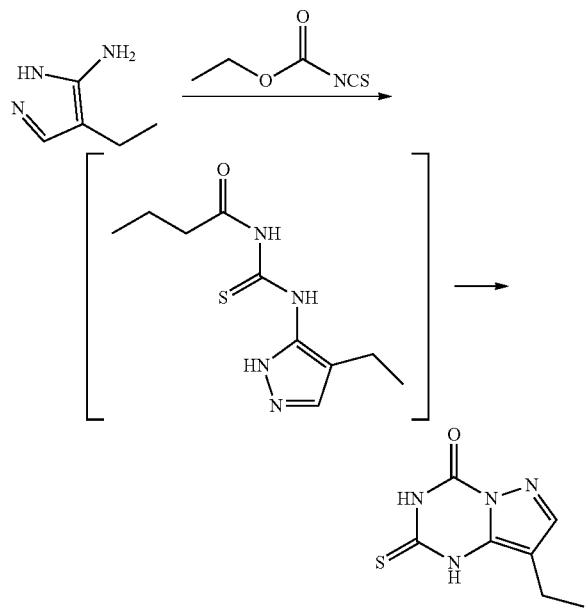

To a solution of 4-ethyl-1H-pyrazol-5-amine (5.0 g, 44.6 mmol) in DCM (20 mL) was added O-ethyl carbonisothiocyanatidate (5.9 g, 45.03 mmol) drop wise at 0° C. The reaction mixture was allowed to stirred at room temperature for 1 h. The solid obtained was filtered and dried to afford the intermediate of N-((4-ethyl-1H-pyrazol-5-yl)carbamothioyl)butyramide (3.5 g, 32.40%) LCMS: m/z=242.8 (M+H)$^+$. The intermediate formed was further dissolved in acetonitrile (100 mL), added K$_2$CO$_3$ (6.2 g, 44.9 mmol) and the reaction mixture was heated at 60° C. for 3 h. After completion of the reaction, the reaction mixture quenched with water and acidified with 2N HCl. The solid obtained was filtered and dried to afford the title compound (2.6 g, 91.22%); LCMS: m/z=197.0 (M+H)$^+$.

Step-4: Synthesis of 8-ethyl-2-(methylthio)pyrazolo[1,5-a][1,3,5]triazin-4(3H)-one

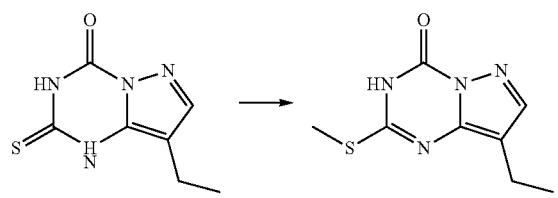

2M NaOH (10 mL, 20 mmol) was added to a stirred solution of 8-ethyl-2-thioxo-2,3-dihydropyrazolo[1,5-a][1,3,5]triazin-4(1H)-one (2.0 g, 10.19 mmol) in ethanol (40 mL) at 0° C. The resulting reaction mixture was stirred at 0° C. for 10 min. Added methyl iodide (1.5 g, 10.50 mmol) at 0° C.; after completion of the addition, the reaction mixture was maintained at room temperature for 4 h. After completion of the reaction, volatiles were removed under reduced pressure and obtained residue was diluted with ice-cold 2N HCl, the solid precipitated was filtered and dried under vacuum to afford the title compound (1.7 g, 79.43%). $^1$HNMR (DMSO-d$_6$): δ 12.73 (s, 1H), 7.90 (s, 1H), 2.58-2.51 (q, 2H), 2.50 (s, 3H), 1.23-1.19 (t, 3H). LCMS: m/z=210.9 (M+H)$^+$.

Step-5: Synthesis of 4-chloro-8-ethyl-2-(methylthio)pyrazolo[1,5-a][1,3,5]triazine

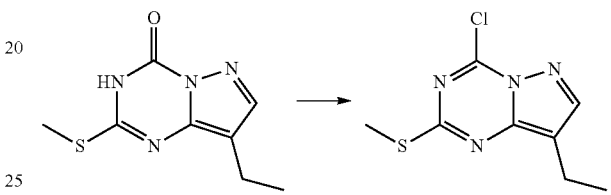

N,N-Diethyl aniline (3.6 g, 24.1 mmol) was added to a stirred solution of 8-ethyl-2-(methylthio)pyrazolo[1,5-a][1,3,5]triazin-4(3H)-one (1.7 g, 8.08 mmol) in POCl$_3$ (35 mL) at 0° C. The reaction mixture was heated at 90° C. for 4 h. After completion of the reaction, the reaction mixture was concentrated under vacuum and diluted with ice-cold water. The aqueous layer was extracted with ethyl acetate (2×50 mL). The combined organic phase was washed with brine, dried over Na$_2$SO$_4$, filtered and concentrated under reduced pressure. The residue was purified using combiflash (0-20% EtOAc/Hexane) to afford desired title compound (1.5 g, 81.52%); LCMS: m/z=228.9 (M+H)$^+$.

The below intermediates-3 and 4 were prepared according to the above protocol (Intermediate-2) by using appropriate reactants, reagents at suitable conditions. The characterization data of the intermediates are summarized herein.

| Int No. | Structure | Analytical Data |
|---|---|---|
| 3 | ![structure] | LCMS: m/z = 192.0 (M − 51)$^+$. |
| 4 | ![structure] | LCMS: m/z = 243.1 (M + 1)$^+$ |

Intermediate-5: Synthesis of tert-butyl (3-(aminomethyl)-4-ethylphenyl)carbamate

Step-1: Synthesis of tert-butyl (4-bromo-3-cyanophenyl)carbamate

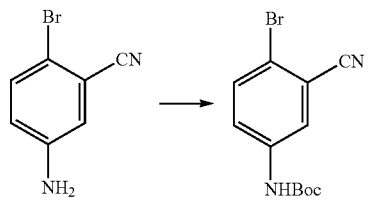 [SMILES: N#Cc1cc(N)ccc1Br ; CC(C)(C)OC(=O)Nc1ccc(Br)c(C#N)c1]

Di-tert-butyl dicarbonate (1.14 g, 4.8 mmol) was added to a solution of 5-amino-2-bromobenzonitrile (0.8 g, 4 mmol) and DMAP (0.58 g, 4.8 mmol) in DCM (20 mL) and the resulting reaction mixture was stirred for 8 h at room temperature. After completion of reaction, the reaction mixture was diluted with ice cold water and extracted with DCM (3×50 mL). The combined organic phase was washed with brine, dried over sodium sulphate, filtered and concentrated under reduced pressure. The residue was purified by 100-200 mesh silica column by eluting with 15% ethyl acetate-hexane to afford the title compound (Ig, 83%). LCMS: m/z=297.15 (M+H)$^+$.

Step-2: Synthesis of tert-butyl (3-cyano-4-ethylphenyl)carbamate

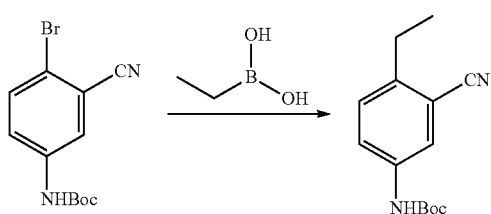

Tert-butyl (4-bromo-3-cyanophenyl)carbamate (4.0 g, 18.6 mmol), Ethyl boronic acid (Ig, 3.3 mmol), $Cs_2CO_3$ (3.21 g, 9.9 mmol) were taken in a pressure vessel. A mixture of toluene (10 mL) and ethanol (1 mL) was added. The suspension was degassed and flushed with nitrogen gas for 15 min. Then $Pd(PPh_3)_4$ (0.38 g, 0.33 mmol) was added, the pressure vessel was sealed and heated overnight at 110° C. After completion of the reaction, cooled to room temperature and was quenched with water and diluted with ethyl acetate. The aqueous layer was separated and extracted with ethyl acetate (2×25 mL). The combined organic phase was washed with brine, dried over $Na_2SO_4$, filtered and concentrated. The residue was purified by 100-200 silica gel column chromatography to afford desired title compound (0.28 g, 66%); LCMS: m/z=247.2 (M+H)$^+$.

Step-3: Synthesis of tert-butyl (3-(aminomethyl)-4-ethylphenyl)carbamate

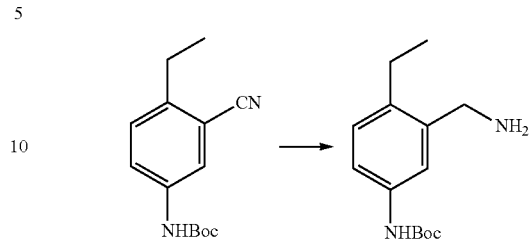

Nickel chloride hexahydrate (0.17 g, 1.2 mmol) was added to a cooled solution of tert-butyl (3-cyano-4-ethylphenyl)carbamate (0.5 g, 2 mmol) in methanol at 0° C. and stirred the reaction mixture for 10 min and added sodium borohydride (0.53 g, 14 mmol) lot wise at 0° C. The resulting reaction mixtures was stirred for 1 h at room temperature and cooled to 0° C. and added diethylene triamine (0.24 g, 2.4 mmol) and stirred for 1 h at room temperature and concentrated under vacuum. The residue was diluted with water, precipitated solid was filtered out and dried. Purified the crude using combiflash to afford the title compound (0.35 g, 65%); LCMS: m/z=251.1 (M+H)$^+$.

The below intermediates-6 and 7 were prepared according to the above protocol (step-1 & 3 of intermediate-5) by using appropriate reactants, reagents at suitable conditions. The characterization data of the intermediates are summarized herein.

| Int No. | Structure | Analytical Data |
|---|---|---|
| 6 | ![structure] | LCMS: m/z = 241 (M + H)$^+$. |
| 7 | ![structure] | LCMS: m/z = 224 (M + H)$^+$. |

Intermediate-8: Synthesis of 1-acryloylpiperidine-4-carboxylic acid

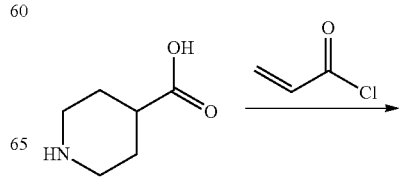

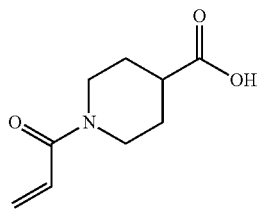

2M NaOH (7.8 mL, 15.5 mmol) was added to a solution of piperidine-4-carboxylic acid (1.0 g, 7.81 mmol) in (20 mL) of THF:Water (6:4) at 0° C. and then stirred for 10 min. Added acryloyl chloride (0.7 g, 7.69 mmol) at 0° C., then the reaction mixture was allowed to room temperature and stirred for 1 h. After completion of the reaction, the reaction mixture was quenched with ice water, adjusted pH to 4 by citric acid and extracted with ethyl acetate (2×100 mL). The combined organic phase was washed with brine, dried over $Na_2SO_4$, filtered and concentrated. The obtained product was triturated with diethyl ether, solid was filtered and dried to afford the title compound (0.45 g, 32.14%). $^1$HNMR (DMSO-$d_6$): δ 12.35 (s, 1H), 6.82-6.73 (m, 1H), 6.08-6.02 (dd, 1H), 5.65-5.61 (dd, 1H), 4.24-4.19 (d, 1H), 3.96-3.91 (d, 1H), 3.15-3.05 (t, 1H), 2.82-2.74 (t, 1H), 2.53-2.44 (m, 1H), 1.84-1.79 (m, 2H), 1.43-1.35 (m, 2H); LCMS: m/z=184 (M+H)$^+$.

The below intermediates-9 to 14 were prepared according to the above protocol (intermediate-8) by using appropriate reactants, reagents at suitable conditions. The characterization data of the intermediates are summarized herein.

| Int No. | Structure | Analytical Data |
|---|---|---|
| 9 | 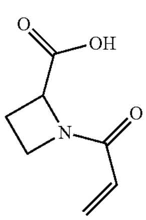 | LCMS: m/z = 156.05 (M + H)$^+$. |
| 10 | 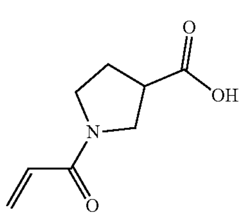 | LCMS: m/z = 170.00 (M + H)$^+$. |
| 11 | 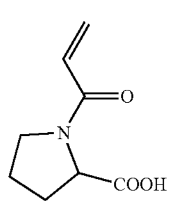 | LCMS: m/z = 170 (M + H)$^+$ |
| 12 | | LCMS: m/z = 185.21 (M + H)$^+$. |
| 13 | | LCMS: m/z = 198.21 (M + H)$^+$. |
| 14 | | LCMS: m/z = 198.21 (M + H)$^+$. |

Intermediate-15: Synthesis of N-(3-aminophenyl)-4-nitrobenzamide

To a cooled solution of 4-nitro benzoic acid (0.3 g, 1.85 mmol) in DMF (2 mL) at 0° C. was added HATU (0.84 g, 2.22 mmol) followed by DIPEA (0.47 mL, 3.7 mmol) and finally added 1,3-diaminobenzene (0.2 g, 1.85 mmol). The reaction mixture was stirred for 1 h at room temperature. The reaction mixture was quenched with ice-water and diluted with ethyl acetate. The aqueous layer was separated and extracted with ethyl acetate (2×25 mL). The combined organic phase was washed with brine, dried over $Na_2SO_4$, filtered and concentrated the crude residue (0.2 g crude). LCMS: m/z=258.10 (M+H)$^+$.

Intermediate-16: Synthesis of tert-butyl (S)-3-(3-(aminomethyl)benzamido)piperidine-1-carboxylate Step-1: Synthesis of tert-butyl (S)-3-(3-cyanobenzamido)piperidine-1-carboxylate

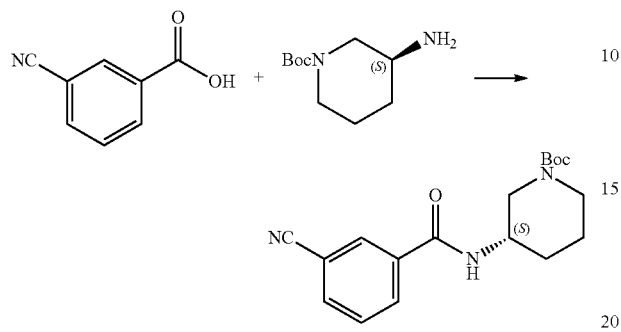

HATU (1.94 g, 5.1 mmol) and DIPEA (1.25 mL, 6.8 mmol) were added to a cooled solution of 3-cyanobenzoic acid (0.5 g, 5.98 mmol) in dry DMF (5 mL) at 0° C. Tert-butyl (S)-3-aminopiperidine-1-carboxylate (0.66 g, 3.4 mmol) was to the reaction mixture and stirred for 2 h at room temperature. After completion of reaction, the reaction mixture was diluted with ice-water and diluted with ethyl acetate. The aqueous layer was separated and extracted with ethyl acetate (2×25 mL). The combined organic phase was washed with brine, dried over Na$_2$SO$_4$, filtered and concentrated the crude residue (0.8 g crude). LCMS: m/z=330 (M+H)$^+$.

Step-2: Synthesis of tert-butyl (S)-3-(3-(aminomethyl)benzamido)piperidine-1-carboxylate

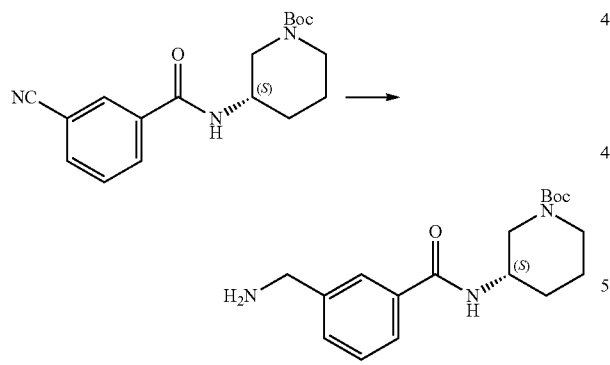

Nickel(II) chloride hexahydrate (0.29 g, 1.23 mmol) was added to a solution of tert-butyl (S)-3-(3-cyanobenzamido) piperidine-1-carboxylate (0.8 g, 2.47 mmol) in MeOH (10 mL) at 0° C., followed by NaBH$_4$ (0.73 g, 19.32 mmol) was added portion wise. The resulting reaction mixture was stirred at ambient temperature for 1 h, then cooled to 0° C. and added diethylenetriamine (0.25 g, 2.46 mmol) and allowed to stir at ambient temperature for 1 h. After completion of the reaction, the reaction mixture was concentrated under vacuum, diluted with ethyl acetate (30 mL), washed with water and brine solution. The organic layer was dried over Na$_2$SO$_4$, filtered and concentrated the crude residue (0.5 g, crude). LCMS: m/z=334 (M+H)$^+$.

The below Intermediate-17 was prepared according to the above protocol (Intermediate-16) by using appropriate reactants, reagents at suitable conditions. The characterization data of the intermediates are summarized herein.

| Int No. | Structure | Analytical Data |
|---|---|---|
| 17 | 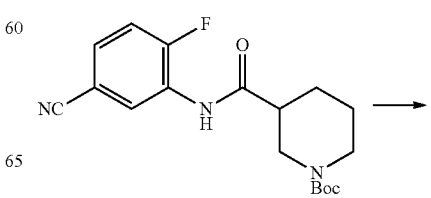 | LCMS: m/z = 334.2 (M + H)$^+$. |

Intermediate-18: Synthesis of tert-butyl 3-((5-(aminomethyl)-2-fluorophenyl)carbamoyl) piperidine-1-carboxylate Step-1: Synthesis of tert-butyl 3-((5-cyano-2-fluorophenyl)carbamoyl)piperidine-1-carboxylate

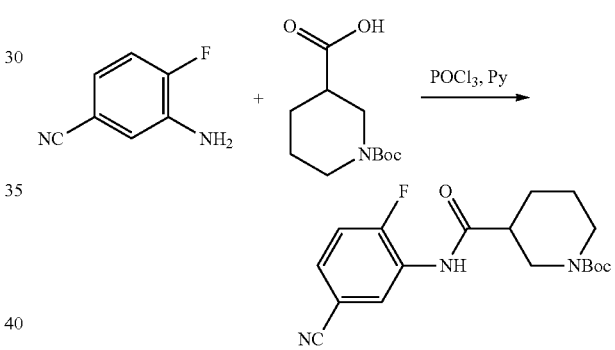

To a cooled solution of 1-(tert-butoxycarbonyl)piperidine-3-carboxylic acid (Ig, 4.3 mmol) in pyridine (5 mL) at 0° C. was added 3-amino-4-fluorobenzonitrile (0.59 g, 4.3 mmol) followed by POCl$_3$ (0.68 g, 4.3 mmol), The reaction mixture was stirred for 2 h at room temperature. The reaction mixture was quenched with ice-water and diluted with ethyl acetate. The aqueous layer was separated and extracted with ethyl acetate (2×25 mL). The combined organic phase was washed with brine, dried over Na$_2$SO$_4$, filtered and concentrated to crude residue (1.1 g). LCMS: m/z=346.15 (M−H)$^+$.

Step-2: Synthesis of tert-butyl 3-((5-(aminomethyl)-2-fluorophenyl)carbamoyl)piperidine-1-carboxylate

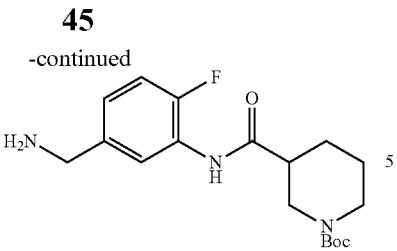

Nickel chloride hexahydrate (0.29 g, 1.21 mmol) was added to a cooled solution of tert-butyl 3-((5-cyano-2-fluorophenyl)carbamoyl)piperidine-1-carboxylate (1.1 g, 3.1 mmol) in methanol at 0° C. and stirred the reaction mixture for 10 min and added sodium borohydride (0.84 g, 22.1 mmol) lot wise at 0° C., stirred the reaction mixture for 1 h at room temperature, further cooled to 0° C. and added diethylenetriamine (0.32 g, 3.1 mmol) and stirred for 1 h at room temperature and concentrated under vacuum. Diluted the reaction mixture with water, solid separated was filtered and dried. The obtained crude was purified by using combiflash to afford the title compound (0.8 g, 72%). LCMS: m/z=352 (M+H)⁺.

The below Intermediates-19 to 20 were prepared according to the above protocol (Intermediate-18) by using appropriate reactants, reagents at suitable conditions. The characterization data of the intermediates are summarized herein.

| Int No. | Structure | Analytical Data |
|---|---|---|
| 19 | 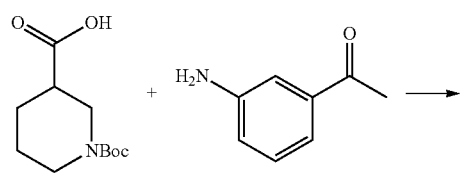 | LCMS: m/z = 336.15 (M − 1)⁺. |
| 20 | 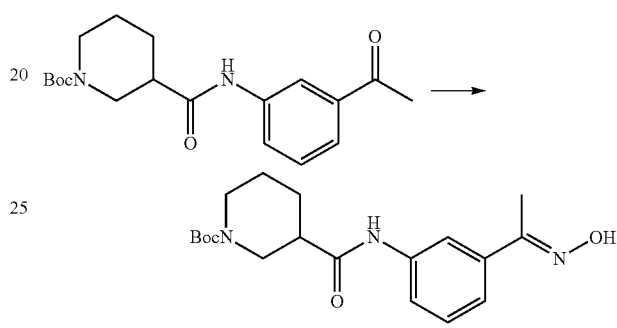 | LCMS: m/z = 335.1 (M + H)⁺. |

Intermediate-21: Synthesis of tert-butyl 3-((3-(1-aminoethyl)phenyl)carbamoyl)piperidine-1-carboxylate Step-1: Synthesis of tert-butyl 3-((3-acetylphenyl)carbamoyl)piperidine-1-carboxylate

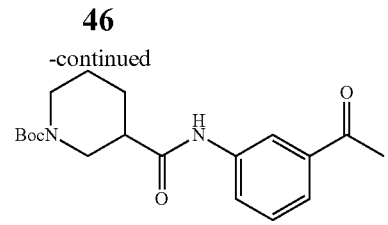

The process of this step was adopted from intermediate-15 (1.2 g). LCMS: m/z=347.1 (M+H)⁺.

Step-2: Synthesis of tert-butyl (E)-3-((3-(1-(hydroxyimino)ethyl)phenyl)carbamoyl) piperidine-1-carboxylate

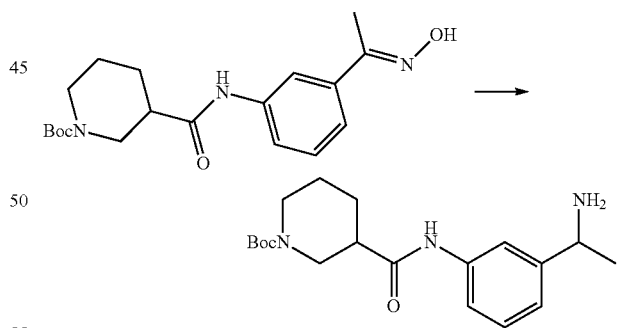

To a solution of tert-butyl 3-((3-acetylphenyl)carbamoyl) piperidine-1-carboxylate (1.2 g, 3.4 mmol) in EtOH (20 mL) was added 50% Aq. NH₂OH solution (0.57 mg, 17.3 mmol) at RT. The reaction mixture was stirred at 80° C. for 2 h. The reaction mixture was concentrated to afford desired title compound (1.1 g, 88%). LCMS: m/z=362.1 (M+H)⁺.

Step-3: Synthesis of tert-butyl 3-((3-(1-aminoethyl)phenyl)carbamoyl)piperidine-1-carboxylate To a solution of tert-butyl (E)-3-((3-(1-(hydroxyimino)ethyl)phenyl)carbamoyl) piperidine-1-carboxylate (1 g, 2.7 mmol) in acetic acid (5 mL) was added zinc (0.905 g, 13.8 mmol). The reaction mixture was stirred at room temperature for 4 h. After completion of the reaction the reaction mixture was filtered through celite and diluted with ethyl acetate. The aqueous layer was separated and extracted with ethyl acetate (2×25 mL). The combined organic phase was washed with brine, dried over Na₂SO₄, filtered and concentrated to afford desired title compound (0.9 g, crude). LCMS: m/z=347.7 (M+H)⁺.

Intermediate-22: Synthesis of tert-butyl 4-(3-aminobenzamido)piperidine-1-carboxylate

Step-1: Synthesis of tert-butyl 4-(3-nitrobenzamido)piperidine-1-carboxylate

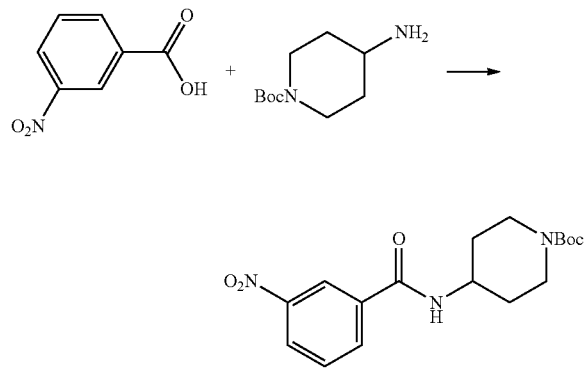

The process of this step was adopted from intermediate-15 (1.2 g crude)

Step-2: Synthesis of tert-butyl 4-(3-aminobenzamido)piperidine-1-carboxylate

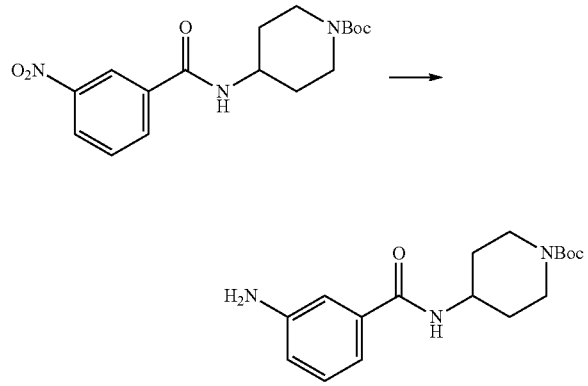

NH$_4$Cl (3.67 g, 68.7 mmol) and Zinc (2.24 g, 34.3 mmol) was sequentially added to a solution of tert-butyl 4-(3-nitrobenzamido)piperidine-1-carboxylate (1.2 g, 3.4 mmol) in mixture of THF:MeOH:water (2:1:1, 40 mL) at 0° C. and the resulting reaction mixture was stirred at ambient temperature for 3 h. After completion of the reaction, the reaction mixture was filtered through celite pad and washed with ethyl acetate. Filtrate was concentrated and quenched with ice-water and diluted with ethyl acetate. The aqueous layer was separated and extracted with ethyl acetate (2×25 mL). The combined organic phase was washed with brine, dried over Na$_2$SO$_4$, filtered and concentrated the crude residue (0.9 g). LCMS: m/z=264.20 (M-tert-Bu+1).

Intermediate-23: Synthesis of 3-fluoro-1-methylpiperidin-4-ol

Step-1: Synthesis of tert-butyl 3-fluoro-4-hydroxypiperidine-1-carboxylate

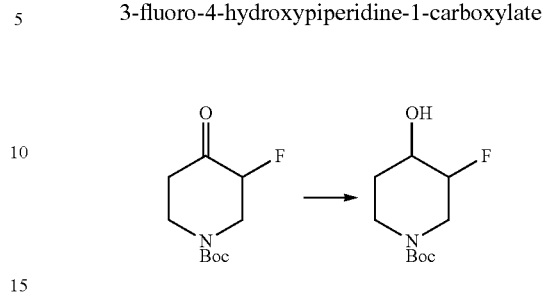

To a solution of tert-butyl 3-fluoro-4-oxopiperidine-1-carboxylate (10 g, 45.87 mmol, WO2015/022662) in MeOH (200 mL) was added sodiumborohydride (2.5 g, 69.44 mmol) lot wise at 0° C. Then the reaction mixture was allowed to stir at room temperature for 1 h. After completion of the reaction, the reaction mixture was concentrated under vacuum and diluted with ice-cold saturated ammonium chloride solution. The aqueous layer was extracted with ethyl acetate (2×50 mL). The combined organic phase was washed with brine, dried over Na$_2$SO$_4$, filtered and concentrated under reduced pressure to afford the title compound (9.1 g, crude). LCMS: m/z=220.0 (M+H)$^+$.

Step-2: Synthesis of tert-butyl 4-(benzyloxy)-3-fluoropiperidine-1-carboxylate

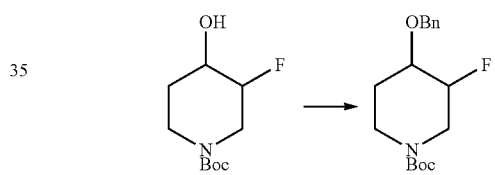

NaH (60%) (2.5 g, 104.16 mmol) was added to a solution of tert-butyl 3-fluoro-4-hydroxypiperidine-1-carboxylate (9.0 g, 0.041 mmol) in DMF (180 mL) under inert atmosphere at 0° C. and stirred for 25 min. Benzylbromide (7.0 g, 0.040 mmol) was added, the resulting reaction mixture was allowed to RT and stirred for 5 h. After completion of the reaction, cooled to room temperature and was quenched with ice-water and diluted with ethyl acetate (25 mL). The aqueous layer was separated and extracted with ethyl acetate (2×100 mL). The combined organic phase was washed with brine, dried over Na$_2$SO$_4$, filtered and concentrated. The residue was purified by column chromatography (0-10% EtOAc/hexane) to afford title compound (10.5 g, 83.33%). LCMS: m/z=310.3 (M+H)$^+$.

Step-3: Synthesis of 4-(benzyloxy)-3-fluoropiperidine

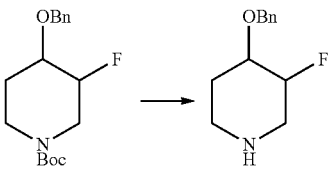 [SMILES: CC(C)(C)OC(=O)N1CCC(OCc2ccccc2)C(F)C1 ; FC1CNCCC1OCc1ccccc1]

To a solution of tert-butyl 4-(benzyloxy)-3-fluoropiperidine-1-carboxylate (10.0 g, 32.32 mmol) in DCM (30 mL) was added TFA (15.0 mL) drop wise at 0° C. Then the reaction mixture was allowed to stirred at room temperature for 5 h. After completion of the reaction, the reaction mixture was concentrated under vacuum and treated with ice-cold NaHCO₃ solution. The aqueous layer was extracted with ethyl acetate (2×50 mL). The combined organic phase was washed with brine, dried over Na₂SO₄, filtered and concentrated under reduced pressure to afford the title compound (7.5 g, crude). LCMS: m/z=209.7 (M+H)⁺.

Step-4: Synthesis of 4-(benzyloxy)-3-fluoro-1-methylpiperidine

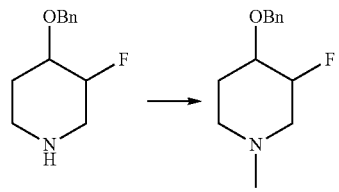 [SMILES: FC1CNCCC1OCc1ccccc1 ; CN1CCC(OCc2ccccc2)C(F)C1]

To a solution of 4-(benzyloxy)-3-fluoropiperidine (8.0 g, 38.27 mmol) in THF (160 mL) was added TEA (3.9 g, 38.61 mmol), followed by dimethylsulfate (4.9 g, 38.84 mmol) at 0° C. Then the reaction mixture was allowed to stirred at room temperature for 2 h. After completion of the reaction, the reaction mixture was concentrated under vacuum and the residue was diluted with water and ethyl acetate, separated the organic phase. The organic phase was washed with brine, dried over Na₂SO₄, filtered and concentrated under reduced pressure to afford the title compound (2.5 g, crude). LCMS: m/z=225.4 (M+H)⁺.

Step-5: Synthesis of 3-fluoro-1-methylpiperidin-4-ol

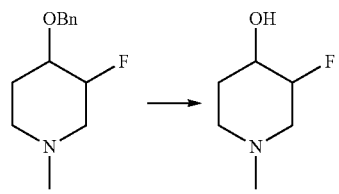

Pd/C (10%) (0.9 g) was added to a solution of 4-(benzyloxy)-3-fluoro-1-methylpiperidine (2.5 g, 11.19 mmol) in ethanol was taken in par shaker (250 mL), applied 50 psi hydrogen pressure, maintained for 24 h at RT. After completion of the reaction, the reaction mixture was filtered through celite pad and the filtrate was concentrated under reduced pressure to afford the title compound (2.0 g, crude). LCMS: m/z=134.1 (M+H)⁺.

Intermediate-24: Synthesis of 8-ethyl-2-(methylthio)-N-(3-nitrobenzyl)pyrazolo[1,5-a][1,3,5]triazin-4-amine

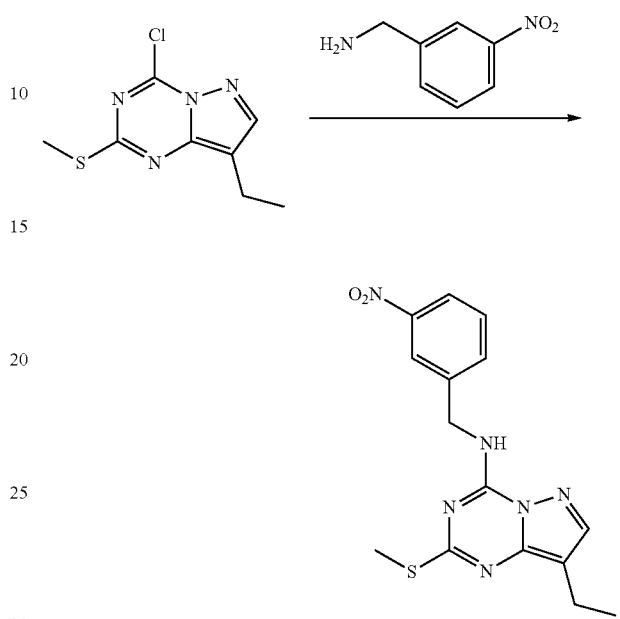

DIPEA (2.0 g, 15.5 mmol) was added to a stirred solution of (3-nitrophenyl) methanamine.HCl (1.45 g, 7.71 mmol) in acetonitrile (50 mL) at 0° C. Then added 4-chloro-8-ethyl-2-(methylthio)pyrazolo[1,5-a][1,3,5]triazine (1.7 g, 7.43 mmol; intermediate-2). The resulting reaction mixture was stirred at ambient temperature for 2 h. After completion of the reaction, concentrated the reaction mixture to remove volatiles and the residue was diluted with ice-cold water, the solid obtained was filtered and dried to afford the title compound (2.4 g, 94.11%). LCMS: m/z=345.2 (M+H)⁺.

The below Intermediates-25 to 28 were prepared according to the above protocol (intermediate-24) by using appropriate reactants, reagents at suitable conditions. The characterization data of the intermediates are summarized herein.

| Int No. | Structure | Analytical Data |
|---|---|---|
| 25 | 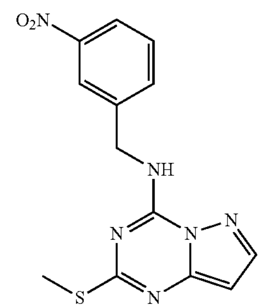 [SMILES: CSc1nc(NCc2cccc([N+](=O)[O-])c2)n2nccc2n1] | LCMS: m/z = 316.9 (M + H)⁺. |

51
-continued

| Int No. | Structure | Analytical Data |
|---|---|---|
| 26 | 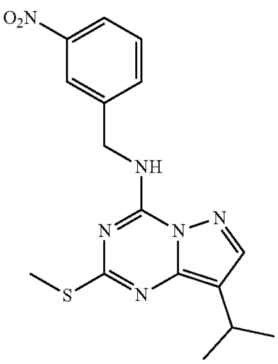 [SMILES: CSc1nc(NCc2cccc([N+](=O)[O-])c2)n2ncc(C(C)C)c2n1] | LCMS: m/z = 359.05 (M + H)⁺. |
| 27 | 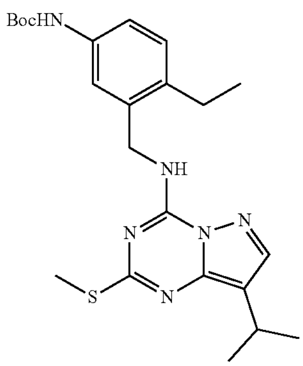 [SMILES: CCc1ccc(NC(=O)OC(C)(C)C)cc1CNc1nc(SC)nc2c(C(C)C)cnn12] | LCMS: m/z = 457.1 (M + H)⁺. |
| 28 | 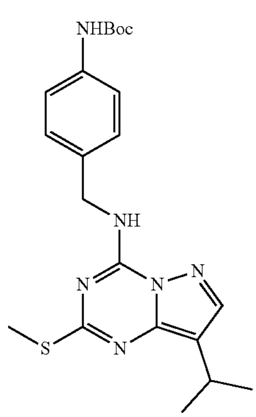 [SMILES: CSc1nc(NCc2ccc(NC(=O)OC(C)(C)C)cc2)n2ncc(C(C)C)c2n1] | LCMS: m/z = 429 (M + H)⁺. |

52

Intermediate-29: Synthesis of N4-(5-amino-2-ethylbenzyl)-8-isopropyl-N2-(tetrahydro-2H-pyran-4-yl)pyrazolo[1,5-a][1,3,5]triazine-2,4-diamine Step-1: Synthesis of tert-butyl (4-ethyl-3-(((8-isopropyl-2-(methylsulfonyl)pyrazolo[1,5-a][1,3,5]triazin-4-yl)amino)methyl)phenyl)carbamate

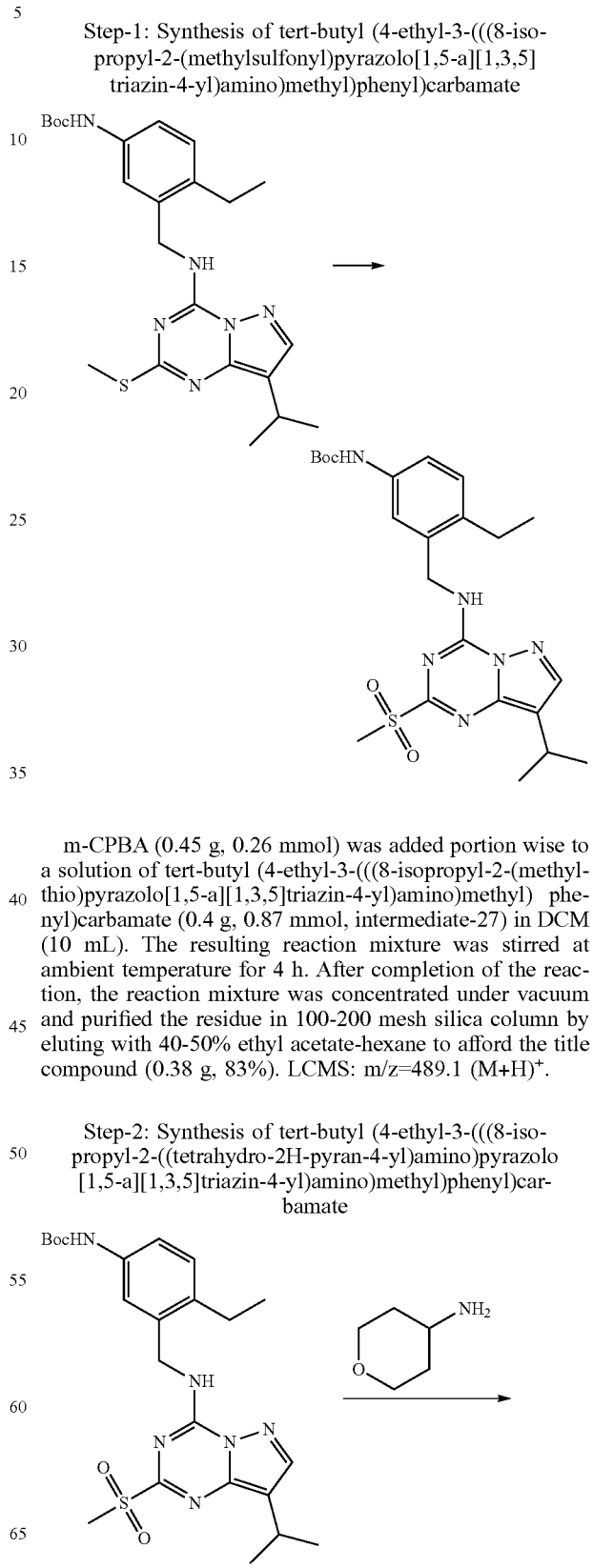

m-CPBA (0.45 g, 0.26 mmol) was added portion wise to a solution of tert-butyl (4-ethyl-3-(((8-isopropyl-2-(methylthio)pyrazolo[1,5-a][1,3,5]triazin-4-yl)amino)methyl) phenyl)carbamate (0.4 g, 0.87 mmol, intermediate-27) in DCM (10 mL). The resulting reaction mixture was stirred at ambient temperature for 4 h. After completion of the reaction, the reaction mixture was concentrated under vacuum and purified the residue in 100-200 mesh silica column by eluting with 40-50% ethyl acetate-hexane to afford the title compound (0.38 g, 83%). LCMS: m/z=489.1 (M+H)⁺.

Step-2: Synthesis of tert-butyl (4-ethyl-3-(((8-isopropyl-2-((tetrahydro-2H-pyran-4-yl)amino)pyrazolo[1,5-a][1,3,5]triazin-4-yl)amino)methyl)phenyl)carbamate

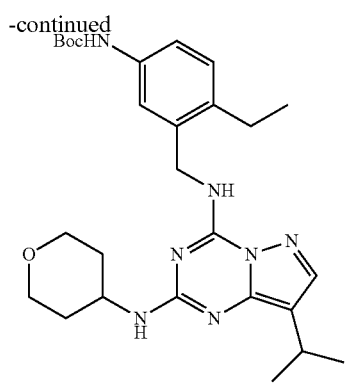

A mixture of 4-aminotetrahydropyran (0.44 g, 4.36 mmol) and tert-butyl (4-ethyl-3-(((8-isopropyl-2-(methylsulfonyl)pyrazolo[1,5-a][1,3,5]triazin-4-yl)amino)methyl)phenyl)carbamate (0.38 g, 0.72 mmol) were heated at 100° C. for 2 h. After completion of the reaction, cooled to room temperature and was quenched with ice-water and diluted with ethyl acetate. The aqueous layer was separated and extracted with ethyl acetate (2×25 mL). The combined organic phase was washed with brine, dried over $Na_2SO_4$, filtered and concentrated. The residue was purified by 100-200 silica gel column chromatography to afford desired title compound (0.28 g, 66%). LCMS: m/z=510.3 $(M+H)^+$.

Step-3: Synthesis of N4-(5-amino-2-ethylbenzyl)-8-isopropyl-N2-(tetrahydro-2H-pyran-4-yl)pyrazolo[1,5-a][1,3,5]triazine-2,4-diamine

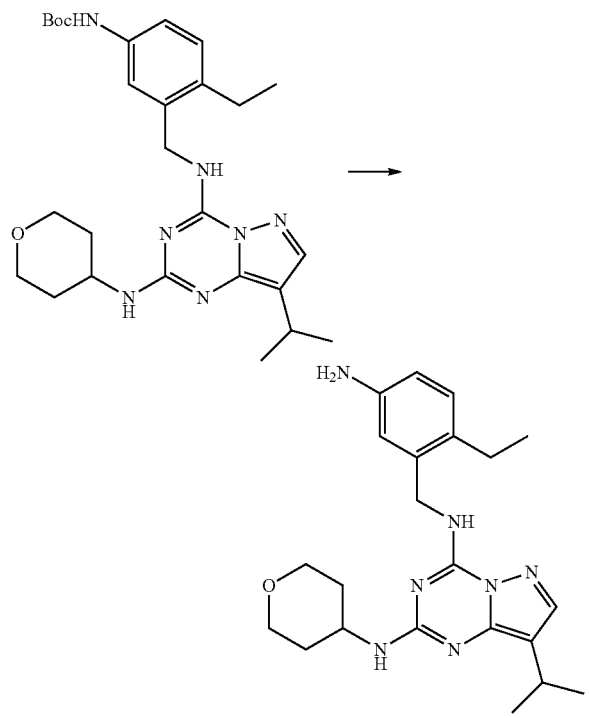

TFA (0.5 mL) was added to a solution of tert-butyl (4-ethyl-3-(((8-isopropyl-2-((tetrahydro-2H-pyran-4-yl)amino)pyrazolo[1,5-a][1,3,5]triazin-4-yl)amino)methyl)phenyl) carbamate (0.28 g, 0.48 mmol) in DCM (2.5 mL) at 0° C. The reaction mixture allowed to stir at room temperature for 2 h. After completion of the reaction, the reaction mixture was concentrated under vacuum to afford desired title compound (0.22 g of TFA salt); LCMS: m/z=410.2 $(M+H)^+$.

The below Intermediates-30 to 32 were prepared according to the above protocol (Intermediate-29) by using appropriate reactants, reagents at suitable conditions. The characterization data of the intermediates are summarized herein.

| Int No. | Structure | Analytical Data |
|---|---|---|
| 30 | ![structure] | LCMS: m/z = 400 (M + H)⁺. |
| 31 | ![structure] | LCMS: m/z = 383.1 (M + H)⁺. |
| 32 | ![structure] | LCMS: m/z = 382 (M + H)⁺. |

Intermediate-33: Synthesis of N4-(3-aminobenzyl)-8-isopropyl-N2-(tetrahydro-2H-pyran-4-yl)pyrazolo[1,5-a][1,3,5]triazine-2,4-diamine

Step-1: Synthesis of 8-isopropyl-2-(methylsulfonyl)-N-(3-nitrobenzyl)pyrazolo[1,5-a][1,3,5]triazin-4-amine

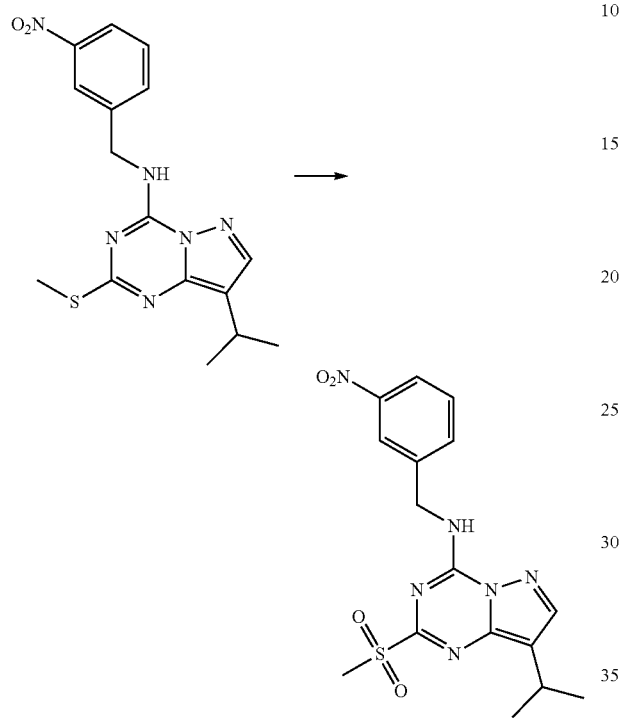

mCPBA (1.73 g, 10.05 mmol) was added portion wise to a solution of 8-isopropyl-2-(methylthio)-N-(3-nitrobenzyl)pyrazolo[1,5-a][1,3,5]triazin-4-amine (1.2 g, 3.35 mmol) in DCM (150 mL). After completion of the reaction, the reaction mixture was extracted with 2M aq. NaOH and DCM. The organic phase was washed with brine, dried over Na$_2$SO$_4$, filtered and concentrated to afford the title compound (1 g, 76%). LCMS: m/z=391.1 (M+H)$^+$.

Step-2: Synthesis of 8-isopropyl-N4-(3-nitrobenzyl)-N2-(tetrahydro-2H-pyran-4-yl)pyrazolo [1,5-a][1,3,5]triazine-2,4-diamine

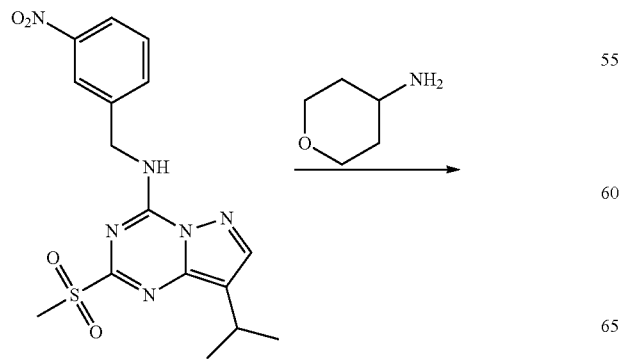

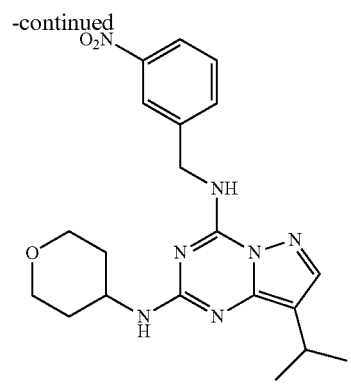

A mixture of 4-aminotetrahydropyran (0.26 g, 2.56 mmol) and 8-isopropyl-2-(methylsulfonyl)-N-(3-nitrobenzyl)pyrazolo[1,5-a][1,3,5]triazin-4-amine (0.2 g, 0.51 mmol) were allowed to heat at 100° C. for 2-12 h. After completion of the reaction, the reaction mixture was cooled to room temperature, quenched with ice-water and diluted with ethyl acetate. The aqueous layer was separated and extracted with ethyl acetate (2×25 mL). The combined organic phase was washed with brine, dried over Na$_2$SO$_4$, filtered and concentrated. The residue was purified by 100-200 silica gel column chromatography to afford desired title compound (0.2 g, 95%). LCMS: m/z=412.49 (M+H)$^+$.

Step-3: Synthesis of N4-(3-aminobenzyl)-8-isopropyl-N2-(tetrahydro-2H-pyran-4-yl) pyrazolo[1,5-a][1,3,5]triazine-2,4-diamine

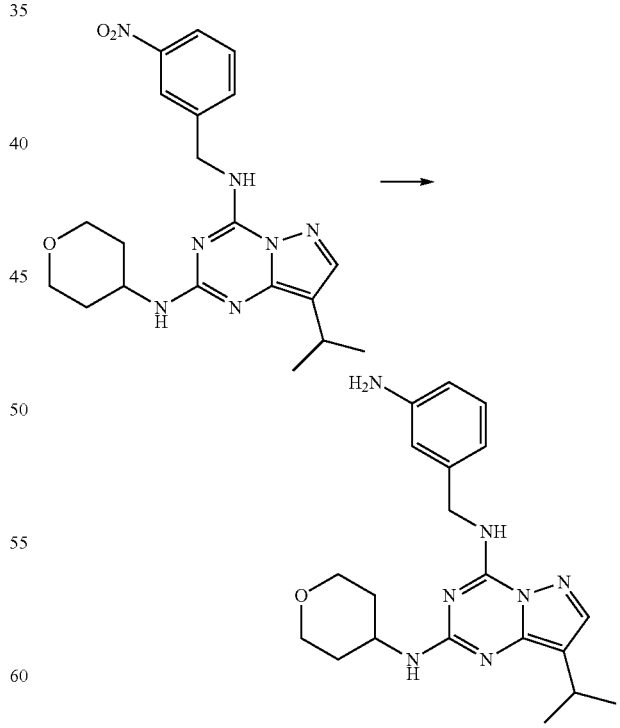

To a solution of 8-isopropyl-2-((1-methylpiperidin-4-yl)oxy)-N-(3-nitrobenzyl)pyrazolo[1,5-a][1,3,5]triazin-4-amine (0.65 g, 1.52 mmol) in THF:MeOH:Water (3:2:1) were added zinc (0.5 g, 7.64 mmol) and ammonium chloride (0.4 g, 7.64 mmol). The reaction mixture was stirred at room temperature for 4 h. After completion of reaction the reaction mixture filtered through celite and diluted with ethyl acetate. The aqueous layer was separated and extracted with ethyl acetate (2×25 mL). The combined organic phase was washed with brine, dried over Na₂SO₄, filtered and concentrated. The residue was purified by 100-200 silica gel column chromatography to afford desired title compound (0.5 g, 83%). LCMS: m/z=382.4 (M+H)⁺.

The below intermediates-34 to 38 were prepared according to the above protocol (intermediate-33) by using appropriate reactants, reagents at suitable conditions. The characterization data of the intermediates are summarized herein.

| Int No. | Structure | Analytical Data |
|---|---|---|
| 34 | 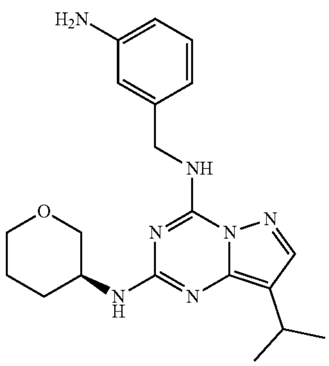 [SMILES: CC(C)c1cnn2c(NCc3cccc(N)c3)nc(N[C@H]3CCCOC3)nc12] | LCMS: m/z = 381 (M + H)⁺. |
| 35 | 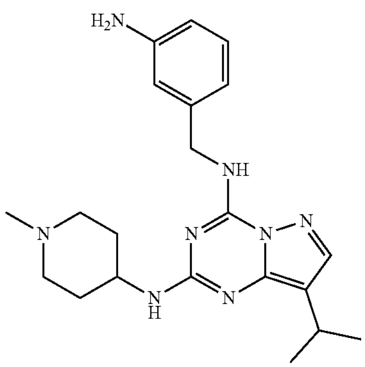 [SMILES: CC(C)c1cnn2c(NCc3cccc(N)c3)nc(NC3CCN(C)CC3)nc12] | LCMS: m/z = 395.21 (M + H)⁺. |
| 36 | 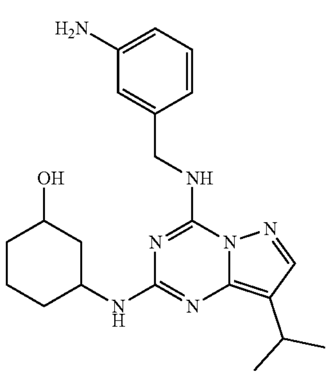 [SMILES: CC(C)c1cnn2c(NCc3cccc(N)c3)nc(NC3CCCC(O)C3)nc12] | LCMS: m/z = 396.65 (M + H)⁺. |
| 37 | | LCMS: m/z = 396.35 (M + H)⁺. |
| 38 | | LCMS: m/z = 499.2 (M + H)⁺. |

Intermediate-39: Synthesis of N4-(3-aminophenyl)-8-isopropyl-N2-(tetrahydro-2H-pyran-4-yl)pyrazolo[1,5-a][1,3,5]triazine-2,4-diamine Step-1: Synthesis of 8-isopropyl-2-(methylthio)-N-(3-nitrophenyl)pyrazolo[1,5-a][1,3,5] triazin-4-amine The process of this step was adopted from intermediate-24 (2 g, 47%). LCMS: m/z=345.0 (M+H)⁺.

Step-2: Synthesis of 8-isopropyl-2-(methylsulfonyl)-N-(3-nitrophenyl)pyrazolo[1,5-a][1,3,5]triazin-4-amine Step-4: Synthesis of N-4-(3-aminophenyl)-8-isopropyl-N2-(tetrahydro-2H-pyran-4-yl)pyrazolo[1,5-a][1,3,5]triazine-2,4-diamine

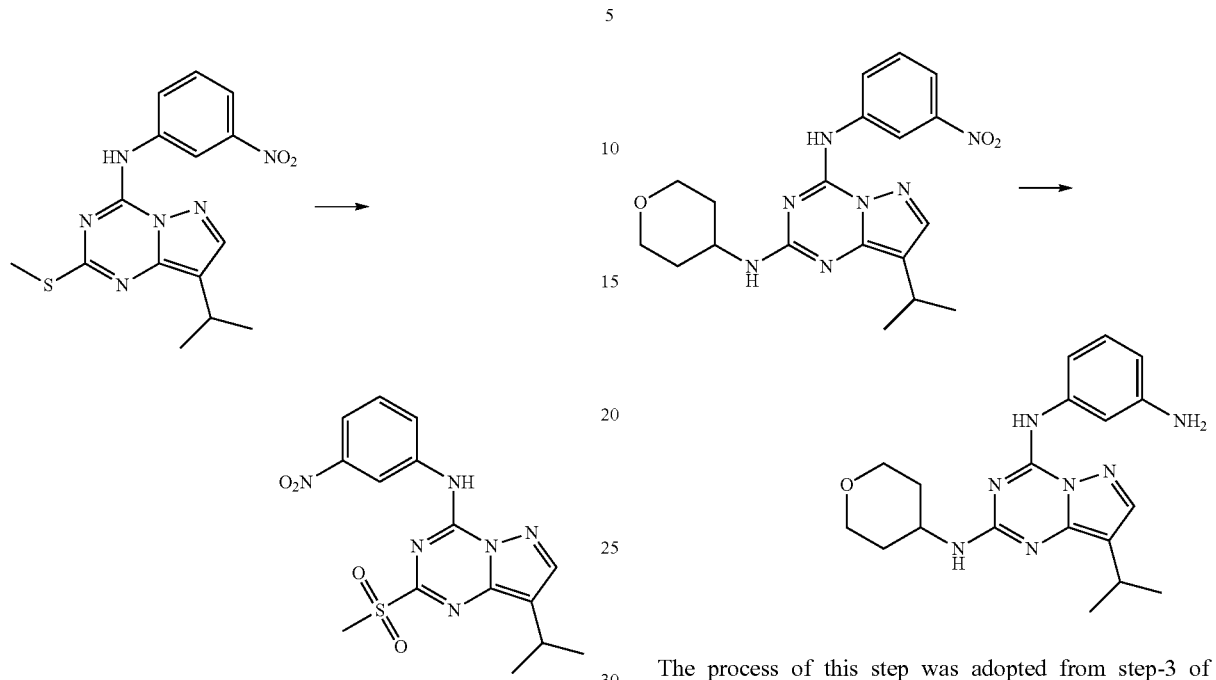

The process of this step was adopted from step-1 of intermediate-29 (2.0 g, 93%). LCMS: m/z=376.95 (M+H)⁺.

Step-3: Synthesis of 8-isopropyl-N4-(3-nitrophenyl)-N2-(tetrahydro-2H-pyran-4-yl)pyrazolo[1,5-a][1,3,5]triazine-2,4-diamine The process of this step was adopted from step-3 of intermediate-33 (0.9 g, 75%). LCMS: m/z=368.5 (M+H)⁺.

Intermediate-40: Synthesis of N-(3-aminobenzyl)-8-ethyl-2-((1-methylpiperidin-4-yl)oxy) pyrazolo[1,5-a][1,3,5]triazin-4-amine Step-1: Synthesis of 8-ethyl-2-(methylsulfonyl)-N-(3-nitrobenzyl)pyrazolo[1,5-a][1,3,5]triazin-4-amine

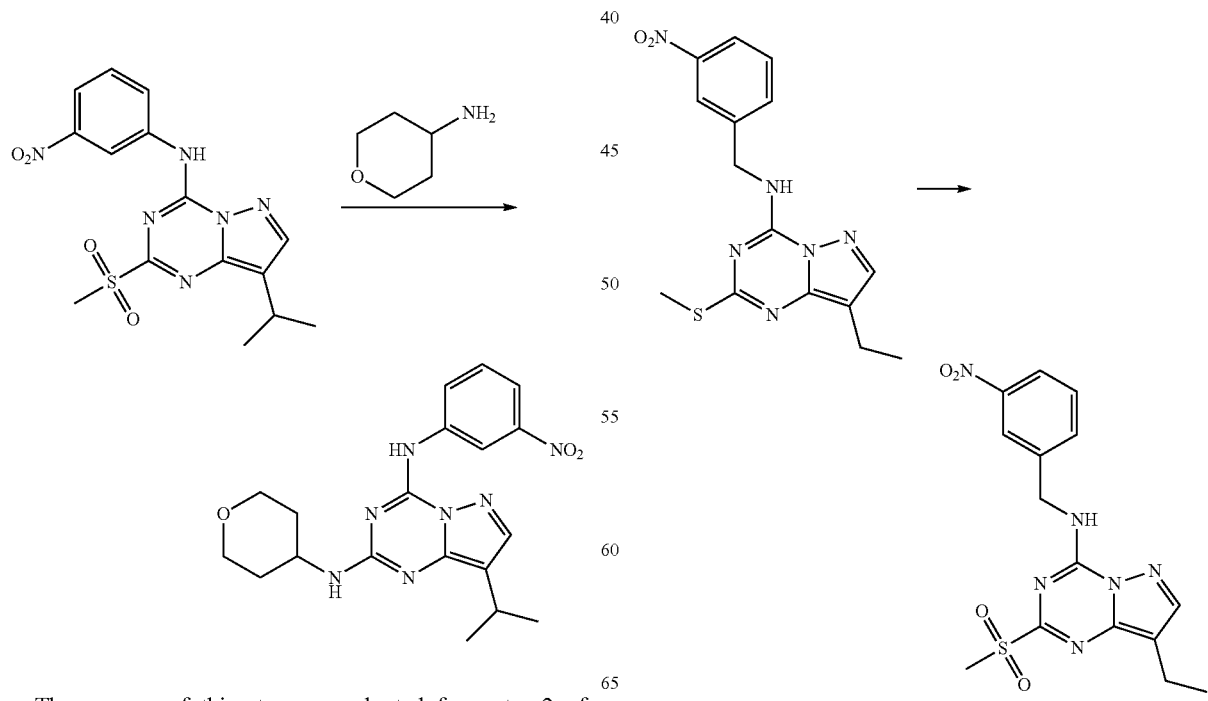

The process of this step was adopted from step-2 of intermediate-29 (1.2 g, 94%). LCMS: m/z=398 (M+H)⁺.

The process of this step was adopted from step-1 of intermediate-29 (1.98 g, 72.52%). LCMS: m/z=377.2 (M+H)⁺.

Step-2: Synthesis of 8-ethyl-2-((1-methylpiperidin-4-yl)oxy)-N-(3-nitrobenzyl)pyrazolo[1,5-a][1,3,5]triazin-4-amine

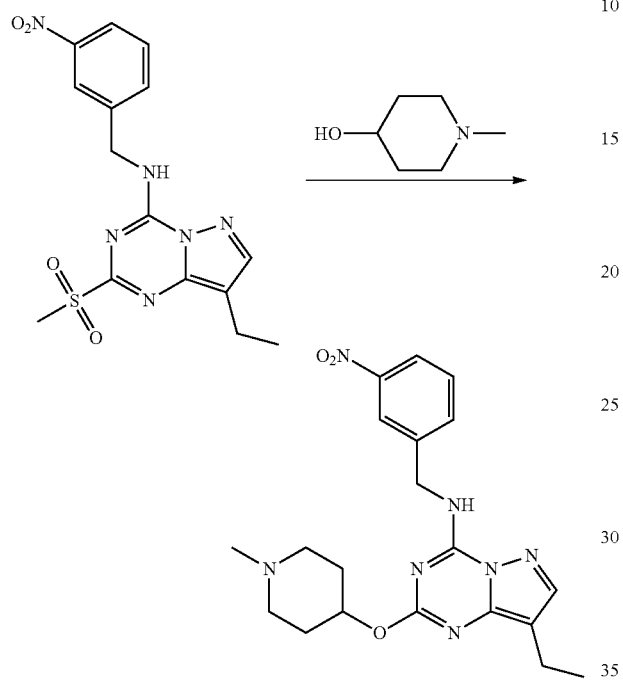

NaH (0.25 g, 10.6 mmol) was added to a solution of 1-methylpiperidin-4-ol (1.2 g, 10.4 mmol) in THF (40 mL) under inert atmosphere at 0° C. and allowed to stir for 25 min. Then 8-ethyl-2-(methylsulfonyl)-N-(3-nitrobenzyl) pyrazolo[1,5-a][1,3,5]triazin-4-amine (1.0 g, 2.65 mmol) was added at same temperature and the resulting reaction mixture was allowed to stir at RT for 2 h. After completion of the reaction, reaction mixture was cooled to room temperature, quenched with ice-water and diluted with ethyl acetate (25 mL). The aqueous layer was separated and extracted with ethyl acetate (2×100 mL). The combined organic phase was washed with brine, dried over Na₂SO₄, filtered and concentrated. The residue was purified by combiflash (0-10% MeOH/DCM) to afford title compound (0.6 g, 55.04%). LCMS: m/z=412.9 (M+H)⁺.

Step-3: Synthesis of N-(3-aminobenzyl)-8-ethyl-2-((1-methylpiperidin-4-yl)oxy)pyrazolo [1,5-a][1,3,5]triazin-4-amine

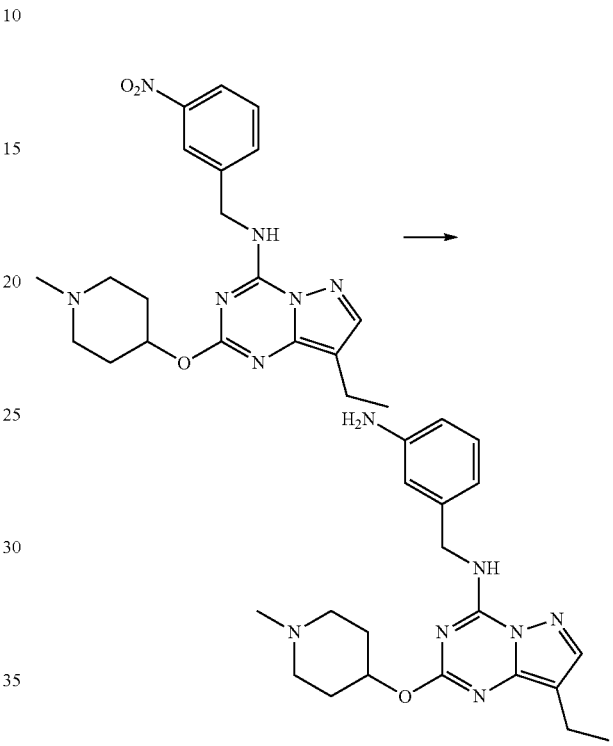

The process of this step was adopted from step-3 of intermediate-33 (0.49 g, 81.66%). LCMS: m/z=381.48 (M+H)⁺.

The below intermediates-41 to 51 were prepared according to the above protocol (intermediate-40) by using appropriate reactants, reagents at suitable conditions. The characterization data of the intermediates are summarized herein.

| Int No. | Structure | Analytical Data |
|---|---|---|
| 41 | 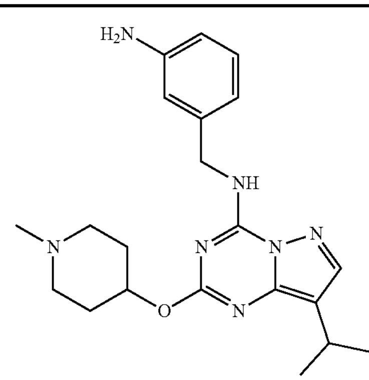 | LCMS: m/z = 396.21 (M + H)⁺. |

-continued

| Int No. | Structure | Analytical Data |
|---|---|---|
| 42 | 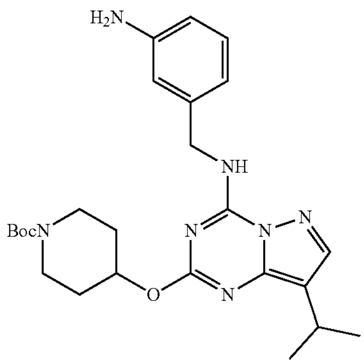 [SMILES: CC(C)c1cnn2c(NCc3cccc(N)c3)nc(OC3CCN(C(=O)OC(C)(C)C)CC3)nc12] | LCMS: m/z = 482.40 (M + H)⁺. |
| 43 | 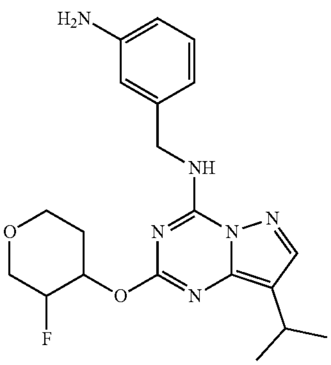 [SMILES: CC(C)c1cnn2c(NCc3cccc(N)c3)nc(OC3CCOCC3F)nc12] | LCMS: m/z = 401.8 (M + H)⁺. |
| 44 | 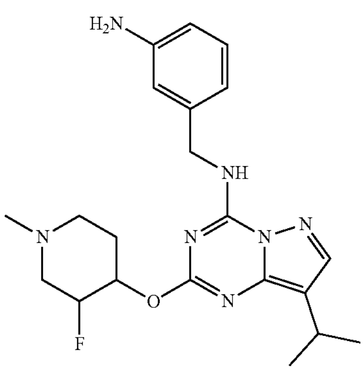 [SMILES: CC(C)c1cnn2c(NCc3cccc(N)c3)nc(OC3CCN(C)CC3F)nc12] | LCMS: m/z = 414.1 (M + H)⁺. |
| 45 | 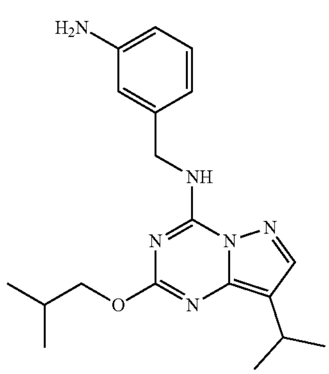 [SMILES: CC(C)COc1nc(NCc2cccc(N)c2)n2ncc(C(C)C)c2n1] | LCMS: m/z = 355.1 (M + H)⁺ |

-continued
| Int No. | Structure | Analytical Data |
|---|---|---|
| 46 | 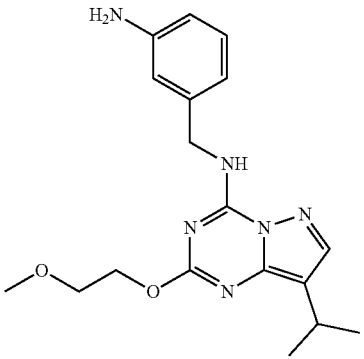 [SMILES: COCCOc1nc(NCc2cccc(N)c2)n2ncc(C(C)C)c2n1] | LCMS: m/z = 357.4 (M + H)+. |
| 47 | 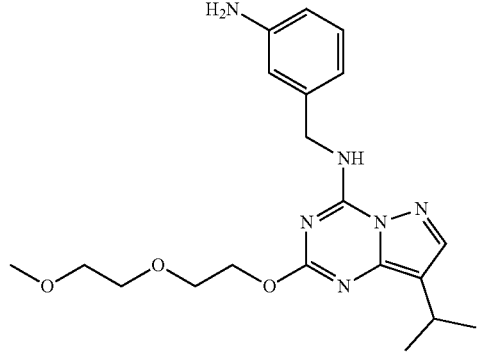 [SMILES: COCCOCCOc1nc(NCc2cccc(N)c2)n2ncc(C(C)C)c2n1] | LCMS: m/z = 399.15 (M − H)+. |
| 48 | 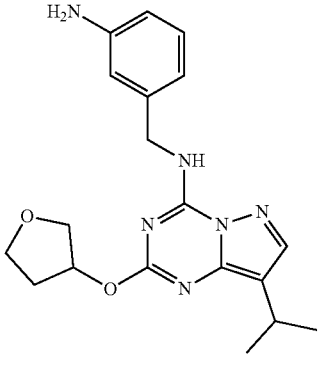 [SMILES: CC(C)c1cnn2c(NCc3cccc(N)c3)nc(OC3CCOC3)nc12] | LCMS: m/z = 369.1 (M + H)+. |
| 49 | 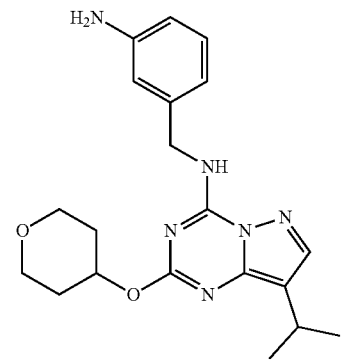 [SMILES: CC(C)c1cnn2c(NCc3cccc(N)c3)nc(OC3CCOCC3)nc12] | LCMS: m/z = 383.21 (M + H)+. |

| Int No. | Structure | Analytical Data |
|---|---|---|
| 50 | 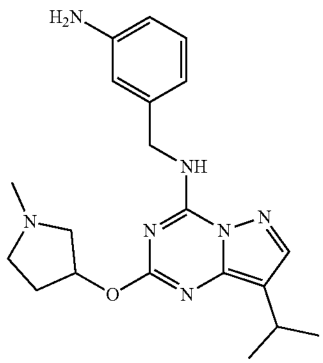 [SMILES: CC(C)c1cnn2c(NCc3cccc(N)c3)nc(OC3CCN(C)C3)nc12] | LCMS: m/z = 382.15 (M + H)+. |
| 51 | 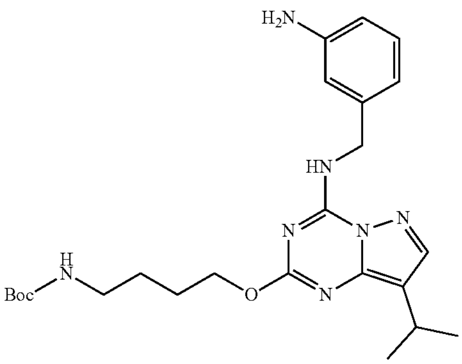 [SMILES: CC(C)c1cnn2c(NCc3cccc(N)c3)nc(OCCCCNC(=O)OC(C)(C)C)nc12] | LCMS: m/z = 470.35 (M + H)+. |

The present invention is further exemplified, but not limited, by the following examples that illustrate the preparation of compounds according to the invention Example-1: Synthesis of 1-acryloyl-N-(3-(((8-isopropyl-2-((tetrahydro-2H-pyran-4-yl)amino)pyrazolo[1,5-a][1,3,5]triazin-4-yl)amino)methyl)phenyl)piperidine-3-carboxamide (Compound-1)

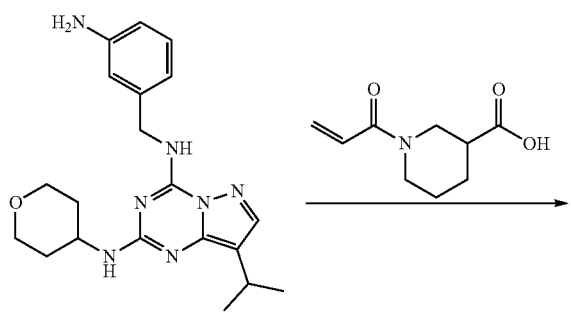

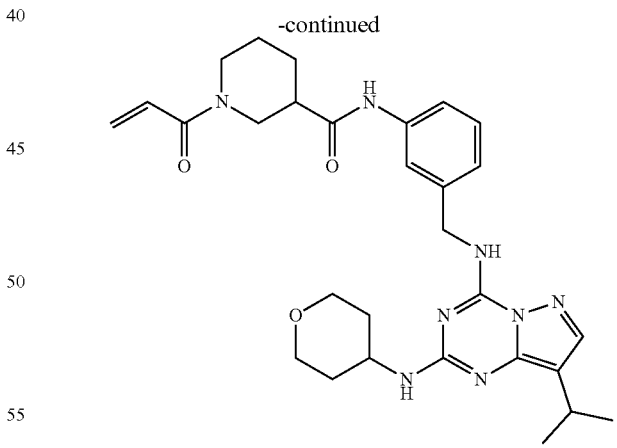

To a cooled solution of 1-acryloylpiperidine-3-carboxylic acid (0.086 g, 0.47 mmol, intermediate-12) in DMF (4 mL) at 0° C. was added HATU (0.22 g, 0.59 mmol) and DIPEA (0.2 mL, 1.18 mmol) and finally added N4-(3-aminobenzyl)-8-isopropyl-N2-(tetrahydro-2H-pyran-4-yl)pyrazolo[1,5-a][1,3,5]triazine-2,4-diamine (0.15 g, 0.39 mmol, intermediate-33). The reaction mixture was stirred for 2 h at room temperature. After completion of the reaction, the reaction mixture was quenched with ice-water and diluted with ethyl acetate. The aqueous layer was separated and extracted with ethyl acetate (2×25 mL). The combined organic phase was washed with brine, dried over Na$_2$SO$_4$, filtered and concentrated to crude residue. The residue was purified by combi-flash to afford the title compound (0.05 g, 25%). $^1$HNMR (DMSO-d$_6$, 400 MHz): δ 9.99-9.96 (d, 1H), 8.95-8.70 (m, 1H), 7.72 (s, 1H), 7.51 (s, 2H), 7.25-7.21 (t, 1H), 7.03-7.01 (d, 1H), 6.90-6.79 (m, 2H), 6.11-6.07 (d, 1H), 5.68-5.63 (t, 1H), 4.59-4.46 (m, 2H), 4.32-4.28 (d, 1H), 4.10-4.00 (m, 2H), 3.82 (s, 3H), 3.18-3.16 (d, 1H), 3.07-3.00 (t, 1H), 2.91 (s, 1H), 2.78-2.67 (m, 1H), 2.46 (m, 1H), 1.95-1.92 (m, 1H), 1.84 (s, 1H), 1.73-1.63 (m, 3H), 1.46-1.35 (m, 3H), 1.23-1.22 (d, 6H); LCMS: m/z=547.9 (M+H)$^+$.

The below compounds were prepared by procedure similar to the one described in Example-1 with appropriate variations in reactants, quantities of reagents, in presence of suitable solvents at suitable reaction conditions. The physicochemical characteristics of the compounds are summarized herein below table.

| Compd No | Compound structure | Analytical data |
|---|---|---|
| 2 | 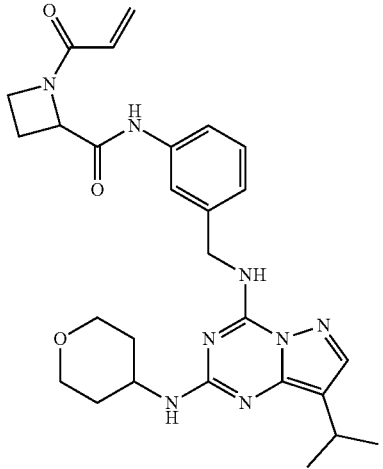 [SMILES: C=CC(=O)N1CCC1C(=O)Nc1cccc(CNc2nc(NC3CCOCC3)nc3c(C(C)C)cnn23)c1] | $^1$H NMR (DMSO-d$_6$, 400 MHz): δ 10.18-10.17 (d, 1H), 7.87-7.34 (m, 3H), 7.27-7.21 (t, 1H), 7.08-7.06 (d, 1H), 6.36-6.29 (m, 1H), 6.13-6.05 (m, 1H) 5.73-5.70 (m, 1H), 5.59-5.56 (t, 1H), 5.06-4.79 (m, 1H), 4.59 (s, 2H), 4.21-4.15 (m, 1H), 3.90-3.80 (m, 3H), 3.37-3.31 (m, 2H), 2.95-2.88 (m, 1H), 2.66-2.58 (m, 1H), 2.21-2.12 (m, 1H), 1.90-1.65 (m, 4H), 1.43 (s, 2H), 1.20 (s, 6H); LCMS: m/z = 519.30 (M + H)$^+$. |
| 3 | 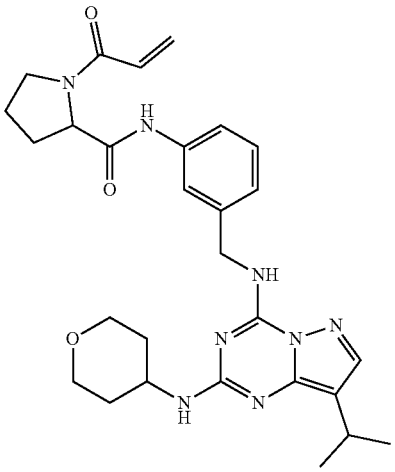 [SMILES: C=CC(=O)N1CCCC1C(=O)Nc1cccc(CNc2nc(NC3CCOCC3)nc3c(C(C)C)cnn23)c1] | $^1$H NMR (DMSO-d$_6$, 400 MHz): δ 10.14 (s, 1H), 10.02 (s, 1H), 8.92 (s, 1H), 8.65 (s, 1H), 7.70 (s, 1H), 7.67-7.48 (m, 3H), 7.24-7.20 (m, 1H), 7.05-7.02 (s, 1H), 6.81 (s, 1H), 6.66-6.54 (m, 1H), 6.14-6.08 (m, 1H), 5.70-5.67 (m, 1H), 4.62-4.58 (m, 2H), 4.47-4.46 (m, 1H), 3.82 (s, 2H), 3.71-3.56 (m, 2H), 2.90 (s, 2H), 2.15-2.08 (m, 2H), 2.02-1.84 (m, 2H), 1.59 (s, 1H), 1.44-1.37 (m, 2H), 1.30-1.23 (m, 6H); LCMS: m/z = 533.3 (M + H)$^+$. |
| 4 | 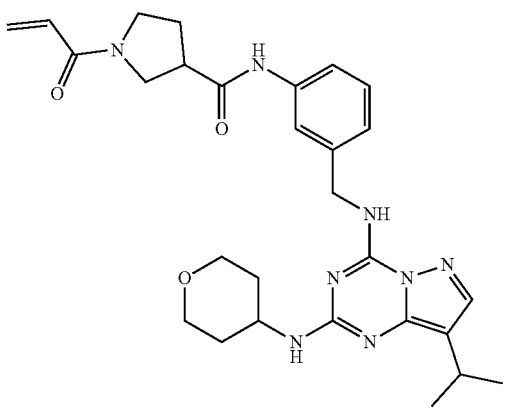 [SMILES: C=CC(=O)N1CCC(C(=O)Nc2cccc(CNc3nc(NC4CCOCC4)nc4c(C(C)C)cnn34)c2)C1] | $^1$H NMR (DMSO-d$_6$, 400 MHz): δ 10.04-10.03 (d, 1H), 8.9 (s, 1H), 7.67 (s, 1H), 7.46 (m, 3H), 7.21-7.17 (t, 1H), 6.99-6.97 (d, 1H), 6.78 (s, 2H), 6.57-6.49 (m, 1H), 6.11-6.06 (m, 1H), 6.06 (s, 1H), 5.63-5.60 (m, 1H), 4.55 (s, 1H), 3.78-3.74 (m, 3H), 3.67-3.63 (m, 2H), 3.58-3.52 (m, 2H), 3.25-3.17 (m, 1H), 3.15-3.13 (m, 1H), 2.86 (s, 2H), 2.16-2.06 (m, 3H), 1.93 (s, 1H), 1.53-1.33 (m, 3H), 1.18 (s, 6H); LCMS: m/z = 533.3 (M + H)$^+$. |

| Compd No | Compound structure | Analytical data |
|---|---|---|
| 5 | 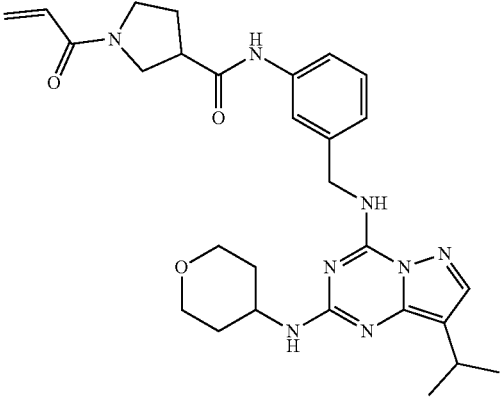 [SMILES: C=CC(=O)N1CCC(C(=O)Nc2cccc(CNc3nc(NC4CCOCC4)nc4c(C(C)C)cnn34)c2)C1] | Isomer-1: ¹H NMR (DMSO-d$_6$, 400 MHz): δ 10.07-10.06 (d, 1H), 8.90 (s, 1H), 7.71 (s, 1H), 7.51 (m, 2H), 7.23-7.21 (t, 1H), 7.03-7.01 (d, 1H), 6.89-6.80 (m, 1H), 6.61-6.53 (m, 1H), 6.15-6.11 (m, 1H), 5.67-5.63 (m, 1H), 4.59 (s, 2H), 3.82-3.62 (m, 3H), 3.58-3.50 (m, 2H), 3.39-3.37 (m, 1H), 3.23-3.06 (m, 2H), 2.89 (s, 2H), 2.19-1.83 (m, 2H), 1.59-1.38 (m, 3H), 1.27-1.23 (d, 2H), 1.11-1.02 (d, 6H); LCMS: m/z = 533.2 (M + H)⁺. |
| 6 | 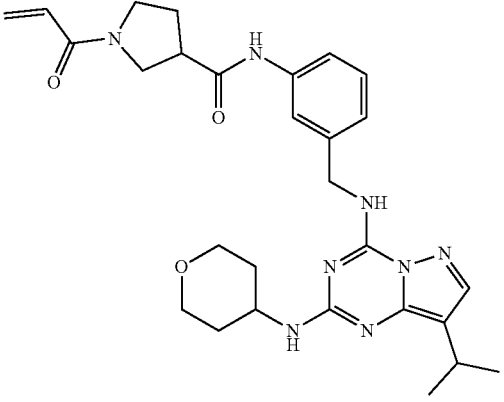 [SMILES: C=CC(=O)N1CCC(C(=O)Nc2cccc(CNc3nc(NC4CCOCC4)nc4c(C(C)C)cnn34)c2)C1] | Isomer-2: ¹H NMR (DMSO-d$_6$, 400 MHz): δ 10.08-10.06 (d, 1H), 8.90 (s, 1H), 7.71 (s, 1H), 7.50 (m, 2H), 7.25-7.21 (t, 1H), 7.03-7.01 (d, 1H), 6.89-6.80 (m, 1H), 6.61-6.53 (m, 1H), 6.15-6.11 (m, 1H), 5.67-5.63 (m, 1H), 4.58 (s, 2H), 3.82-3.62 (m, 5H), 3.58-3.50 (m, 2H), 3.39-3.37 (m, 1H), 3.23-3.07 (m, 1H), 2.89 (s, 1H), 2.19-1.99 (m, 4H), 1.59-1.38 (m, 2H), 1.27-1.23 (d, 2H), 1.23 (s, 6H); LCMS: m/z = 533.25 (M + H)⁺. |
| 7 | 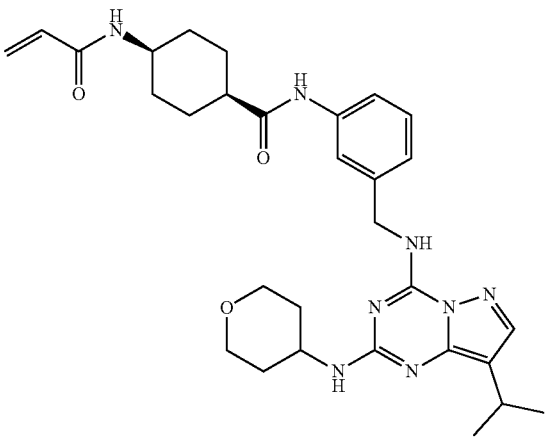 [SMILES: C=CC(=O)N[C@H]1CC[C@@H](C(=O)Nc2cccc(CNc3nc(NC4CCOCC4)nc4c(C(C)C)cnn34)c2)CC1] | ¹H NMR (DMSO-d$_6$, 400 MHz): δ 9.80 (s, 1H), 8.90 (s, 1H), 8.65 (s, 1H), 8.02-8.00 (d, 1H), 7.71 (s, 1H), 7.50 (s, 2H), 7.23-7.19 (t, 1H), 6.99-6.97 (d, 1H), 6.82 (s, 1H), 6.39-6.32 (m, 1H), 6.08-6.03 (d, 1H), 5.56-5.52 (m, 1H), 4.59 (s, 2H), 4.05-4.00 (m, 1H), 3.87-3.83 (m, 4H), 2.90 (s, 1H), 2.38-2.36 (m, 1H), 1.82-1.69 (m, 6H), 1.59-1.53 (m, 6H), 1.19 (s, 6H); LCMS: m/z = 561.4 (M + H)⁺. |

| Compd No | Compound structure | Analytical data |
|---|---|---|
| 8 | 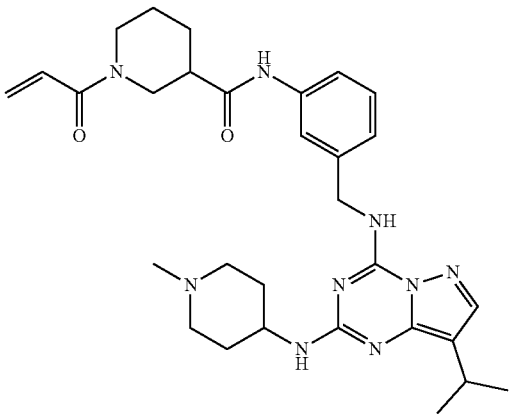 [SMILES: C=CC(=O)N1CCCC(C(=O)Nc2cccc(CNc3nc(NC4CCN(C)CC4)nc4c(C(C)C)cnn34)c2)C1] | $^1$H NMR (DMSO-d$_6$, 400 MHz): δ 10.00-9.97 (d, 1H), 8.91-8.64 (m, 1H), 7.71 (s, 1H), 7.51 (s, 2H), 7.25-7.23 (t, 1H), 7.02 (s, 1H), 6.90-6.75 (m, 2H), 6.11-6.07 (d, 1H), 5.69-5.63 (t, 1H), 4.60 (s, 2H), 4.49-4.28 (m, 1H), 4.13-4.00 (m, 2H), 3.65 (s, 3H), 3.23-3.16 (m, 2H), 3.07-3.01 (t, 1H), 2.90 (s, 1H), 2.78-2.67 (m, 3H), 2.42 (s, 1H), 2.20 (s, 3H), 2.04-1.85 (m, 4H), 1.73-1.67 (m, 3H), 1.49-1.34 (m, 4H), 1.23 (s, 6H); LCMS: m/z = 560.5 (M + H)$^+$. |
| 9 | 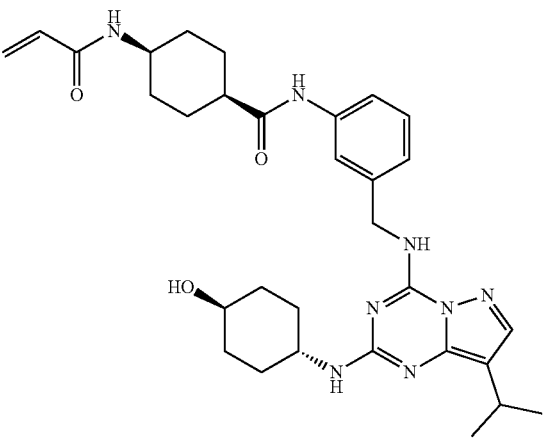 [SMILES: C=CC(=O)N[C@H]1CC[C@@H](C(=O)Nc2cccc(CNc3nc(N[C@H]4CC[C@H](O)CC4)nc4c(C(C)C)cnn34)c2)CC1] | $^1$H NMR (DMSO-d$_6$, 400 MHz): δ 9.80 (s, 1H), 8.02-8.00 (d, 1H), 7.87 (s, 1H), 7.72 (s, 1H), 7.61 (t, 1H), 7.50 (s, 2H), 7.23-7.19 (t, 2H), 7.08 (s, 1H), 6.96 (s, 2H), 6.38-6.31 (m, 1H), 6.08-6.03 (m, 1H), 5.55-5.52 (m, 1H), 4.59-4.57 (m, 2H), 3.87 (s, 1H), 3.38 (s, 2H), 2.91 (s, 2H), 2.67 (s, 2H), 2.32 (s, 2H), 1.90-1.68 (m, 6H), 1.53-1.40 (m, 3H), 1.22-1.20 (d, 7H); LCMS: m/z = 575.0 (M + H)$^+$. |
| 10 & 11 | 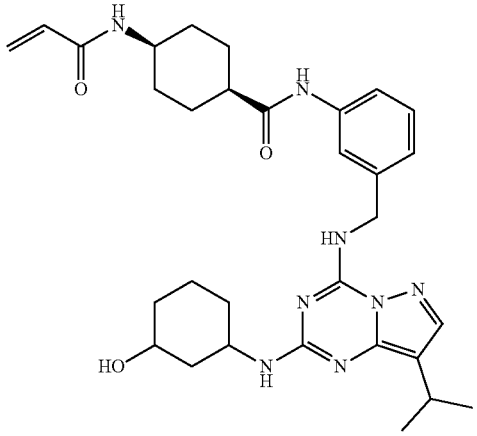 [SMILES: C=CC(=O)N[C@H]1CC[C@@H](C(=O)Nc2cccc(CNc3nc(NC4CCCC(O)C4)nc4c(C(C)C)cnn34)c2)CC1] | Isomer-1: $^1$H NMR (DMSO-d$_6$, 400 MHz): δ 9.80 (s, 1H), 8.60 (s, 1H), 8.02-8.00 (d, 1H), 7.70 (s, 1H), 7.50 (m, 2H), 7.23-7.19 (t, 1H), 6.98 (s, 1H), 6.55 (m, 1H), 6.39-6.32 (m, 1H), 6.08-6.03 (m, 1H), 5.56-5.53 (d, 1H), 4.60 (s, 4H), 4.11-4.09 (m, 1H), 3.89 (s, 1H), 3.69 (s, 1H), 3.43-3.42 (m, 1H), 3.17-3.16 (d, 2H), 2.91 (s, 2H), 2.67 (s, 2H), 2.38-2.37 (m, 1H), 1.83-1.69 (m, 5H), 1.60-1.50 (m, 4H), 1.23 (s, 6H); LCMS: m/z = 575.40 (M + H)$^+$.<br>Isomer-2: $^1$H NMR (DMSO-d$_6$, 400 MHz): δ 9.79 (s, 1H), 8.60 (s, 1H), 8.02-8.01 (d, 1H), 7.69 (s, 1H), 7.55-7.53 (m, 2H), 7.23-7.19 (t, 1H), 6.98 (s, 1H), 6.55 (m, 1H), 6.39-6.32 (m, 1H), 6.08-6.04 (m, 1H), 5.56-5.53 (d, 1H), 4.60 (s, 2H), 4.38 (s, 1H), 4.13-4.09 (m, 2H), 3.90 (m, 2H), 3.17-3.16 (d, 2H), 2.91 (s, 1H), 2.67 (s, 2h), 2.38 (s, 1H), 1.80-1.68 (m, 4H), 1.60-1.36 (m, 7H), 1.23 (s, 6H); LCMS: m/z = 575.30 (M + H)$^+$. |

| Compd No | Compound structure | Analytical data |
|---|---|---|
| 12 & 13 | 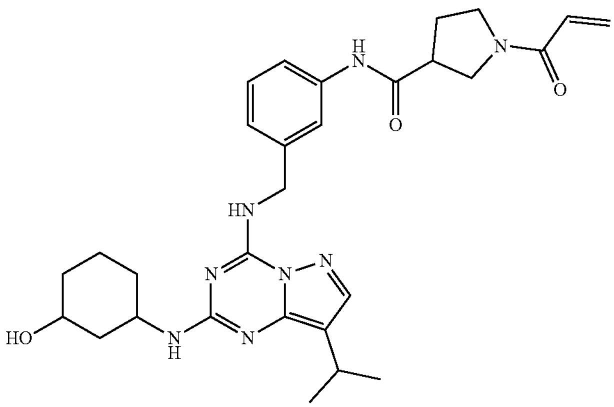 [SMILES: C=CC(=O)N1CCC(C(=O)Nc2cccc(CNc3nc(NC4CCCC(O)C4)nc4c(C(C)C)cnn34)c2)C1] | Isomer-1: $^1$H NMR (DMSO-d$_6$, 400 MHz): δ 10.03 (s, 1H), 8.57 (s, 1H), 7.66 (s, 1H), 7.53-7.40 (m, 2H), 7.21-7.18 (t, 1H), 6.99 (s, 1H), 6.69 (s, 1H), 6.58-6.50 (m, 1H), 6.11-6.07 (m, 1H), 5.64-5.60 (m, 1H), 4.56 (s, 2H), 3.79-3.59 (m, 3H), 3.55-3.39 (m, 2H), 3.20-3.04 (m, 3H), 2.85 (s, 2H), 2.17-1.91 (m, 4H), 1.73-1.61 (m, 5H), 1.18 (s, 6H); LCMS: m/z = 546.90 (M + H)$^+$. Isomer-2: $^1$H NMR (DMSO-d$_6$, 400 MHz): δ 10.04-10.02 (d, 1H), 8.54 (s, 1H), 7.65 (s, 1H), 7.50-7.48 (m, 2H), 7.21-7.18 (t, 1H), 6.98 (s, 1H), 6.57-6.51 (m, 2H), 6.11-6.06 (m, 1H), 5.64-5.60 (m, 1H), 4.56-4.35 (m, 3H), 4.09-4.05 (m, 1H), 3.89 (s, 1H), 3.79-3.59 (m, 2H), 3.55-3.42 (m, 2H), 3.18-3.04 (m, 2H), 2.16-1.91 (m, 3H), 1.77-1.53 (m, 4H), 1.41-1.32 (m, 3H), 1.19 (s, 6H); LCMS: m/z = 547.20 (M + H)$^+$. |

Example-2: Synthesis of 1-acryloyl-N-(3-(((2-(((3R,4R)-3-fluoropiperidin-4-yl)amino)-8-isopropylpyrazolo[1,5-a][1,3,5]triazin-4-yl)amino)methyl)phenyl)pyrrolidine-3-carboxamide (Compound-14)

Step-1: Synthesis of tert-butyl (3R,4R)-4-((4-((3-(1-acryloylpyrrolidine-3-carboxamido) benzyl)amino)-8-isopropylpyrazolo[1,5-a][1,3,5]triazin-2-yl)amino)-3-fluoropiperidine-1-carboxylate

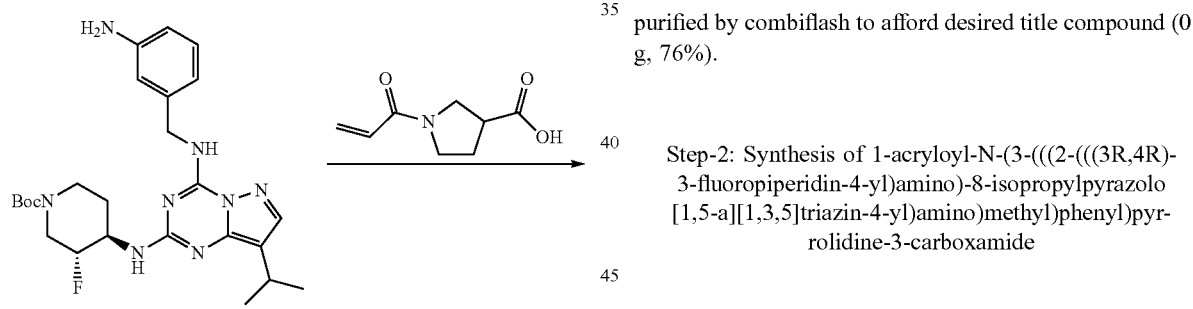

To a cooled solution of 1-acryloylpyrrolidine-3-carboxylic acid (0.05 g, 0.30 mmol, intermediate-10) in DMF (2 mL) at 0° C. was added HATU (0.11 g, 0.30 mmol) and DIPEA (0.07 mL, 0.40 mmol) and finally added tert-butyl (3R,4R)-4-((4-((3-aminobenzyl)amino)-8-isopropylpyrazolo[1,5-a][1,3,5]triazin-2-yl)amino)-3-fluoropiperidine-1-carboxylate (0.1 g, 0.20 mmol, intermediate-38). The reaction mixture was stirred for 2 h at room temperature. The reaction mixture was quenched with ice-water and diluted with ethyl acetate. The aqueous layer was separated and extracted with ethyl acetate (2×20 mL). The combined organic phase was washed with brine, dried over Na$_2$SO$_4$, filtered and concentrated to crude residue. The residue was purified by combiflash to afford desired title compound (0.1 g, 76%).

Step-2: Synthesis of 1-acryloyl-N-(3-(((2-(((3R,4R)-3-fluoropiperidin-4-yl)amino)-8-isopropylpyrazolo[1,5-a][1,3,5]triazin-4-yl)amino)methyl)phenyl)pyrrolidine-3-carboxamide

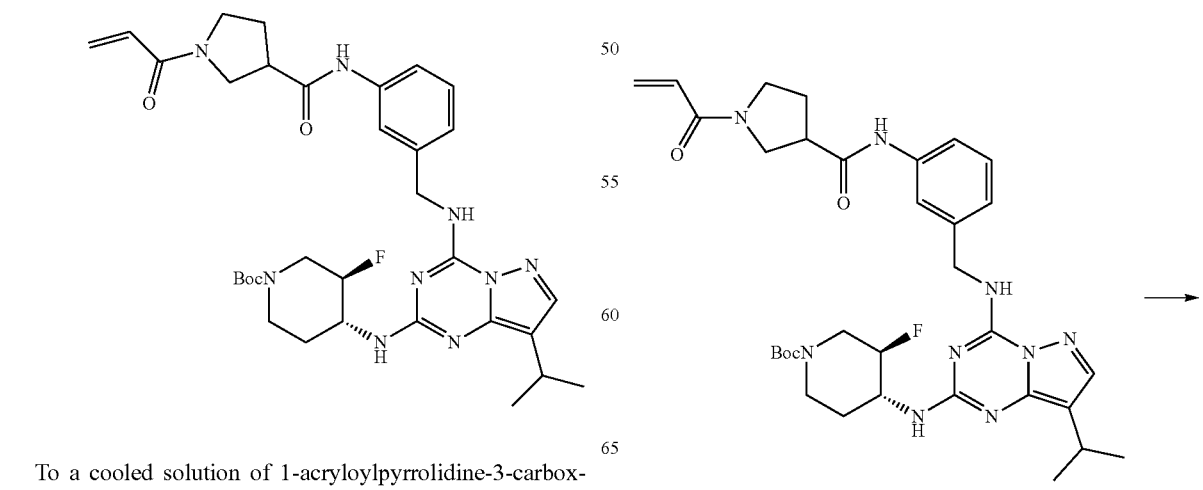

-continued

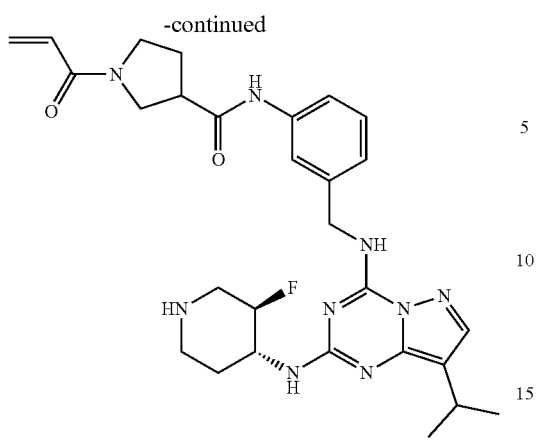

TFA (1 mL) was added to a solution of tert-butyl (3R,4R)-4-((4-(((3-(1-acryloylpyrrolidine-3-carboxamido)benzyl)amino)-8-isopropylpyrazolo[1,5-a][1,3,5]triazin-2-yl)amino)-3-fluoropiperidine-1-carboxylate (0.1 g, 0.15 mmol) in DCM (5 mL) at 0° C. Then the reaction mixture allowed stirring at room temperature for 12 h. After completion of the reaction, the reaction mixture was evaporated to afford amine. The residue was purified by prep. HPLC (Method: A: 0.1% TFA, B: Acetonitrile:MeOH, Column: XBRIDGE C-18 (19 mm*150 mm, 5 μm)) to afford desired title compound (0.04 g, 50%). ¹HNMR (DMSO-$d_6$, 400 MHz): δ 10.09-10.07 (d, 1H), 8.80 (s, 3H), 7.79 (s, 1H), 7.62-7.51 (m, 2H), 7.26-7.22 (t, 1H), 7.09-6.96 (m, 1H), 6.61-6.54 (m, 1H), 6.15-6.10 (m, 1H), 5.75-5.65 (m, 2H), 4.63 (s, 2H), 4.25 (m, 2H), 3.82-3.63 (m, 3H), 3.66-3.45 (m, 2H), 3.37-3.10 (m, 4H), 2.93-2.90 (t, 2H), 2.22-1.92 (m, 2H), 1.71 (s, 2H), 1.39 (s, 6H); LCMS: m/z=550.65 (M+H)⁺.

The below compounds were prepared by procedure similar to the one described in Example-2 with appropriate variations in reactants, quantities of reagents, in presence of suitable solvents at suitable reaction conditions. The physicochemical characteristics of the compounds are summarized herein below table.

Example-3: Synthesis of 1-acryloyl-N-(3-(((8-isopropyl-2-(((S)-tetrahydro-2H-pyran-3-yl)amino)pyrazolo[1,5-a][1,3,5]triazin-4-yl)amino)methyl)phenyl)piperidine-2-carboxamide (Compound-16)

Step-1: Synthesis of tert-butyl 2-((3-(((8-isopropyl-2-(((S)-tetrahydro-2H-pyran-3-yl)amino)pyrazolo[1,5-a][1,3,5]triazin-4-yl)amino)methyl)phenyl)carbamoyl)piperidine-1-carboxylate

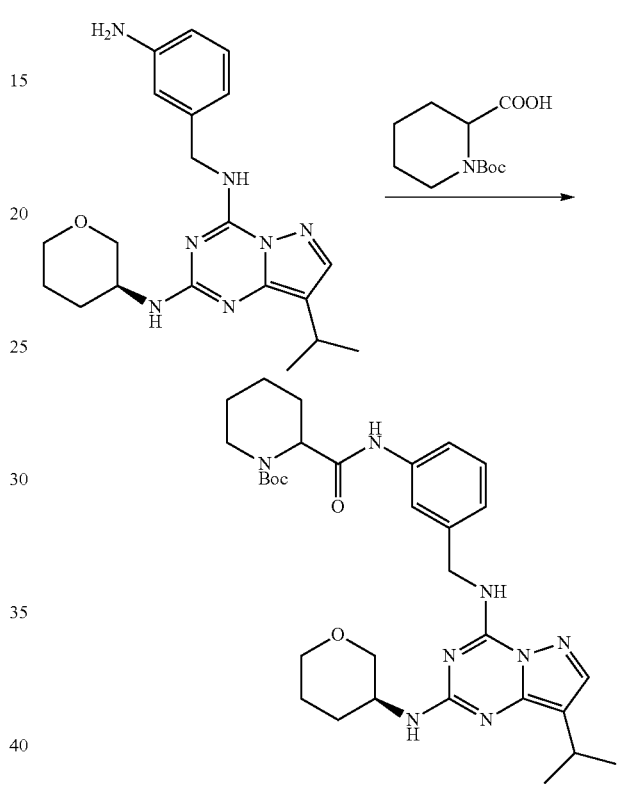

| Compd No | Compound structure | Analytical data |
|---|---|---|
| 15 | ![structure] | ¹H NMR (DMSO-$d_6$, 400 MHz): δ 10.07-10.05 (d, 1H), 8.54 (s, 1H), 7.78-7.70 (m, 4H), 7.48 (m, 2H), 7.23-7.19 (m, 1H), 7.07 (s, 1H), 6.99 (s, 1H), 6.57-6.51 (m, 1H), 6.12-6.07 (d, 1H), 5.65-5.62 (m, 1H), 4.57 (s, 3H), 3.36-3.33 (m, 3H), 3.19-3.05 (m, 3H), 2.92-2.87 (m, 2H), 2.14-2.04 (m, 2H), 1.96-1.28 (m, 4H), 1.19 (s, 8H); LCMS: m/z = 546.25 (M + H)⁺. |

To a cooled solution of 1-(tert-butoxycarbonyl)piperidine-2-carboxylic acid (0.13 g, 0.577 mmol) in DMF (10 mL) at 0° C. was added HATU (0.26 g, 0.68 mmol) followed by DIPEA (0.2 mL, 1.04 mmol) and finally added (S)—N4-(3-aminobenzyl)-8-isopropyl-N2-(tetrahydro-2H-pyran-3-yl)pyrazolo[1,5-a][1,3,5]triazine-2,4-diamine (0.2 g, 0.524 mmol, intermediate-34). The reaction mixture was stirred for 1 h at room temperature. The reaction mixture was quenched with ice-water and diluted with ethyl acetate. The aqueous layer was separated and extracted with ethyl acetate (2×25 mL). The combined organic phase was washed with brine, dried over Na$_2$SO$_4$, filtered and concentrated the crude residue was purified by 100-200 silica gel column chromatography to afford desired title compound (0.14 g, 42%). LCMS: m/z=593 (M+H)$^+$.

Step-2: Synthesis of N-(3-(((8-isopropyl-2-(((S)-tetrahydro-2H-pyran-3-yl)amino)pyrazolo[1,5-a][1,3,5]triazin-4-yl)amino)methyl)phenyl)piperidine-2-carboxamide

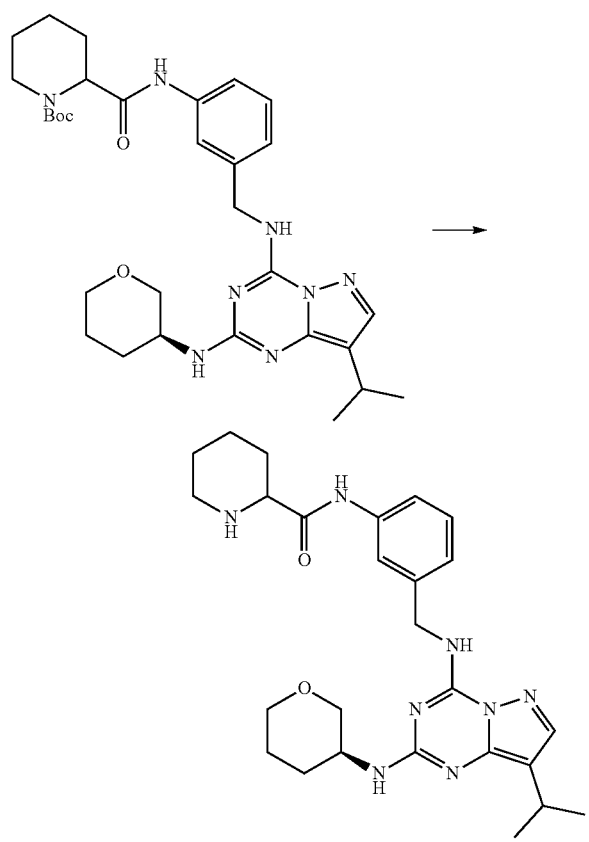

TFA (0.5 mL) was added to a solution of tert-butyl 2-((3-(((8-isopropyl-2-(((S)-tetrahydro-2H-pyran-3-yl)amino)pyrazolo[1,5-a][1,3,5]triazin-4-yl)amino)methyl)phenyl) carbamoyl)piperidine-1-carboxylate (0.14 g, 0.23 mmol) in DCM (5 mL) at 0° C. Then the reaction mixture allowed to stir at room temperature for 2 h. After completion of the reaction, the reaction mixture was concentrated under vacuum, to afford desired title compound (0.12 g, crude). LCMS: m/z=493 (M+H)$^+$.

Step-3: Synthesis of 1-acryloyl-N-(3-(((8-isopropyl-2-(((S)-tetrahydro-2H-pyran-3-yl)amino)pyrazolo[1,5-a][1,3,5]triazin-4-yl)amino)methyl)phenyl)piperidine-2-carboxamide

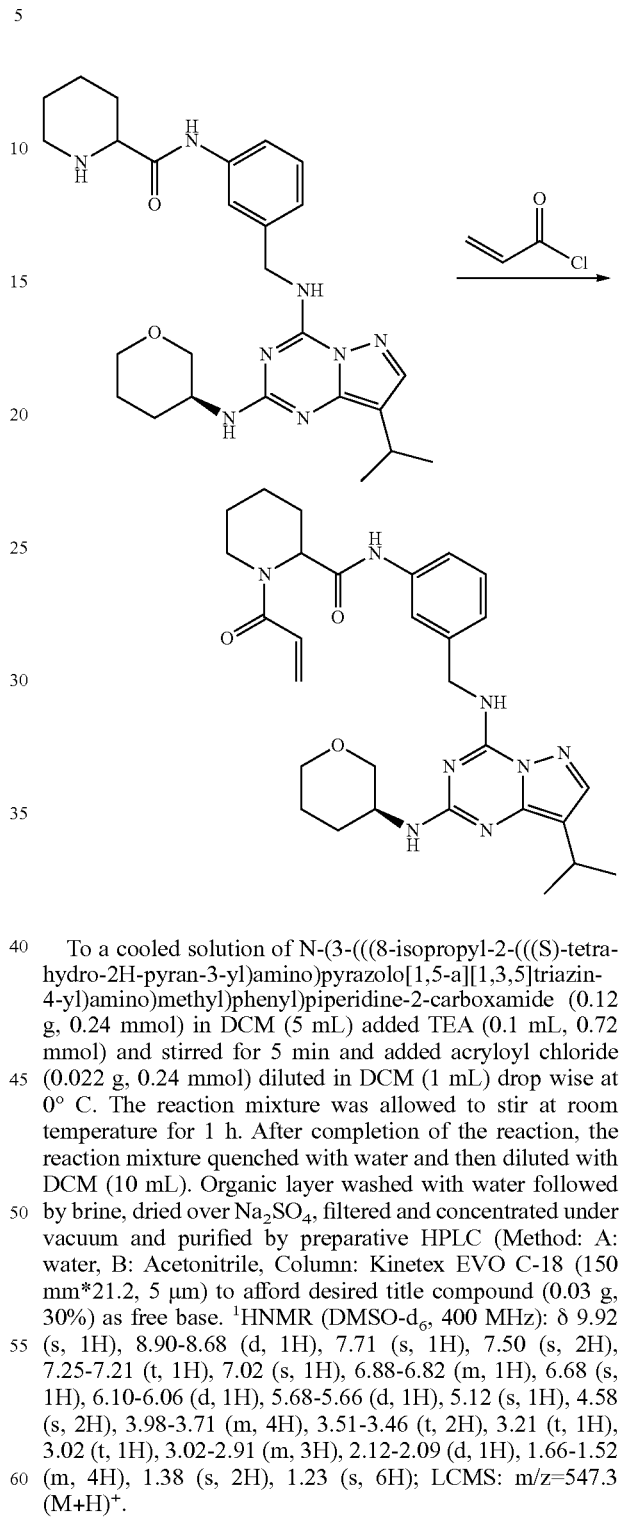

To a cooled solution of N-(3-(((8-isopropyl-2-(((S)-tetrahydro-2H-pyran-3-yl)amino)pyrazolo[1,5-a][1,3,5]triazin-4-yl)amino)methyl)phenyl)piperidine-2-carboxamide (0.12 g, 0.24 mmol) in DCM (5 mL) added TEA (0.1 mL, 0.72 mmol) and stirred for 5 min and added acryloyl chloride (0.022 g, 0.24 mmol) diluted in DCM (1 mL) drop wise at 0° C. The reaction mixture was allowed to stir at room temperature for 1 h. After completion of the reaction, the reaction mixture quenched with water and then diluted with DCM (10 mL). Organic layer washed with water followed by brine, dried over Na$_2$SO$_4$, filtered and concentrated under vacuum and purified by preparative HPLC (Method: A: water, B: Acetonitrile, Column: Kinetex EVO C-18 (150 mm*21.2, 5 µm) to afford desired title compound (0.03 g, 30%) as free base. $^1$HNMR (DMSO-d$_6$, 400 MHz): δ 9.92 (s, 1H), 8.90-8.68 (d, 1H), 7.71 (s, 1H), 7.50 (s, 2H), 7.25-7.21 (t, 1H), 7.02 (s, 1H), 6.88-6.82 (m, 1H), 6.68 (s, 1H), 6.10-6.06 (d, 1H), 5.68-5.66 (d, 1H), 5.12 (s, 1H), 4.58 (s, 2H), 3.98-3.71 (m, 4H), 3.51-3.46 (t, 2H), 3.21 (t, 1H), 3.02 (t, 1H), 3.02-2.91 (m, 3H), 2.12-2.09 (d, 1H), 1.66-1.52 (m, 4H), 1.38 (s, 2H), 1.23 (s, 6H); LCMS: m/z=547.3 (M+H)$^+$.

The below compounds were prepared by procedure similar to the one described in Example-3 with appropriate variations in reactants, quantities of reagents, in presence of suitable solvents at suitable reaction conditions. The physicochemical characteristics of the compounds are summarized herein below table.

| Compd. No. | Compound structure | Analytical data |
|---|---|---|
| 17 | 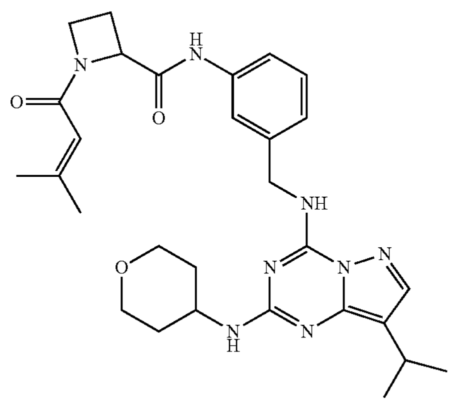 [SMILES: CC(C)=CC(=O)N1CCC1C(=O)Nc1cccc(CNc2nc(NC3CCOCC3)nc3c(C(C)C)cnn23)c1] | ¹H NMR (DMSO-d₆, 400 MHz): δ 7.69 (s, 1H), 7.57 (m, 1H), 7.44 (m, 1H), 7.24 (m, 1H), 7.04 (m, 1H), 5.65 (s, 1H), 5.41 (s, 1H), 4.88 (m, 1H), 4.56 (m, 2H), 4.08 (m, 1H), 3.78 (m, 3H), 3.42 (m, 3H), 2.88 (m, 2H), 2.13 (m, 1H), 2.09 (m, 3H), 1.96 (m, 3H), 1.63 (m, 2H), 1.42 (m, 2H), 1.20 (d, 6H), 1.08 (m, 2H); LCMS: m/z = 547.7 (M + H)⁺. |
| 18 | 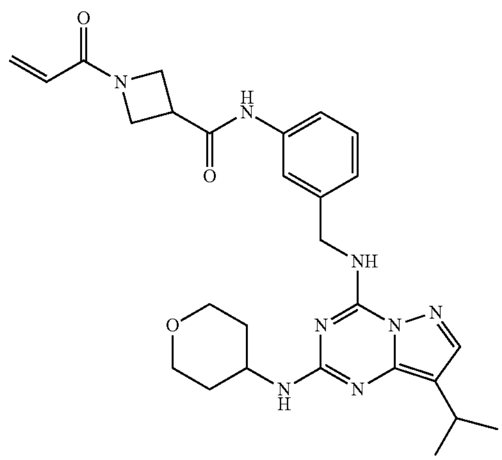 [SMILES: C=CC(=O)N1CC(C(=O)Nc2cccc(CNc3nc(NC4CCOCC4)nc4c(C(C)C)cnn34)c2)C1] | ¹H NMR (DMSO-d₆, 400 MHz): δ 10.08 (s, 1H), 8.70 (s, 1H), 7.71 (s, 1H), 7.5-7.48 (m, 2H), 7.26 (t, 1H), 7.04 (d, 1H), 6.90 (m, 1H), 6.34 (m, 1H), 6.12 (d, 1H), 5.68 (d, 1H), 4.59-4.40 (m, 2H), 4.37 (t, 1H), 4.35 (t, 1H), 4.08 (m, 1H), 4.03 (m, 1H), 3.94 (m, 3H), 3.52 (m, 2H), 2.90 (m, 2H), 1.98-1.92 (m, 2H), 1.6-1.4 (m, 2H), 1.23-1.07 (d, 6H); LCMS: m/z = 518.7(M + H)⁺. |
| 19 | 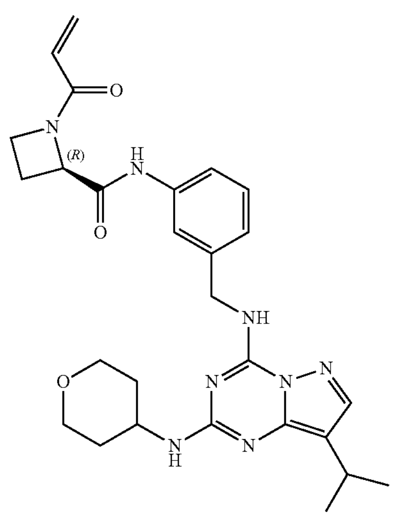 | ¹H NMR (DMSO-d₆, 400 MHz): δ 10.15 (s, 1H), 8.70 (s, 1H), 7.70 (s, 1H), 7.54 (s, 2H), 7.26-7.22 (t, 1H), 7.05-7.03 (d, 1H), 6.81 (s, 1H), 6.36-6.29 (m, 1H), 6.13-6.05 (m, 1H), 5.72-5.55 (m, 1H), 5.05-4.78 (m, 1H), 4.58 (s, 2H), 4.20-4.15 (m, 1H), 3.90-3.81 (m, 4H), 2.49-2.44 (m, 2H), 2.21-2.07 (m, 1H), 1.81-1.72 (m, 2H), 1.44-1.37 (m, 4H), 1.21 (s, 6H); LCMS: m/z = 519.20 (M + H)⁺. |

| Compd. No. | Compound structure | Analytical data |
|---|---|---|
| 20 | 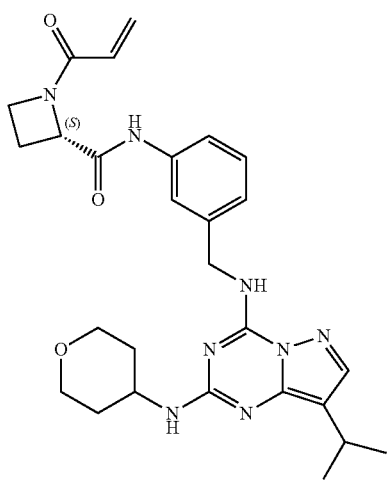 | $^1$H NMR (DMSO-d$_6$, 400 MHz): δ 10.15 (s, 1H), 8.70 (d, 1H), 7.70 (s, 1H), 7.52-7.48 (s, 2H), 7.23 (t, 1H), 7.05 (d, 1H), 6.90-6.75 (m, 1H), 6.36-6.30 (m, 1H), 6.13-6.05 (m, 1H) 5.72-5.55 (m, 1H), 5.05-4.78 (m, 1H), 4.58 (brs, 2H), 4.20-4.15 (m, 1H), 3.90-3.81 (m, 3H), 2.89 (brs, 1H), 2.49-2.44 (m, 2H), 2.21-2.12 (m, 1H), 1.81-1.74 (m, 2H), 1.65-1.30 (m, 4H), 1.22 (s, 6H); LCMS: m/z = 519.15 (M + H)$^+$. |
| 21 | 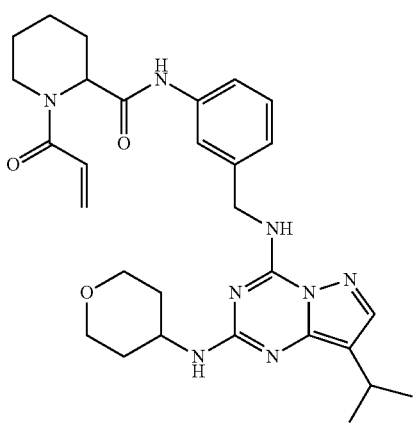 [SMILES: C=CC(=O)N1CCCCC1C(=O)Nc1cccc(CNc2nc(NC3CCOCC3)nc3c(C(C)C)cnn23)c1] | $^1$H NMR (DMSO-d$_6$, 400 MHz): δ 8.66-8.62 (m, 2H), 7.71 (s, 1H), 7.64-7.53 (m, 2H), 7.25-7.21 (t, 1H), 7.03 (m, 1H), 6.89-6.82 (m, 2H), 6.10 (d, 1H), 5.69-5.66 (d, 1H), 5.12-5.11 (d, 2H), 4.58 (m, 2H), 3.98-3.95 (d, 1H), 3.82 (m, 3H), 3.51-3.46 (m, 1H), 2.99-2.90 (m, 2H), 2.12-2.09 (d, 1H), 1.82 (m, 1H), 1.66-1.62 (m, 4H), 1.38 (m, 4H), 1.23 (d, 6H); LCMS: m/z = 547.0 (M + H)$^+$. |
| 22 | 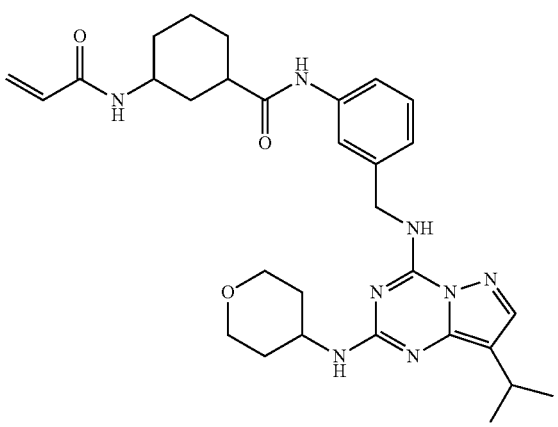 [SMILES: C=CC(=O)NC1CCCC(C(=O)Nc2cccc(CNc3nc(NC4CCOCC4)nc4c(C(C)C)cnn34)c2)C1] | $^1$H NMR (DMSO-d$_6$, 400 MHz): δ 9.87 (s, 1H), 8.9-8.98 (m, 2H), 7.71 (s, 1H), 7.50 (m, 2H), 7.22 (t, 1H), 7.0 (d, 1H), 6.90 (m, 1H), 6.81 (m, 1H), 6.21 (m, 1H), 6.08 (d, 1H), 5.57 (d, 1H), 4.57 (m, 2H), 3.82-3.65 (m, 5H), 2.9 (m, 1H), 1.90-1.87 (m, 6H), 1.62-1.45 (m, 2H), 1.36-1.29 (m, 3H), 1.27-1.23 (d, 6H), 1.1-1.08 (m, 2H); LCMS: m/z = 561.7 (M + H)$^+$. |

| Compd. No. | Compound structure | Analytical data |
|---|---|---|
| 23 | 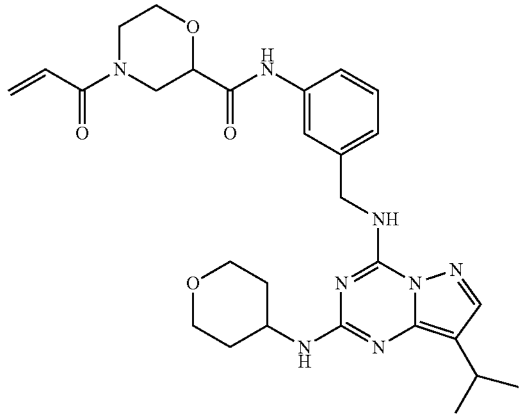 [SMILES: C=CC(=O)N1CCOC(C(=O)Nc2cccc(CNc3nc(NC4CCOCC4)nc4c(C(C)C)cnn34)c2)C1] | $^1$H NMR (DMSO-d$_6$, 400 MHz): δ 9.85 (d, 1H), 8.80 (d, 1H), 7.72 (s, 1H), 7.62-7.57 (m, 2H), 7.25 (t, 1H), 7.07 (d, 1H), 6.85-6.79 (m, 2H), 6.19-6.11 (m, 1H), 5.74-5.72 (d, 1H), 4.60-4.51 (m, 3H), 4.12-3.83 (m, 4H), 3.90-3.70 (m, 3H), 3.55 (t, 1H), 3.10-2.80 (m, 3H), 1.82 (brs, 1H), 1.65-1.35 (m, 4H), 1.24 (s, 6H); LCMS: m/z = 549.70 (M + H)$^+$. |
| 24 | 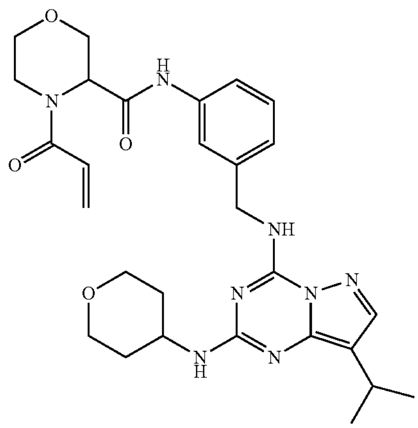 [SMILES: C=CC(=O)N1CCOCC1C(=O)Nc1cccc(CNc2nc(NC3CCOCC3)nc3c(C(C)C)cnn23)c1] | $^1$H NMR (DMSO-d$_6$, 400 MHz): δ 9.96 (s, 1H), 8.70 (d, 1H), 7.71 (s, 1H), 7.65-7.45 (m, 2H), 7.24 (t, 1H), 7.04 (brs, 1H), 6.89-6.82 (m, 2H) 6.17-6.13 (m, 1H), 5.75-5.66 (m, 1H), 4.87-4.85 (m, 1H), 4.59 (brs, 2H), 4.29-4.26 (d, 1H), 3.89-3.65 (m, 6H), 3.60-3.45 (m, 1H), 2.90 (brs, 1H), 2.45-2.55 (m, 2H), 1.82 (brs, 1H), 1.70-1.30 (m, 4H), 1.22 (d, 6H); LCMS: m/z = 549.40 (M + H)$^+$. |
| 25 | 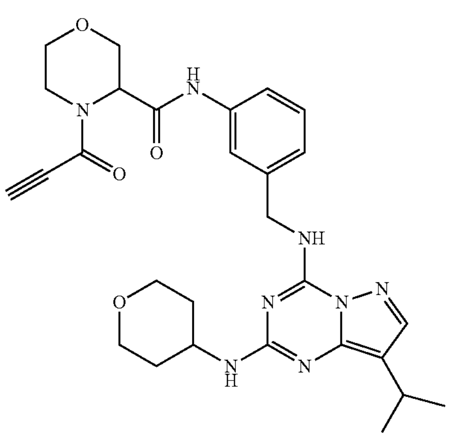 [SMILES: C#CC(=O)N1CCOCC1C(=O)Nc1cccc(CNc2nc(NC3CCOCC3)nc3c(C(C)C)cnn23)c1] | $^1$H NMR (DMSO-d$_6$, 400 MHz): δ 10.14-10.09 (d, 1H), 8.95 (s, 1H), 8.70 (s, 1H), 7.71 (s, 1H), 7.49 (m, 2H), 7.27-7.23 (t, 1H), 7.06 (s, 1H), 6.81 (s, 1H), 4.80-4.79 (d, 1H), 4.70 (s, 1H), 4.60 (s, 2H), 4.35-4.26 (m, 1H), 4.03-3.99 (t, 1H), 3.90-3.73 (m, 4H), 3.69-3.45 (m, 1H), 3.49-3.43 (m, 1H), 2.67 (s, 1H), 1.82 (s, 2H), 1.63 (s, 1H), 1.45 (m, 3H), 1.22 (s, 6H); LCMS: m/z = 547.70 (M + H)$^+$. |

| Compd. No. | Compound structure | Analytical data |
|---|---|---|
| 26 | 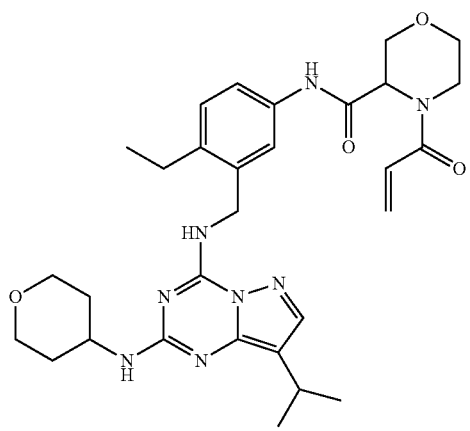 [SMILES: C=CC(=O)N1CCOCC1C(=O)Nc1ccc(CC)c(CNc2nc(NC3CCOCC3)nc3c(C(C)C)cnn23)c1] | $^1$H NMR (DMSO-d$_6$, 400 MHz): δ 9.63 (s, 1H), 8.13 (s, 1H), 7.67 (s, 1H), 7.53-7.51 (m, 1H), 7.42-7.41 (d, 1H), 7.15-7.12 (d, 1H), 6.41-6.39 (m, 1H), 6.12-6.07 (m, 1H), 5.69-5.66 (d, 1H), 4.80 (s, 1H), 4.68-4.66 (d, 2H), 4.31-4.28 (m, 2H), 3.86-3.64 (m, 6H), 3.68-3.64 (m, 1H), 3.46-3.31 (m, 3H), 3.0-2.95 (m, 2H), 2.75-2.67 (m, 2H), 1.93-1.81 (m, 2H), 1.55-1.46 (m, 2H), 1.18 (s, 6H), 1.18-1.16 (m, 3H); LCMS: m/z = 577.5 (M + H)$^+$. |
| 27 | 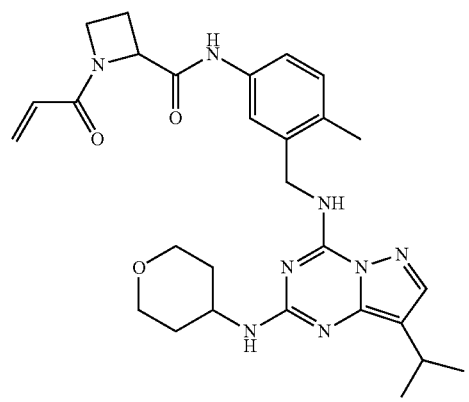 | $^1$HNMR (DMSO-d$_6$, 400 MHz): δ 10.06 (s, 1H), 8.60 (s, 1H), 7.73-7.72 (m, 1H), 7.58 (s, 1H), 7.33 (s, 1H), 7.11-7.09 (d, 1H), 6.79 (s, 1H), 6.55 (s, 1H), 6.34-6.27 (m, 1H), 6.11-6.04 (m, 1H), 5.71-5.68 (m, 1H), 5.56-5.53 (t, 1H), 5.01-4.97(m, 1H), 4.78-4.75 (m, 1H), 4.56-4.54 (d, 2H), 4.19-4.10 (m, 1H), 3.89-3.81 (m, 2H), 3.17-3.15 (d, 1H), 2.91 (s, 2H), 2.59-2.41 (m, 2H), 2.38 (s, 3H), 2.05-2.17 (m, 1H), 2.08 (m, 1H), 1.81 (s, 1H), 1.44 (s, 2H),.1.24 (s, 6H); LCMS: m/z = 532.9 (M + H)$^+$. |
| 28 | 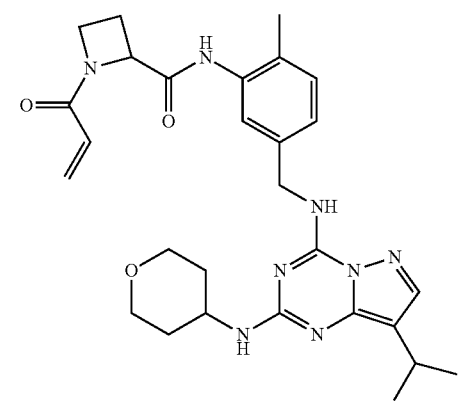 [SMILES: C=CC(=O)N1CCC1C(=O)Nc1cc(CNc2nc(NC3CCOCC3)nc3c(C(C)C)cnn23)ccc1C] | $^1$H NMR (DMSO-d$_6$, 400 MHz): δ 9.64 (s, 1H), 8.90-8.64 (m, 1H), 7.69 (s, 1H), 7.57 (m, 1H), 7.33 (m, 1H), 7.14-7.13 (m, 2H), 6.83 (m, 1H), 6.37 (m, 1H), 6.18-6.04 (m, 1H), 5.75 (d, 1H), 5.61 (d, 1H), 5.10 (m, 1H), 4.95 (t, 1H), 4.53 (m, 2H), 4.21-4.17 (t, 2H), 3.93-3.85 (m, 4H), 2.89 (m, 1H), 2.14 (s, 3H), 1.81-1.67 (m, 2H), 1.44 (m, 2H), 1.21 (d, 6H); LCMS: m/z = 533.2(M + H)$^+$. |

| Compd. No. | Compound structure | Analytical data |
|---|---|---|
| 29 | 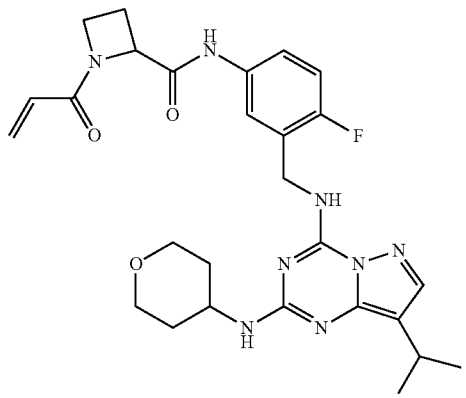 [SMILES: C=CC(=O)N1CCC1C(=O)Nc1ccc(F)c(CNc2nc(NC3CCOCC3)nc3c(C(C)C)cnn23)c1] | $^1$H NMR (DMSO-$d_6$, 400 MHz): δ 10.19 (s, 1H), 8.66 (d, 1H), 7.74 (s, 1H), 7.58 (m, 2H), 7.18-7.13 (t, 1H), 6.83 (m, 1H), 6.54 (s, 1H), 6.35-6.29 (m, 1H), 6.13-6.05 (m, 1H), 5.72-5.69 (m, 1H), 5.58-5.56 (m, 1H), 5.02-4.98 (m, 1H), 4.77-4.74 (m, 1H), 4.65 (s, 2H), 4.21-4.14 (m, 1H), 3.89-3.83 (m, 3H), 2.41 (m, 1H), 2.20-2.18 (m, 1H), 1.83 (m, 2H), 1.59-1.479 (m, 3H), 1.24 (s, 6H); LCMS: m/z = 537 (M + H)$^+$. |
| 30 | 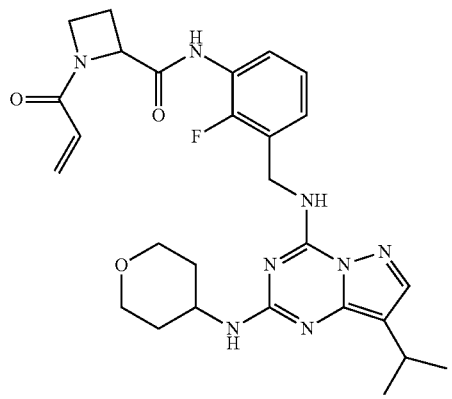 [SMILES: C=CC(=O)N1CCC1C(=O)Nc1cccc(CNc2nc(NC3CCOCC3)nc3c(C(C)C)cnn23)c1F] | $^1$H NMR (DMSO-$d_6$, 400 MHz): δ 10.05 (d, 1H), 9.00-8.52 (m, 1H), 7.9 (m, 1H), 7.72 (s, 1H), 7.10 (m, 2H), 6.89 (m, 1H), 6.39 (m, 1H), 6.21 (d, 1H), 6.10 (d, 1H), 5.78 (d, 1H), 5.06 (m, 1H), 4.67 (m, 2H), 4.22 (t, 2H), 3.91-3.81 (m, 4H), 2.9 (m, 2H), 2.33 (m, 1H), 1.81 (m, 1H), 1.44 (m, 3H), 1.22 (d, 6H); LCMS: m/z = 537.65 (M + H)$^+$. |
| 31 | 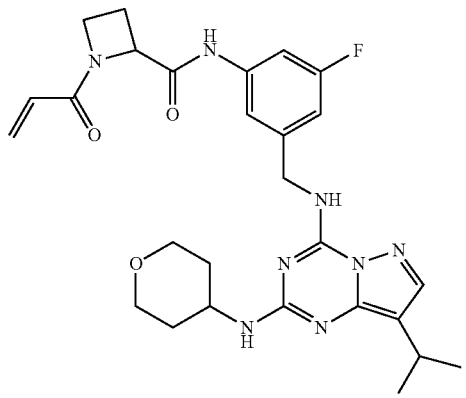 [SMILES: C=CC(=O)N1CCC1C(=O)Nc1cc(F)cc(CNc2nc(NC3CCOCC3)nc3c(C(C)C)cnn23)c1] | $^1$H NMR (DMSO-$d_6$, 400 MHz): δ 10.36 (s, 1H), 8.81 (d, 1H), 7.72 (s, 1H), 7.58-7.20 (m, 2H), 6.91-6.80 (m, 2H), 6.36-6.29 (m, 1H), 6.13-6.06 (m, 1H), 5.73-5.56 (m, 1H), 5.05-4.759 (m, 1H), 4.58 (brs, 2H), 4.21-4.10 (m, 1H), 3.90-3.83 (m, 3H), 3.17-3.15 (m, 2H), 2.90 (brs, 1H), 2.32-2.08 (m, 3H), 1.92-1.82 (m, 1H), 1.56-1.37 (m, 3H), 1.22 (s, 6H); LCMS: m/z = 537.3 (M + H)$^+$. |

| Compd. No. | Compound structure | Analytical data |
|---|---|---|
| 32 | 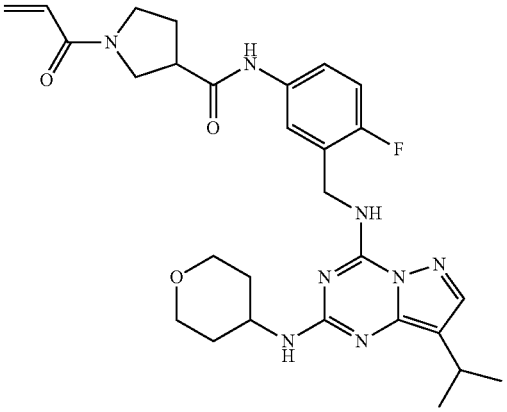 [SMILES: C=CC(=O)N1CCC(C(=O)Nc2ccc(F)c(CNc3nc(NC4CCOCC4)nc4c(C(C)C)cnn34)c2)C1] | ¹H NMR (DMSO-d₆, 400 MHz): δ 10.13 (s, 1H), 8.7 (d, 1H), 7.70-7.40 (m, 3H), 7.12 (t, 1H), 6.83 (m, 1H), 6.59-6.52 (m, 1H), 6.13-6.09 (m, 1H), 5.63-5.62 (m, 1H), 4.64 (s, 2H), 3.79-3.59 (m, 5H), 3.49-3.43 (m, 2H), 3.33-3.04(m, 2H), 3.04(s, 2H) 2.16-1.80 (m, 4H), 1.55-1.34 (m, 3H), 1.23 (s, 6H); LCMS: m/z = 551.45(M + H)⁺. |
| 33 | 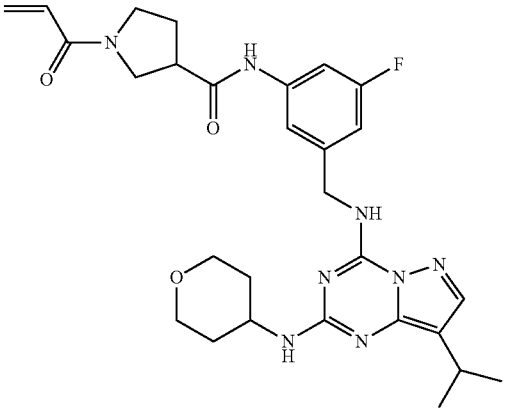 [SMILES: C=CC(=O)N1CCC(C(=O)Nc2cc(F)cc(CNc3nc(NC4CCOCC4)nc4c(C(C)C)cnn34)c2)C1] | ¹H NMR (DMSO-d₆, 400 MHz): δ 10.25 (d, 1H), 8.8 (d, 1H), 7.69 (s, 1H), 7.49-7.16 (m, 2H), 7.00-6.70 (m, 2H), 6.56-6.49 (m, 1H), 6.11-6.06 (m, 1H), 5.64-5.60 (m, 1H), 4.54 (s, 2H), 3.77-3.73 (m, 3H), 3.67-3.43(m, 4H), 3.30-3.12(m, 2H), 3.05(s, 1H) 2.15-1.90 (m, 4H), 1.52-1.33 (m, 3H), 1.19 (s, 6H); LCMS: m/z = 551.3(M + H)⁺. |
| 34 | 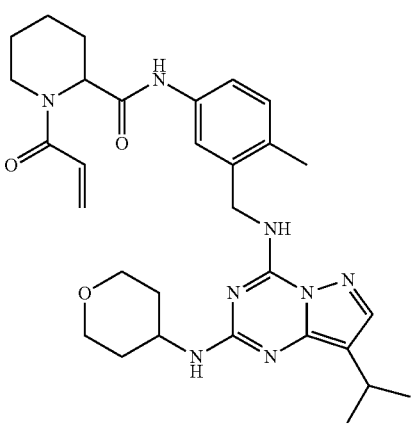 [SMILES: C=CC(=O)N1CCCCC1C(=O)Nc1ccc(C)c(CNc2nc(NC3CCOCC3)nc3c(C(C)C)cnn23)c1] | ¹HNMR (DMSO-d₆, 400 MHz): δ 9.82 (s, 1H), 8.56 (d, 1H), 7.72 (s, 1H), 7.56 (m, 2H), 7.27 (m, 2H), 7.08-7.06 (d, 2H), 6.85-6.79 (m, 3H), 6.00 (d, 1H), 5.66-5.63 (d, 1H), 5.07 (s, 1H), 4.55-4.53 (d, 3H), 4.30-(m, 1H), 3.94-3.91 (d, 1H), 3.82 (m, 4H), 3.46 (m, 1H), 3.16-2.91 (m, 2H), 2.31-2.25 (m, 3H), 2.13-1.97 (m, 2H), 1.82 (s, 2H), 1.63-1.54 (m, 2H), 1.23-1.22 (d, 6H); LCMS: m/z = 561.1 (M + H)⁺. |

| Compd. No. | Compound structure | Analytical data |
|---|---|---|
| 35 | 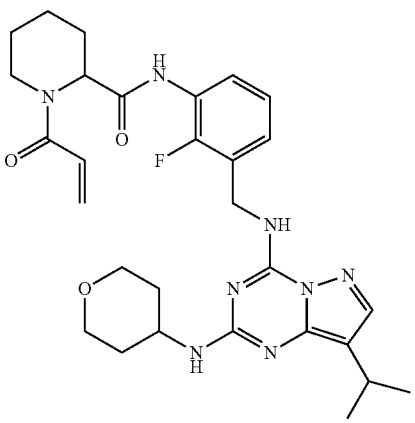 [SMILES: C=CC(=O)N1CCCCC1C(=O)Nc1cccc(CNc2nc(NC3CCOCC3)nc3c(C(C)C)cnn23)c1F] | $^1$H NMR (DMSO-$d_6$, 400 MHz): δ 9.70 (d, 1H), 8.60-8.90 (d, 1H), 7.70 (s, 1H), 7.50 (s, 1H), 7.06 (m, 2H), 6.85 (m, 2H), 6.09-6.05 (d, 1H), 5.67-5.64 (d, 1H), 5.24 (s, 1H), 4.63 (s, 2H), 3.90 (d, 1H), 3.78 (m, 4H), 2.90 (m, 1H), 2.29-2.28 (d, 2H), 1.8 (m, 1H), 1.62 (m, 4H), 1.37 (m, 4H), 1.19 (s, 6H); LCMS: m/z = 565.45 (M + H)$^+$. |
| 36 | 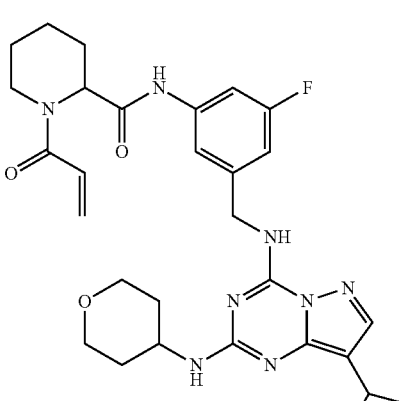 | $^1$H NMR (DMSO-$d_6$, 400 MHz): δ 10.14 (s, 1H), 8.70 (s, 1H), 7.71 (s, 1H), 7.50-7.28 (m, 2H), 6.87-6.80 (m, 3H), 6.53 (s, 2H), 6.09-6.05 (d, 1H) 5.68-5.65 (m, 1H), 5.08-5.07 (d, 1H), 4.56 (s, 2H), 3.97-3.81 (m, 4H), 3.45 (m, 1H), 3.32 (s, 1H), 2.89 (s, 2H), 2.09-2.06 (d, 1H), 1.81 (s, 1H), 1.65-1.58 (m, 3H), 1.37-1.35 (d, 3H), 1.22 (s, 6H); LCMS: m/z = 565.75 (M + H)$^+$. |
| 37 | 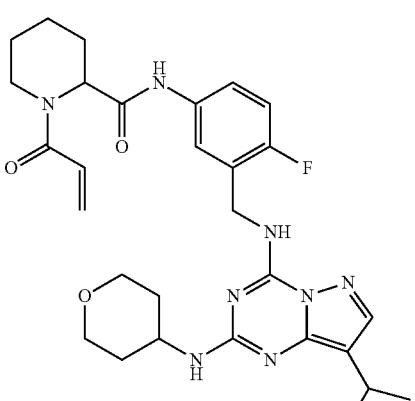 | $^1$H NMR (DMSO-$d_6$, 400 MHz): δ 9.97 (s, 1H), 8.96-8.65 (d, 1H), 7.75-7.43 (m, 3H), 7.16-7.12 (t, 1H), 6.94-6.82 (m, 2H), 6.10-6.03 (m, 1H), 5.69-5.67 (d, 1H), 5.09 (s, 1H), 4.80-4.68 (m, 2H), 3.98-3.83 (m, 4H), 2.93 (m, 2H), 2.19-1.99 (m, 2H), 1.84 (s, 1H), 1.66-1.62 (m, 3H), 1.38-1.25 (m, 8H); LCMS: m/z = 565.2 (M + H)$^+$. |

| Compd. No. | Compound structure | Analytical data |
|---|---|---|
| 38 | 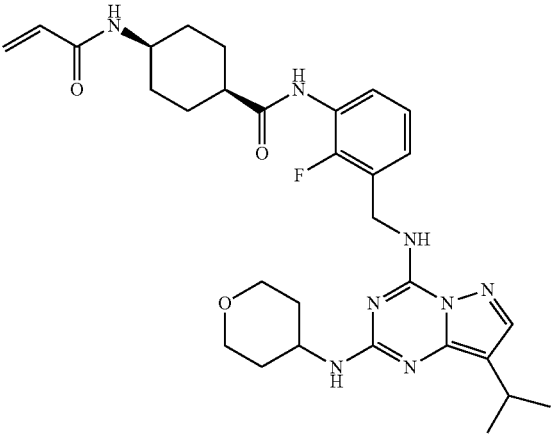 [SMILES: C=CC(=O)N[C@H]1CC[C@@H](C(=O)Nc2cccc(CNc3nc(NC4CCOCC4)nc4c(C(C)C)cnn34)c2F)CC1] | ¹H NMR (DMSO-d$_6$, 400 MHz): δ 9.55 (s, 1H), 9.00-8.52 (m, 1H), 8.01-7.99 (d, 1H), 7.68 (s, 1H), 7.60 (m, 1H), 7.02 (m, 2H), 6.90 (m, 1H), 6.35-6.28 (m, 1H), 6.05-6.00 (dd, 1H), 5.52-5.49 (dd, 1H), 4.63 (s, 2H), 3.84-3.77 (m, 3H), 3.36-3.33 (m, 2H), 3.25 (m, 1H), 2.80 (m, 1H), 2.51-2.48 (m, 1H), 1.79-1.74 (m, 3H), 1.67-1.65 (m, 2H), 1.60-1.49 (m, 3H), 1.40 (m, 2H), 1.18 (d, 6H), 1.05-1.03 (t, 2H); LCMS: m/z = 579.3 (M + H)⁺. |
| 39 | 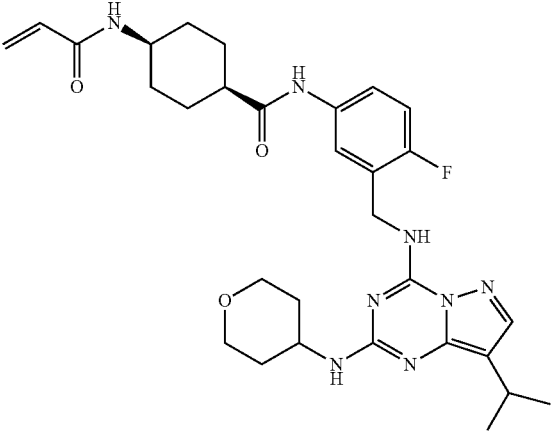 [SMILES: C=CC(=O)N[C@H]1CC[C@@H](C(=O)Nc2ccc(F)c(CNc3nc(NC4CCOCC4)nc4c(C(C)C)cnn34)c2)CC1] | ¹H NMR (DMSO-d$_6$, 400 MHz): δ 9.84 (s, 1H), 8.7 (d, 1H), 8.00 (d, 1H), 7.74 (s, 1H), 7.07-7.04 (m, 2H), 7.10 (t, 1H), 6.90 (m, 1H), 6.37-6.31 (m, 1H), 6.07-6.02 (m, 1H), 5.55-5.52 (m, 1H), 4.63 (s, 2H), 3.86-3.60 (m, 4H), 3.20 (s, 1H), 2.90 (s, 2H), 2.67-2.52 (s, 3H), 1.90-1.60 (m, 5H), 1.59-1.40 (m, 5H), 1.23 (s, 6H); LCMS: m/z = 579.35 (M + H)⁺. |
| 40 | 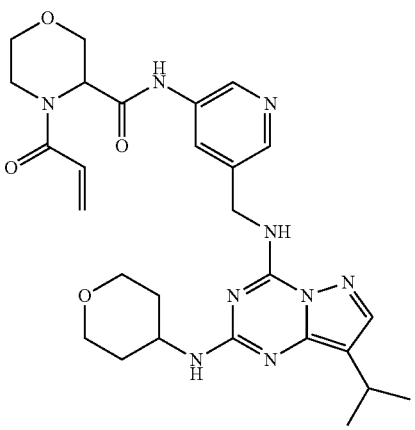 [SMILES: C=CC(=O)N1CCOCC1C(=O)Nc1cncc(CNc2nc(NC3CCOCC3)nc3c(C(C)C)cnn23)c1] | ¹H NMR (DMSO-d$_6$, 400 MHz): δ 10.06 (s, 1H), 8.76 (s, 1H), 8.61 (s, 1H), 8.47 (s, 1H), 8.18 (s, 1H), 7.80 (s, 1H), 6.9-0-6.80 (m, 1H), 6.60-6.58 (d, 1H), 6.27-6.23 (d, 1H), 5.85-5.82 (d, 1H), 5.00 (d, 1H), 4.79-4.77 (d, 2H), 4.51-4.47 (d, 1H), 4.04-3.97 (m, 5H), 3.86-3.82 (m, 1H), 3.62-3.48 (m, 3H), 3.14-3.06 (m, 2H), 1.97-1.94 (d, 2H), 1.68-1.63 (m, 2H), 1.40-1.38 (d, 6H); LCMS: m/z = 550.3 (M + H)⁺. |

-continued

| Compd. No. | Compound structure | Analytical data |
|---|---|---|
| 40A | 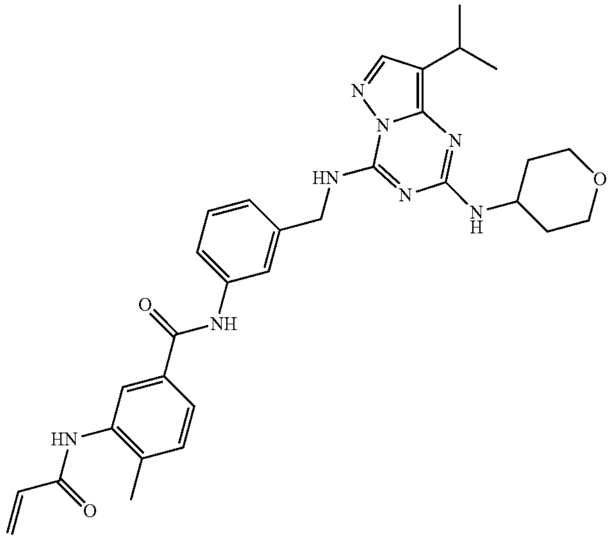 [SMILES: C=CC(=O)Nc1cc(C(=O)Nc2cccc(CNc3nc(NC4CCOCC4)nc4c(C(C)C)cnn34)c2)ccc1C] | LCMS: m/z = 569.5 (M + H)+. |
| 40B | 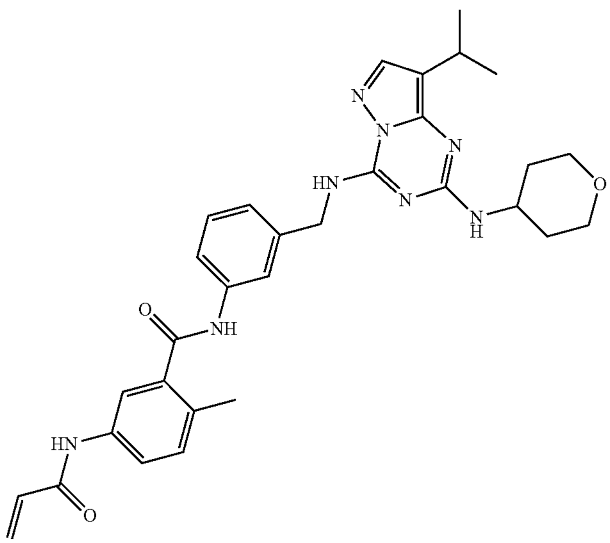 [SMILES: C=CC(=O)Nc1ccc(C)c(C(=O)Nc2cccc(CNc3nc(NC4CCOCC4)nc4c(C(C)C)cnn34)c2)c1] | LCMS: m/z = 569.5 (M + H)+. |
| 40C | 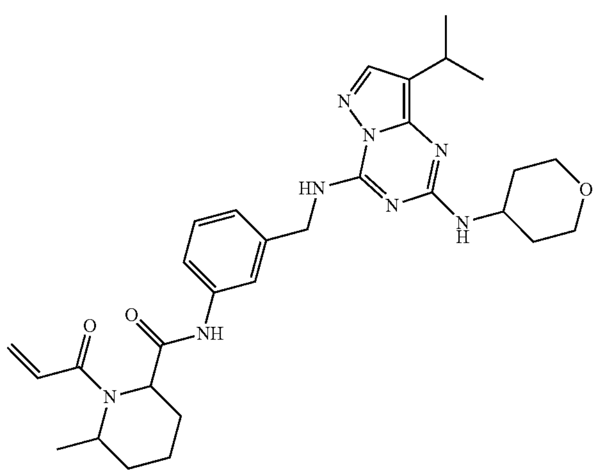 [SMILES: C=CC(=O)N1C(C)CCCC1C(=O)Nc1cccc(CNc2nc(NC3CCOCC3)nc3c(C(C)C)cnn23)c1] | LCMS: m/z = 561.25 (M + H)+. |

| Compd. No. | Compound structure | Analytical data |
|---|---|---|
| 40D | 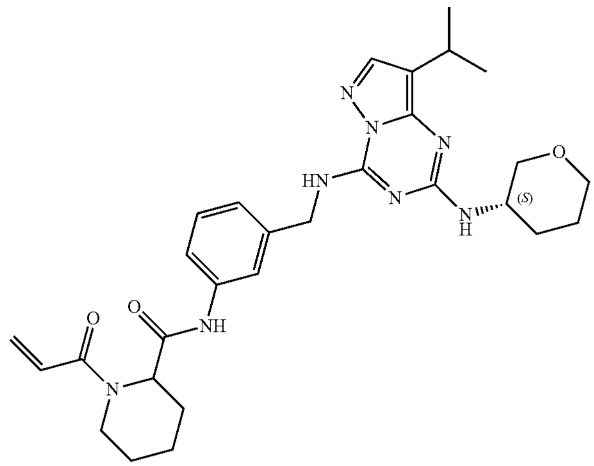 | LCMS: m/z = 547.30 (M + H)⁺. |
| 40E | 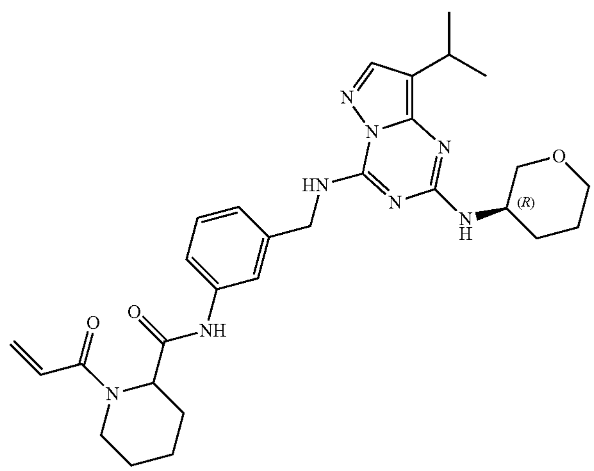 | LCMS: m/z = 547.70 (M + H)⁺. |

Example-4: Synthesis of (S)—N-(1-acryloylpiperidin-3-yl)-3-(((8-isopropyl-2-((tetrahydro-2H-pyran-4-yl)amino)pyrazolo[1,5-a][1,3,5]triazin-4-yl)amino)methyl)benzamide (Compound-41)

Step-1: Synthesis of tert-butyl (S)-3-(3-(((8-isopropyl-2-(methylthio)pyrazolo[1,5-a][1,3,5]triazin-4-yl)amino)methyl)benzamido)piperidine-1-carboxylate

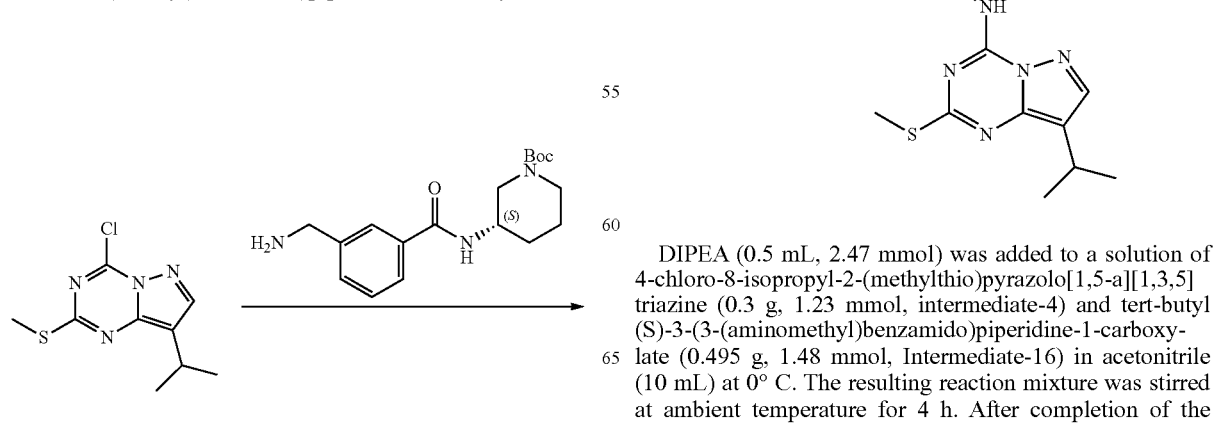

DIPEA (0.5 mL, 2.47 mmol) was added to a solution of 4-chloro-8-isopropyl-2-(methylthio)pyrazolo[1,5-a][1,3,5]triazine (0.3 g, 1.23 mmol, intermediate-4) and tert-butyl (S)-3-(3-(aminomethyl)benzamido)piperidine-1-carboxylate (0.495 g, 1.48 mmol, Intermediate-16) in acetonitrile (10 mL) at 0° C. The resulting reaction mixture was stirred at ambient temperature for 4 h. After completion of the reaction, the reaction mixture was concentrated under vacuum and purified by column chromatography using 100-200 silica gel to afford the title compound (0.4 g, 66%). LCMS: m/z=540 (M+H)$^+$.

Step-2: Synthesis of tert-butyl (S)-3-(3-(((8-isopropyl-2-(methylsulfonyl)pyrazolo[1,5-a][1,3,5]triazin-4-yl)amino)methyl)benzamido)piperidine-1-carboxylate

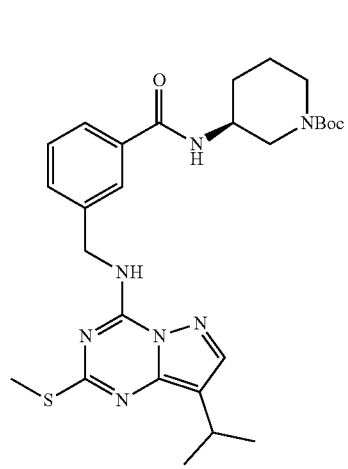

Step-3: Synthesis of tert-butyl (S)-3-(3-(((8-isopropyl-2-((tetrahydro-2H-pyran-4-yl)amino)pyrazolo[1,5-a][1,3,5]triazin-4-yl)amino)methyl)benzamido)piperidine-1-carboxylate

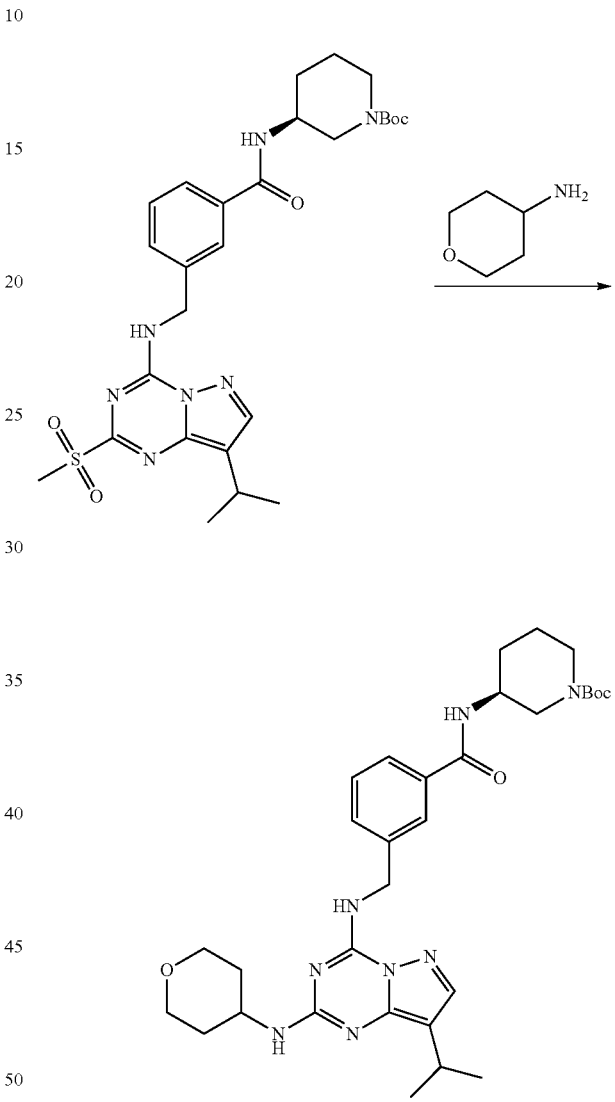

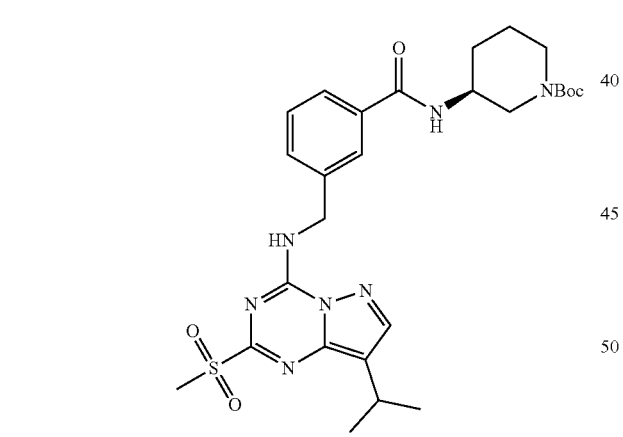

mCPBA (1.53 g, 5.79 mmol) was added portion wise to a solution of tert-butyl (S)-3-(3-(((8-isopropyl-2-(methylthio)pyrazolo[1,5-a][1,3,5]triazin-4-yl)amino)methyl)benzamido) piperidine-1-carboxylate (0.8 g, 1.44 mmol) in DCM (10 mL) and stirred for overnight at RT. After completion of the reaction, the reaction mixture was extracted with 2M aq. NaOH and DCM (10 mL). The organic phase was washed with brine, dried over Na$_2$SO$_4$, filtered and concentrated to afford the title compound (0.7 g, crude). LCMS: m/z=572 (M+H)$^+$.

A mixture of 4-aminotetrahydropyran (0.25 g, 2.45 mmol) and tert-butyl (S)-3-(3-(((8-isopropyl-2-(methylsulfonyl)pyrazolo[1,5-a][1,3,5]triazin-4-yl)amino)methyl)benzamido) piperidine-1-carboxylate (0.35 g, 0.614 mmol) were allowed to heat at 100° C. for 2 h. After completion of the reaction, the reaction mixture was cooled to room temperature and quenched with ice-water and diluted with ethyl acetate. The aqueous layer was separated and extracted with ethyl acetate (2×25 mL). The combined organic phase was washed with brine, dried over Na$_2$SO$_4$, filtered and concentrated. The residue was purified by 100-200 silica gel column chromatography to afford desired title compound (0.16 g, 44%). LCMS: m/z=592.9 (M+H)$^+$.

103

Step-4: Synthesis of (S)-3-(((8-isopropyl-2-((tetra-hydro-2H-pyran-4-yl)amino)pyrazolo[1,5-a][1,3,5]triazin-4-yl)amino)methyl)-N-(piperidin-3-yl)benzamide

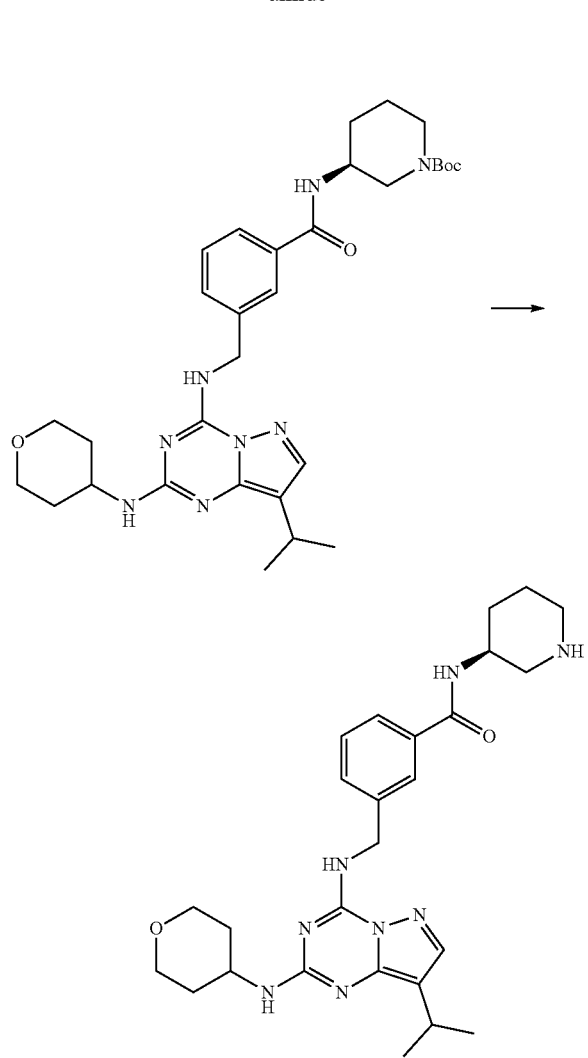

The process of this step was adopted from step-2 of example-3 (0.10 g crude). LCMS: m/z=493.4 (M+H)⁺.

104

Step-5: Synthesis of (S)—N-(1-acryloylpiperidin-3-yl)-3-(((8-isopropyl-2-((tetrahydro-2H-pyran-4-yl)amino)pyrazolo[1,5-a][1,3,5]triazin-4-yl)amino)methyl)benzamide

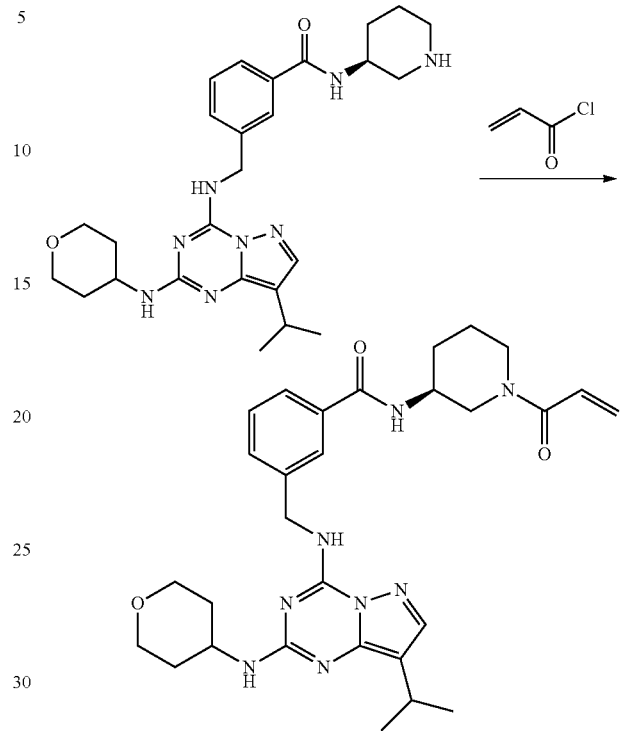

The process of this step was adopted from step-3 of example-3. The obtained crude compound was purified by preparative HPLC (Method: A: water, B: Acetonitrile, Column: X Bridge C-18 (150 mm*21.2, 5 μm) to afford the desired title compound (0.014 g, 20%). ¹HNMR (DMSO-d₆, 400 MHz): δ 9.00 (s, 1H), 8.75 (s, 1H), 8.32-8.30 (m, 1H), 7.84 (s, 1H), 7.71-7.68 (m, 2H), 7.51-7.49 (m, 1H), 7.41-7.37 (m, 1H), 6.92-6.67 (m, 2H), 6.07-6.03 (t, 1H), 5.65-5.61 (m, 1H), 4.69 (s, 2H), 3.96-3.79 (m, 6H), 3.17-3.15 (d, 1H), 2.89 (s, 2H), 1.92-1.76 (m, 3H), 1.64-1.57 (m, 2H), 1.42 (s, 2H), 1.28-1.21 (m, 7H); LCMS: m/z=546.8 (M+H)⁺.

The below compounds were prepared by procedure similar to the one described in Example-4 with appropriate variations in reactants, quantities of reagents in presence of suitable solvents at suitable reaction conditions. The physicochemical characteristics of the compounds are summarized herein below table.

| Compd. No. | Compound structure | Analytical data |
|---|---|---|
| 42 | 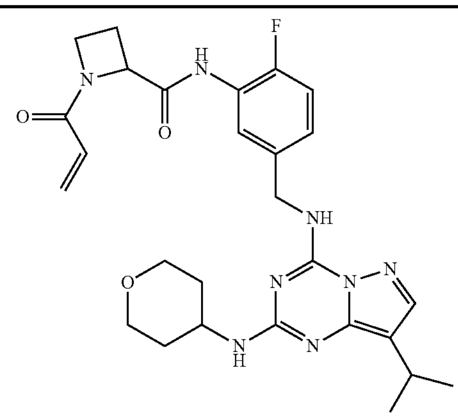 | ¹H NMR (DMSO-d₆, 400 MHz): δ 10.09 (d, 1H), 9.02-8.4 (m, 1H), 8.22-7.90 (m, 1H), 7.69 (s, 1H), 7.22-7.14 (m, 2H), 7.10-6.4 (m, 1H), 6.36 (m, 1H), 6.18 (m, 1H), 5.75 (d, 1H), 5.03 (m, 1H), 4.84 (m, 2H), 4.20 (t, 1H), 3.88-3.82 (m, 3H), 3.33 (m, 1H), 2.88 (m, 1H), 2.66 (m, 1H), 2.29 (m, 1H), 1.82-1.62 (m, 2H), 1.63-1.43 (m, 2H), 1.20 (d, 6H), 1.08 (m, 2H); LCMS: m/z = 537.7(M + H)⁺. |

| Compd. No. | Compound structure | Analytical data |
|---|---|---|
| 43 | 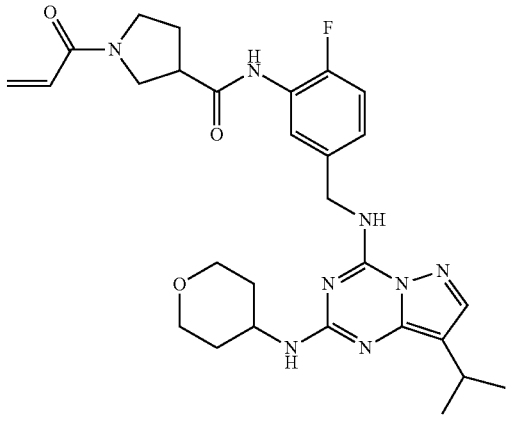 [SMILES: C=CC(=O)N1CCC(C(=O)Nc2cc(CNc3nc(NC4CCOCC4)nc4c(C(C)C)cnn34)ccc2F)C1] | ¹H NMR (DMSO-d₆, 400 MHz): δ 9.88 (s, 1H), 8.9 (m, 1H), 7.93-7.85 (m, 1H), 7.70 (s, 1H), 7.21-7.14 (m, 2H), 6.92-6.89 (m, 1H), 6.61-6.53 (m, 1H), 6.15-6.10 (dd, 1H), 5.68-5.64 (dd, 1H), 4.53 (s, 2H), 3.83-3.79 (m, 3H), 3.71-3.66 (m, 2H), 3.55-3.51 (m, 2H), 3.46-3.27 (m, 3H), 2.88 (m, 1H), 2.22-2.15 (m, 2H), 1.98-1.97 (m, 2H), 1.83-1.64 (m, 2H), 1.43-1.20 (dd, 6H); LCMS: m/z = 551.3 (M + H)⁺. |
| 44 | 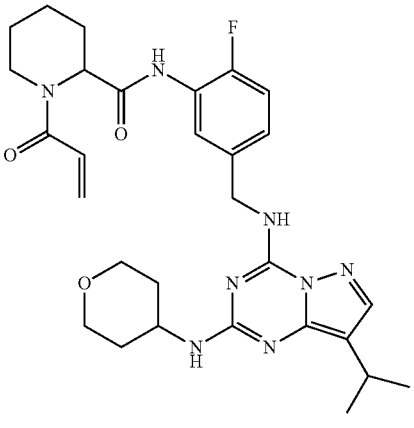 [SMILES: C=CC(=O)N1CCCCC1C(=O)Nc1cc(CNc2nc(NC3CCOCC3)nc3c(C(C)C)cnn23)ccc1F] | ¹H NMR (DMSO-d₆, 400 MHz): δ 9.72-9.67 (d, 1H), 8.70 (s, 1H), 7.69 (s, 2H), 7.20-7.15 (m, 3H), 6.87-6.80 (m, 2H), 6.54 (s, 3H), 6.11-6.06 (d, 1H), 5.69-5.65 (m, 1H), 5.24-5.23 (d, 1H), 4.53 (s, 2H), 4.04 (s, 2H), 3.98-3.95 (d, 1H), 3.82 (s, 2H), 2.88 (s, 1H), 2.16-2.12 (d, 1H), 1.81 (s, 1H), 1.64 (m, 3H), 1.41-1.38 (m, 3H), 1.20-1.19 (d, 6H); LCMS: m/z = 565.75 (M + H)⁺; |
| 45 | 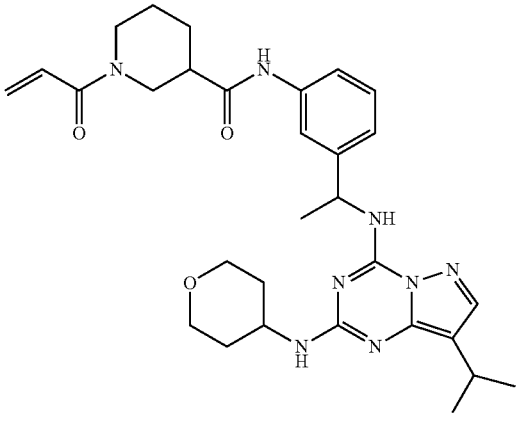 [SMILES: C=CC(=O)N1CCCC(C(=O)Nc2cccc(C(C)Nc3nc(NC4CCOCC4)nc4c(C(C)C)cnn34)c2)C1] | ¹H NMR (DMSO-d₆, 400 MHz): δ9.95-9.93 (d, 1H), 8.50 (m, 1H), 7.66 (s, 1H), 7.41 (m, 1H), 7.18 (m, 1H), 7.07-7.06 (m, 1H), 6.85-6.74 (m, 2H), 6.06-6.02 (d, 1H), 5.64-5.59 (t, 1H), 5.1 (m, 1H), 4.45-4.42 (d, 1H), 4.28-4.24 (d, 1H), 4.06-3.96 (m, 1H), 3.81-3.67 (m, 3H), 3.36 (m, 1H), 2.99-2.84 (m, 3H), 2.67-2.50 (m, 1H), 1.91-1.69 (m, 4H), 1.51-1.45 (m, 3H), 1.39-1.36 (m, 3H), 1.30 (d, 6H), 1.06-1.02 (m, 2H); LCMS: m/z = 561.35 (M + H)⁺. |

Example-5: Synthesis of 3-(((8-isopropyl-2-((tetra-hydro-2H-pyran-4-yl)amino)pyrazolo[1,5-a][1,3,5]triazin-4-yl)amino)methyl)phenyl 4-acryloylpiperazine-1-carboxylate (Compound-46)

Step-1: Synthesis of 3-(((8-isopropyl-2-(methylthio)pyrazolo[1,5-a][1,3,5]triazin-4-yl)amino)methyl)phenol

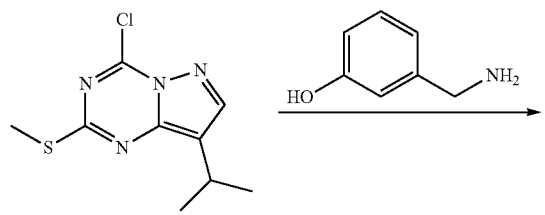

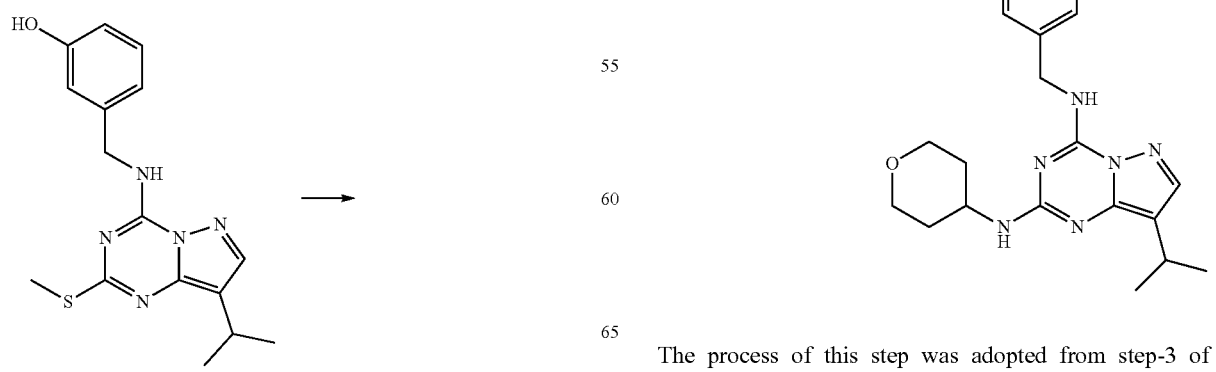

The process of this step was adopted from step-1 of example-4 (0.5 g, 73%). LCMS: m/z=330.2 (M+H)$^+$.

Step-2: Synthesis of 3-(((8-isopropyl-2-(methylsulfonyl)pyrazolo[1,5-a][1,3,5]triazin-4-yl)amino)methyl)phenol

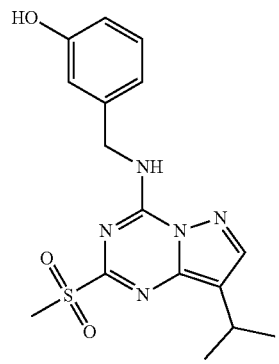

The process of this step was adopted from step-2 of example-4 (0.35 g, 63%). LCMS: m/z=362.3 (M+H)$^+$.

Step-3: Synthesis of 3-(((8-isopropyl-2-((tetrahydro-2H-pyran-4-yl)amino)pyrazolo[1,5-a][1,3,5]triazin-4-yl)amino)methyl)phenol

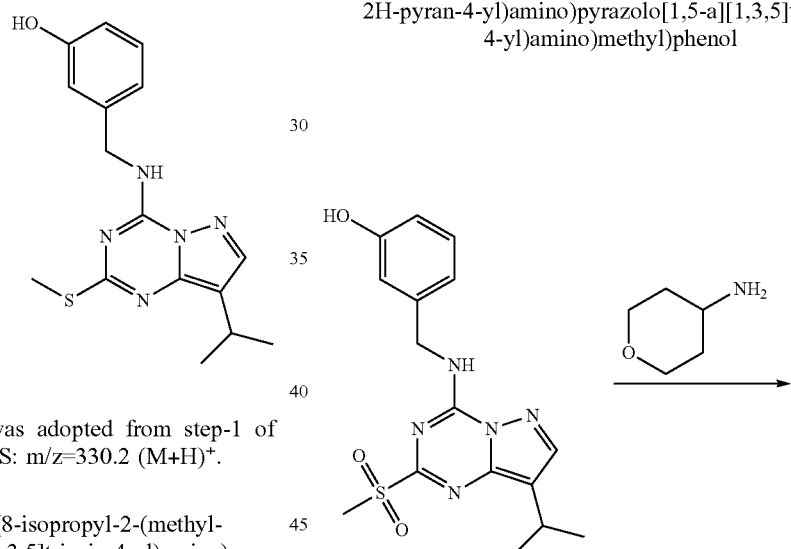

The process of this step was adopted from step-3 of example-4 (0.22 g, 70%). LCMS: m/z=383.2 (M+H)$^+$

Step-4: Synthesis of 1-(tert-butyl) 4-(3-(((8-isopropyl-2-((tetrahydro-2H-pyran-4-yl)amino) pyrazolo [1,5-a][1,3,5]triazin-4-yl)amino)methyl)phenyl) piperazine-1,4-dicarboxylate

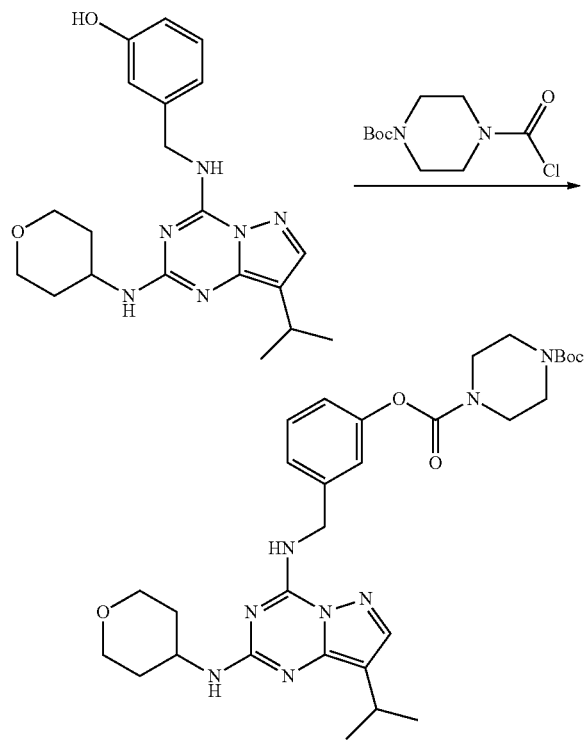

To a solution of 3-(((8-isopropyl-2-((tetrahydro-2H-pyran-4-yl)amino)pyrazolo[1,5-a][1,3,5]triazin-4-yl)amino) methyl)phenol (0.227 g, 0.59 mmol) in 10 mL DCM, was added DMAP (0.086 g, 0.70 mmol), followed by tert-butyl 4-(chlorocarbonyl)piperazine-1-carboxylate (0.147 g, 0.59 mmol, synthesized according to procedure depicted in US2007/270433A1). Reaction mixture was stirred for 4 h at RT. After completion of reaction, reaction mixture was quenched to ice cold water and partitioned between water and DCM. The product was extracted with DCM (3×25 ml), washed with brine, dried over sodium sulphate, filtered and concentrated to dryness. The product was purified by 100-200 mesh silica column by eluting with 30%-50% ethyl acetate-hexane to afford the title compound (0.15 g, 42%). LCMS: m/z=595.8 (M+H)+.

Step-5: Synthesis of 3-(((8-isopropyl-2-((tetrahydro-2H-pyran-4-yl)amino)pyrazolo[1,5-a][1,3,5]triazin-4-yl)amino)methyl)phenyl piperazine-1-carboxylate

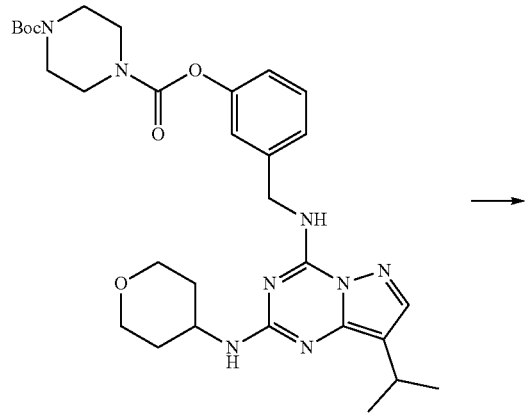

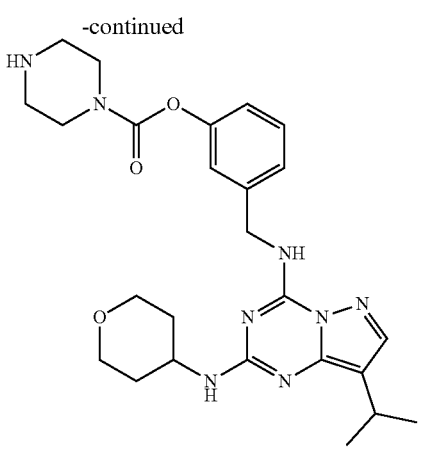

The process of this step was adopted from step-2 of example-3 (0.1 g of TFA salt). LCMS: m/z=495.4 (M+H)+.

Step-6: Synthesis of 3-(((8-isopropyl-2-((tetrahydro-2H-pyran-4-yl)amino)pyrazolo[1,5-a][1,3,5]triazin-4-yl)amino)methyl)phenyl 4-acryloylpiperazine-1-carboxylate

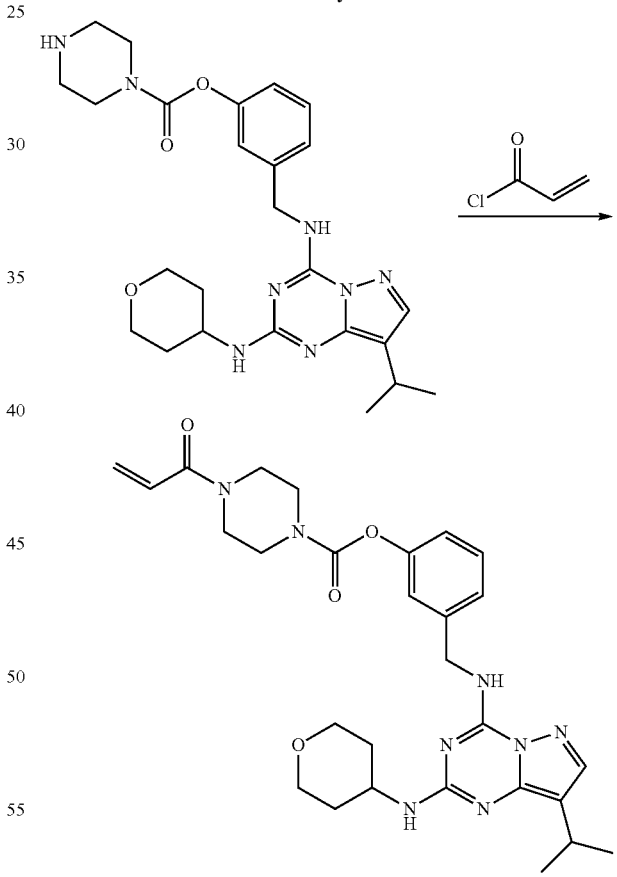

The process of this step was adopted from step-3 of example-3. The obtained crude compound was purified by preparative HPLC (0.01% NH$_4$OH in water, B: Acetonitrile, Column: Gemini NX C-18 (21.2 mm*150 mm, 5 μm)) to afford desired title compound (0.035 g, 26%). $^1$HNMR (DMSO-d$_6$, 400 MHz): δ 8.95-8.66 (d, 1H), 7.68 (s, 1H), 7.31-7.14 (m, 1H), 7.17 (s, 1H), 7.08 (s, 1H), 7.98-7.96 (d, 1H), 6.90-6.87 (m, 1H), 6.81-6.74 (m, 1H), 6.52 (s, 1H), 6.13-6.08 (m, 1H), 5.70-5.67 (m, 1H), 4.62-4.56 (m, 2H), 3.80-3.78 (m, 4H), 3.60-3.56 (m, 6H), 3.40-3.33 (m, 2H), 2.86 (s, 1H), 1.80-1.60 (m, 1H), 1.50-1.38 (m, 4H) 1.18 (s, 6H); LCMS: m/z=549.6 (M+H)+.

Example-6: Synthesis of 3-acrylamido-N-(3-(((8-isopropyl-2-((tetrahydro-2H-pyran-4-yl)amino)pyrazolo[1,5-a][1,3,5]triazin-4-yl)amino)methyl)phenyl)benzamide (Compound-47)

Step-1: Synthesis of N-(3-(((8-isopropyl-2-((tetrahydro-2H-pyran-4-yl)amino)pyrazolo[1,5-a][1,3,5]triazin-4-yl)amino)methyl)phenyl)-3-nitrobenzamide

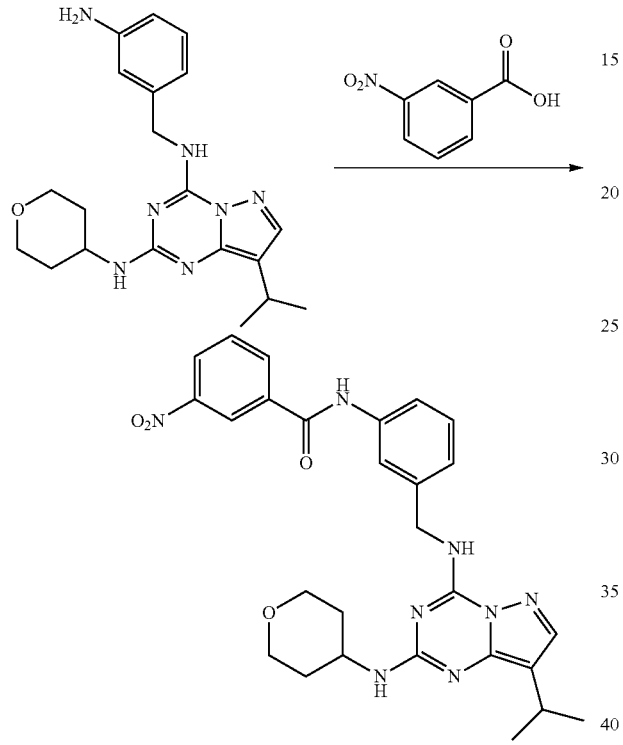

The process of this step was adopted from step-1 of example-3 (0.38 g). LCMS: m/z=531.60 (M+H)+.

Step-2: Synthesis of 3-amino-N-(3-(((8-isopropyl-2-((tetrahydro-2H-pyran-4-yl)amino) pyrazolo[1,5-a][1,3,5]triazin-4-yl)amino)methyl)phenyl)benzamide

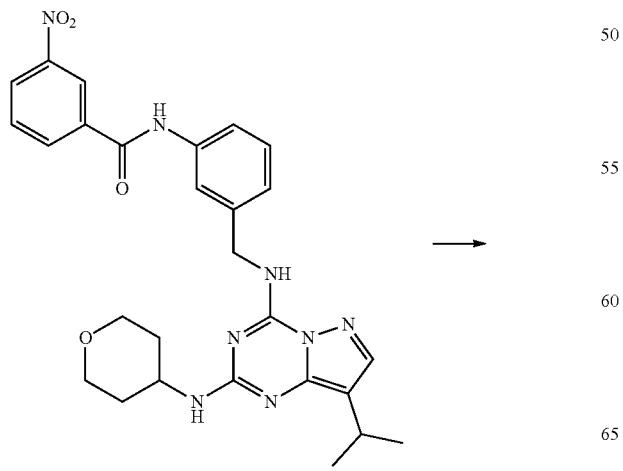

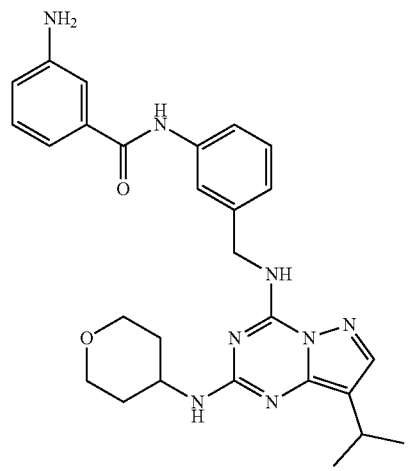

To a solution of N-(3-(((8-isopropyl-2-((tetrahydro-2H-pyran-4-yl)amino)pyrazolo [1,5-a][1,3,5]triazin-4-yl) amino)methyl)phenyl)-3-nitrobenzamide (0.38 g, 0.71 mmol) in THF:MeOH:Water (3:2:1) were added zinc (0.465 g, 7.1 mmol) and ammonium chloride (0.76 g, 14.3 mmol). The reaction mixture was stirred at room temperature for 4 h. After completion of reaction, the reaction mixture filtered through celite and diluted with ethyl acetate. The aqueous layer was separated and extracted with ethyl acetate (2×25 mL). The combined organic phase was washed with brine, dried over Na₂SO₄, filtered and concentrated. The residue was purified by 100-200 silica gel column chromatography to afford desired title compound (0.3 g, 70%). LCMS: m/z=501.20 (M+H)+.

Step-3: Synthesis of 3-acrylamido-N-(3-(((8-isopropyl-2-((tetrahydro-2H-pyran-4-yl)amino) pyrazolo[1,5-a][1,3,5]triazin-4-yl)amino)methyl)phenyl)benzamide

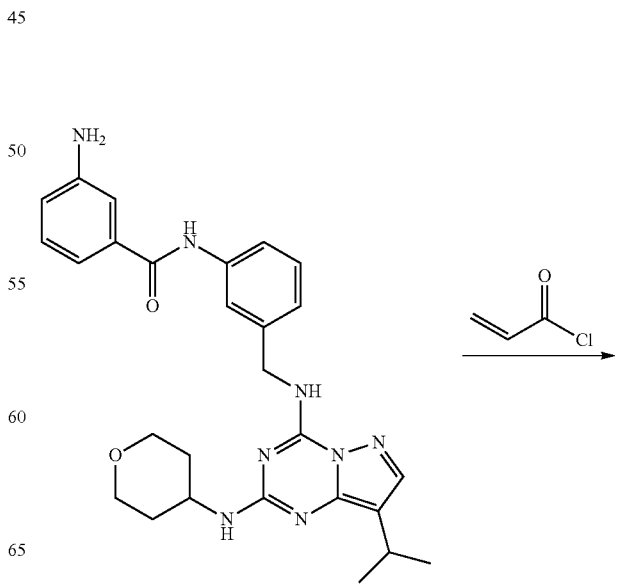

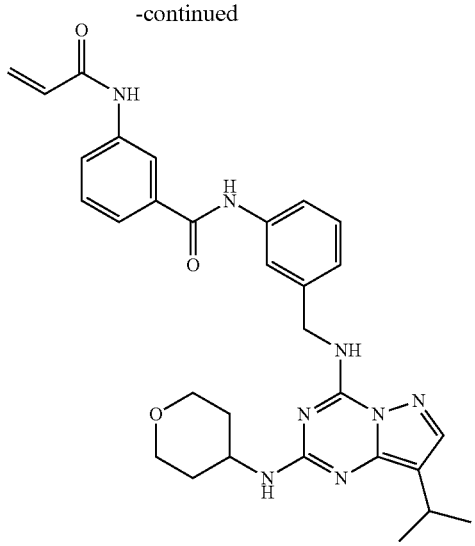

The process of this step was adopted from step-3 of example-3. The obtained crude compound was purified by preparative HPLC (Method: A: water, B: Acetonitrile-Methanol, Column: ZORBAX XDB C-18 (21.1 mm*150 mm, 5 μm) to afford desired title compound (0.022 g, 25%). HNMR (DMSO-$d_6$, 400 MHz): δ 10.33 (s, 1H), 10.26 (s, 1H), 8.11 (s, 1H), 7.91 (d, 1H), 7.70 (m, 2H), 7.61-7.59 (d, 2H), 7.47 (t, 1H), 7.28 (t, 1H), 7.08 (m, 1H), 6.70 (m, 1H), 6.53 (m, 1H), 6.30 (d, 1H), 5.79-5.75 (m, 2H), 4.62 (m, 2H), 3.81 (m, 3H), 2.90 (m, 1H), 1.81-1.50 (m, 3H), 1.49-1.2 (m, 3H), 1.21 (d, 6H); LCMS: m/z=555.2 (M+H)$^+$.

The below compound was prepared by procedure similar to the one described in Example-6 with appropriate variations in reactants, quantities of reagents, in presence of suitable solvents at suitable reaction conditions. The physicochemical characteristics of the compounds are summarized herein below table.

| Compd. No. | Compound structure | Analytical data |
|---|---|---|
| 48 | 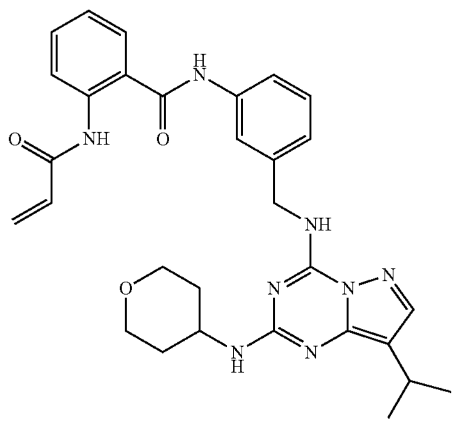 [SMILES: C=CC(=O)Nc1ccccc1C(=O)Nc1cccc(CNc2nc(NC3CCOCC3)nc3c(C(C)C)cnn23)c1] | $^1$H NMR (DMSO-$d_6$, 400 MHz): δ 10.63 (s, 1H), 10.44 (s, 1H), 8.18 (d, 1H), 7.74 (m, 2H), 7.54 (t, 2H), 7.31 (m, 1H), 7.25 (m, 1H), 7.12 (m, 2H), 6.40 (m, 1H), 6.21 (d, 1H), 5.76 (d, 1H), 4.62 (m, 2H), 3.88-3.79 (m, 4H), 2.96 (m, 2H), 1.81 (m, 3H), 1.45 (m, 3H), 1.20 (d, 6H); LCMS: m/z = 555.20 (M + H)$^+$. |
| 48A | 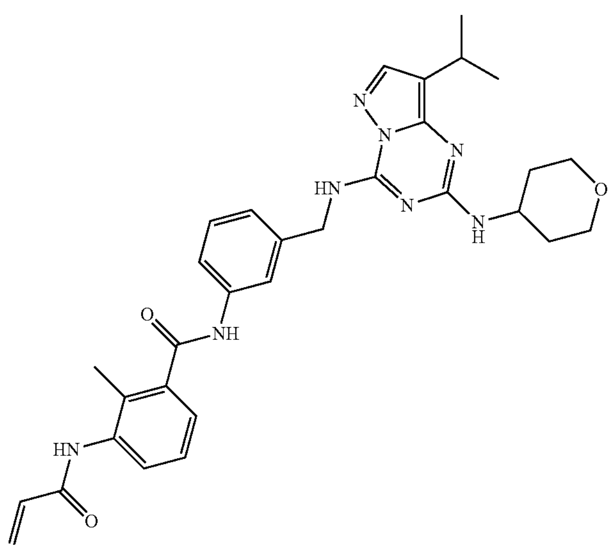 [SMILES: C=CC(=O)Nc1cccc(C(=O)Nc2cccc(CNc3nc(NC4CCOCC4)nc4c(C(C)C)cnn34)c2)c1C] | LCMS: m/z = 569.30 (M + H)$^+$. |

Example-7: Synthesis of (E)-4-((3-(((8-isopropyl-2-((tetrahydro-2H-pyran-4-yl)amino) pyrazolo[1,5-a][1,3,5]triazin-4-yl)amino)methyl)phenyl)amino)-N,N-dimethylbut-2-enamide (Compound-49)

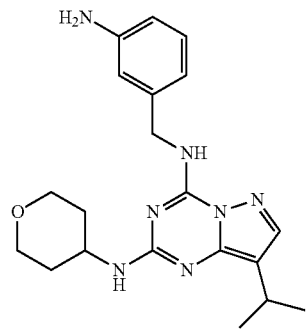

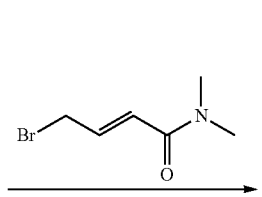

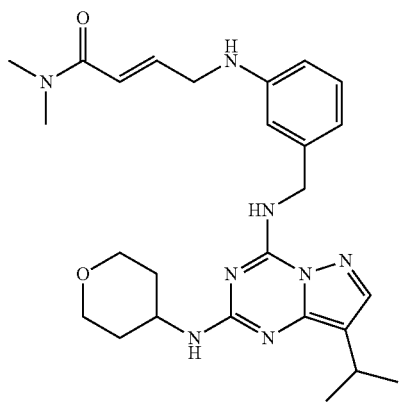

To a solution of N4-(3-aminobenzyl)-8-isopropyl-N2-(tetrahydro-2H-pyran-4-yl)pyrazolo[1,5-a][1,3,5]triazine-2,4-diamine (0.1 g, 0.26 mmol, intermediate-33) and (E)-4-bromo-N,N-dimethylbut-2-enamide (0.061 g, 31.4 mmol) in CAN (3 mL) was added K$_2$CO$_3$ (0.157 g, 1.136 mmol) at RT, then stirred at 80° C. for 4 h. After reaction completion, the reaction mixture was cooled to room temperature, quenched with water and diluted with ethyl acetate. The aqueous layer was separated and extracted with ethyl acetate (2×15 mL). The combined organic phase was washed with brine, dried over Na$_2$SO$_4$, filtered and concentrated. The residue was purified by preparative HPLC (Method: A: 0.02% NH$_3$ in water, B: ACN, Column: Gemini NX C18: 150 mm*21.2 mm) to afford desired title compound (0.028 g, 20%). $^1$H NMR (DMSO-d$_6$, 400 MHz): δ 8.40-8.80 (d, 1H), 7.70 (s, 1H), 7.02-6.99 (t, 1H), 6.84 (s, 1H), 6.66-6.63 (m, 2H), 6.60-6.54 (d, 2H), 6.44-6.42 (d, 1H), 5.99 (s, 1H), 4.44 (s, 2H), 3.89 (s, 5H), 3.30 (m, 4H), 2.89 (s, 4H), 2.82 (s, 3H), 1.89 (s, 1H), 1.23 (s, 1H), 1.10 (s, 6H); LCMS: m/z=493.6 (M+H)$^+$.

Example-8: Synthesis of (E)-4-(diethylamino)-N-(3-(((8-isopropyl-2-((tetrahydro-2H-pyran-4-yl)amino) pyrazolo[1,5-a][1,3,5]triazin-4-yl)amino)methyl)phenyl)but-2-enamide (Compound-50)

Step-1: Synthesis of (E)-4-bromo-N-(3-(((8-isopropyl-2-((tetrahydro-2H-pyran-4-yl)amino) pyrazolo[1,5-a][1,3,5]triazin-4-yl)amino)methyl)phenyl)but-2-enamide

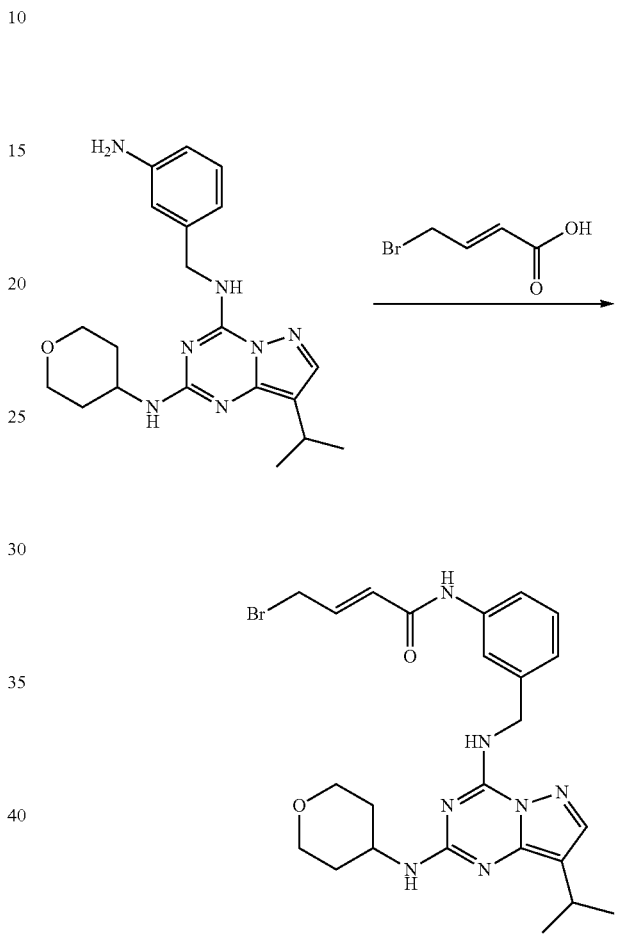

To a cooled solution of (E)-4-bromobut-2-enoic acid (0.86 g, 5.24 mmol) in DCM (10 mL) was added 2 drops of DMF and followed by oxalyl chloride (0.9 mL, 10.49 mmol) at 0° C., then stirred at RT for 1 h, evaporated the solvent completely under vacuum and dissolved again in DCM (5 mL). In another flask, a solution of N4-(3-aminobenzyl)-8-isopropyl-N2-(tetrahydro-2H-pyran-4-yl)pyrazolo[1,5-a][1,3,5]triazine-2,4-diamine (1 g, 2.62 mmol, Intermediate-33) in DCM (10 mL) and DIPEA (1.45 mL, 7.87 mmol) was cooled to 0° C. To this the above acid chloride in DCM was added slowly drop wise, reaction mixture was allowed to stirred at RT for 1 h. After completion of the reaction, the reaction mixture quenched with water and then diluted with DCM (20 mL). The organic layer washed with water followed by brine, dried over Na$_2$SO$_4$, filtered and concentrated, the residue was purified by 100-200 mesh silica gel column chromatography to afford desired title compound (0.7 g, 60%). LCMS: m/z=530.05 (M+H)$^+$.

Step-2: Synthesis of (E)-4-(diethylamino)-N-(3-(((8-isopropyl-2-((tetrahydro-2H-pyran-4-yl)amino)pyrazolo[1,5-a][1,3,5]triazin-4-yl)amino)methyl)phenyl)but-2-enamide

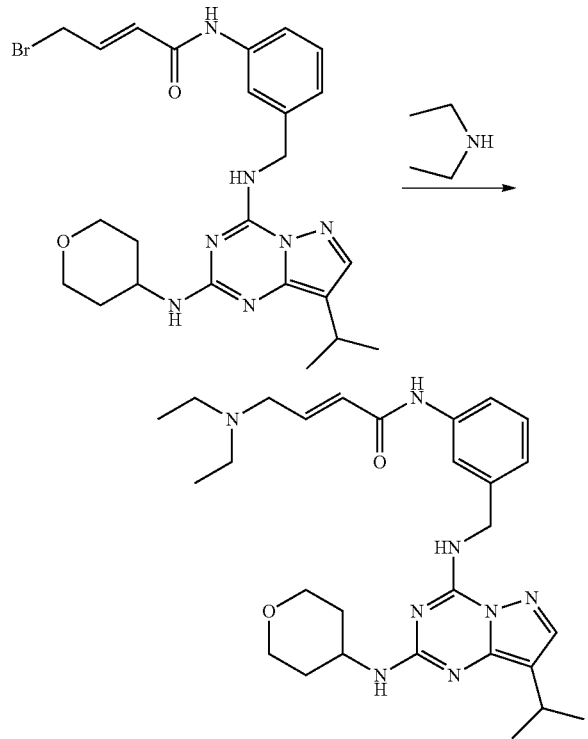

To a stirred solution of (E)-4-bromo-N-(3-(((8-isopropyl-2-((tetrahydro-2H-pyran-4-yl)amino)pyrazolo[1,5-a][1,3,5]triazin4yl)amino)methyl)phenyl)butenamide (0.15 g, 0.28 mmol) and diethylamine (0.042 g, 0.568 mmol) in ACN (3 mL) was added $K_2CO_3$ (0.1 g, 0.71 mmol) at RT, then stirred at 80° C. for 2 h. After completion of reaction, the reaction mixture was cooled to room temperature, quenched with water and diluted with ethyl acetate. The aqueous layer was separated and extracted with ethyl acetate (2×15 mL). The combined organic phase was washed with brine, dried over $Na_2SO_4$, filtered and concentrated. The residue was purified by preparative HPLC (Method: A: 0.1% TFA in water, B: Acetonitrile, Column: X Bridge: 150 mm*19.0 mm) to afford desired title compound as TFA salt, after that passed this TFA salt through Vari pure basic resin column to remove TFA to afford final compound (0.027 g, 54%). $^1$HNMR (DMSO-$d_6$, 400 MHz): $^1$HNMR (DMSO-$d_6$, 400 MHz): δ 10.35 (s, 1H), 9.70 (s, 1H), 9.60 (s, 1H), 8.90 (s, 1H), 7.95 (s, 1H), 7.75 (s, 1H), 7.55 (m, 1H), 7.34-7.30 (t, 1H), 7.15 (s, 1H), 6.81-6.73 (m, 1H), 6.53-6.49 (d, 1H), 4.66 (s, 2H), 4.02-4.00 (t, 2H), 3.92-3.91 (m, 2H), 3.82 (m, 3H), 3.20 (s, 2H), 3.18-3.14 (m, 4H), 3.02-2.97 (m, 1H), 1.69 (s, 1H), 1.48 (s, 2H), 1.27-1.23 (m, 10H); LCMS: m/z=521.65 $(M+H)^+$.

The below compounds were prepared by procedure similar to the one described in Example-8 with appropriate variations in reactants, quantities of reagents in presence of suitable solvents at suitable reaction conditions. The physicochemical characteristics of the compounds are summarized herein below table.

| Compd. No. | Compound structure | Analytical data |
|---|---|---|
| 51 | (morpholine-containing structure) | $^1$H NMR (DMSO-$d_6$, 400 MHz): δ 10.30-10.10 (d, 1H), 9.50 (s, 1H), 8.74 (s, 2H), 7.86-7.54 (m, 3H), 7.30 (t, 1H), 7.12 (s, 1H), 6.90-6.73 (m, 2H), 6.47-6.43 (d, 1H), 4.63 (s, 2H), 4.01 (s, 3H), 3.90-3.70 (m, 5H), 3.12 (s, 3H), 2.94 (s, 2H), 2.00 (s, 1H), 1.84 (s, 1H), 1.66 (s, 1H), 1.46 (s, 2H), 1.24 (s, 6H); LCMS: m/z = 535.7 $(M + H)^+$. |
| 52 | (ethylpiperazine-containing structure) | $^1$H NMR (DMSO-$d_6$, 400 MHz): δ 10.03 (s, 1H), 7.71 (s, 1H), 7.77-7.75 (m, 2H), 7.26-7.22 (t, 1H), 7.03-7.02 (d, 1H), 6.9-6.8 (m, 1H), 6.72-6.65 (m, 1H), 6.24-6.21 (d, 1H), 4.60 (d, 2H), 3.90-3.80 (m, 3H), 3.35-3.30 (m, 3H), 3.08-3.07 (d, 2H), 2.907 (s, 1H), 2.67 (s, 1H), 2.45-2.33 (m, 5H), 2.32-2.28 (m, 2H), 1.83 (s, 1H), 1.60-1.45 (m, 2H), 1.23 (s, 7H), 0.99-0.95 (t, 3H); LCMS: m/z = 562.35 $(M + H)^+$. |

| Compd. No. | Compound structure | Analytical data |
|---|---|---|
| 53 | 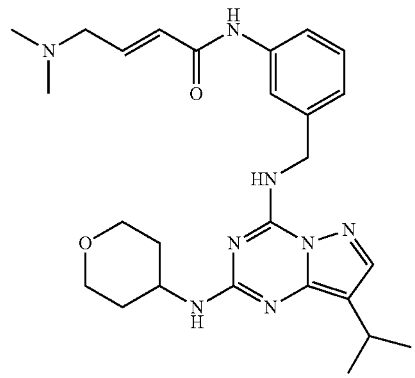 [SMILES: CC(C)c1cnn2c(NCc3cccc(NC(=O)/C=C/CN(C)C)c3)nc(NC3CCOCC3)nc12] | ¹H NMR (DMSO-d₆, 400 MHz): δ 9.96 (s, 1H), 8.90 (s, 1H), 8.6 (s, 1H), 7.67 (s, 1H), 7.60-7.50 (m, 1H), 7.22-7.18 (m, 1H), 6.99-6.97 (m, 1H), 6.88-6.77 (m, 1H), 6.69-6.64 (m, 1H), 6.20-6.16 (m, 1H), 4.58-4.52 (m, 2H), 3.80-3.72 (m, 3H), 3.44-3.33 (m, 2H), 2.95-2.92 (m, 2H), 2.88-2.82 (m, 1H), 2.22-2.20 (m, 6H), 1.81-1.75 (m, 1H), 1.60-1.50 (m, 2H), 1.35-1.49 (m, 2H), 1.18 (s, 6H); LCMS: m/z = 493.6 (M + H)⁺. |
| 54 | 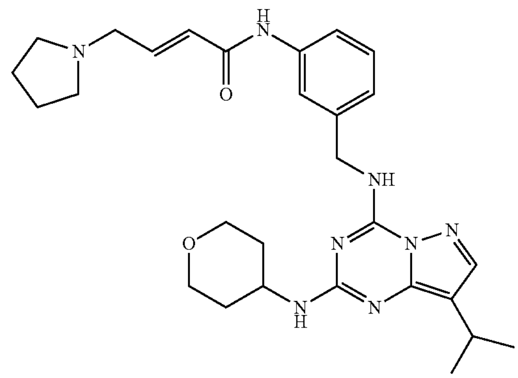 [SMILES: CC(C)c1cnn2c(NCc3cccc(NC(=O)/C=C/CN4CCCC4)c3)nc(NC3CCOCC3)nc12] | ¹H NMR (DMSO-d₆, 400 MHz): δ 10.03 (s, 1H), 8.65 (s, 1H), 7.71 (s, 1H), 7.56 (m, 2H), 7.25-7.21 (t, 1H), 7.02-7.01 (d, 1H), 6.83 (s, 1H), 6.77-6.71 (m, 1H), 6.26-6.22 (d, 1H), 4.59 (s, 2H), 3.82 (s, 3H), 3.20-3.16 (m, 2H), 2.90 (s, 1H), 2.54-2.32 (m, 4H), 1.82 (s, 1H), 1.72-1.68 (m, 4H), 1.59 (s, 1H), 1.45 (s, 2H), 1.37 (s, 2H), 1.22 (s, 6H); LCMS: m/z = 519.30 (M + H)⁺. |
| 55 | 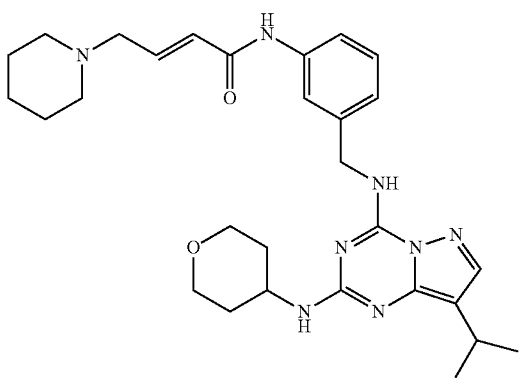 [SMILES: CC(C)c1cnn2c(NCc3cccc(NC(=O)/C=C/CN4CCCCC4)c3)nc(NC3CCOCC3)nc12] | ¹HNMR (DMSO-d₆, 400 MHz): δ 10.23 (s, 1H), 8.90 (s, 1H), 8.65 (s, 1H), 7.71 (s, 1H), 7.55 (m, 2H), 7.25-7.21 (t, 1H), 7.03 (s, 1H), 6.83 (s, 1H), 6.73-6.66 (m, 1H), 6.23-6.19 (d, 1H), 4.59 (s, 2H), 3.82 (s, 4H), 3.05-3.03 (m, 2H), 2.90 (s, 1H), 2.32 (s, 4H), 1.82 (s, 1H), 1.52-1.47 (m, 6H), 1.39-1.37 (d, 3H), 1.22 (s, 6H); LCMS: m/z = 533.20 (M + H)⁺. |
| 56 | 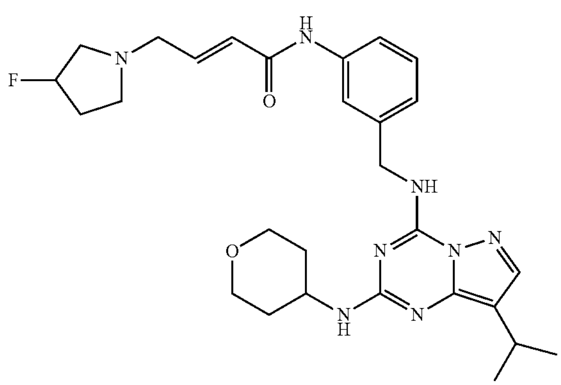 [SMILES: CC(C)c1cnn2c(NCc3cccc(NC(=O)/C=C/CN4CCC(F)C4)c3)nc(NC3CCOCC3)nc12] | ¹HNMR (DMSO-d₆, 400 MHz): δ 10.05 (s, 1H), 8.65 (s, 1H), 7.71 (s, 1H), 7.56 (m, 2H), 7.25-7.21 (t, 1H), 7.03-7.01 (d, 1H), 6.83 (s, 1H), 6.76-6.70 (m, 1H), 6.27-6.23 (d, 1H), 5.26-5.11 (m, 1H), 4.59 (s, 2H), 3.82 (s, 3H), 3.24-3.18 (m, 4H), 2.87-2.78 (m, 3H), 2.66-2.58 (m, 2H), 2.34-2.28 (m, 1H), 2.17-2.08 (m, 1H), 1.93-1.81 (m, 2H), 1.59-1.37 (m, 2H), 1.22 (s, 6H); LCMS: m/z = 537.60 (M + H)⁺. |

| Compd. No. | Compound structure | Analytical data |
|---|---|---|
| 57 | 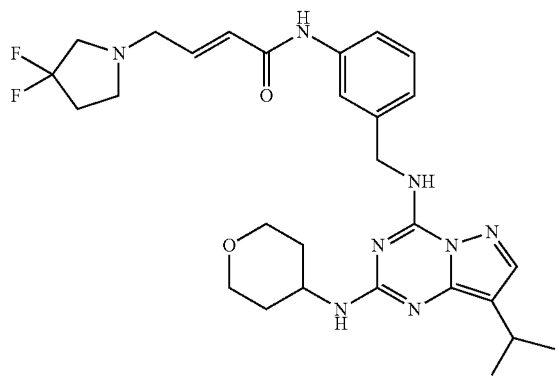 [SMILES: CC(C)c1cnn2c(NCc3cccc(NC(=O)/C=C/CN4CCC(F)(F)C4)c3)nc(NC3CCOCC3)nc12] | ¹HNMR (DMSO-d₆, 400 MHz): δ 10.05 (s, 1H), 8.92 (s, 1H), 8.65 (s, 1H), 7.71 (s, 1H), 7.58-7.54 (m, 2H), 7.26-7.22 (t, 1H), 7.03-7.01 (d, 1H), 6.82 (s, 1H), 6.73-6.67 (m, 1H), 6.27-6.23 (d, 1H), 4.59 (s, 2H), 3.82 (s, 3H), 3.26-3.25 (m, 2H), 2.93-2.87 (t, 3H), 2.74-2.70 (m, 2H), 2.33-2.19 (m, 2H), 1.83 (s, 1H), 1.58 (s, 1H), 1.45 (s, 1H), 1.36 (s, 2H), 1.22 (s, 6H); LCMS: m/z = 555.60 (M + H)⁺. |
| 58 | 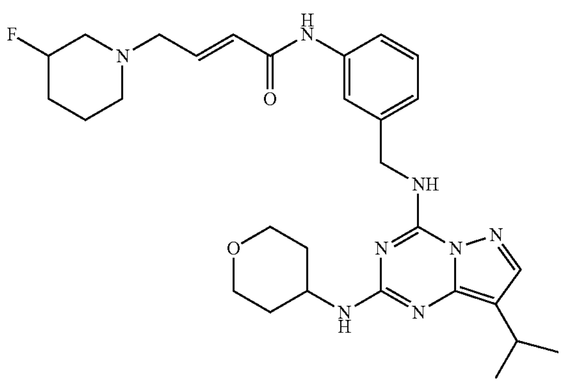 [SMILES: CC(C)c1cnn2c(NCc3cccc(NC(=O)/C=C/CN4CCCC(F)C4)c3)nc(NC3CCOCC3)nc12] | ¹HNMR (DMSO-d₆, 400 MHz): δ 10.05 (s, 1H), 8.66 (s, 1H), 7.71 (s, 1H), 7.60-7.50 (m, 2H), 7.27-7.23 (t, 1H), 7.05 (s, 1H), 6.89-6.82 (m, 1H), 6.73-6.68 (m, 1H), 6.32 (s, 1H), 4.60 (s, 2H), 3.81 (s, 4H), 3.20-3.16 (m, 2H), 2.67-2.55 (m, 2H), 2.33-2.32 (m, 2H), 2.90 (s, 2H), 1.81 (s, 4H), 1.58 (s, 2H), 1.44 (s, 2H), 1.36 (s, 1H), 1.22 (s, 6H); LCMS: m/z = 551.20 (M + H)⁺. |
| 59 | 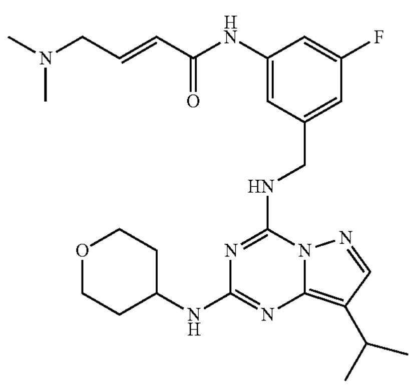 [SMILES: CC(C)c1cnn2c(NCc3cc(F)cc(NC(=O)/C=C/CN(C)C)c3)nc(NC3CCOCC3)nc12] | ¹H NMR (DMSO-d₆, 400 MHz): δ 10.13 (s, 1H), 8.95 (s, 1H), 8.70 (s, 1H), 7.72 (s, 1H), 7.61 (s, 1H), 7.30-7.20 (m, 1H), 6.87-6.85 (d, 2H), 6.75-6.68 (m, 1H), 6.22-6.18 (d, 1H), 4.59 (s, 2H), 3.82-3.75 (d, 3H), 3.03-3.01 (d, 2H), 2.90 (s, 1H), 2.66 (s, 1H), 2.32 (s, 1H), 2.14 (s, 5H), 1.82 (s, 2H), 1.60 (s, 2H), 1.45 (s, 2H), 1.22 (s, 6H); LCMS: m/z = 511.20 (M + H)⁺. |
| 60 | 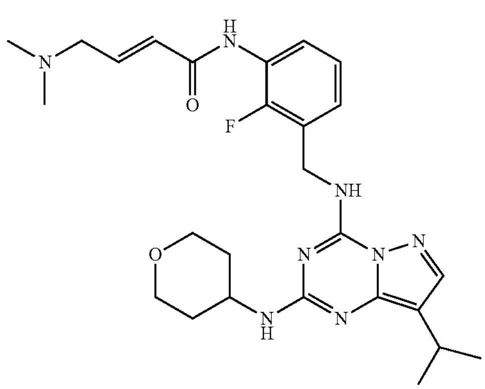 [SMILES: CC(C)c1cnn2c(NCc3cccc(NC(=O)/C=C/CN(C)C)c3F)nc(NC3CCOCC3)nc12] | ¹H NMR (DMSO-d₆, 400 MHz): δ 9.84 (s, 2H), 8.90 (s, 1H), 8.65 (s, 2H), 7.80 (s, 2H), 7.72 (s, 1H), 7.08 (s, 3H), 6.90 (s, 2H), 6.75-6.70 (m, 2H), 6.45-6.41 (d, 2H), 4.67 (s, 2H), 3.90-3.70 (m, 5H), 3.03-3.00 (d, 2H), 2.67 (s, 2H), 2.20 (s, 6H), 2.12-1.97 (m, 2H), 1.81 (s, 2H), 1.55-1.45 (m, 4H), 1.23 (s, 8H); LCMS: m/z = 511.2(M + H)⁺. |

| Compd. No. | Compound structure | Analytical data |
|---|---|---|
| 61 | 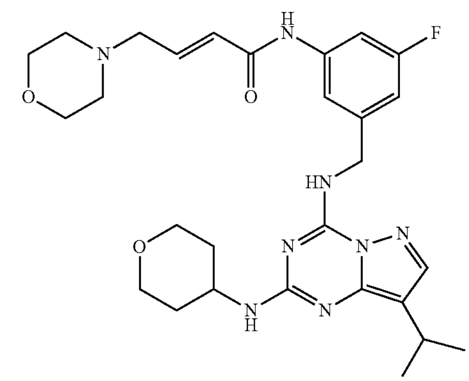 | $^1$H NMR (DMSO-d$_6$, 400 MHz): δ 10.13 (s, 1H), 8.95 (s, 1H), 8.70 (s, 1H), 7.72 (s, 1H), 7.61 (s, 1H), 7.30-7.20 (m, 1H), 6.87-6.85 (d, 2H), 6.75-6.68 (m, 1H), 6.23-6.20 (d, 1H), 4.59 (s, 2H), 3.82-3.75 (d, 3H), 3.58-3.56 (m, 4H), 3.34-3.29 (m, 1H), 3.10-3.08 (m, 2H), 2.90 (s, 1H), 2.36 (s, 4H), 1.86 (s, 1H), 1.53-1.35 (m, 3H), 1.22 (s, 6H); LCMS: m/z = 533.30 (M + H)$^+$. |
| 62 | 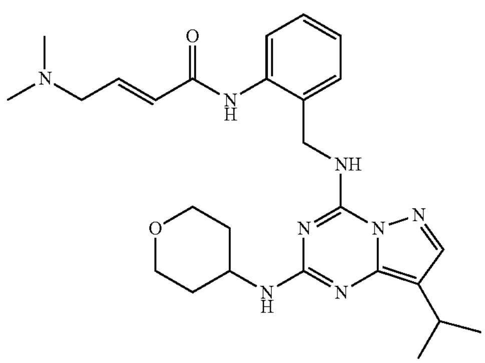 [SMILES: CC(C)c1cnn2c(NCc3ccccc3NC(=O)/C=C/CN(C)C)nc(NC3CCOCC3)nc12] | $^1$HNMR (DMSO-d$_6$, 400 MHz): δ 9.70 (s, 1H), 8.85 (s, 1H), 8.58 (s, 1H), 7.71 (s, 1H), 7.51-7.49 (d, 1H), 7.33-7.31 (d, 1H), 7.26-7.22 (t, 1H), 7.13 (s, 1H), 6.87 (s, 1H), 6.77-6.71 (m, 1H), 6.49-6.45 (d, 1H), 4.60-4.59 (d, 2H), 3.82 (s, 3H), 2.91-2.90 (m, 1H), 2.66 (s, 1H), 2.40 (s, 6H), 2.33 (s, 2H), 1.83 (s, 1H), 1.46 (s, 2H), 1.23-1.21 (d, 7H); LCMS: m/z = 493.20 (M + H)$^+$. |
| 63 | 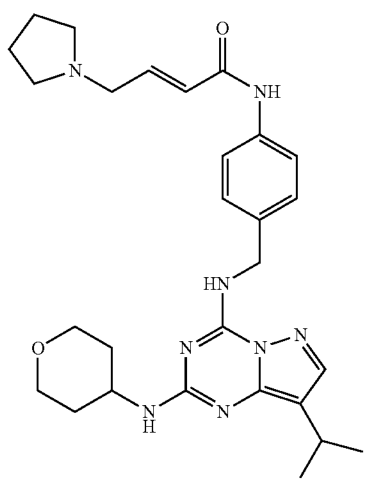 [SMILES: CC(C)c1cnn2c(NCc3ccc(NC(=O)/C=C/CN4CCCC4)cc3)nc(NC3CCOCC3)nc12] | $^1$H NMR (DMSO-d$_6$, 400 MHz): δ 10.03 (s, 1H), 8.80-8.60 (d, 1H), 7.69 (s, 1H), 7.58-7.56 (d, 2H), 7.30-7.27 (d, 2H), 6.90-6.71 (m, 2H), 6.27-6.22 (d, 1H), 4.53 (s, 2H), 3.85-3.82 (d, 2H), 3.43 (s, 2H), 3.21-3.19 (d, 3H), 2.90 (s, 1H), 1.83 (s, 1H), 1.69 (s, 6H), 1.44 (m, 3H), 1.22 (s, 8H); LCMS: m/z = 519.25 (M + H)$^+$. |

Example-9: Synthesis of (E)-1-(4-(dimethylamino) but-2-enoyl)-N-(2-fluoro-5-(((8-isopropyl-2-((tetrahydro-2H-pyran-4-yl)amino)pyrazolo[1,5-a][1,3,5] triazin-4-yl)amino) methyl)phenyl) pyrrolidine-3-carboxamide (Compound-64)

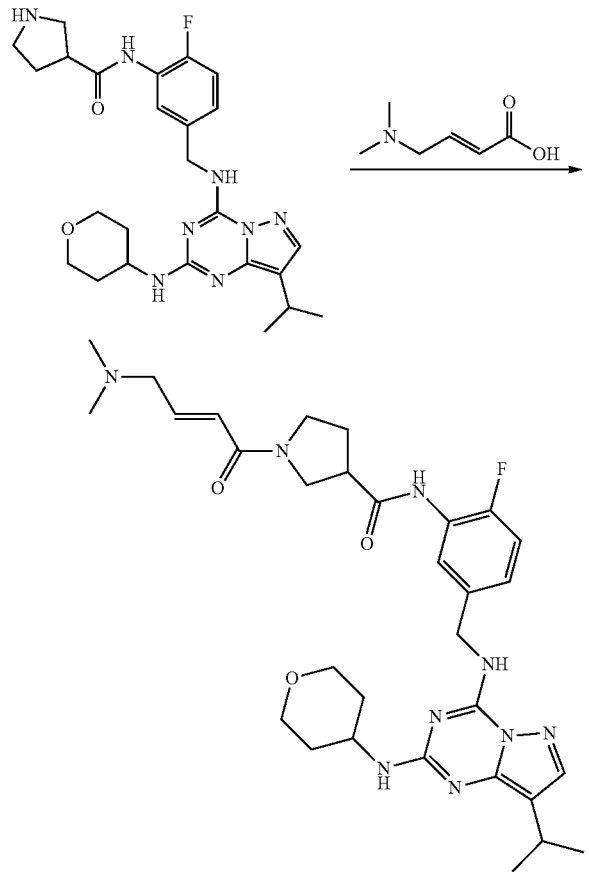

To a cooled solution of (E)-4-(dimethylamino)but-2-enoic acid hydrochloride (0.050 g, 0.3 mmol) in DMF (2 mL) at 0° C. was added HATU (0.137 g, 0.30 mmol) followed by DIPEA (0.1 mL, 0.6 mmol) and finally added N-(2-fluoro-5-(((8-isopropyl-2-((tetrahydro-2H-pyran-4-yl)amino)pyrazolo[1,5-a][1,3,5]triazin-4-yl)amino)methyl)phenyl)pyrrolidine-3-carboxamide (0.150 g, 0.3 mmol; this was prepared by using the procedure of example-3). The reaction mixture was stirred for 2 h at room temperature. The reaction mixture was quenched with ice-water and diluted with ethyl acetate. The aqueous layer was separated and extracted with ethyl acetate (2×25 mL). The combined organic phase was washed with brine, dried over $Na_2SO_4$, filtered and concentrated and purified by preparative HPLC (Method: A: 0.01% in ammonia in water, B: Acetonitrile-MeOH, Column: EVO C-18 (150 mm*21.2, 5 μm) to afford desired title compound (0.04 g, 24%). $^1$HNMR (DMSO-$d_6$, 400 MHz): δ 9.98-9.88 (s, 1H), 9.00 (s, 1H), 8.60 (s, 1H), 7.85 (m, 1H), 7.70 (s, 1H), 7.22-7.15 (m, 2H), 6.64 (m, 1H), 6.63-6.58 (m, 1H), 6.38-6.33 (dd, 1H), 4.54 (s, 2H), 3.82-3.78 (m, 3H), 3.67-3.60 (m, 2H), 3.54 (m, 2H), 3.53-3.51 (m, 1H), 3.34-3.27 (m, 1H), 3.02-3.01 (d, 2H), 2.89 (m, 1H), 2.20-2.14 (m, 7H), 2.00-1.98 (m, 1H), 1.83 (m, 1H), 1.64 (m, 1H), 1.45 (m, 2H), 1.21 (d, 6H); LCMS: m/z=608.75 (M+H)$^+$.

The below compounds were prepared by procedure similar to the one described in Example-9 with appropriate variations in reactants, quantities of reagents in presence of suitable solvents at suitable reaction conditions. The physicochemical characteristics of the compounds are summarized herein below table.

| Compd. No. | Compound structure | Analytical data |
|---|---|---|
| 65 | 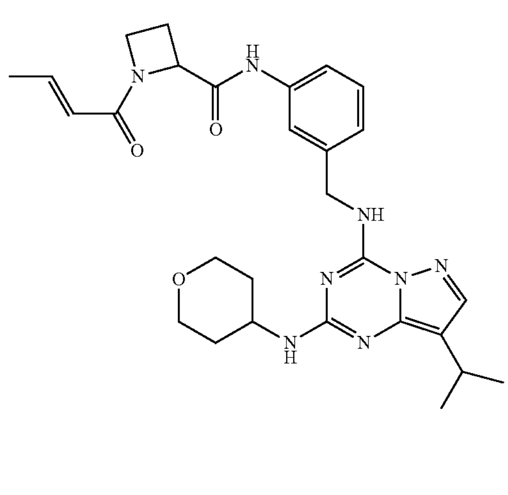 [SMILES: C/C=C/C(=O)N1CCC1C(=O)Nc1cccc(CNc2nc(NC3CCOCC3)nc3c(C(C)C)cnn23)c1] | $^1$H NMR (DMSO-$d_6$, 400 MHz): δ 10.23-10.20 (m, 1H), 8.88-8.72 (s, 1H), 7.76 (s, 1H), 7.60 (s, 2H), 7.32-7.30 (m, 1H), 7.10 (s, 1H), 6.90 (s, 1H), 6.72 (m, 1H), 6.09-6.05 (d, 1H), 5.80 (t, 1H), 5.10-4.89 (m, 1H), 4.64 (s, 2H), 4.20-4.19 (m, 1H), 3.90-3.86 (m, 3H), 2.95 (s, 2H), 2.57-2.50 (m, 2H), 2.22 (m, 2H), 1.90-1.88 (d, 3H), 1.78-1.76 (d, 1H), 1.50 (s, 3H), 1.28 (s, 6H); LCMS: m/z = 533.2 (M + H)$^+$. |

-continued

| Compd. No. | Compound structure | Analytical data |
|---|---|---|
| 66 | 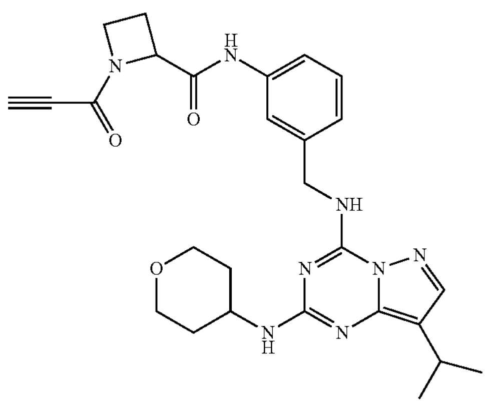 [SMILES: C#CC(=O)N1CCC1C(=O)Nc1cccc(CNc2nc(NC3CCOCC3)nc3c(C(C)C)cnn23)c1] | $^1$H NMR (DMSO-d$_6$, 400 MHz): δ 10.19-10.14 (d, 1H), 8.9-8.6 (d, 1H), 7.72 (s, 1H), 7.55 (m, 2H), 7.28-7.24 (t, 1H), 7.10-7.06 (m, 1H), 6.90-6.60 (m, 1H), 6.65 (s, 3H), 4.98-4.77 (m, 1H), 4.60 (s, 2H), 4.31 (s, 1H), 4.16-4.12 (m, 1H), 3.93-3.82 (m, 3H), 2.91 (m, 1H), 2.23-2.14 (m, 1H), 1.84-1.80 (m, 2H), 1.46-1.37 (m, 2H), 1.24 (s, 6H); LCMS: m/z = 517.1 (M + H)$^+$. |
| 67 | 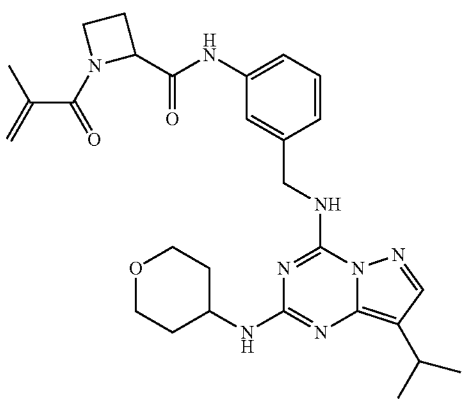 [SMILES: C=C(C)C(=O)N1CCC1C(=O)Nc1cccc(CNc2nc(NC3CCOCC3)nc3c(C(C)C)cnn23)c1] | $^1$H NMR (DMSO-d$_6$, 400 MHz): δ 10.06 (s, 1H), 9.0-8.65 (m, 2H), 7.70 (s, 1H), 7.50 (m, 2H), 7,26 (t, 1H), 7.04 (d, 1H), 6.81 (m, 1H), 5.46 (d, 1H), 5.18 (d, 1H), 4.95 (m, 1H), 4.77 (m, 1H), 4.58 (m, 2H), 4.18 (m, 1H), 3.93-3.80 (m, 4H), 2.89 (m, 1H), 2.15 (m, 2H), 1.81 (m, 3H), 1.68 (m, 2H), 1.45 (m, 2H), 1.22 (d, 6H); LCMS: m/z = 533.25 (M + H)$^+$. |
| 68 | 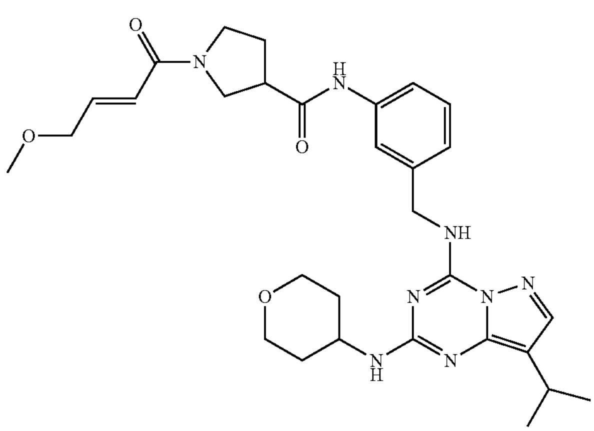 [SMILES: COC/C=C/C(=O)N1CCC(C(=O)Nc2cccc(CNc3nc(NC4CCOCC4)nc4c(C(C)C)cnn34)c2)C1] | $^1$H NMR (DMSO-d$_6$, 400 MHz): δ 10.05 (s, 1H), 8.90 (s, 1H), 8.60 (s, 1H), 7.71 (s, 1H), 7.50 (s, 1H), 7.23 (t, 1H), 7.03 (s, 1H), 6.80 (s, 1H), 6.68-6.64 (d, 1H), 6.39-6.38 (d, 1H), 4.58 (s, 2H), 4.05 (s, 2H), 3.81-3.76 (m, 3H), 3.65-3.62 (t, 2H), 3.55-3.53 (m, 2H), 3.35-3.36 (m, 3H), 3.10 (m, 2H), 2.90 (s, 1H), 2.10 (m, 2H), 2.80 (m, 2H), 1.62-1.45 (m, 3H), 1.23 (s, 6H); LCMS: m/z = 577.2 (M + H)$^+$. |

| Compd. No. | Compound structure | Analytical data |
|---|---|---|
| 69 | 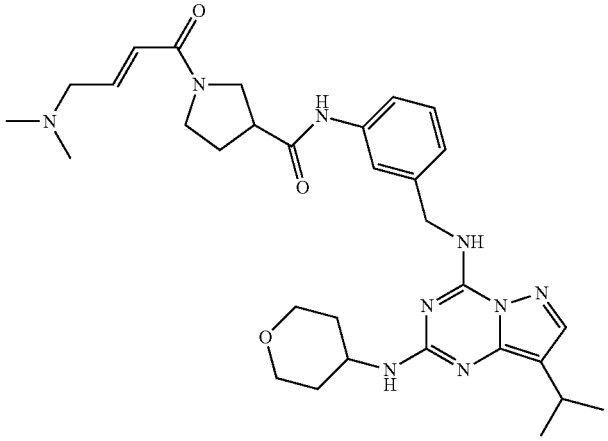 [SMILES: CC(C)c1cnn2c(NCc3cccc(NC(=O)C4CCN(C(=O)/C=C/CN(C)C)C4)c3)nc(NC3CCOCC3)nc12] | $^1$H NMR (DMSO-d$_6$, 400 MHz): δ 10.06 (s, 1H), 8.9 (s, 1H), 7.71 (s, 1H), 7.51 (m, 2H), 7.25-7.21 (t, 1H), 7.03-7.01 (d, 1H), 6.85 (s, 1H), 6.62-6.56 (m, 1H), 6.68-6.33 (m, 1H), 4.59 (s, 2H), 3.81-3.76 (m, 4H), 3.67-3.61 (m, 2H), 3.54-3.43 (m, 2H), 3.21-3.08 (m, 2H), 30.3-3.01 (d, 2H), 2.90 (s, 1H), 2.18-2.13 (m, 7H), 1.98-1.90 (m, 2H), 1.60-1.49 (m, 3H), 1.22 (s, 6H); LCMS: m/z = 590.5 (M + H)$^+$. |
| 70 | 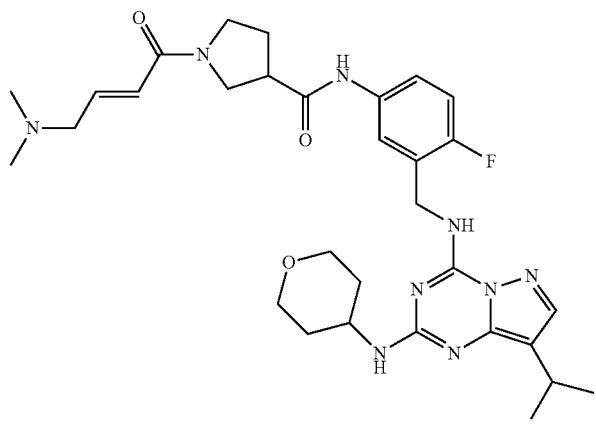 [SMILES: CC(C)c1cnn2c(NCc3cc(NC(=O)C4CCN(C(=O)/C=C/CN(C)C)C4)ccc3F)nc(NC3CCOCC3)nc12] | $^1$H NMR (DMSO-d$_6$, 400 MHz): δ 10.04 (s, 1H), 8.90-8.60 (m, 2H), 7.70 (s, 2H), 7.51 (s, 1H), 7.35 (s, 1H), 7.11-7.06 (t, 1H), 6.79 (s, 2H), 6.59-6.53 (m, 1H), 6.32-6.27 (d, 1H), 4.61 (s, 2H), 3.77-3.70 (m, 4H), 3.63-3.60 (m, 2H), 3.58-3.53 (m, 1H), 3.48-3.38 (m, 2H), 3.29-3.08 (m, 2H), 3.01-2.95 (m, 2H), 2.86 (s, 2H), 2.11-1.90 (m, 6H), 1.87-1.77 (m, 1H), 1.52-1.19 (m,3H), 1.19 (s, 6H); LCMS: m/z = 608.3 (M + H)$^+$. |
| 71 | 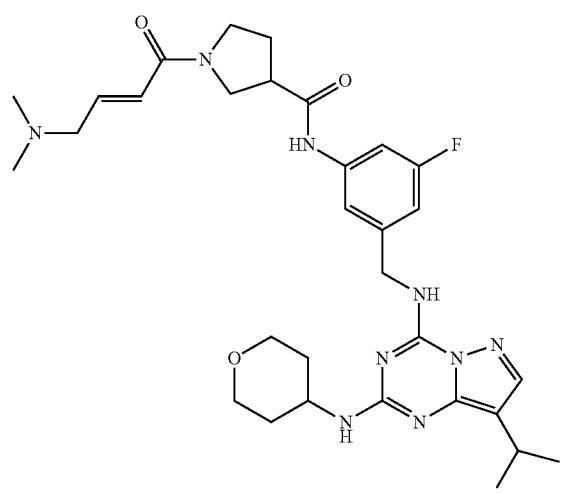 [SMILES: CC(C)c1cnn2c(NCc3cc(F)cc(NC(=O)C4CCN(C(=O)/C=C/CN(C)C)C4)c3)nc(NC3CCOCC3)nc12] | $^1$H NMR (DMSO-d$_6$, 400 MHz): δ 10.23 (s, 1H), 8.90-8.65 (d, 1H), 7.68 (s, 1H), 7.50 (s, 1H), 7.16 (s, 1H), 6.84-6.81 (d, 2H), 6.60-6.53 (m, 1H), 6.32-6.28 (d, 1H), 4.55 (s, 2H), 3.76-3.71 (m, 3H), 3.60-3.56 (m, 1H), 3.51-3.45 (m, 1H), 3.43-3.46 (m, 1H), 3.29-3.13 (m, 1H), 3.05-3.02 (m, 2H), 2.87 (s, 1H), 2.63 (s, 2H), 2.28 (s, 2H), 2.14-1.89 (m, 7H), 1.79 (s, 1H); 1.52-1.32 (s, 3H), 1.19 (s, 6H); LCMS: m/z = 608.3 (M + H)$^+$. |

| Compd. No. | Compound structure | Analytical data |
|---|---|---|
| 72 | 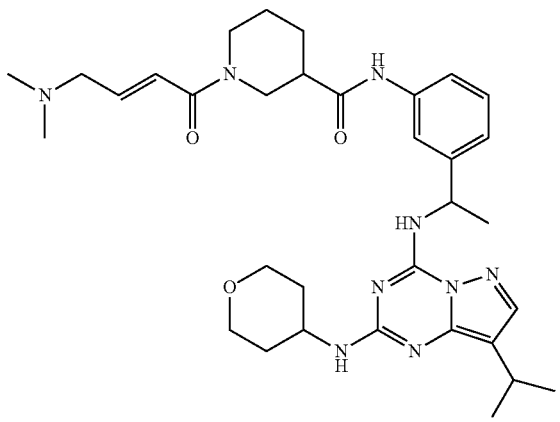 [SMILES: CC(C)c1cnn2c(NC(C)c3cccc(NC(=O)C4CCCN(C(=O)/C=C/CN(C)C)C4)c3)nc(NC3CCOCC3)nc12] | $^1$H NMR (DMSO-d$_6$, 400 MHz): δ 9.97 (s, 1H), 8.6 (s, 1H), 8.5 (s, 1H), 7.71 (s, 1H), 7.52-7.42 (m, 3H), 7.22 (m, 1H), 7.12-7.10 (d, 1H), 6.80 (m, 1H), 6.62-6.59 (m, 2H), 5.40 (s, 1H), 5.10 (s, 1H), 4.5 (m, 1H), 4.32 (m, 1H), 4.04-4.01 (m, 1H), 3.85-3.72 (m, 3H), 3.33-2.97 (m, 3H), 2.88 (m, 2H), 2.13-2.09 (m, 6H), 1.92 (m, 1H), 1.74-1.68 (m, 3H), 1.56-1.54 (d, 2H), 1.49-1.41 (m, 2H), 1.21 (d, 6H), 1.10-1.06 (t, 2H); LCMS: m/z = 618.5 (M + H)$^+$. |
| 73 | 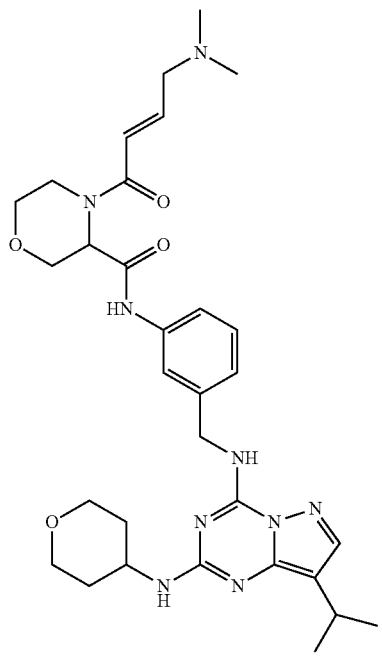 [SMILES: CC(C)c1cnn2c(NCc3cccc(NC(=O)C4COCCN4C(=O)/C=C/CN(C)C)c3)nc(NC3CCOCC3)nc12] | $^1$H NMR (DMSO-d$_6$, 400 MHz): δ 10.04 (s, 1H), 8.95-8.65 (m, 1H), 7.70 (s, 1H), 7.48 (m, 2H), 7.26-7.22 (t, 1H), 7.04 (s, 1H), 6.64 (s, 1H), 4.85-4.84 (d, 1H), 4.59 (s, 1H), 4.26-4.23 (d, 1H), 3.85-3.82 (d, 4H), 3.69-3.63 (d, 1H), 3.34 (s, 1H), 3.03 (s, 2H), 2.95-2.90 (m, 1H), 2.55-2.54 (m, 2H), 2.45 (s, 2H), 2.33-2.32 (m, 2H), 2.13 (s, 4H), 2.04 (s, 2H), 1.81 (s, 2H), 1.60 (s, 1H), 1.45 (s, 2H), 1.21 (s, 6H); LCMS: m/z = 606.30 (M + H)$^+$. |
| 74 | 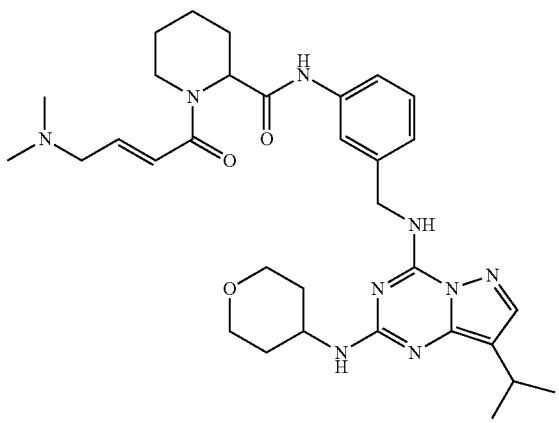 [SMILES: CC(C)c1cnn2c(NCc3cccc(NC(=O)C4CCCCN4C(=O)/C=C/CN(C)C)c3)nc(NC3CCOCC3)nc12] | $^1$H NMR (DMSO-d$_6$, 400 MHz): δ 9.92 (s, 1H), 8.94 (s, 1H), 8.60 (s, 1H), 7.71 (s, 1H), 7.49 (s, 1H), 7.28 (t, 2H), 7.02 (s, 1H), 6.88-6.81 (m, 1H), 6.66-6.44 (m, 1H), 5.11 (s, 1H), 4.80-4.58 (m, 3H), 3.96-3.83 (m, 4H), 3.02-3.01 (d, 1H), 2.94-2.90 (d, 2H), 2.67 (s, 3H), 2.32 (s, 3H), 2.13 (s, 4H), 2.04-1.98 (s, 1H), 1.82 (s, 1H), 1.66-1.61 (d, 3H), 1.44-1.37 (m, 3H), 1.22 (s, 6H); LCMS: m/z = 604.25 (M + H)$^+$. |

| Compd. No. | Compound structure | Analytical data |
|---|---|---|
| 75 | 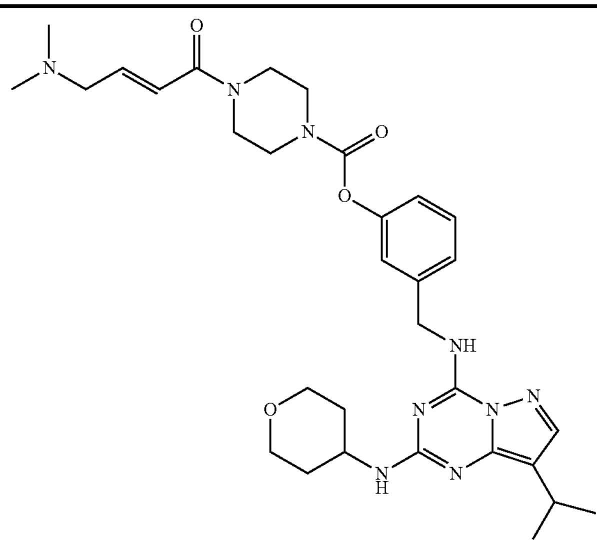 | $^1$H NMR (DMSO-d$_6$, 400 MHz): δ 8.37 (s, 1H), 8.21 (s, 1H), 7.66 (s, 1H), 7.35-7.31 (m, 1H), 7.24-7.22 (m, 1H), 7.18 (s, 1H), 7.04-7.01 (d, 1H), 6.67-6.61 (m, 1H), 6.51-6.47 (m, 1H), 4.65 (s, 2H), 3.86-3.84 (m, 3H), 3.64-3.63 (m, 4H), 3.56-3.52 (m, 4H), 3.42-3.35 (m, 4H), 3.10-3.06 (m, 1H)), 2.18 (s, 6H), 1.84-1.81 (m, 2H), 1.55-1.46 (m, 2H), 1.26-1.24 (d, 6H); LCMS: m/z = 606.2 (M + H)$^+$. |

Example-10: Synthesis of (E)-1-(4-(dimethyl-amino)-4-oxobut-2-en-1-yl)-N-(3-(((8-isopropyl-2-((tetrahydro-2H-pyran-4-yl)amino)pyrazolo[1,5-a][1,3,5]triazin-4-yl)amino) methyl)phenyl)azetidine-2-carboxamide (Compound-76)

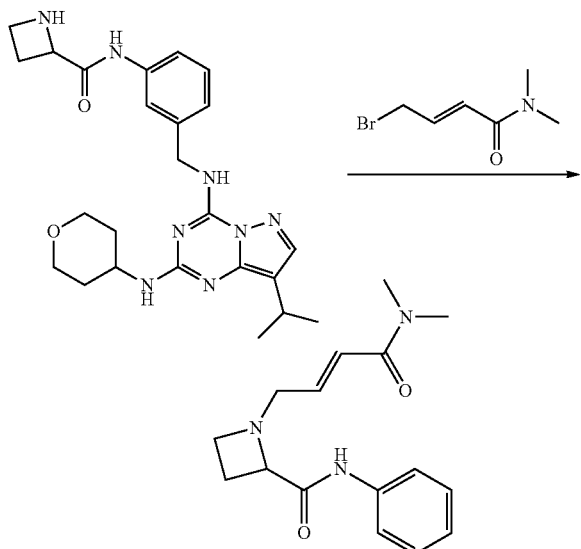

To a stirred solution of N-(3-(((8-isopropyl-2-((tetra-hydro-2H-pyran-4-yl)amino)pyrazolo[1,5-a][1,3,5]triazin-4-yl)amino)methyl)phenyl)azetidine-2-carboxamide (0.1 g, 0.21 mmol) in ACN (3 mL) was added DIPEA (0.07 mL, 0.43 mmol) and (E)-4-bromo-N,N-dimethylbut-2-enamide (0.05 g, 0.25 mmol) at 0° C. The reaction mixture was stirred for 12 h at RT. Water was added and extracted with dichloromethane. The aqueous layer was separated and extracted with dichloromethane (2×25 mL). The combined organic phase was washed with brine, dried over Na$_2$SO$_4$, filtered and concentrated to afford crude residue. The residue was purified by prep. HPLC (Method: A: 0.02% Ammonia in water, B: Acetonitrile, Column: WATER X BRIDGE (19 mm*150 mm, 5 μm)) to afford desired title compound (0.05 g, 41%). $^1$HNMR (DMSO-d$_6$, 400 MHz): δ 9.63 (s, 1H), 8.90-8.60 (m, 1H), 7.70-7.53 (m, 3H), 7.25-7.21 (t, 1H), 7.04 (s, 1H), 6.84 (s, 1H), 6.55 (s, 2H), 4.58 (s, 2H), 3.80 (s, 3H), 3.67-3.63 (t, 1H), 3.35-3.19 (m, 5H), 2.96-2.90 (m, 5H), 2.79 (s, 3H), 2.66 (s, 1H), 2.32-2.65 (m, 1H), 2.13-2.09 (m, 1H), 1.82 (s, 2H), 1.45-1.32 (m, 2H), 1.22 (s, 6H); LCMS: m/z=576.45 (M+H)$^+$.

Example-11: Synthesis of (E)-N-(3-(((8-isopropyl-2-((tetrahydro-2H-pyran-4-yl)amino) pyrazolo[1,5-a][1,3,5]triazin-4-yl)amino)methyl)phenyl)-1-(4-(pyrrolidin-1-yl)but-2-enoyl)piperidine-2-carboxamide (Compound-77)

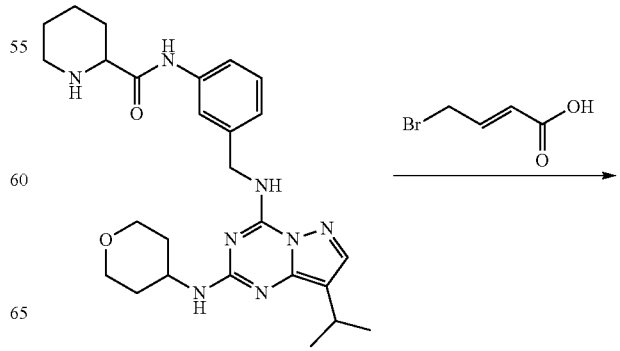

1H), 7.24-7.20 (t, 1H), 7.03 (s, 1H), 6.89-6.81 (d, 2H), 6.63 (s, 1H), 5.11 (s, 1H), 4.57 (m, 2H), 3.95-3.92 (m, 4H), 3.40-3.39 (m, 2H), 3.19-3.18 (d, 1H), 3.00 (s, 1H), 2.89 (s, 1H), 2.67 (s, 1H), 2.42 (s, 3H), 2.33-2.32 (d, 1H), 2.11-2.08 (d, 1H), 1.98 (s, 1H), 1.83-1.61 (m, 6H), 1.53 (s, 3H), 1.37 (s, 3H), 1.23 (s, 6H); LCMS: m/z=630.3 (M+H)$^+$.

Example-12: Synthesis of N-(3-(((8-isopropyl-2-((tetrahydro-2H-pyran-4-yl)amino)pyrazolo [1,5-a][1,3,5]triazin-4-yl)amino)methyl)phenyl)-1-(vinylsulfonyl)piperidine-2-carboxamide (Compound-78)

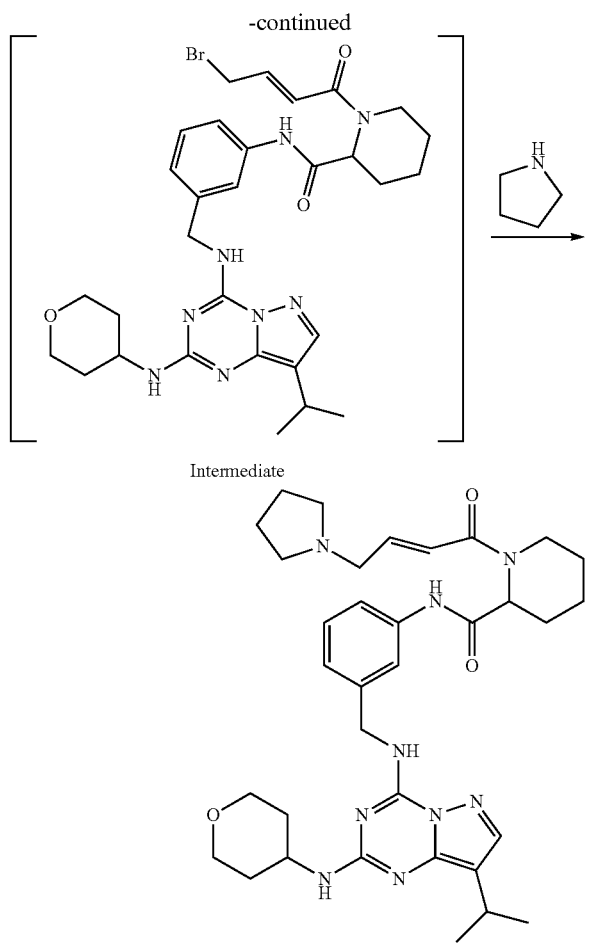

Intermediate

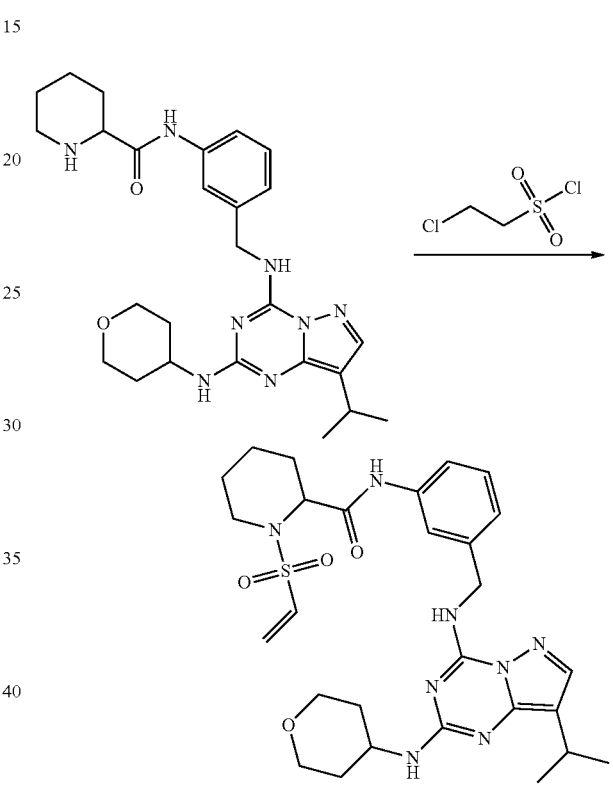

To a cooled solution of (E)-4-bromobut-2-enoic acid (0.28 g, 1.71 mmol) in DMF (10 mL) at 0° C. was added HATU (0.65 g, 1.71 mmol) followed by DIPEA (0.31 mL, 1.71 mmol) and finally added N-(3-(((8-isopropyl-2-((tetrahydro-2H-pyran-4-yl)amino)pyrazolo[1,5-a][1,3,5]triazin-4-yl)amino)methyl)phenyl)piperidine-2-carboxamide (0.42 g, 0.855 mmol). The reaction mixture was stirred for 1 h at room temperature. The reaction mixture was quenched with ice-water and diluted with ethyl acetate. The aqueous layer was separated and extracted with ethyl acetate (2×25 mL). The combined organic phase was washed with brine, dried over Na$_2$SO$_4$, filtered and concentrated the crude residue was purified by 100-200 silica gel column chromatography to afford desired intermediate (0.3 g, 46%). LCMS: m/z=641 (M+2H)$^+$. The intermediate was dissolved in ACN (5 mL) and pyrrolidine (0.067 g, 0.93 mmol) and K$_2$CO$_3$ (0.13 g, 0.93 mmol) was added at RT, stirred at 80° C. for 2 h. After reaction completion, the reaction mixture was cooled to room temperature, quenched with water and diluted with ethyl acetate. The aqueous layer was separated and extracted with ethyl acetate (2×15 mL). The combined organic phase was washed with brine, dried over Na$_2$SO$_4$, filtered and concentrated. The residue was purified by preparative HPLC (Method: A: 0.01% TFA in water, B: MeOH:CAN (1:1), Column: Zorbax XDB C18: 150 mm*21.2 mm) to afford desired title compound as TFA salt, after that passed this TFA salt through Vari pure basic resin column to removal the TFA from compound to afford final compound (0.04 g, 26%). $^1$HNMR (DMSO-d$_6$, 400 MHz): δ 9.91 (s, 1H), 8.95-8.66 (d, 1H), 7.70 (s, 1H), 7.64 (s, 1H), 7.54-7.48 (m, To the solution of N-(3-(((8-isopropyl-2-((tetrahydro-2H-pyran-4-yl)amino)pyrazolo[1,5-a][1,3,5]triazin-4-yl)amino) methyl)phenyl)piperidine-2-carboxamide (0.15 g, 0.3 mmol; prepared according to procedure of example-3) in DCM (10 mL) was added Et$_3$N (0.123 mL, 0.9 mmol) and 2-chloroethane-1-sulfonyl chloride (0.5 g, 0.3 mmol) at 0° C. After stirring 2 h at room temperature, the reaction mixture was quenched with ice-water and diluted with DCM. The aqueous layer was separated and extracted with DCM (2×25 mL). The combined organic phase was washed with brine, dried over Na$_2$SO$_4$, filtered and concentrated the crude residue was purified by preparative HPLC (Method: A: water, B: ACN, Column: Zorbax XDB C18 (21.2 mm×150 mm, 5) to afford desired title compound (0.025 g, 10.5%). $^1$HNMR (DMSO-d$_6$, 400 MHz): δ 9.99 (s, 1H), 8.80 (d, 1H), 7.71 (s, 1H), 7.60-7.40 (m, 2H), 7.23 (t, 1H), 7.04-7.02 (d, 1H), 6.95-6.75 (m, 1H), 6.66-6.60 (m, 1H), 6.05-5.96 (m, 2H), 4.58 (brs, 2H), 4.49-4.48 (d, 1H), 3.90-3.70 (m, 4H), 3.55-3.45 (m, 2H), 2.89 (brs, 1H), 2.03-2.00 (m, 1H), 1.85-1.58 (m, 6H), 1.39-133 (m, 4H), 1.22 (s, 6H); LCMS: m/z=583.0 (M+H)$^+$.

Example-13: Synthesis of N-(2-((3-(((8-isopropyl-2-((tetrahydro-2H-pyran-4-yl)amino)pyrazolo[1,5-a][1,3,5]triazin-4-yl)amino)methyl)phenyl)amino)-2-oxoethyl)acrylamide (Compound-79)

Step-1: Synthesis of tert-butyl (2-((3-(((8-isopropyl-2-((tetrahydro-2H-pyran-4-yl)amino)pyrazolo[1,5-a][1,3,5]triazin-4-yl)amino)methyl)phenyl)amino)-2-oxoethyl)carbamate

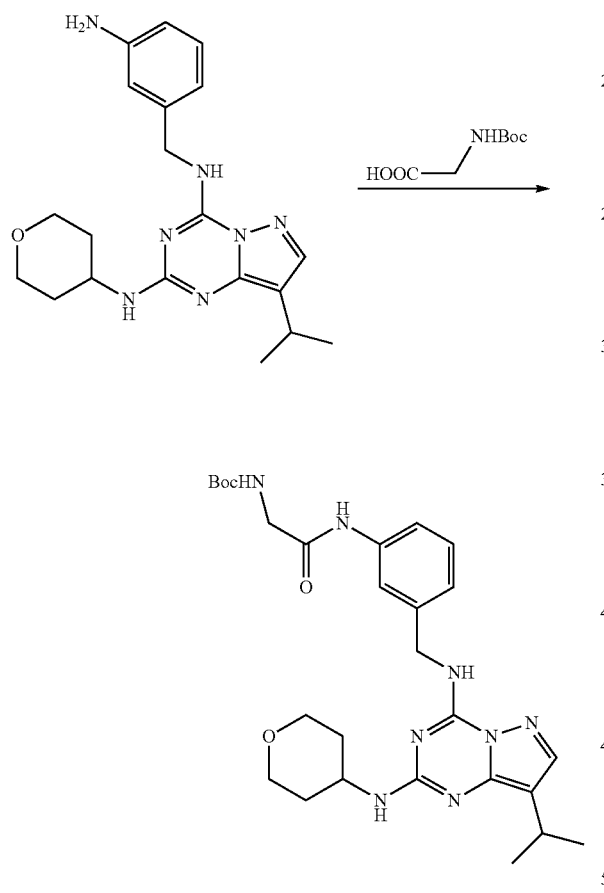

To a cooled solution of (tert-butoxycarbonyl)glycine (0.033 g, 0.3 mmol) in DMF (5 mL) at 0° C. was added HATU (0.152 g, 0.4 mmol) followed by DIPEA (0.1 mL, 0.62 mmol) and finally added N4-(3-aminobenzyl)-8-isopropyl-N2-(tetrahydro-2H-pyran-4-yl)pyrazolo[1,5-a][1,3,5]triazine-2,4-diamine (0.1 g, 0.26 mmol; Intermediate-33). The reaction mixture was stirred for 1 h at room temperature. The reaction mixture was quenched with ice-water and diluted with ethyl acetate. The aqueous layer was separated and extracted with ethyl acetate (2×25 mL). The combined organic phase was washed with brine, dried over Na$_2$SO$_4$, filtered and concentrated the crude residue was purified by 100-200 silica gel column chromatography to afford desired title compound (0.12 g, crude). LCMS: m/z=539 (M+H)$^+$.

Step-2: Synthesis of 2-amino-N-(3-(((8-isopropyl-2-((tetrahydro-2H-pyran-4-yl)amino)pyrazolo[1,5-a][1,3,5]triazin-4-yl)amino)methyl)phenyl)acetamide

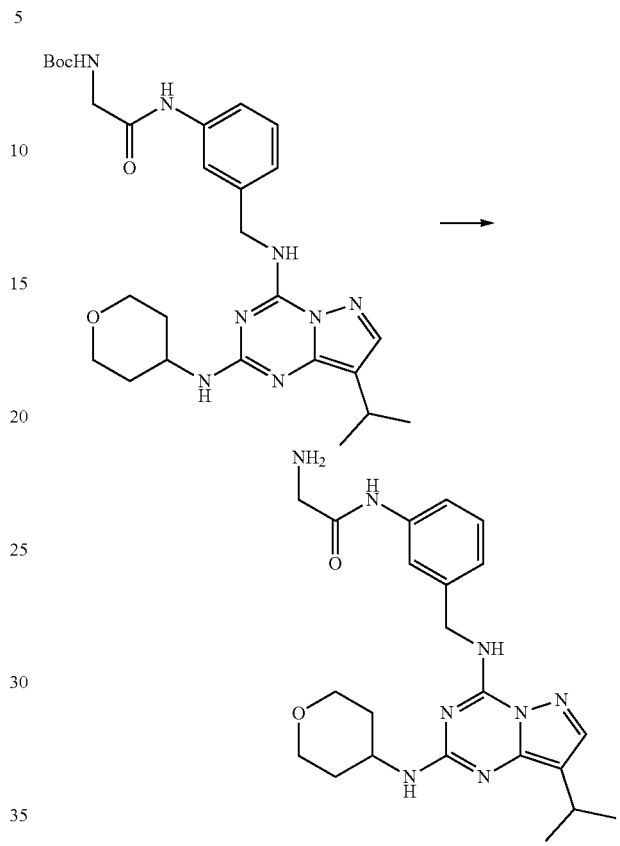

TFA (1 mL) was added to a solution of tert-butyl (2-((3-(((8-isopropyl-2-((tetrahydro-2H-pyran-4-yl)amino)pyrazolo[1,5-a][1,3,5]triazin-4-yl)amino)methyl)phenyl)amino)-2-oxoethyl)carbamate (0.15 g, 0.34 mmol) in DCM (3 mL) at 0° C. Then the reaction mixture allowed to stir at room temperature for 2 h. After completion of the reaction, the reaction mixture was concentrated under vacuum to afford desired title compound (0.15 g, crude). LCMS: m/z=439 (M+H)$^+$.

Step-3: Synthesis of N-(2-((3-(((8-isopropyl-2-((tetrahydro-2H-pyran-4-yl)amino)pyrazolo [1,5-a][1,3,5]triazin-4-yl)amino)methyl)phenyl)amino)-2-oxoethyl)acrylamide

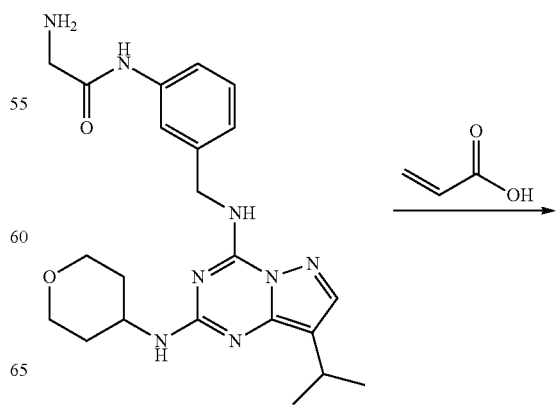

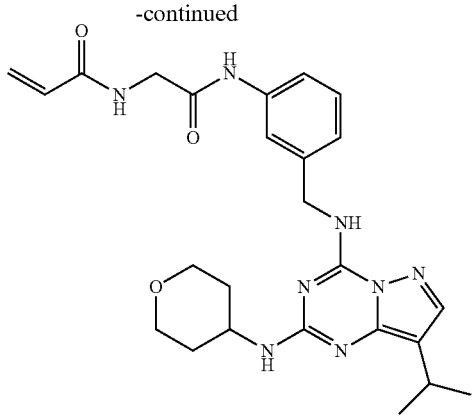

To a cooled solution of 2-amino-N-(3-(((8-isopropyl-2-((tetrahydro-2H-pyran-4-yl)amino)pyrazolo[1,5-a][1,3,5]triazin-4-yl)amino)methyl)phenyl)acetamide (0.127 g, 0.28 mmol) in DCM (5 mL) added TEA (0.08 mL, 0.56 mmol) and stirred for 5 min and added acryloyl chloride (0.026 g, 0.28 mmol) drop wise at 0° C. The reaction mixture was allowed to stir at room temperature for 1 h. After completion of the reaction, the reaction mixture quenched with water and then diluted with DCM (10 mL). Organic layer washed with water followed by brine, dried over $Na_2SO_4$, filtered and concentrated under vacuum and purified by preparative HPLC (Method: A: 0.02% in ammonia in water, B: MeOH: Acetonitrile (1:1), Column: Gemini NX C-18 (150 mm*21.2, 5 μm) to afford the title compound (0.043 g, 43%) as free base. $^1$HNMR (DMSO-$d_6$, 400 MHz): δ 10.08 (s, 1H), 9.92 (s, 1H), 8.50-8.47 (t, 1H), 7.76 (s, 1H), 7.52 (s, 2H), 7.31-7.27 (t, 1H), 7.08 (s, 1H), 6.85 (s, 1H), 6.41-6.34 (m, 1H), 6.17-6.12 (m, 1H), 5.68-5.65 (m, 1H), 4.64 (s, 2H), 3.99-3.97 (d, 2H), 3.87 (s, 3H), 2.95 (s, 3H), 1.87 (s, 2H), 1.50 (s, 2H), 1.28 (s, 6H); LCMS: m/z=493.3 (M+H)$^+$.

The below compounds were prepared by procedure similar to the one described in Example-13 with appropriate variations in reactants, quantities of reagents, in presence of suitable solvents at suitable reaction conditions. The physicochemical characteristics of the compounds are summarized herein below table.

| Compd. No. | Compound structure | Analytical data |
|---|---|---|
| 80 | 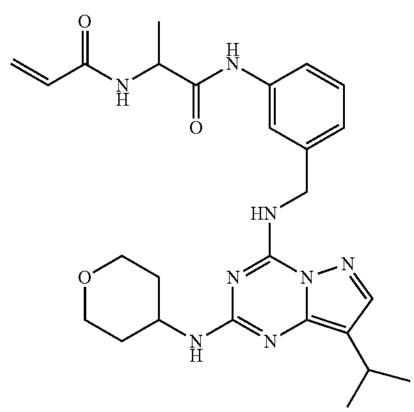 [SMILES: C=CC(=O)NC(C)C(=O)Nc1cccc(CNc2nc(NC3CCOCC3)nc3c(C(C)C)cnn23)c1] | $^1$H NMR (DMSO-$d_6$, 400 MHz): δ 10.05 (s, 1H), 8.70 (s, 1H), 8.40-8.38 (d, 1H), 7.70 (s, 1H), 7.51 (s, 1H), 7.24-7.21 (t, 1H), 7.03-7.00 (d, 1H), 6.82 (s, 1H), 6.36-6.29 (m, 1H), 6.10-6.05 (m, 1H), 5.60-5.57 (m, 1H), 4.58 (s, 1H), 4.50-4.43 (m, 1H), 3.81 (s, 3H), 3.32 (s, 2H), 2.89 (s, 2H), 2.66 (s, 1H), 2.32 (s, 1H), 1.82 (s, 3H), 1.44 (m, 2H), 1.22 (s, 6H); LCMS: m/z = 507.20 (M + H)$^+$. |
| 81 | 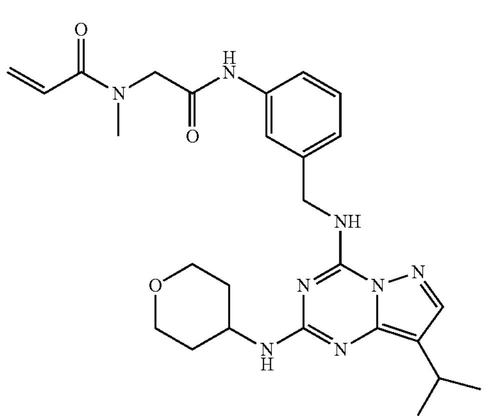 [SMILES: C=CC(=O)N(C)CC(=O)Nc1cccc(CNc2nc(NC3CCOCC3)nc3c(C(C)C)cnn23)c1] | $^1$H NMR (DMSO-$d_6$, 400 MHz): δ 10.09 (d, 1H), 9.0-8.50 (m, 1H), 7.70 (s, 1H), 7.48 (m, 2H), 7.23 (m, 1H), 7.02 (m, 1H), 6.84 (m, 2H), 6.62 (m, 1H), 6.14 (m, 1H), 5.72 (d, 1H), 4.58 (m, 2H), 4.23 (s, 2H), 3.81 (m, 3H), 3.32 (m, 1H), 3.10 (m, 2H), 2.87 (m, 2H), 1.82 (m, 2H), 1.44 (m, 2H), 1.22 (d, 6H); LCMS: m/z = 507.20 (M + H)$^+$. |

| Compd. No. | Compound structure | Analytical data |
|---|---|---|
| 82 | 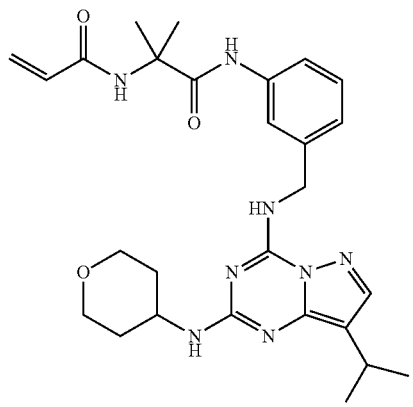 [SMILES: C=CC(=O)NC(C)(C)C(=O)Nc1cccc(CNc2nc(NC3CCOCC3)nc3c(C(C)C)cnn23)c1] | ¹H NMR (DMSO-d₆, 400 MHz): δ 9.39 (s, 1H), 9.0-8.5 (m, 2H), 8.15 (s, 1H), 7.69 (s, 1H), 7.57-7.46 (m, 2H), 7.20 (t, 1H), 6.98 (m, 1H), 6.82 (m, 2H), 6.33 (m, 1H), 6.05 (d, 1H), 5.57 (d, 1H), 4.56 (m, 2H), 3.81 (m, 3H), 2.89 (m, 2H), 1.82 (m, 3H), 1.41 (d, 6H), 1.22 (m, 6H); LCMS: m/z = 521.2 (M + H)⁺. |
| 83 | 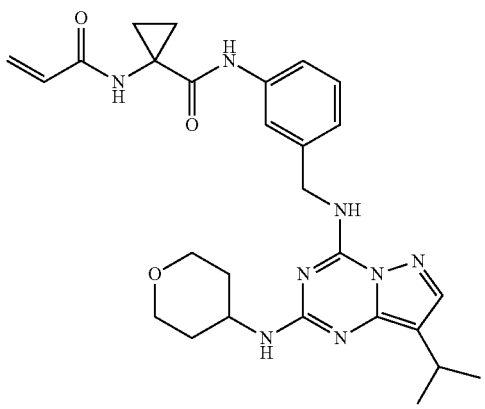 | ¹H NMR (DMSO-d₆, 400 MHz): δ 9.49 (s, 1H), 8.59 (s, 2H), 7.69 (s, 1H), 7.56 (m, 1H), 7.52 (m, 1H), 7.23 (t, 1H), 7.03 (m, 1H), 6.81 (m, 1H), 6.25 (m, 1H), 6.05 (d, 1H), 5.61 (d, 1H), 4.57 (m, 2H), 3.81 (m, 3H), 2.89 (m, 2H), 1.82 (m, 3H), 1.37 (m, 4H), 1.22 (d, 6H), 0.94 (m, 2H); LCMS: m/z = 519.4 (M + H)⁺. |
| 84 | 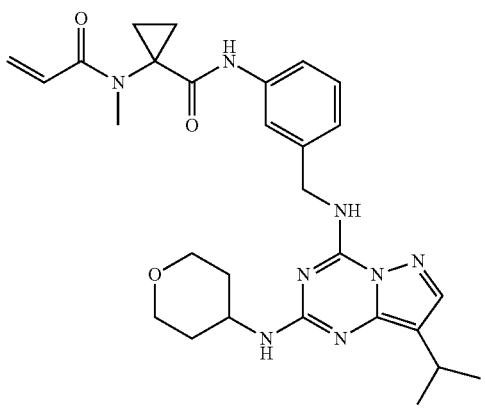 [SMILES: C=CC(=O)N(C)C1(C(=O)Nc2cccc(CNc3nc(NC4CCOCC4)nc4c(C(C)C)cnn34)c2)CC1] | ¹H NMR (DMSO-d₆, 400 MHz): δ 7.69 (s, 1H), 7.57 (m, 2H), 7.42 (m, 1H), 7.23 (t, 1H), 7.06 (d, 1H), 6.7 (m, 1H), 6.64 (m, 1H), 6.15 (m, 1H), 5.67 (d, 1H), 4.55 (m, 2H), 3.79 (m, 3H), 3.35-3.29 (m, 3H), 2.91 (m, 4H), 1.77 (m, 2H), 1.57 (m, 2H), 1.44 (m, 4H), 1.19 (d, 6H); LCMS: m/z = 533.7 (M + H)⁺. |

Example-14: Synthesis of 4-acrylamido-N-(3-(((8-isopropyl-2-((tetrahydro-2H-pyran-4-yl)amino)pyrazolo[1,5-a][1,3,5]triazin-4-yl)amino)methyl)phenyl)-1-methyl-1H-pyrazole-3-carboxamide (Compound-85)

Step-1: Synthesis of N-(3-(((8-isopropyl-2-((tetrahydro-2H-pyran-4-yl)amino)pyrazolo[1,5-a][1,3,5]triazin-4-yl)amino)methyl)phenyl)-1-methyl-4-nitro-1H-pyrazole-3-carboxamide

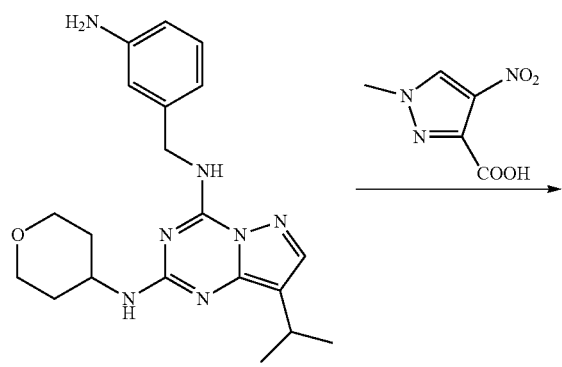

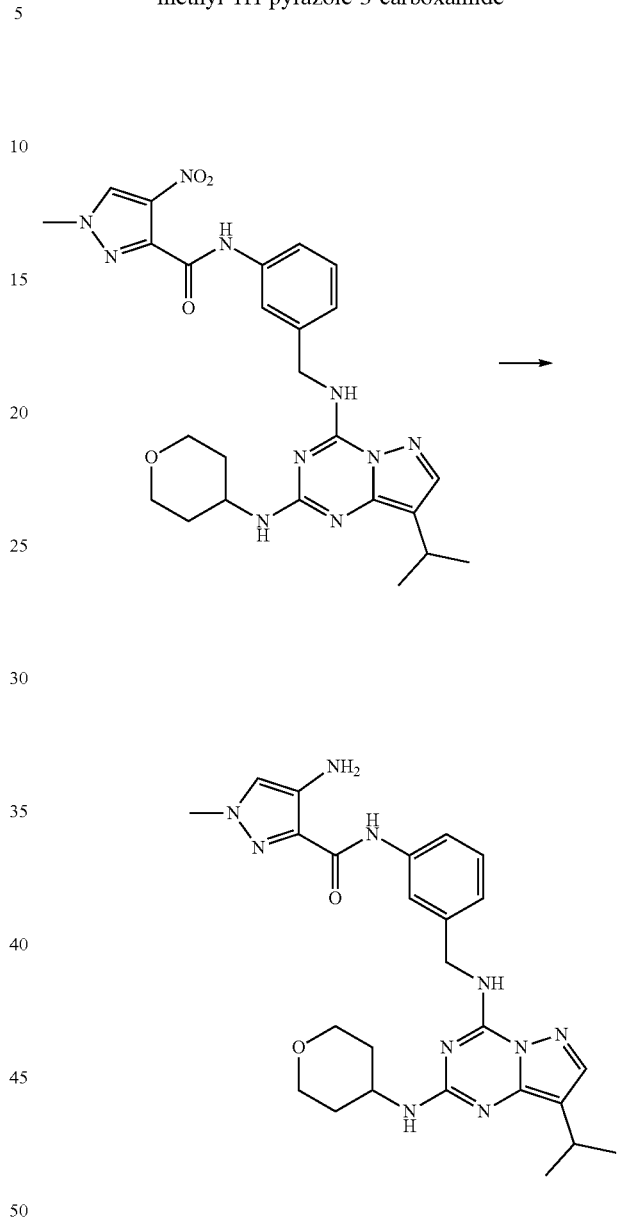

To a cooled solution of 1-methyl-4-nitro-1H-pyrazole-3-carboxylic acid (0.108 g, 0.62 mmol; US 2009/156582A1) in DMF (10 mL) at 0° C. was added HATU (0.3 g, 0.78 mmol) followed by DIPEA (0.2 mL, 1.04 mmol) and finally added N4-(3-aminobenzyl)-8-isopropyl-N2-(tetrahydro-2H-pyran-4-yl)pyrazolo[1,5-a][1,3,5]triazine-2,4-diamine (0.2 g, 0.52 mmol; intermediate-33). The reaction mixture was stirred for 1 h at room temperature. The reaction mixture was quenched with ice-water and diluted with ethyl acetate. The aqueous layer was separated and extracted with ethyl acetate (2×25 mL). The combined organic phase was washed with brine, dried over $Na_2SO_4$, filtered and concentrated the crude residue was purified by 100-200 silica gel column chromatography to afford the title compound (0.23 g, 82%). LCMS: m/z=535.1 $(M+H)^+$.

Step-2: Synthesis of: 4-amino-N-(3-(((8-isopropyl-2-((tetrahydro-2H-pyran-4-yl)amino) pyrazolo[1,5-a][1,3,5]triazin-4-yl)amino)methyl)phenyl)-1-methyl-1H-pyrazole-3-carboxamide To a solution of N-(3-(((8-isopropyl-2-((tetrahydro-2H-pyran-4-yl)amino)pyrazolo[1,5-a][1,3,5]triazin-4-yl)amino) methyl)phenyl)-1-methyl-4-nitro-1H-pyrazole-3-carboxamide (0.35 g, 0.655 mmol) in THF:MeOH:Water (3:2:1 ratio, 15 mL) were added zinc (0.43 g, 6.554 mmol) and ammonium chloride (0.7 g, 13.1 mmol). The reaction mixture was stirred at room temperature for 4 h. After completion of reaction the reaction mixture filtered through celite bed and diluted with ethyl acetate. The aqueous layer was separated and extracted with ethyl acetate (2×25 mL). The combined organic phase was washed with brine, dried over $Na_2SO_4$, filtered and concentrated. The residue was purified by 100-200 silica gel column chromatography to afford desired title compound (0.3 g, 90%). LCMS: m/z=504.9 $(M+H)^+$.

Step-3: Synthesis of 4-acrylamido-N-(3-(((8-isopropyl-2-((tetrahydro-2H-pyran-4-yl)amino)pyrazolo[1,5-a][1,3,5]triazin-4-yl)amino)methyl)phenyl)-1-methyl-1H-pyrazole-3-carboxamide

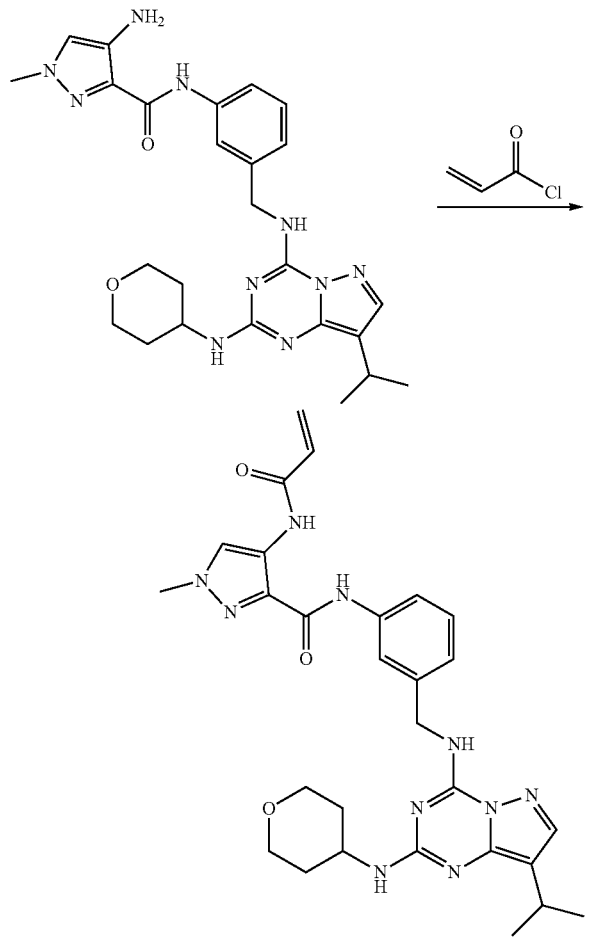

To a cooled solution of 4-amino-N-(3-(((8-isopropyl-2-((tetrahydro-2H-pyran-4-yl)amino)pyrazolo[1,5-a][1,3,5]triazin-4-yl)amino)methyl)phenyl)-1-methyl-1H-pyrazole-3-carboxamide (0.2 g, 0.39 mmol) in DCM (5 mL) was added TEA (0.01 mL, 0.79 mmol) and stirred for 5 min and added acryloyl chloride (0.035 g, 0.39 mmol) in DCM (1 mL) drop wise at 0° C. The reaction mixture was allowed to stir at room temperature for 1 h. After completion of the reaction, the reaction mixture quenched with water and then diluted with DCM (10 mL). Organic layer washed with water followed by brine, dried over $Na_2SO_4$, filtered and concentrated under vacuum and purified by combiflash column by using 100-200 silica gel and ethyl acetate and hexane as eluent to afford the title compound (0.062 g, 28%) $^1$H NMR (DMSO-$d_6$, 400 MHz): δ 10.29 (s, 1H), 9.85 (s, 1H), 8.95-8.70 (m, 1H), 8.42 (s, 1H), 7.90 (s, 1H), 7.74 (s, 2H), 7.32-7.30 (t, 1H), 7.13 (s, 1H), 6.89 (s, 1H), 6.68-6.64 (m, 1H), 6.31-6.26 (d, 1H), 5.82-5.79 (d, 1H), 4.67 (s, 2H), 4.00 (s, 4H), 3.87 (s, 4H), 2.93 (s, 2H), 1.90 (s, 2H), 1.52 (s, 2H), 1.28 (s, 6H); LCMS: m/z=559.1 (M+H)$^+$.

Example-15: Synthesis of 1-acryloyl-N-(3-((8-isopropyl-2-((tetrahydro-2H-pyran-4-yl)amino)pyrazolo[1,5-a][1,3,5]triazin-4-yl)amino)phenyl)azetidine-2-carboxamide (Compound-86)

Step-1: Synthesis of tert-butyl 2-((3-((8-isopropyl-2-((tetrahydro-2H-pyran-4-yl)amino) pyrazolo[1,5-a][1,3,5]triazin-4-yl)amino)phenyl)carbamoyl)azetidine-1-carboxylate

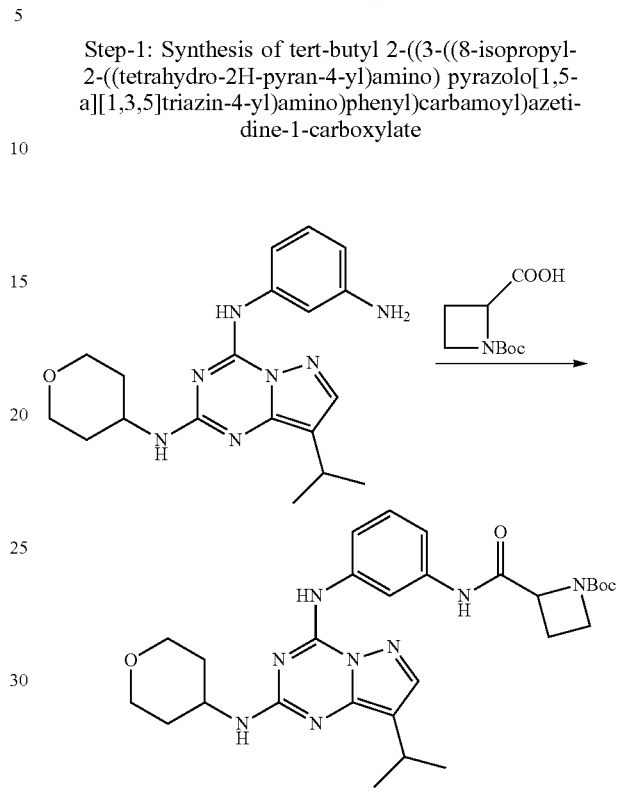

The process of this step was adopted from step-1 of example-3 (0.18 g, 48%). LCMS: m/z=551.6 (M+H)$^+$.

Step-2: Synthesis of N-(3-((8-isopropyl-2-((tetrahydro-2H-pyran-4-yl)amino)pyrazolo[1,5-a][1,3,5]triazin-4-yl)amino)phenyl)azetidine-2-carboxamide

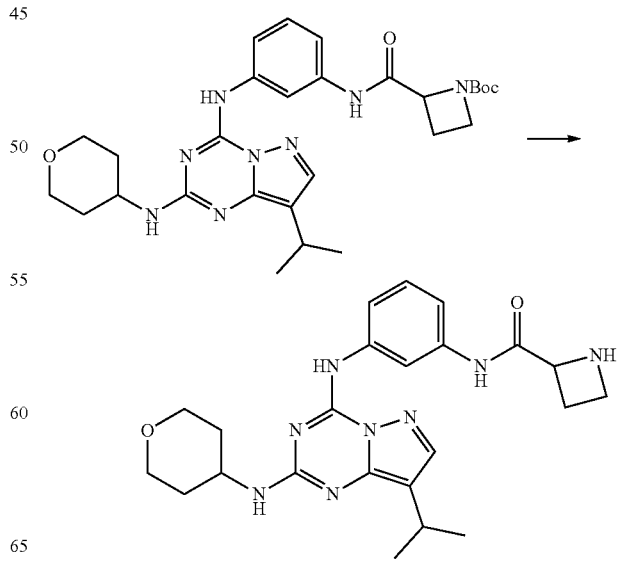

147

The process of this step was adopted from step-2 of example-3 (0.11 g crude). LCMS: m/z=451.3 (M+H)+.

Step-3: Synthesis of 1-acryloyl-N-(3-((8-isopropyl-2-((tetrahydro-2H-pyran-4-yl)amino)pyrazolo[1,5-a][1,3,5]triazin-4-yl)amino)phenyl)azetidine-2-carboxamide

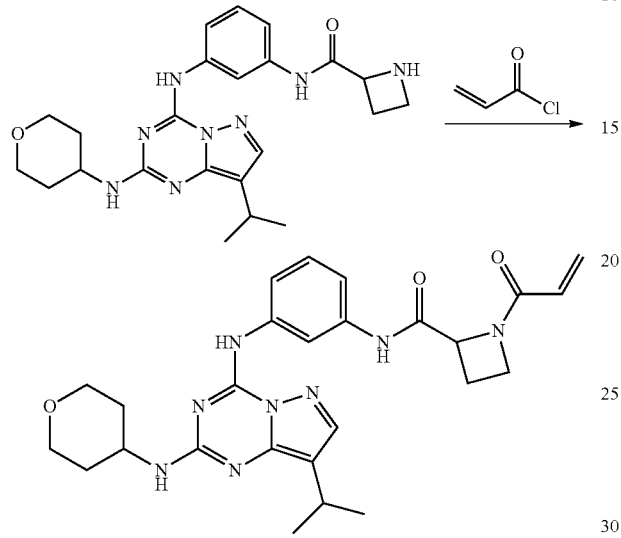

The process of this step was adopted from step-3 of example-3. The obtained crude compound was purified by preparative HPLC (Method: A: water, B: Acetonitrile-Methanol, Column: KINETEX C18: 21.2 mm*150 mm) to afford desired title compound (0.035 g, 35%). $^1$H NMR (DMSO-d$_6$, 400 MHz): δ 10.3-10.1 (m, 1H), 7.82 (s, 1H), 7.50-7.70 (m, 1H), 7.34-7.30 (t, 1H), 7.20-6.90 (d, 1H), 6.40-6.33 (m, 1H), 6.18-6.10 (m, 1H), 5.77-5.62 (m, 1H), 5.61-4.90 (m, 1H), 4.88-4.22 (m, 1H), 4.20-3.91 (m, 4H), 3.42-3.30 (m, 2H), 3.30-2.96 (m, 1H), 2.92-2.68 (m, 2H), 2.34-2.33 (m, 2H), 2.26 (s, 1H), 1.87 (s, 2H), 1.48 (s, 2H), 1.27-1.25 (d, 6H); LCMS: m/z=505.3 (M+H)+.

The below compound was prepared by procedure similar to the one described in Example-15 with appropriate variations in reactants, quantities of reagents, in presence of suitable solvents at suitable reaction conditions. The physicochemical characteristics of the compounds are summarized herein below table.

148

Example-16: Synthesis of 1-acryloyl-N-(3-(((8-ethyl-2-((1-methylpiperidin-4-yl)oxy)pyrazolo [1,5-a][1,3,5]triazin-4-yl)amino)methyl)phenyl)piperidine-4-carboxamide (Compound-88)

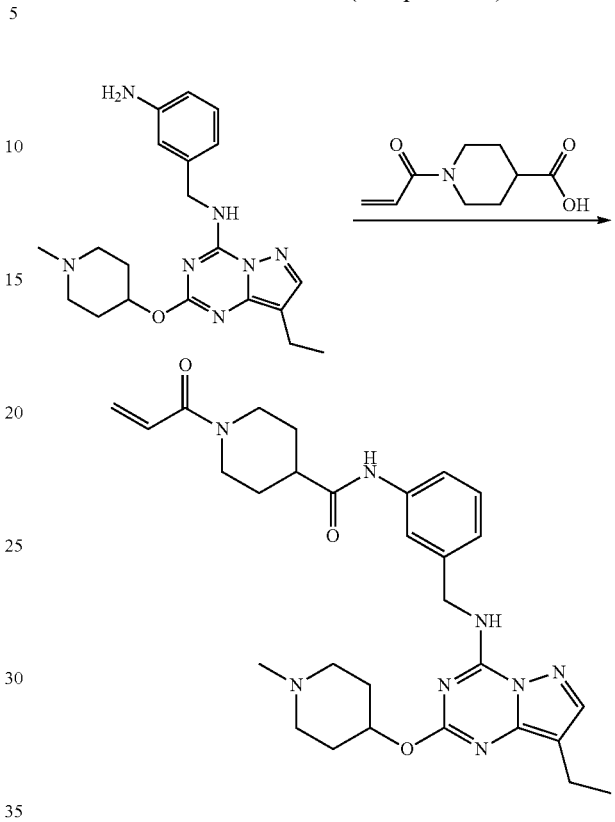

HATU (0.15 g, 0.39 mmol) followed by DIPEA (0.15 g, 1.16 mmol) was added to a cooled solution of 1-acryloylpiperidine-4-carboxylic acid (0.08 g, 0.43 mmol) in dry DMF (5 mL) at 0° C. N-(3-aminobenzyl)-8-ethyl-2-((1-methylpiperidin-4-yl)oxy)pyrazolo[1,5-a][1,3,5]triazin-4-amine (0.15 g, 0.39 mmol, intermediate-40) was added to above reaction mixture and the resulting reaction mixture was stirred for 1 h at room temperature. After completion of reaction, the reaction mixture was quenched with ice-water and diluted with ethyl acetate. The aqueous layer was separated and extracted with ethyl acetate (2×50 mL). The combined organic phase was washed with brine, dried over Na$_2$SO$_4$, filtered and concentrated. The residue was purified by prep. HPLC Column: XBRIDGE (19 mm×150 mm),

| Compd No | Compound structure | Analytical data |
|---|---|---|
| 87 | 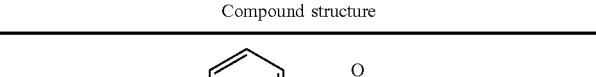 | $^1$H NMR (DMSO-d$_6$, 400 MHz): δ 10.1-9.87 (m, 2H), 8.25 (s, 1H), 8.05-8.04 (d, 1H), 7.81 (s, 2H), 7.52 (s, 1H), 7.29-7.25 (t, 1H), 7.20 (s, 1H), 6.90 (s, 1H), 5.57-5.54 (m, 1H), 3.91-3.85 (m, 4H), 2.96-2.93 (m, 2H), 2.67 (s, 1H), 2.33 (s, 2H), 1.84-1.74 (m, 6H), 1.63-1.48 (m, 6H), 1.26-1.24 (d, 6H); LCMS: m/z = 547.75 (M + H)+. |

0.01% HCOOH (A), Acetonitrile (B) to afford desired title compound (0.04 g, 18.69%). ¹HNMR (DMSO-d₆, 400 MHz): δ 9.93 (s, 1H), 9.30-9.27 (t, 1H), 7.94 (s, 1H), 7.55 (s, 1H), 7.51-7.49 (d, 1H), 7.25-7.21 (t, 1H), 7.01-6.99 (d, 1H), 6.84-6.77 (m, 1H), 6.11-6.06 (m, 1H), 5.68-5.64 (m, 1H), 4.90 (s, 1H), 4.61-4.60 (d, 2H), 4.44-4.41 (d, 1H), 4.10-4.07 (d, 1H), 3.15-3.05 (m, 2H), 2.74-2.52 (m, 4H), 2.35-2.25 (m, 4H), 1.95-1.85 (m, 2H), 1.81-1.78 (d, 2H), 1.75-1.65 (m, 3H), 1.55-1.35 (m, 3H), 1.23-1.17 (m, 3H); LCMS: m/z=548.1 (M+1)+.

The below compounds were prepared by procedure similar to the one described in Example-16 with appropriate variations in reactants, quantities of reagents, in presence of suitable solvents at suitable reaction conditions. The physicochemical characteristics of the compounds are summarized herein below table.

| Compd. No. | Compound structure | Analytical data |
|---|---|---|
| 89 | 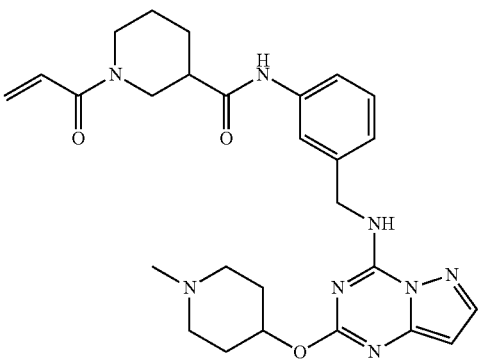 [SMILES: C=CC(=O)N1CCCC(C(=O)Nc2cccc(CNc3nc(OC4CCN(C)CC4)nc4ccnn34)c2)C1] | ¹H NMR (DMSO-d₆, 400 MHz): δ 10.05-9.97 (d, 1H), 9.39-9.36 (t, 1H), 8.05 (s, 1H), 7.53-7.51 (m, 2H), 7.27-7.23 (t, 1H), 7.04-7.02 (d, 1H), 6.95-6.75 (m, 1H), 6.17 (s, 1H), 6.11-6.07 (d, 1H), 5.68-5.55 (t, 1H), 4.95-4.81 (m, 1H), 4.64-4.62 (d, 2H), 4.51-4.22 (m, 1H), 4.15-3.95 (m, 1H), 3.29-3.15 (m, 1H), 3.15-2.95 (m, 1H), 2.85-2.55 (m, 2H), 2.49-2.35 (m, 1H), 2.25-2.05 (m, 4H), 1.95-1.85 (m, 2H), 1.80-1.55 (m, 3H), 1.45-1.15 (m, 3H), 0.88-0.84 (t, 1H); LCMS: m/z = 519 (M + H)⁺. |
| 90 | 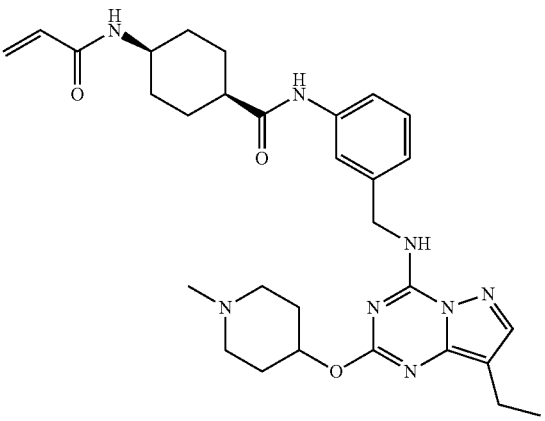 [SMILES: C=CC(=O)N[C@H]1CC[C@@H](C(=O)Nc2cccc(CNc3nc(OC4CCN(C)CC4)nc4c(CC)cnn34)c2)CC1] | ¹H NMR (DMSO-d₆, 400 MHz): δ 9.80 (s, 1H), 9.28-9.25 (t, 1H), 8.03-8.01 (d, 1H), 7.94 (s, 1H), 7.56-7.54 (d, 1H), 7.50 (s, 1H), 7.24-7.20 (t, 1H), 6.99-6.97 (d, 1H), 6.38-6.31 (m, 1H), 6.08-6.01 (m, 1H), 5.55-5.52 (m, 1H), 4.95-4.75 (m, 1H), 4.61-4.60 (d, 2H), 3.88 (s, 1H), 2.67-2.52 (m, 3H), 2.49-2.18 (m, 1H), 2.11-1.92 (m, 4H), 1.90-1.49 (m, 11H), 1.29-1.19 (m, 3H), 0.87-0.82 (m, 3H); LCMS: m/z = 561.2 (M + H)⁺. |
| 91 | 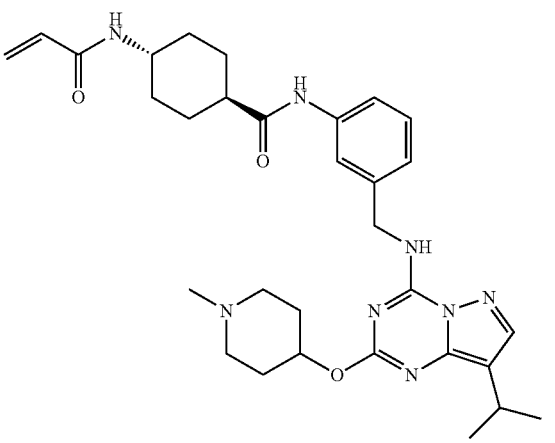 [SMILES: C=CC(=O)N[C@H]1CC[C@H](C(=O)Nc2cccc(CNc3nc(OC4CCN(C)CC4)nc4c(C(C)C)cnn34)c2)CC1] | ¹H NMR (DMSO-d₆, 400 MHz): δ 9.77 (s, 1H), 7.95-7.93 (d, 1H), 7.88 (s, 1H), 7.48-7.46 (m, 2H), 7.19-7.15 (t, 1H), 6.95-6.93 (d, 1H), 6.16-6.10 (m, 1H), 6.03-5.98 (m, 1H), 5.52-5.49 (m, 1H), 4.78 (m, 2H), 4.55 (s, 4H), 2.94-2.90 (m, 2H), 2.55 (m, 2H), 2.28-2.20 (m, 1H), 2.11 (s, 3H), 2.07-2.04 (m, 3H), 1.88-1.79 (m, 3H), 1.58-1.56 (m, 2H), 1.44-1.41 (d, 2H), 1.22-1.13 (m, 8H); LCMS: m/z = 575.4 (M + H)⁺. |

| Compd. No. | Compound structure | Analytical data |
|---|---|---|
| 92 & 93 | 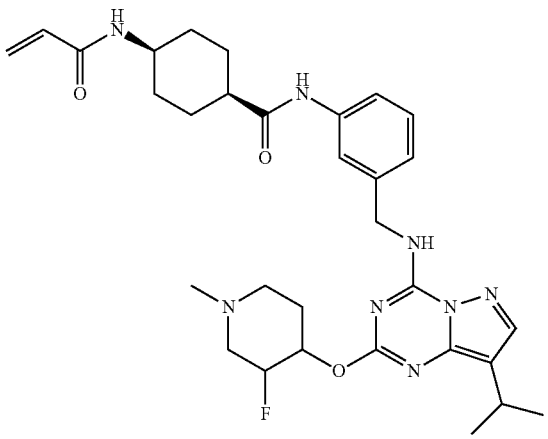 [SMILES: C=CC(=O)N[C@H]1CC[C@@H](C(=O)Nc2cccc(CNc3nc(OC4CCN(C)CC4F)nc4c(C(C)C)cnn34)c2)CC1] | Isomer-I: ¹H NMR (DMSO-d₆, 400 MHz): δ 9.81 (s, 1H), 9.38-9.37 (t, 1H), 8.03-8.01 (d, 1H), 7.96 (s, 1H), 7.57-7.55 (d, 1H), 7.50 (s, 1H), 7.25-7.21 (t, 1H), 7.00-6.99 (d, 1H), 6.39-6.32 (m, 1H), 5.56-5.53 (d, 1H), 4.95-4.90 (m, 1H), 4.75-4.61 (m, 3H), 3.89 (s, 1H), 3.00-2.95 (m, 2H), 2.67-2.60 (m, 1H), 2.38-2.33 (m, 2H), 2.22 (s, 3H), 2.18-2.07 (m, 3H), 1.80-1.54 (m, 9H), 1.27-1.25 (d, 6H); LCMS: m/z = 594.5 (M + H)⁺.<br>Isomer-2: ¹H NMR (DMSO-d₆, 400 MHz): δ 9.81 (s, 1H), 9.37-9.34 (t, 1H), 8.03-8.01 (d, 1H), 7.96 (s, 1H), 7.57-7.55 (d, 1H), 7.52 (s, 1H), 7.25-7.21 (t, 1H), 7.00-6.99 (d, 1H), 6.39-6.32 (m, 1H), 5.56-5.53 (d, 1H), 4.98-4.91 (m, 1H), 4.79 (s, 1H), 4.63-4.61 (d, 2H), 3.89 (s, 1H), 3.01-2.88 (m, 2H), 2.67-2.62 (m, 1H), 2.28-2.23 (m, 2H), 2.18 (s, 3H), 2.17-2.07 (m, 2H), 1.95-1.56 (m, 10H), 1.27-1.25 (d, 6H); LCMS: m/z = 594.5 (M + H)⁺. |
| 94 | 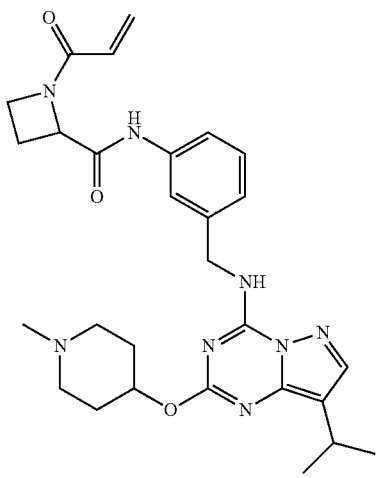 [SMILES: C=CC(=O)N1CCC1C(=O)Nc1cccc(CNc2nc(OC3CCN(C)CC3)nc3c(C(C)C)cnn23)c1] | ¹H NMR (DMSO-d₆, 400 MHz): δ 10.16 (s, 1H), 9.31-9.28 (t, 1H), 7.92 (s, 1H), 7.55-7.54 (m, 2H), 7.29-7.25 (t, 1H), 7.05-7.03 (d, 1H), 6.37-6.30 (m, 1H), 6.14-6.06 (m, 2H), 5.73-5.74 (m, 1H), 4.83-4.79 (m, 2H), 4.62-4.61 (d, 1H), 4.19-4.18 (m, 2H), 3.90 (m, 1H), 2.98-2.94 (m, 1H), 2.67-2.59 (m, 2H), 2.15-2.06 (m, 5H), 1.93-1.91 (m, 2H), 1.63-1.60 (d, 2H), 1.26-1.24 (d, 6H); LCMS: m/z = 533.2 (M + H)⁺. |
| 95 | 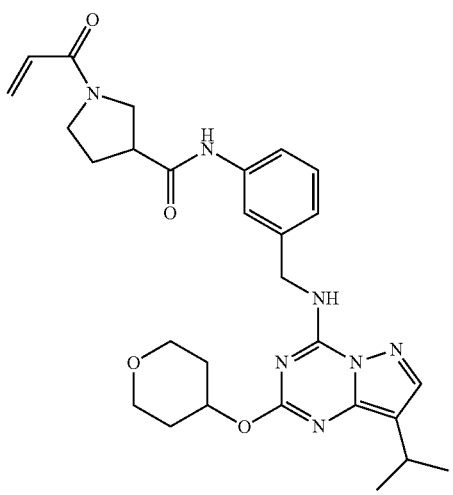 [SMILES: C=CC(=O)N1CCC(C(=O)Nc2cccc(CNc3nc(OC4CCOCC4)nc4c(C(C)C)cnn34)c2)C1] | ¹H NMR (DMSO-d₆, 400 MHz): δ 10.05-10.03 (d, 1H), 9.30-9.27 (t, 1H), 7.90 (s, 1H), 7.51-7.47 (m, 2H), 7.23-7.19 (t, 1H), 7.00-6.98 (d, 1H), 6.57-6.50 (m, 1H), 6.11-6.06 (m, 1H), 5.63-5.60 (d, 1H), 5.00-4.95 (m, 1H), 4.56 (s, 2H), 3.79-3.74 (m, 2H), 3.68-3.63 (m, 2H), 3.58-3.48 (m, 4H), 3.17-3.05 (m, 1H), 2.96-2.90 (m, 1H), 2.13-2.02 (m, 2H), 2.02-1.93 (m, 2H), 1.58-1.51 (m, 2H), 1.22-1.20 (d, 6H); LCMS: m/z = 534.3 (M + H)⁺. |

-continued

| Compd. No. | Compound structure | Analytical data |
|---|---|---|
| 96 | 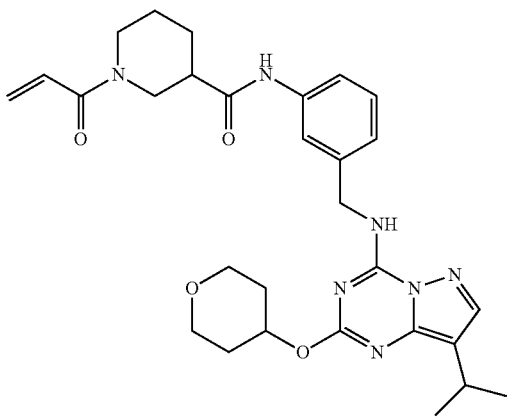 [SMILES: C=CC(=O)N1CCCC(C(=O)Nc2cccc(CNc3nc(OC4CCOCC4)nc4c(C(C)C)cnn34)c2)C1] | ¹H NMR (DMSO-d₆, 400 MHz): δ 10.00-9.98 (d, 1H), 9.34-9.31 (t, 1H), 7.95 (s, 1H), 7.51 (s, 2H), 7.27-7.22 (m, 2H), 7.10 (s, 1H), 7.03-7.01 (d, 1H), 6.97 (s, 1H), 6.90-6.79 (m, 1H), 6.11-6.07 (d, 1H), 5.68-5.63 (t, 1H), 5.02 (s, 1H), 4.62-4.61 (d, 2H), 4.49-4.28 (m, 2H), 4.10-4.00 (m, 2H), 3.84-3.80 (m, 1H), 3.23-3.17 (m, 1H), 3.07-2.94 (m, 2H), 2.78-2.67 (m, 1H), 2.33 (m, 1H), 1.97-1.94 (m, 2H), 1.73-1.56 (m, 4H), 1.27-1.25 (d, 6H); LCMS: m/z = 548.4 (M + H)⁺. |
| 97 | 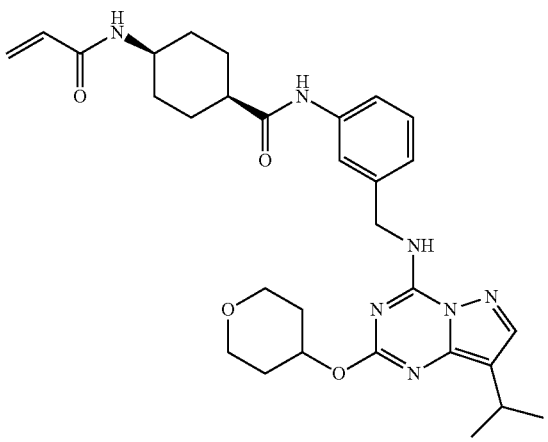 [SMILES: C=CC(=O)N[C@H]1CC[C@@H](C(=O)Nc2cccc(CNc3nc(OC4CCOCC4)nc4c(C(C)C)cnn34)c2)CC1] | ¹H NMR (DMSO-d₆, 400 MHz): δ 9.81 (s, 1H), 9.31-9.28 (t, 1H), 8.32 (s, 1H), 8.02-8.00 (d, 1H), 7.94 (s, 1H), 7.55-7.51 (m, 2H), 7.25-7.21 (t, 1H), 7.00-6.98 (d, 1H), 6.39-6.32 (m, 1H), 6.08-6.03 (m, 1H), 5.56-5.53 (m, 1H), 5.04-4.99 (m, 1H), 4.61-4.60 (d, 2H), 3.88-3.79 (m, 3H), 3.46-3.40 (t, 2H), 3.05-2.94 (m, 1H), 2.38 (m, 1H), 1.98-1.94 (m, 2H), 1.80-1.70 (m, 4H), 1.63-1.50 (m, 5H), 1.26-1.25 (d, 6H); LCMS: m/z = 562.4 (M + H)⁺. |
| 98 & 99 | 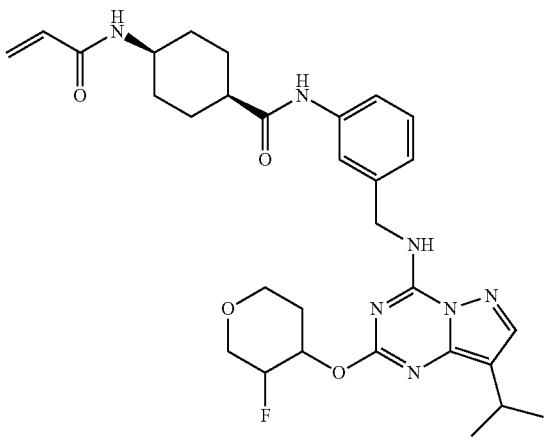 [SMILES: C=CC(=O)N[C@H]1CC[C@@H](C(=O)Nc2cccc(CNc3nc(OC4CCOCC4F)nc4c(C(C)C)cnn34)c2)CC1] | Isomer-1: ¹H NMR (CDCl₃-d₆, 400 MHz): δ 7.72 (s, 1H), 7.63 (s, 1H), 7.41-7.35 (m, 2H), 7.29-7.26 (m, 1H), 7.08-7.06 (d, 1H), 6.95-6.85 (m, 1H), 6.29-6.24 (m, 1H), 6.11-6.04 (m, 1H), 5.95-5.85 (d, 1H), 5.63-5.60 (m, 1H), 5.40-5.25 (m, 1H), 4.85-4.74 (m, 2H), 4.15-3.85 (m, 3H), 3.65-3.55 (m, 2H), 3.09-3.06 (m, 1H), 2.38-2.36 (m, 2H), 1.88-1.80 (m, 8H), 1.29-1.27 (d, 6H); LCMS: m/z = 580.1 (M + H)⁺.<br>Isomer-2: ¹HNMR (CDCl₃-d₆, 400 MHz): δ 7.71 (s, 1H), 7.56 (s, 1H), 7.47 (s, 1H), 7.43-7.41 (d, 1H), 7.27-7.23 (m, 3H), 7.04-7.02 (m, 2H), 6.28-6.23 (m, 1H), 6.10-6.03 (m, 1H), 5.94-5.84 (d, 1H), 5.62-5.59 (d, 1H), 5.35-4.90 (m, 2H), 4.76-4.73 (m, 2H), 4.25-4.05 (m, 3H), 3.75-3.51 (m, 2H), 3.06-3.02 (m, 1H), 2.45-2.35 (m, 2H), 2.05-1.70 (m, 7H), 1.28-1.27 (d, 6H); LCMS: m/z = 580.1 (M + H)⁺. |

| Compd. No. | Compound structure | Analytical data |
|---|---|---|
| 100 | 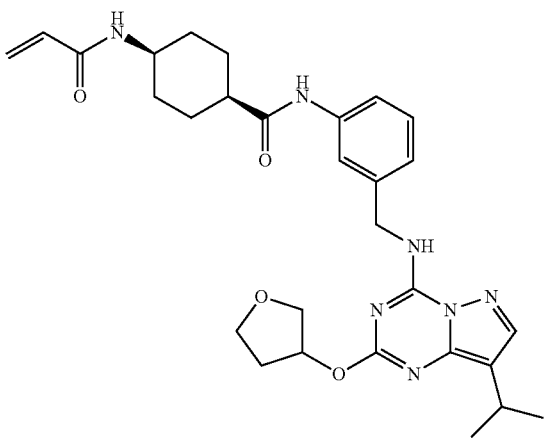 [SMILES: C=CC(=O)N[C@H]1CC[C@@H](C(=O)Nc2cccc(CNc3nc(OC4CCOC4)nc4c(C(C)C)cnn34)c2)CC1] | $^1$H NMR (DMSO-d$_6$, 400 MHz): δ 9.76 (s, 1H), 9.26 (t, 1H), 7.98-7.96 (d, 1H), 7.90 (s, 1H), 7.53-7.51 (d, 1H), 7.46 (s, 1H), 7.20-7.17 (m, 1H), 6.96-6.94 (d, 1H), 6.34-6.27 (m, 1H), 6.04-5.99 (dd, 1H), 5.51-5.48 (dd, 1H), 5.37-5.35 (m, 1H), 4.57-4.56 (d, 2H), 3.84-3.80 (m, 2H), 3.77-3.66 (m, 3H), 2.15-2.12 (m, 2H), 1.98-1.96 (m, 2H), 1.75-1.64 (m, 4H), 1.51-1.45 (m, 4H), 1.23-1.21 (d, 6H); LCMS: m/z = 548.1 (M + H)$^+$. |
| 101 | 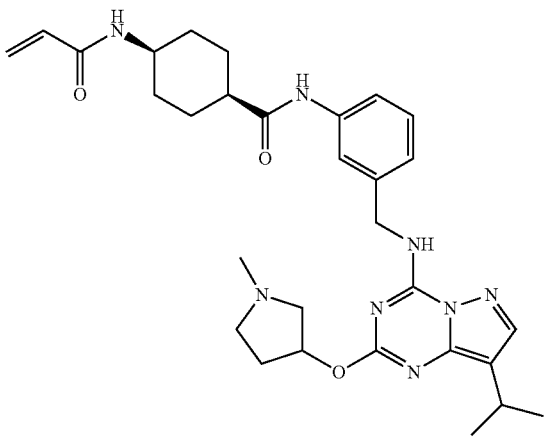 [SMILES: C=CC(=O)N[C@H]1CC[C@@H](C(=O)Nc2cccc(CNc3nc(OC4CCN(C)C4)nc4c(C(C)C)cnn34)c2)CC1] | $^1$H NMR (DMSO-d$_6$, 400 MHz): δ 9.81 (s, 1H), 9.27 (t, 1H), 8.03-8.01 (d, 1H), 7.94 (s, 1H), 7.58-7.56 (d, 1H), 7.49 (s, 1H), 7.25-7.21 (t, 1H), 7.00-6.98 (d, 1H), 6.39-6.32 (m, 1H), 6.08-6.03 (dd, 1H), 5.55-5.52 (dd, 1H), 5.37 (m, 1H), 4.61-4.60 (d, 2H), 3.9 (m, 1H), 3.40-3.38 (m, 2H), 2.99-2.96 (m, 1H), 2.67 (m, 1H), 2.66-2.64 (m, 2H), 2.37-2.35 (m, 2H), 2.25 (m, 3H), 1.80-1.77 (m, 3H), 1.58-1.53 (m, 3H), 1.27-1.26 (d, 6H), 1.10-1.07 (t, 2H); LCMS: m/z = 560.8 (M + H)$^+$. |
| 102 | 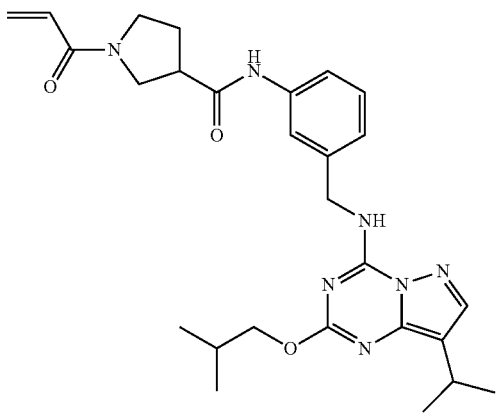 [SMILES: C=CC(=O)N1CCC(C(=O)Nc2cccc(CNc3nc(OCC(C)C)nc4c(C(C)C)cnn34)c2)C1] | $^1$H NMR (DMSO-d$_6$, 400 MHz): δ 10.08-10.07 (d, 1H), 9.27-9.24 (t, 1H), 7.94 (s, 1H), 7.54 (s, 2H), 7.27-7.23 (t, 1H), 7.05-7.03 (d, 1H), 6.61-6.54 (m, 1H), 6.15-6.10 (m, 1H), 5.76-5.64 (m, 1H), 4.63-4.62 (d, 2H), 4.03-4.01 (d, 2H), 3.80-3.63 (m, 2H), 3.57-3.47 (m, 2H), 3.21-3.08 (m, 1H), 3.02-2.96 (m, 1H), 2.18-1.94 (m, 3H), 1.27-1.25 (m, 6H), 0.94-0.92 (d, 6H); LCMS: m/z = 506.4 (M + H)$^+$. |

| Compd. No. | Compound structure | Analytical data |
|---|---|---|
| 103 | 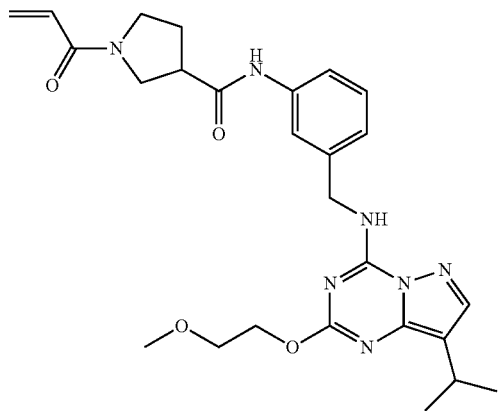 [SMILES: C=CC(=O)N1CCC(C(=O)Nc2cccc(CNc3nc(OCCOC)nc4c(C(C)C)cnn34)c2)C1] | $^1$H NMR (DMSO-d$_6$, 400 MHz): δ 10.09 (d, 1H), 9.32 (t, 1H), 7.95 (s, 1H), 7.57 (d, 1H), 7.51 (d, 1H), 7.27 (t, 1H), 7.05 (d, 1H), 6.62 (m, 1H), 6.15 (d, 1H), 5.67 (d, 1H), 4.63-4.61 (d, 2H), 4.36-4.34 (d, 2H), 3.72-3.67 (m, 3H), 3.59-3.53 (m, 1H), 3.46-3.26 (m, 6H), 3.20 (m, 1H), 2.18-2.08 (m, 2H), 1.27-1.25 (d, 6H); LCMS: m/z = 506.15 (M − H)$^-$. |
| 104 | 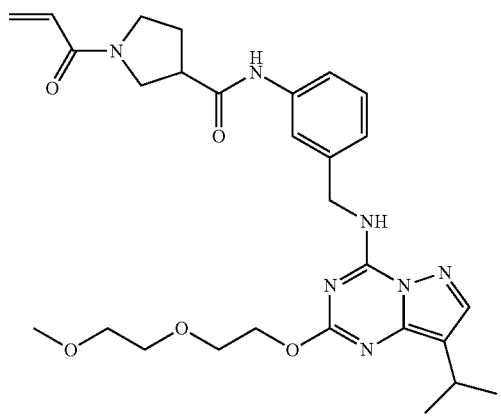 [SMILES: C=CC(=O)N1CCC(C(=O)Nc2cccc(CNc3nc(OCCOCCOC)nc4c(C(C)C)cnn34)c2)C1] | $^1$H NMR (DMSO-d$_6$, 400 MHz): δ 10.08 (d, 1H), 9.32 (t, 1H), 7.95 (s, 1H), 7.57 (s, 1H), 7.50 (s, 1H), 7.27 (t, 1H), 7.04 (d, 1H), 6.61 (m, 1H), 6.15 (d, 1H), 5.6 (d, 1H), 4.63-4.61 (d, 2H), 4.35-4.33 (d, 2H), 3.82-3.5 (m, 3H), 3.53-3.42 (m, 3H), 3.41-3.30 (m, 2H), 3.21-2.97 (m, 6H), 3.00 (m, 1H), 2.19-2.09 (m, 2H), 1.33-1.25 (d, 6H); LCMS: m/z = 550.2 (M− H)$^-$; |
| 105 | 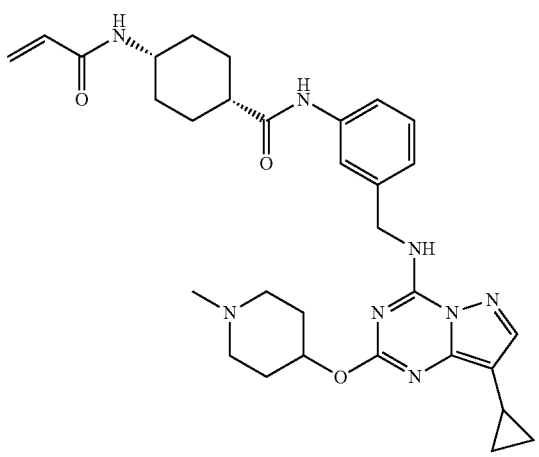 [SMILES: C=CC(=O)N[C@H]1CC[C@@H](C(=O)Nc2cccc(CNc3nc(OC4CCN(C)CC4)nc4c(C5CC5)cnn34)c2)CC1] | $^1$H NMR (DMSO-d$_6$, 400 MHz): δ 9.80 (s, 1H), 9.30-9.15 (t, 1H), 8.02-8.01 (d, 1H), 7.85 (s, 1H), 7.55-7.53 (d, 1H), 7.49 (s, 1H), 7.24-7.20 (t, 1H), 6.98-6.96 (d, 1H), 6.38-6.32 (m, 1H), 6.08-6.03 (m, 1H), 5.56-5.52 (m, 1H), 4.81-4.80 (m, 1H), 4.60-4.59 (d, 2H), 3.88 (s, 1H), 2.67-2.58 (m, 2H), 2.45-2.25 (m, 1H), 2.16 (s, 3H), 2.10-2.05 (t, 2H), 1.92-1.85 (m, 2H), 1.80-1.50 (m, 10H), 1.10-1.07 (t, 1H), 0.84-0.74 (m, 4H); LCMS: m/z = 572.9 (M + H)$^+$. |

Example-17: Synthesis of 1-acryloyl-N-(3-(((8-isopropyl-2-(piperidin-4-yloxy)pyrazolo[1,5-a][1,3,5]triazin-4-yl)amino)methyl)phenyl)piperidine-4-carboxamide (Compound-106)

Step-1: Synthesis of tert-butyl 4-((4-((3-(1-acryloylpiperidine-4-carboxamido)benzyl)amino)-8-isopropylpyrazolo[1,5-a][1,3,5]triazin-2-yl)oxy)piperidine-1-carboxylate

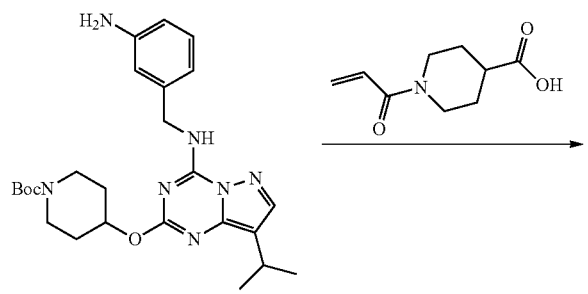

The process of this step was adopted from example-16. The obtained crude compound was purified by combiflash to afford the title compound (0.1 g, 50%). LCMS: m/z=647.4 (M+H)+.

Step-2: Synthesis of 1-acryloyl-N-(3-(((8-isopropyl-2-(piperidin-4-yloxy)pyrazolo[1,5-a][1,3,5]triazin-4-yl)amino)methyl)phenyl)piperidine-4-carboxamide

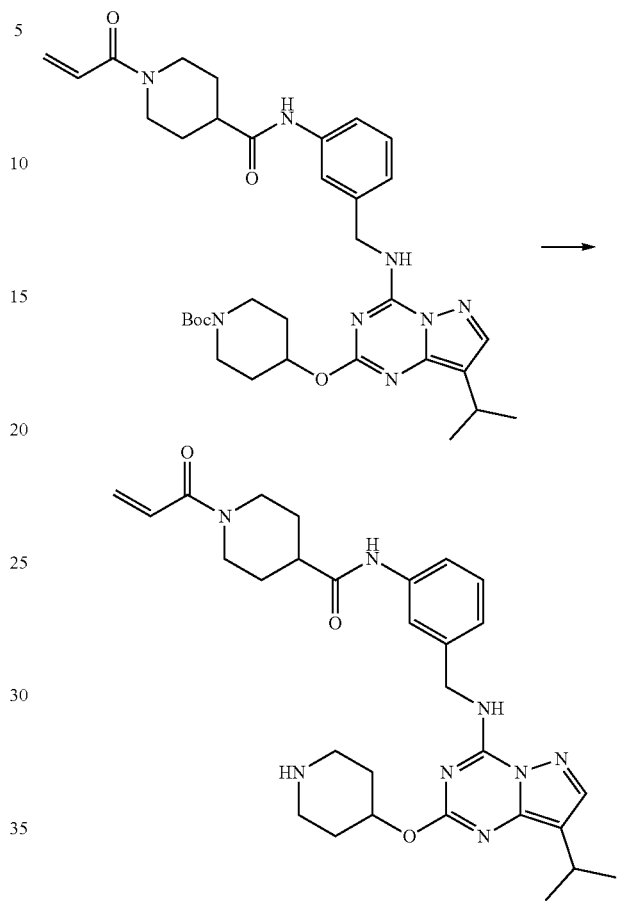

TFA (1 mL) was added to a solution of tert-butyl 4-((4-((3-(1-acryloylpiperidine-4-carboxamido)benzyl)amino)-8-isopropylpyrazolo[1,5-a][1,3,5]triazin-2-yl)oxy)piperidine-1-carboxylate (0.1 g, 0.15 mmol) in DCM (10 mL) at 0° C. Then the reaction mixture allowed to stir at room temperature for 2 h. After completion of the reaction, the reaction mixture was concentrated under vacuum and purified by prep. HPLC (Method: A: 0.01% Ammonia in water, B: Acetonitrile-Methanol, Column: EVA-C-18 (21.2 mm*150 mm, 5 μm)) to afford desired title compound (0.06 g, 22%). $^1$H NMR (DMSO-d$_6$, 400 MHz): δ 9.93 (s, 1H), 9.39-9.36 (t, 1H), 8.48 (s, 1H), 8.38 (s, 1H), 7.97 (s, 1H), 7.59 (s, 1H), 7.48-7.46 (d, 1H), 7.25-7.21 (t, 1H), 7.02-7.00 (d, 1H), 6.84-6.77 (m, 1H), 6.11-6.07 (m, 1H), 5.68-5.65 (m, 1H), 5.11 (s, 1H), 4.63-4.61 (d, 2H), 4.45-4.42 (d, 1H), 4.11-4.08 (m, 2H), 3.23 (m, 2H), 3.11-3.08 (m, 3H), 3.01-2.94 (m, 1H), 2.70-2.64 (m, 1H), 2.33 (m, 1H), 2.08 (m, 2H), 1.86-1.78 (m, 3H), 1.49-1.40 (m, 2H), 1.27-1.25 (d, 5H); LCMS: m/z=547.4 (M+H)+.

The below compound was prepared by procedure similar to the one described in Example-17 with appropriate variations in reactants, quantities of reagents, in presence of suitable solvents at suitable reaction conditions. The physicochemical characteristics of the compounds are summarized herein below table.

| Compd. No. | Compound structure | Analytical data |
|---|---|---|
| 107 | 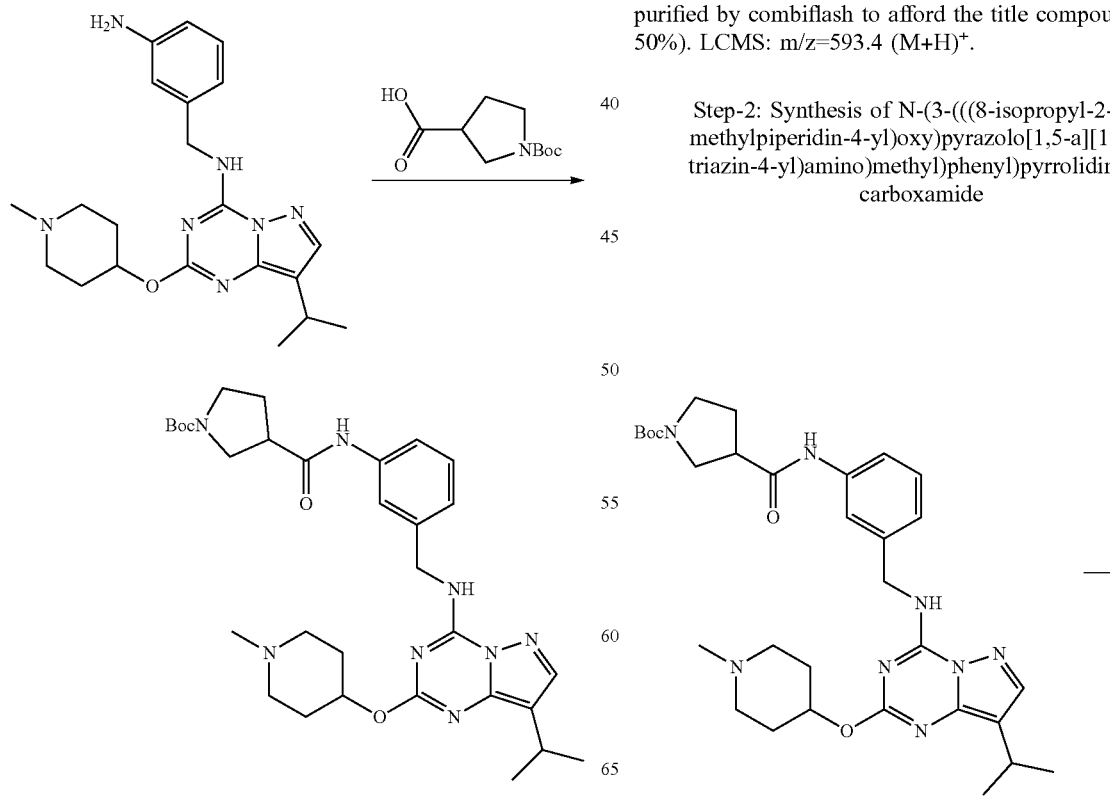 | ¹H NMR (DMSO-d₆, 400 MHz): δ 9.92 (s, 1H), 8.36 (s, 1H), 7.95 (s, 1H), 7.53-7.52 (m, 2H), 7.25-7.21 (t, 1H), 7.01-6.99 (d, 1H), 6.84-6.77 (m, 1H), 6.11-6.06 (m, 1H), 5.67-5.64 (m, 1H), 4.60 (s, 2H), 4.44-4.41 (d, 1H), 4.26-4.23 (t, 2H), 4.10-4.07 (m, 2H), 3.6 (s, 2H), 3.16-2.95 (m, 3H), 2.78-2.75 (t, 1H), 2.70-2.57 (m, 2H), 1.81-1.68 (m, 3H), 1.65-1.59 (m, 2H), 1.51-1.43 (m, 2H), 1.27-1.25 (d, 6H); LCMS: m/z = 535.4 (M + H)⁺. |

Example-18: Synthesis of 1-acryloyl-N-(3-(((8-isopropyl-2-((1-methylpiperidin-4-yl)oxy) pyrazolo[1,5-a][1,3,5]triazin-4-yl)amino)methyl)phenyl)pyrrolidine-3-carboxamide (Compound-108)

Step-1: Synthesis of tert-butyl 3-((3-(((8-isopropyl-2-((1-methylpiperidin-4-yl)oxy)pyrazolo[1,5-a][1,3,5]triazin-4-yl)amino)methyl)phenyl)carbamoyl)pyrrolidine-1-carboxylate To a cooled solution of 1-(tert-butoxycarbonyl)pyrrolidine-3-carboxylic acid (0.16 g, 0.75 mmol) in DMF (4 mL) at 0° C. was added HATU (0.36 g, 0.94 mmol) and DIPEA (0.21 mL, 1.26 mmol) and finally added N-(3-aminobenzyl)-8-isopropyl-2-((1-methylpiperidin-4-yl)oxy)pyrazolo[1,5-a][1,3,5]triazin-4-amine (0.25 g, 0.63 mmol, Intermediate-41). The reaction mixture was stirred for 2 h at room temperature. The reaction mixture was quenched with ice-water and diluted with ethyl acetate. The aqueous layer was separated and extracted with ethyl acetate (2×25 mL). The combined organic phase was washed with brine, dried over Na₂SO₄, filtered and concentrated to crude residue. The residue was purified by combiflash to afford the title compound (0.1 g, 50%). LCMS: m/z=593.4 (M+H)⁺.

Step-2: Synthesis of N-(3-(((8-isopropyl-2-((1-methylpiperidin-4-yl)oxy)pyrazolo[1,5-a][1,3,5]triazin-4-yl)amino)methyl)phenyl)pyrrolidine-3-carboxamide

163

-continued

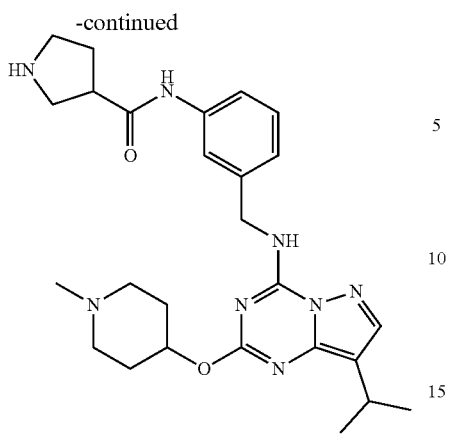

TFA (3 mL) was added to a solution of tert-butyl 3-((3-(((8-isopropyl-2-((1-methylpiperidin-4-yl)oxy)pyrazolo[1,5-a][1,3,5]triazin-4-yl)amino)methyl)phenyl) carbamoyl)pyrrolidine-1-carboxylate (0.3 g, 0.50 mmol) in DCM (10 mL) at 0° C. Then the reaction mixture allowed to stir at room temperature for 2 h. After completion of the reaction, the reaction mixture was concentrated under vacuum (0.25 g, Crude). LCMS: m/z=493.4 (M+H)$^+$.

Step-3: Synthesis of 1-acryloyl-N-(3-(((8-isopropyl-2-((1-methylpiperidin-4-yl)oxy)pyrazolo [1,5-a][1,3,5]triazin-4-yl)amino)methyl)phenyl)pyrrolidine-3-carboxamide

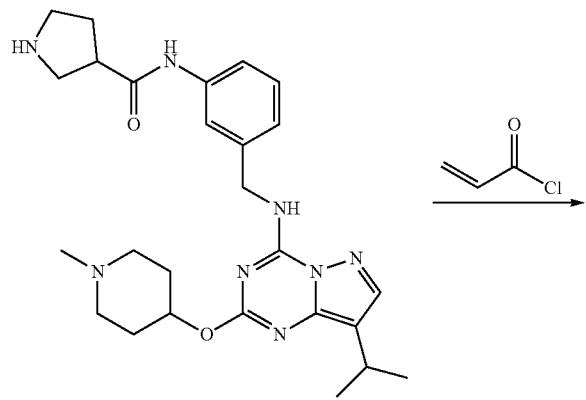

164

-continued

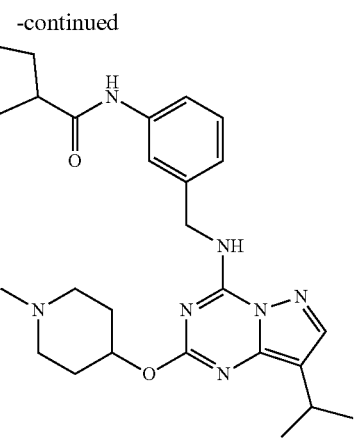

To a solution of N-(3-(((8-isopropyl-2-((1-methylpiperidin-4-yl)oxy)pyrazolo[1,5-a][1,3,5]triazin-4-yl)amino)methyl)phenyl)pyrrolidine-3-carboxamide (0.25 g, 0.50 mmol) in DCM (10 mL) was added DIPEA (0.17 mL, 1.0 mmol) and acryloyl chloride (0.05 g, 0.55 mmol) at 0° C. The reaction mixture was stirred for 2 h at rt. Water was added and extracted with ethyl acetate. The aqueous layer was separated and extracted with dichloromethane (2×25 mL). The combined organic phase was washed with brine, dried over $Na_2SO_4$, filtered and concentrated to afford crude and purified by prep. HPLC (Method: A: 0.01% Ammonia in water, B: Acetonitrile-Methanol, Column: EVA-C-18 (21.2 mm*150 mm, 5 μm) to afford desired title compound (0.06 g, 22%). LCMS: m/z=547.21 (M+H)$^+$. $^1$HNMR (DMSO-d$_6$, 400 MHz): δ 10.50 (s, 1H), 9.95 (s, 1H), 8.18 (s, 2H), 8.06-8.02 (m, 2H), 7.94 (s, 1H), 7.50-7.48 (d, 1H), 7.34-7.30 (m, 2H), 6.36-6.33 (m, 1H), 6.09-6.04 (m, 1H), 5.56-5.53 (m, 1H), 4.90 (s, 1H), 3.91 (m, 2H), 3.03-2.99 (m, 2H), 2.71-2.67 (m, 3H), 2.01-1.99 (m, 3H), 1.84-1.57 (m, 8H), 1.29-1.27 (d, 6H); LCMS: m/z=547.4 (M+H)$^+$.

The below compounds were prepared by procedure similar to the one described in Example-18 with appropriate variations in reactants, quantities of reagents, in presence of suitable solvents at suitable reaction conditions. The physicochemical characteristics of the compounds are summarized herein below table.

| Compd. No. | Compound structure | Analytical data |
|---|---|---|
| 109 & 110 | 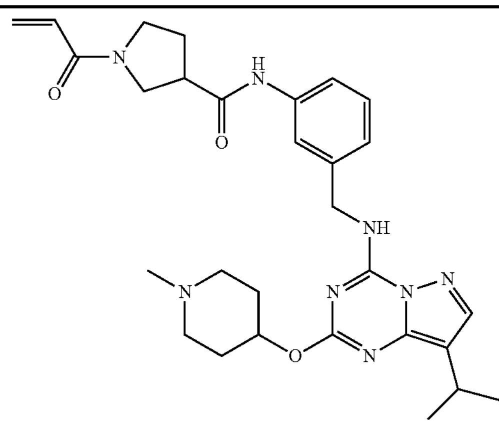 | Isomer-1: $^1$HNMR (DMSO-d$_6$, 400 MHz): δ 10.09-10.07 (d, 1H), 9.31-9.28 (t, 1H), 7.93 (s, 1H), 7.53-7.50 (m, 2H), 7.26-7.22 (t, 1H), 7.02-7.01 (d, 1H), 6.60-6.53 (m, 1H), 6.14-6.10 (m, 1H), 5.67-5.64 (m, 1H), 4.85 (s, 1H), 4.59 (d, 2H), 3.79-3.77 (m, 1H), 3.69-3.62 (m, 2H), 3.58-3.49 (m, 2H), 3.20-3.07 (m, 2H), 3.03-2.92 (m, 2H), 2.69 (s, 1H), 2.20-2.05 (m, 6H), 1.97-1.91 (m, 2H), 1.63 (s, 2H), 1.29-1.24 (m, 6H); LCMS: m/z = 547.0 (M + H)$^+$. Isomer-2: $^1$HNMR (DMSO-d$_6$, 400 MHz): δ 10.09-10.07 (d, 1H), 9.30-9.27 (t, 1H), 7.93 (s, 1H), 7.53-7.50 (m, 2H), 7.26-7.22 (t, 1H), 7.02-7.00 (d, 1H), 6.60-6.53 (m, 1H), 6.14-6.10 (m, 1H), 5.66-5.64 (m, 1H), 4.84 (s, 1H), 4.61-4.59 (d, 2H), 3.79-3.77 (m, 1H), 3.69-3.62 (m, 2H), 3.58-3.48 (m, 3H), 3.20-3.07 (m, 1H), 2.97-2.92 (m, 2H), 2.69 (s, 2H), 2.19-2.07 (m, 5H), 1.99-1.91 (m, 2H), 1.64-1.62 (m, 2H), 1.25-1.24 (m, 6H); LCMS: m/z = 547.0 (M + H)$^+$; |

-continued
| Compd. No. | Compound structure | Analytical data |
|---|---|---|
| 111 | 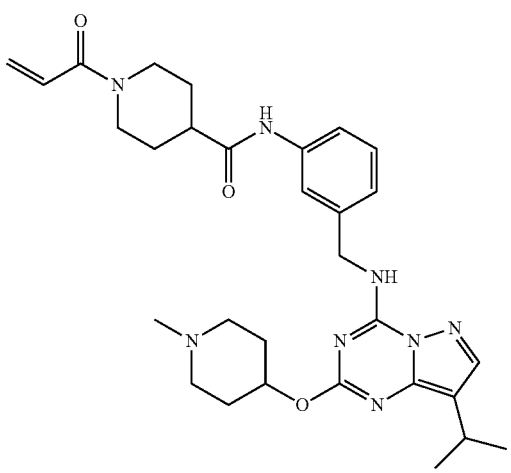 [SMILES: C=CC(=O)N1CCC(C(=O)Nc2cccc(CNc3nc(OC4CCN(C)CC4)nc4c(C(C)C)cnn34)c2)CC1] | $^1$H NMR (DMSO-d$_6$, 400 MHz): δ 9.90 (s, 1H), 9.27 (s, 1H), 7.86 (s, 1H), 7.51 (s, 2H), 7.23-7.19 (t, 1H), 6.99-6.98 (d, 1H), 6.83-6.76 (t, 1H), 6.10-6.05 (m, 1H), 5.66-5.63 (m, 1H), 4.83-4.79 (m, 1H), 4.58 (s, 2H), 4.43-4.40 (d, 1H), 4.10-4.06 (d, 1H), 3.15 (s, 1H), 3.09-3.03 (s, 1H), 2.98-2.91 (m, 1H), 2.66-2.53 (m, 4H), 2.14 (s, 2H), 2.09-2.04 (t, 2H), 1.91-1.81 (m, 2H), 1.89-1.80 (m, 2H), 1.63-1.56 (m, 2H), 1.50-1.40 (m, 2H), 1.24-1.23 (d, 6H); LCMS: m/z = 561.4 (M + H)$^+$. |
| 112 | 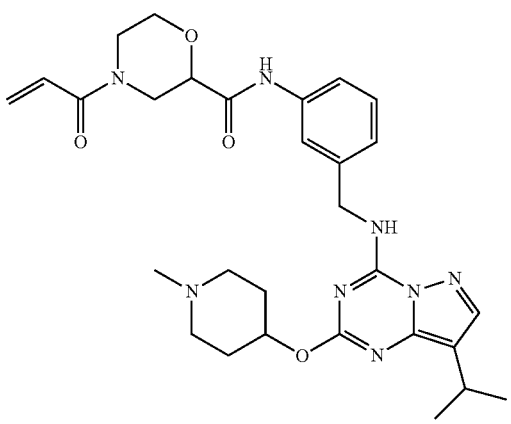 [SMILES: C=CC(=O)N1CCOC(C(=O)Nc2cccc(CNc3nc(OC4CCN(C)CC4)nc4c(C(C)C)cnn34)c2)C1] | $^1$H NMR (DMSO-d$_6$, 400 MHz): δ 9.89-9.81 (d, 1H), 9.27 (s, 1H), 7.93 (s, 1H), 7.63-7.58 (m, 2H), 7.28-7.24 (m, 1H), 7.06-6.04 (m, 1H), 6.85-6.78 (m, 1H), 6.18-6.11 (m, 1H), 5.75-5.73 (m, 1H), 4.85-4.80 (m, 1H), 4.61-4.50 (m, 2H), 4.11-3.94 (m, 1H), 3.57-3.39 (m, 1H), 3.42-3.35 (m, 1H), 3.0-2.95 (m, 1H), 2.60-2.58 (m, 2H), 2.25 (s, 3H), 2.22-2.1 (m, 2H), 1.95-1.75 (m, 2H), 1.63-1.60 (m, 2H), 1.18 (s, 6H); LCMS: m/z = 563.5 (M + H)$^+$. |
| 113 | 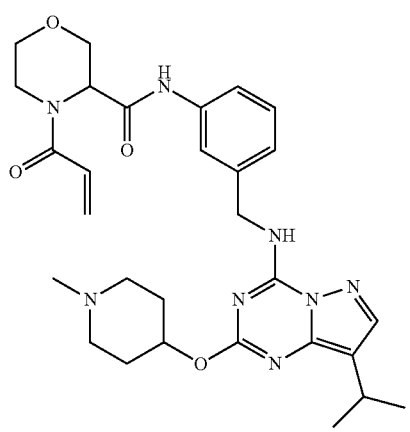 [SMILES: C=CC(=O)N1CCOCC1C(=O)Nc1cccc(CNc2nc(OC3CCN(C)CC3)nc3c(C(C)C)cnn23)c1] | $^1$H NMR (DMSO-d$_6$, 400 MHz): δ 10.05 (s, 1H), 9.32-9.29 (t, 1H), 7.93 (s, 1H), 7.52-7.48 (m, 2H), 7.28-7.24 (t, 1H), 7.05-7.03 (d, 1H), 6.89-6.82 (m, 1H), 6.17-6.13 (m, 1H), 5.76-5.73 (d, 1H), 4.87-4.86 (m, 1H), 4.62-4.61 (d, 2H), 4.29-4.26 (d, 1H), 4.12-4.11 (d, 1H), 3.89-3.84 (t, 2H), 3.70-3.64 (m, 2H), 3.17-3.16 (d, 2H), 3.00-2.93 (m, 3H), 2.67-2.62 (m, 2H), 2.18-2.13 (m, 3H), 1.92 (s, 3H), 1.26-1.24 (d, 6H); LCMS: m/z = 563.70 (M + H)$^+$. |

| Compd. No. | Compound structure | Analytical data |
|---|---|---|
| 114 | 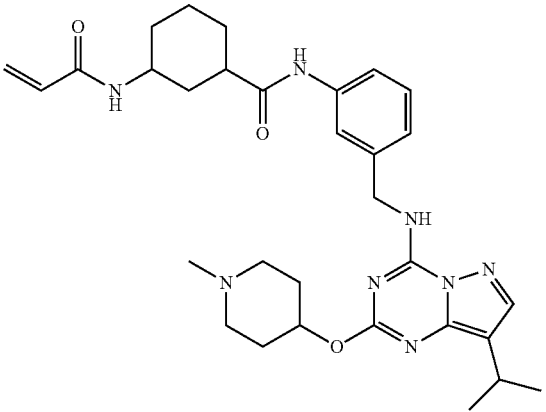 [SMILES: C=CC(=O)NC1CCCC(C(=O)Nc2cccc(CNc3nc(OC4CCN(C)CC4)nc4c(C(C)C)cnn34)c2)C1] | $^1$H NMR (CDCl$_3$-d$_6$, 400 MHz): δ 7.83 (s, 1H), 7.71-7.67 (m, 2H), 7.36-7.34 (d, 1H), 7.05-7.03 (d, 1H), 6.96-6.94 (m, 1H), 6.27-6.23 (m, 1H), 6.13-6.07 (m, 2H), 5.62-5.59 (m, 1H), 5.15 (s, 1H), 4.72-4.71 (d, 1H), 3.96-3.90 (m, 2H), 3.05-2.94 (m, 2H), 2.49 (s, 3H), 2.45-2.42 (m, 1H), 2.30-2.20 (m, 4H), 2.10-1.65 (m, 9H), 1.51-1.44 (m, 2H), 1.28-1.20 (m, 6H); LCMS: m/z = 574.9 (M + H)$^+$. |
| 115 | 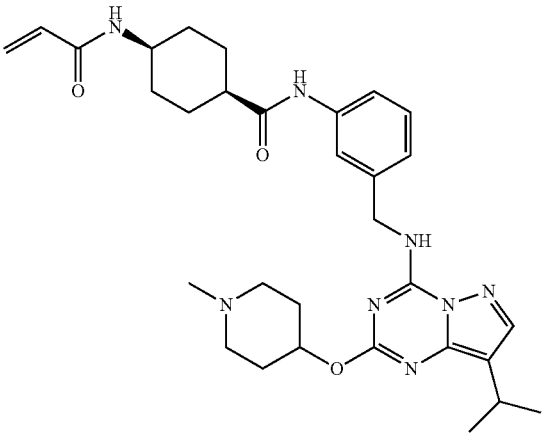 [SMILES: C=CC(=O)N[C@H]1CC[C@@H](C(=O)Nc2cccc(CNc3nc(OC4CCN(C)CC4)nc4c(C(C)C)cnn34)c2)CC1] | $^1$H NMR (DMSO-d$_6$, 400 MHz): δ 10.13 (s, 1H), 9.31-9.28 (t, 1H), 7.93 (s, 1H), 7.62-7.63 (m, 1H), 7.56 (s, 1H), 7.29-7.25 (t, 1H), 7.05-7.03 (d, 1H), 6.43-6.36 (m, 1H), 6.25-6.20 (m, 1H), 5.74-5.71 (m, 1H), 4.83-4.81 (m, 1H), 4.63-4.61 (d, 2H), 3.87 (s, 1H), 3.16 (d, 1H), 2.98-2.93 (m, 1H), 2.67-2.60 (m, 2H), 2.35 (m, 2H), 2.16-2.10 (m, 4H), 1.92-1.90 (m, 2H), 1.79-1.52 (m, 10H), 1.26-1.25 (d, 6H); LCMS: m/z = 575.1 (M + H)$^+$. |

Example-19: Synthesis of 1-acryloyl-N-(3-(((8-isopropyl-2-((1-methylpiperidin-4-yl)oxy)pyrazolo[1,5-a][1,3,5]triazin-4-yl)amino)methyl)phenyl)piperidine-3-carboxamide (Compound-116)

Step-1: Synthesis of tert-butyl 3-((3-(((8-isopropyl-2-(methylthio)pyrazolo[1,5-a][1,3,5]triazin-4-yl)amino) methyl)phenyl)carbamoyl)piperidine-1-carboxylate

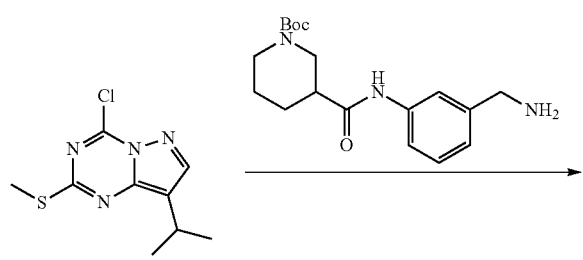

-continued

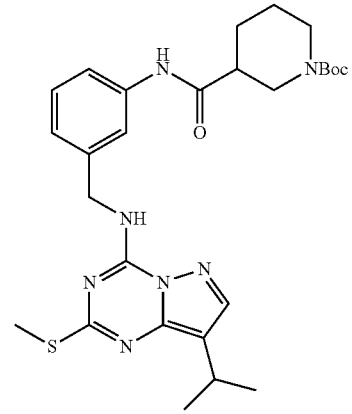

DIPEA (1.2 mL, 7.23 mmol) was added to a stirred solution of 4-chloro-8-isopropyl-2-(methylthio)pyrazolo[1,5-a][1,3,5]triazine (0.35 g, 1.44 mmol; intermediate-4) and tert-butyl 3-((3-(aminomethyl)phenyl)carbamoyl)piperidine-1-carboxylate (0.48 g, 1.44 mmol, intermediate-17) in acetonitrile (10 mL) at 0° C. The resulting reaction mixture was stirred at ambient temperature for 4 h. After completion of the reaction, the reaction mixture was concentrated under vacuum and purified the residue in 100-200 mesh silica column by eluting with 15% ethyl acetate-hexane to afford the title compound (0.5 g, 64%). LCMS: m/z=540.1 (M+H)+.

Step-2: Synthesis of tert-butyl 3-((3-(((8-isopropyl-2-(methylsulfonyl)pyrazolo[1,5-a][1,3,5]triazin-4-yl)amino) methyl)phenyl)carbamoyl)piperidine-1-carboxylate Step-3: Synthesis of tert-butyl 3-((3-(((8-isopropyl-2-((1-methylpiperidin-4-yl)oxy)pyrazolo[1,5-a][1,3,5]triazin-4-yl)amino)methyl)phenyl)carbamoyl)piperidine-1-carboxylate

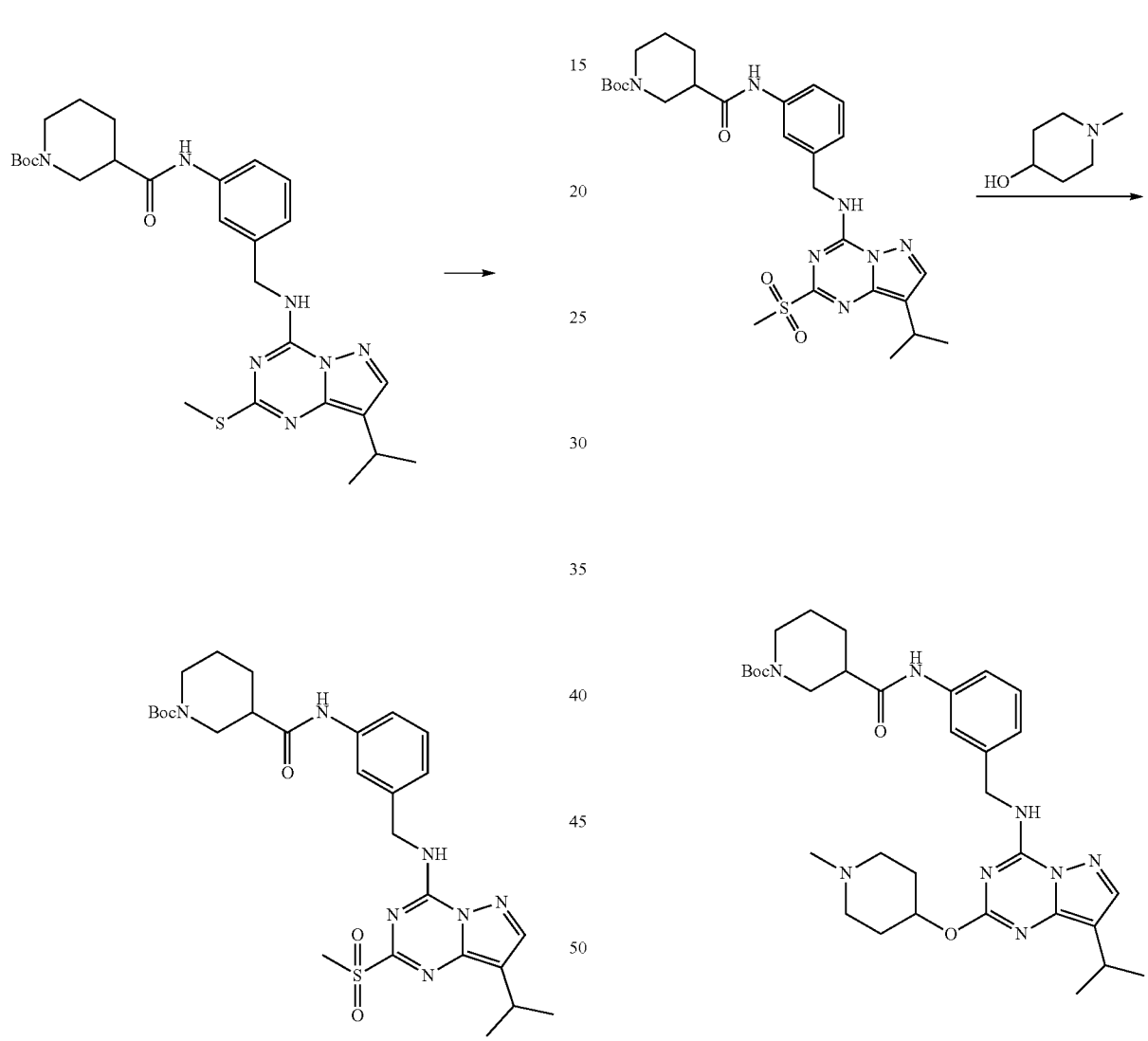

mCPBA (0.48 g, 2.78 mmol) was added portion wise to a stirred solution of tert-butyl 3-((3-(((8-isopropyl-2-(methylthio)pyrazolo[1,5-a][1,3,5]triazin-4-yl)amino)methyl) phenyl) carbamoyl) piperidine-1-carboxylate (0.5 g, 0.92 mmol) in DCM (100 mL). After reaction completion the reaction mixture was extracted with 2M aq. NaOH and DCM. The organic phase was washed with brine, dried over Na₂SO₄, filtered and concentrated to afford the title compound (0.5 g, 94%). LCMS: m/z=572.2 (M+H)+.

NaH (0.042 g, 1.05 mmol) was added to DMSO (4 mL) under inert atmosphere and stirred for 15 min. 1-Methylpiperidin-4-ol (0.12 g, 1.05 mmol) was added to the reaction mixture and stirring continued for 10 min. Added tert-butyl 3-((3-(((8-isopropyl-2-(methylsulfonyl)pyrazolo[1,5-a][1,3,5]triazin-4-yl)amino)methyl)phenyl)carbamoyl) piperidine-1-carboxylate (0.2 g, 0.35 mmol) and stirring continued for 10 min. The reaction mixture was heated to 60° C. for 1 h. After completion of the reaction, the reaction mixture was cooled to room temperature, quenched with ice-water and diluted with ethyl acetate. The aqueous layer was separated and extracted with ethyl acetate (2×25 mL). The combined organic phase was washed with brine, dried over Na₂SO₄, filtered and concentrated. The residue was purified by 100-200 mesh silica gel column chromatography to afford desired title compound (0.2 g, 94%). LCMS: m/z=607.2 (M+H)⁺.

Step-4: Synthesis of N-(3-(((8-isopropyl-2-((1-methylpiperidin-4-yl)oxy)pyrazolo[1,5-a][1,3,5]triazin-4-yl)amino)methyl)phenyl)piperidine-3-carboxamide

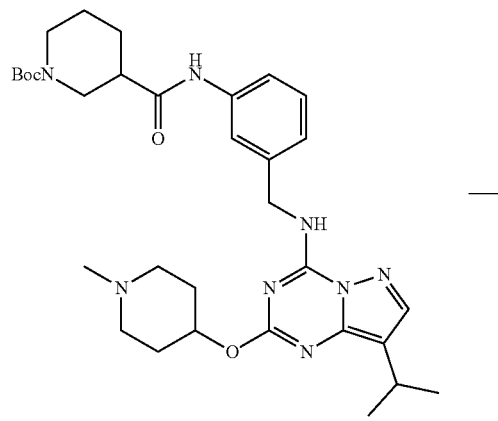

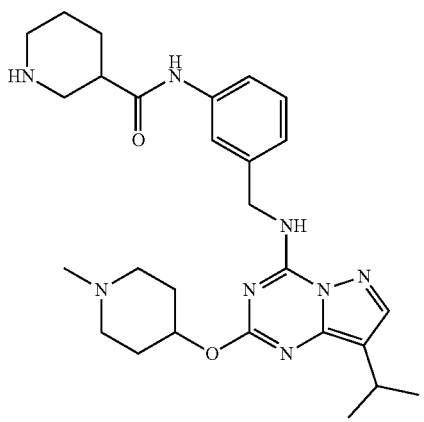

The process of this step was adopted from step-2 of example-18 (0.15 g crude). LCMS: m/z=507.2 (M+H)⁺.

Step-5: Synthesis of 1-acryloyl-N-(3-(((8-isopropyl-2-((1-methylpiperidin-4-yl)oxy)pyrazolo [1,5-a][1,3,5] triazin-4-yl)amino)methyl)phenyl)piperidine-3-carboxamide

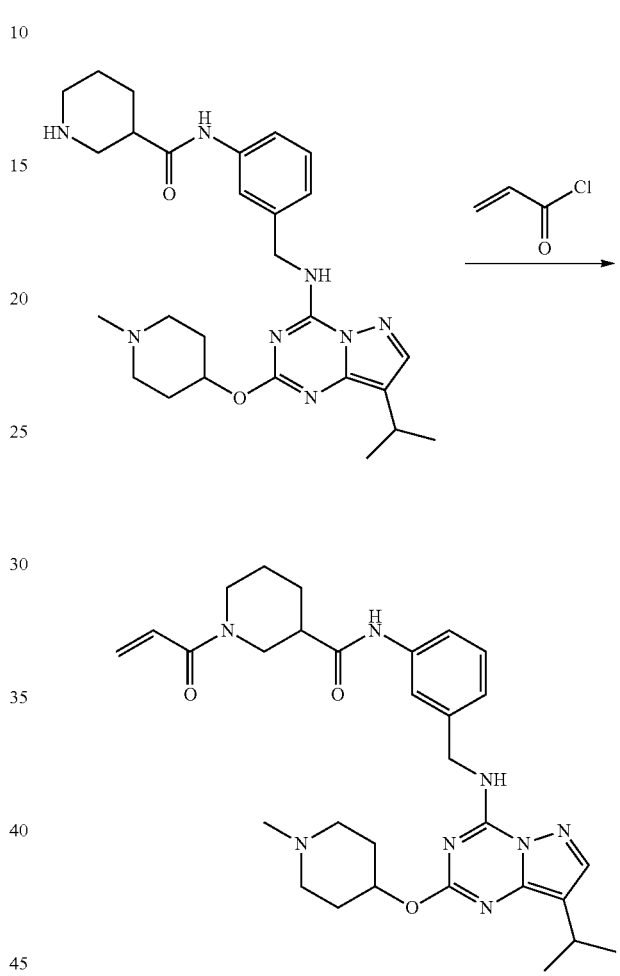

The process of this step was adopted from step-3 of example-18. The obtained crude compound was purified by preparative HPLC (Method: A: 5 mm ammonium acetate in water, B: Acetonitrile-Methanol, Column: Zorbax XDB-C-18 (150 mm*21.2 mm, 5 μm)) to afford desired title compound as acetate salt (0.02 g, 18%). ¹HNMR (DMSO-d₆, 400 MHz): δ 10.0 (d, 1H), 7.93 (s, 1H), 7.49-7.52 (m, 2H), 7.24 (t, 1H), 7.0 (d, 1H), 6.83-6.85 (m, 2H), 6.08 (m, 1H), 5.63 (t, 1H), 4.82-4.83 (m, 1H), 4.61 (s, 2H), 4.43-4.5 (m, 1H), 4.29-4.32 (m, 1H), 4.0-4.1 (m, 1H), 2.93-3.06 (m, 1H), 2.59-2.62 (m, 2H), 2.16 (s, 2H), 2.06-2.11 (m, 2H), 1.91-1.93 (m, 2H), 1.84 (s, 6H), 1.60-1.84 (m, 3H), 1.26 (dd, 6H). LCMS: m/z=561.25 (M+H)⁺.

The below compounds were prepared by procedure similar to the one described in Example-19 with appropriate variations in reactants, quantities of reagents, in presence of suitable solvents at suitable reaction conditions. The physicochemical characteristics of the compounds are summarized herein below table.

| Compd. No. | Compound structure | Analytical data |
|---|---|---|
| 117 | 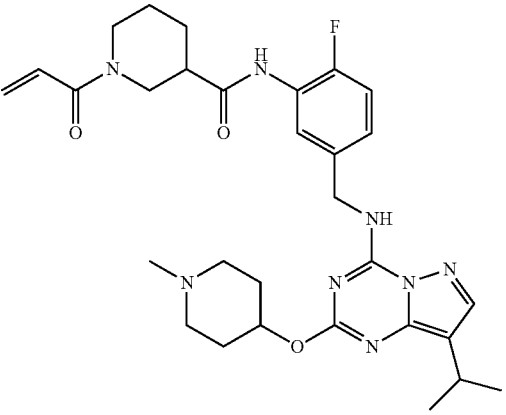 [SMILES: C=CC(=O)N1CCCC(C(=O)Nc2cc(CNc3nc(OC4CCN(C)CC4)nc4c(C(C)C)cnn34)ccc2F)C1] | $^1$H NMR (DMSO-$d_6$, 400 MHz): δ 9.78-9.77 (d, 1H), 9.33-9.30 (t, 1H), 7.92 (s, 1H), 7.90-7.80 (m, 1H), 7.21-7.12 (m, 2H), 6.95-6.75 (m, 1H), 6.15-6.00 (m, 1H), 5.75-5.55 (t, 1H), 4.85-4.75 (m, 1H), 4.58-4.57 (d, 2H), 4.55-3.95 (m, 2H), 3.40-3.36 (m, 1H), 3.35-3.15 (m, 1H), 3.05-2.95 (m, 1H), 2.74-2.60 (m, 4H), 2.16-2.08 (m, 4H), 1.95-1.91 (m, 3H), 1.71-1.60 (m, 4H), 1.45-1.35 (m, 1H), 1.25-1.24 (d, 6H); LCMS: m/z = 578.8 (M + H)$^+$. |
| 118 | 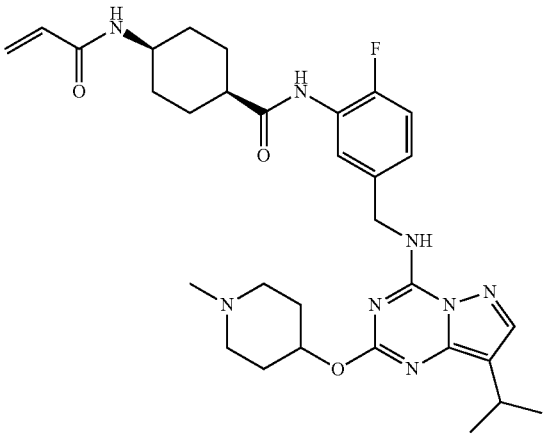 [SMILES: C=CC(=O)N[C@H]1CC[C@@H](C(=O)Nc2cc(CNc3nc(OC4CCN(C)CC4)nc4c(C(C)C)cnn34)ccc2F)CC1] | $^1$H NMR (DMSO-$d_6$, 400 MHz): δ 9.56 (s, 1H), 9.32-9.28 (t, 1H), 8.01-8.00 (d, 1H), 7.92 (s, 1H), 7.79-7.77 (d, 1H), 7.20-7.15 (t, 1H), 7.12-7.10 (m, 1H), 6.37-6.31 (m, 1H), 6.08-6.03 (dd, 1H), 5.55-5.52 (dd, 1H), 4.84 (m, 1H), 4.58-4.57 (d, 2H), 3.87 (m, 1H), 2.97-2.93 (m, 1H), 2.66-2.60 (m, 2H), 2.16-2.10 (m, 4H), 1.94-1.91 (m, 3H), 1.80-1.77 (m, 3H), 1.64-1.54 (m, 8H), 1.25-1.23 (d, 6H); LCMS: m/z = 593.25 (M + H)$^+$. |
| 119 | 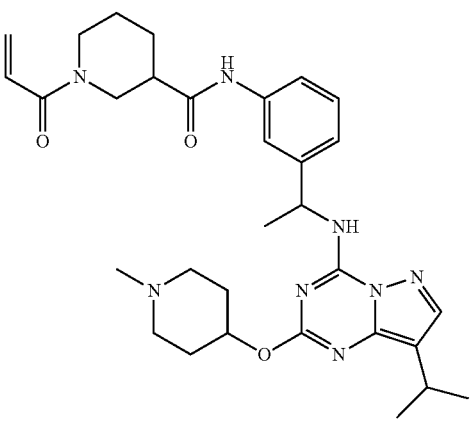 [SMILES: C=CC(=O)N1CCCC(C(=O)Nc2cccc(C(C)Nc3nc(OC4CCN(C)CC4)nc4c(C(C)C)cnn34)c2)C1] | $^1$H NMR (DMSO-$d_6$, 400 MHz): δ 10.01-9.98 (d, 1H), 9.12 (s, 1H), 7.93 (s, 1H), 7.63-7.60 (d, 1H), 7.48-7.47 (d, 1H), 7.27-7.23 (t, 1H), 7.13-7.11 (d, 1H), 6.90-6.79 (m, 1H), 6.11-6.07 (d, 1H), 5.69-5.63 (t, 1H), 5.28-5.26 (m, 1H), 4.80 (m, 1H), 4.50-4.47 (m, 1H), 4.33-4.29 (m, 1H), 4.11-4.00 (m, 1H), 3.23-3.17 (m, 1H), 2.99-2.94 (m, 1H), 2.78-2.67 (m, 4H), 2.17 (s, 3H), 2.11-2.08 (m, 2H), 1.95 (m, 2H), 1.83 (m, 1H), 1.70-1.66 (m, 3H), 1.63-1.58 (d, 3H), 1.56 (m, 1H), 1.26-1.24 (d, 6H); LCMS: m/z = 575.35 (M + H)$^+$. |

Example-20: Synthesis of 2-(1-acryloylpiperidine-3-carboxamido)-5-(((8-isopropyl-2-((1-methylpiperidin-4-yl)oxy)pyrazolo[1,5-a][1,3,5]triazin-4-yl)amino)methyl)pyridine 1-oxide (Compound-120)

Step-1: Synthesis of tert-butyl 3-((5-(((8-isopropyl-2-(methylthio)pyrazolo[1,5-a][1,3,5]triazin-4-yl)amino)methyl)pyridin-2-yl)carbamoyl)piperidine-1-carboxylate

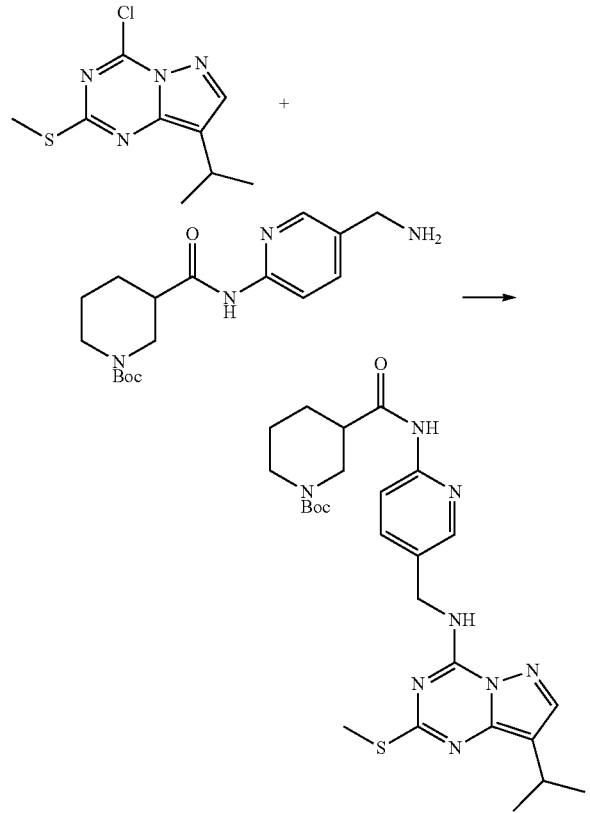

The process of this step was adopted from step-1 of example-19 (0.58 g, 52%). LCMS: m/z=540.9 (M+H)$^+$.

Step-2: Synthesis of 2-(1-(tert-butoxycarbonyl)piperidine-3-carboxamido)-5-(((8-isopropyl-2-(methylsulfonyl)pyrazolo[1,5-a][1,3,5]triazin-4-yl)amino)methyl)pyridine 1-oxide

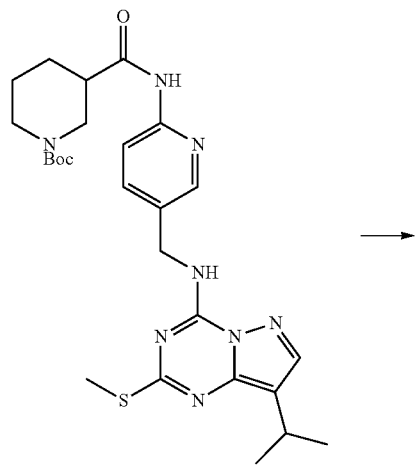

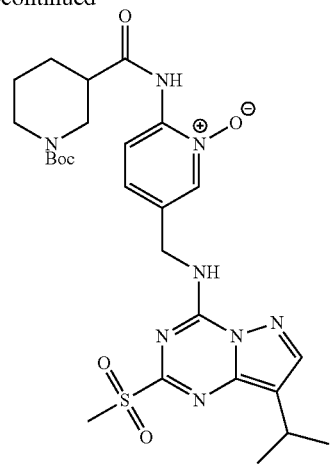

The process of this step was adopted from step-2 of example-19 (0.6 g). LCMS: m/z=589.35 (M+H)$^+$.

Step-3: Synthesis of 2-(1-(tert-butoxycarbonyl)piperidine-3-carboxamido)-5-(((8-isopropyl-2-((1-methylpiperidin-4-yl)oxy)pyrazolo[1,5-a][1,3,5]triazin-4-yl)amino)methyl)pyridine 1-oxide

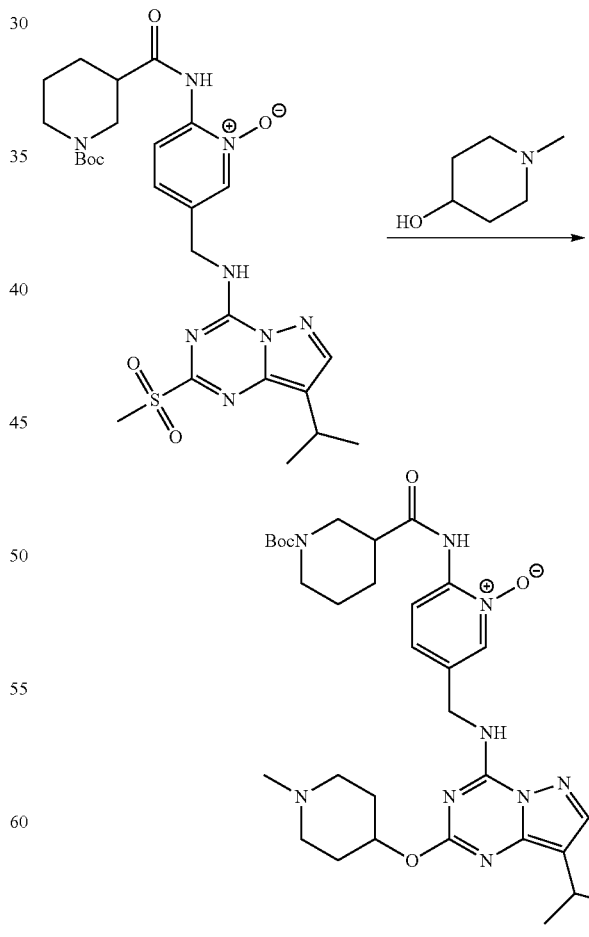

The process of this step was adopted from step-3 of example-19 (0.5 g, 50%). LCMS: m/z=624.45 (M+H)$^+$.

Step-4: Synthesis of 5-((((8-isopropyl-2-((1-methylpiperidin-4-yl)oxy)pyrazolo[1,5-a][1,3,5]triazin-4-yl)amino)methyl)-2-(piperidine-3-carboxamido)pyridine 1-oxide

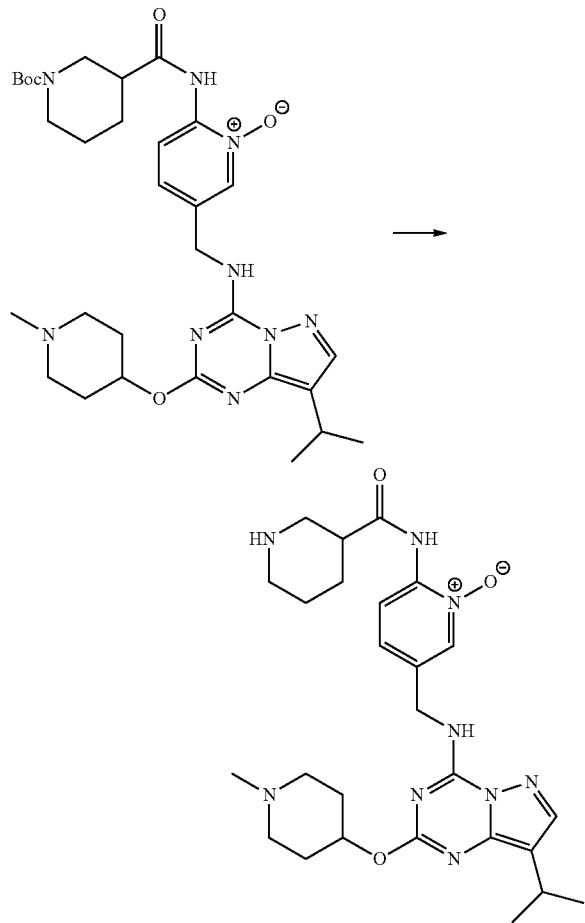

The process of this step was adopted from step-2 of example-18 (0.4 g crude). LCMS: m/z=524.1 (M+H).

Step-5: Synthesis of 1-acryloyl-N-(5-(((8-isopropyl-2-((1-methylpiperidin-4-yl)oxy)pyrazolo[1,5-a][1,3,5]triazin-4-yl)amino)methyl)-1-(11-oxidanyl)-1l4-pyridin-2-yl)piperidine-3-carboxamide

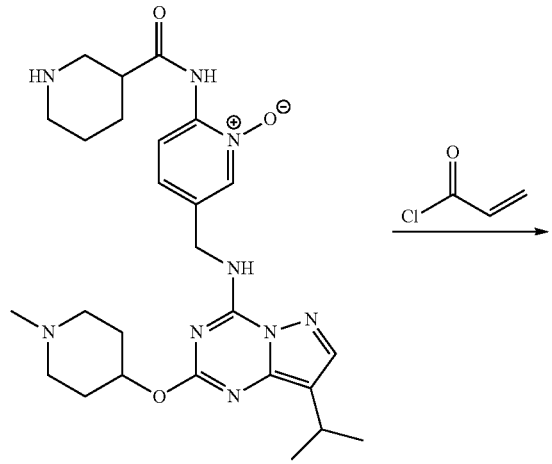

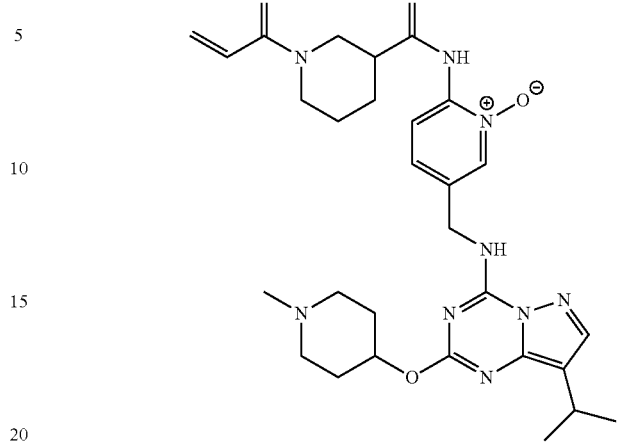

The process of this step was adopted from step-3 of example-18. The obtained crude compound was purified by preparative HPLC (Method: A: 0.01% Ammonia in water, B: Acetonitrile, Column: KINETEX EVO C-18 (21.1 mm*150 mm, 5 μm) to afford desired title compound (0.007 g, 10.2%). $^1$HNMR (DMSO-$d_6$, 400 MHz): δ 10.62-10.56 (m, 1H), 9.26 (s, 1H), 8.36 (s, 1H), 8.22-8.20 (d, 1H), 7.93 (s, 1H), 7.40-7.38 (d, 1H), 6.88-6.78 (m, 1H), 6.1-6.03 (t, 1H), 5.68-5.61 (m, 1H), 4.84 (m, 1H), 4.58 (s, 1H), 4.46-4.43 (m, 1H), 4.19-3.95 (m, 1H), 2.99-2.92 (m, 1H), 2.85-2.79 (m, 1H), 2.66-2.59 (m, 2H), 2.16-2.13 (m, 3H), 1.95-1.92 (m, 2H), 1.67-1.62 (m, 2H), 1.36 (m, 1H), 1.25-1.24 (d, 6H), 1.53 (m, 2H), 1.29-1.27 (d, 6H); LCMS: m/z=578.4 (M+H)$^+$.

Example-21: Synthesis of 3-((((8-isopropyl-2-((1-methylpiperidin-4-yl)oxy)pyrazolo[1,5-a][1,3,5]triazin-4-yl)amino)methyl)phenyl 4-acryloylpiperazine-1-carboxylate (Compound-121)

Step-1: Synthesis of 3-3-((((8-isopropyl-2-((1-methylpiperidin-4-yl)oxy)pyrazolo[1,5-a][1,3,5]triazin-4-yl)amino)methyl)phenol

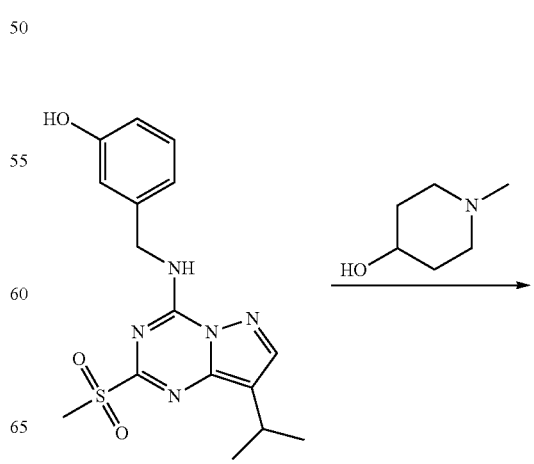

-continued

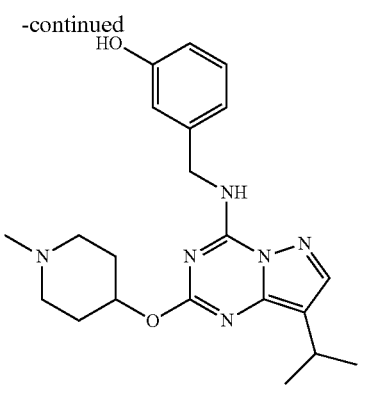

The process of this step was adopted from step-3 of example-19 (0.25 g, 60%). LCMS: m/z=397.4 (M+H)⁺.

Step-2: Synthesis of 1-(tert-butyl) 4-(3-(((8-isopropyl-2-((1-methylpiperidin-4-yl)oxy) pyrazolo[1,5-a][1,3,5]triazin-4-yl)amino)methyl)phenyl)piperazine-1,4-dicarboxylate

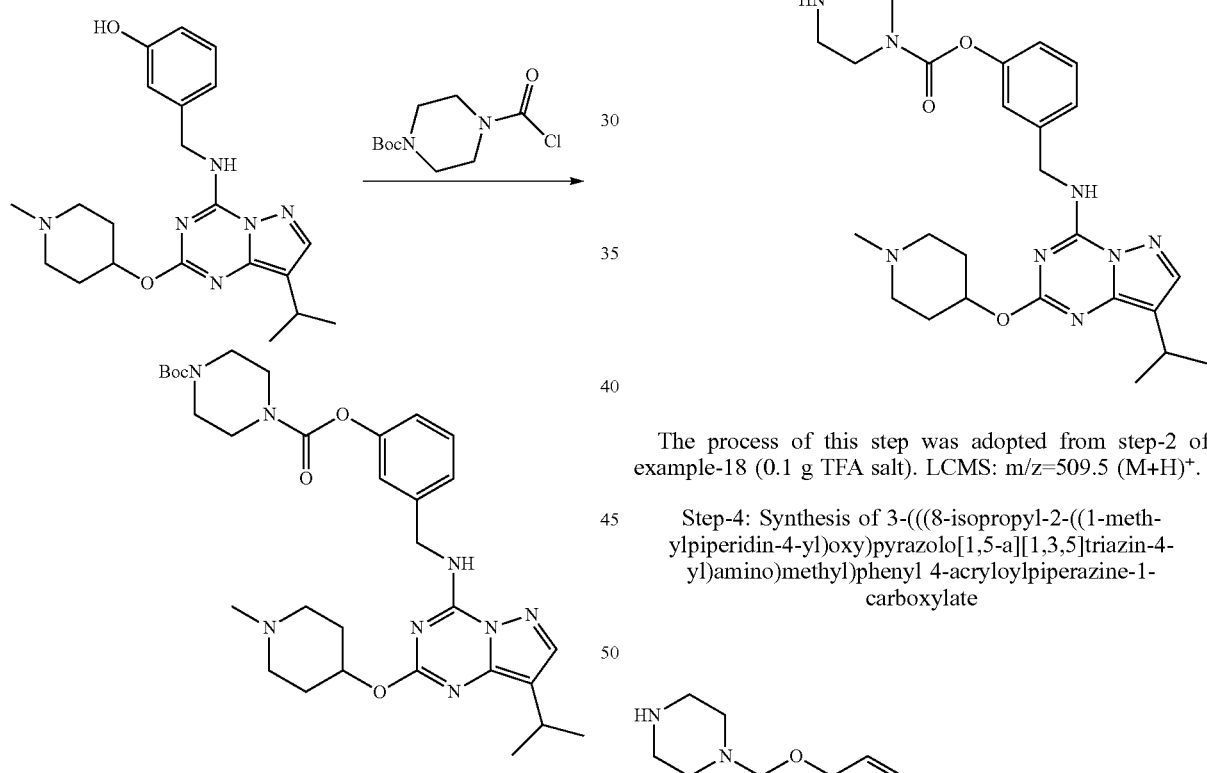

To a solution of 3-(((8-isopropyl-2-((1-methylpiperidin-4-yl)oxy)pyrazolo[1,5-a][1,3,5]triazin-4-yl)amino)methyl)phenol (0.25 g, 0.63 mmol) in 10 mL MDC, was added DMAP (0.092 g, 0.75 mmol), followed by tert-butyl 4-(chlorocarbonyl)piperazine-1-carboxylate (Synthesized according to literature procedure explained in US2007/270433A1) (0.157 g, 0.63 mmol). Reaction mixture was stirred for 4 h at RT and then mixture was quenched to ice cold water and partitioned between water and MDC. The product was extracted three times with MDC (25 ml×3), washed with brine, dried over sodium sulphate, filtered and concentrated to dryness. The product was purified by combiflash column by eluting with 30%-50% ethyl acetate-hexane to afford the title compound (0.22 g, 57%). LCMS: m/z=609.5 (M+H)⁺.

Step-3: Synthesis of 3-(((8-isopropyl-2-((1-methylpiperidin-4-yl)oxy)pyrazolo[1,5-a][1,3,5]triazin-4-yl)amino)methyl)phenyl piperazine-1-carboxylate

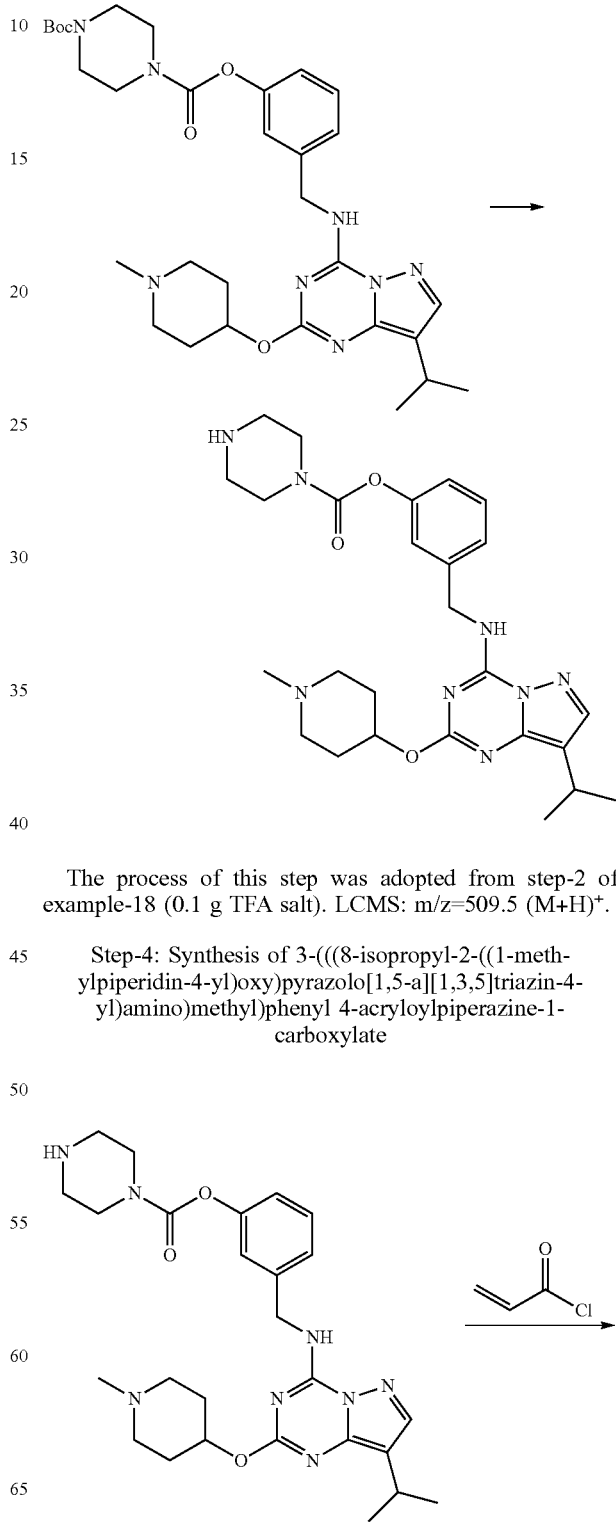

The process of this step was adopted from step-2 of example-18 (0.1 g TFA salt). LCMS: m/z=509.5 (M+H)⁺.

Step-4: Synthesis of 3-(((8-isopropyl-2-((1-methylpiperidin-4-yl)oxy)pyrazolo[1,5-a][1,3,5]triazin-4-yl)amino)methyl)phenyl 4-acryloylpiperazine-1-carboxylate -continued

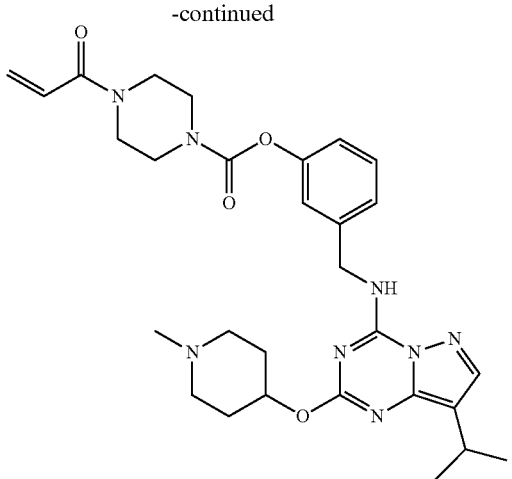

The process of this step was adopted from step-3 of example-18. The obtained crude compound was purified by preparative HPLC (0.01% NH4OH in water, B: Acetonitrile, Column: Gemini NX C-18 (21.2 mm*150 mm, 5 μm) to afford desired title compound (0.25 g, 12%). ¹HNMR (DMSO-d$_6$, 400 MHz): δ 9.33-9.30 (m, 1H), 7.93 (s, 1H), 7.36-7.33 (m, 1H), 7.22-7.20 (m, 1H), 7.12 (s, 1H), 6.85-6.78 (m, 1H), 6.17-6.12 (m, 1H), 5.74-5.72 (m, 1H), 4.88-4.75 (m, 1H), 4.65-4.64 (m, 2H), 3.65-3.60 (m, 5H), 3.44-3.38 (m, 4H), 3.30-2.93 (m, 1H), 2.71-2.60 (m, 2H), 2.20 (s, 3H), 2.0-1.90 (m, 2H), 1.72-1.61 (m, 2H), 1.18 (s, 6H); LCMS: m/z=563.5 (M+H)⁺.

Example-22: Synthesis of (E)-1-(4-(dimethylamino) but-2-enoyl)-N-(3-(((8-isopropyl-2-((1-methyl-piperidin-4-yl)oxy)pyrazolo[1,5-a][1,3,5]triazin-4-yl) amino)methyl)phenyl)-piperidine-3-carboxamide (Compound-122)

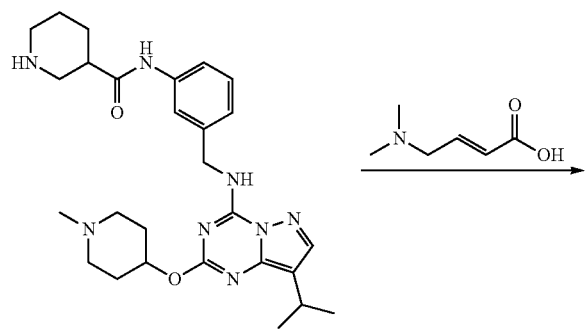

-continued

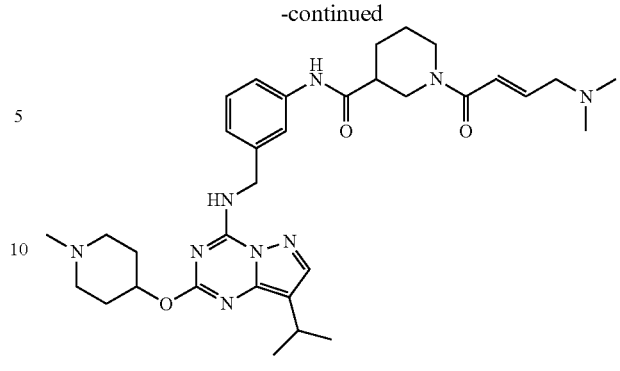

To a stirred solution of (E)-4-(dimethylamino)but-2-enoic acid (0.02 g, 0.118 mmol) in DMF (4 mL) was added HATU (0.067 g, 0.177 mmol) followed by DIPEA (0.04 mL, 0.23 mmol) and finally added N-(3-(((8-isopropyl-2-((1-methylpiperidin-4-yl)oxy)pyrazolo[1,5-a][1,3,5]triazin-4-yl) amino)methyl)phenyl)piperidine-3-carboxamide (0.06 g, 0.118 mmol, step-4 product of example-19). The reaction mixture was stirred for 1 h at room temperature. The reaction mixture was quenched with ice-water and diluted with ethyl acetate. The aqueous layer was separated and extracted with ethyl acetate (2×25 mL). The combined organic phase was washed with brine, dried over Na$_2$SO$_4$, filtered and concentrated. The residue was purified by prep. HPLC (Method: A: 0.1% TFA in water, B: Acetonitrile-Methanol, Column: X bridge C-18 (150 mm*19 mm, 5 μm)) to afford desired title compound (0.15 g, 23%). 1HNMR (DMSO-d$_6$, 400 MHz): δ 10.01 (s, 1H), 7.98 (s, 1H), 7.47-7.57 (m, 2H), 7.26 (t, 1H), 7.03 (d, 1H), 6.94 (t, 1H), 6.56-6.57 (m, 1H), 5.21 (s, 1H), 5.02-5.03 (m, 1H), 4.65-4.66 (m, 2H), 4.47 (d, 1H), 4.25 (d, 1H), 4.06-4.07 (m, 2H), 3.87-3.89 (m, 3H), 3.40-3.41 (m, 4H), 2.97-2.99 (m, 2H), 2.76-2.77 (m, 6H), 2.28 (d, 2H), 2.28 (d, 2H), 1.99 (d, 2H), 1.80 (m, 3H), 1.66 (m, 1H), 1.26 (d, 6H). LCMS: m/z=618.25 (M+H)⁺.

The below compounds were prepared by procedure similar to the one described in Example-22 with appropriate variations in reactants, quantities of reagents, in presence of suitable solvents at suitable reaction conditions. The physicochemical characteristics of the compounds are summarized herein below table.

| Compd. No. | Compound structure | Analytical data |
|---|---|---|
| 123 | ![structure] | ¹H NMR (DMSO-d$_6$, 400 MHz): δ 9.77 (s, 1H), 9.31 (s, 1H), 7.92 (s, 1H), 7.85 (m, 1H), 7.21-7.16 (t, 1H), 7.13-7.12 (m, 1H), 6.59 (m, 2H), 4.85-4.83 (m, 1H), 4.57 (s, 2H), 4.44 (d, 1H), 4.2 (d, 1H), 4.01 (t, 1H), 2.98-2.92 (m, 4H), 2.72-2.66 (m, 4H), 2.16 (s, 3H), 2.12-2.09 (m, 7H), 1.92 (m, 3H), 1.72-1.61 (m, 4H), 1.32 (m, 1H), 1.25-1.23 (d, 6H); LCMS: m/z = 636.40 (M + H)⁺. |

| Compd. No. | Compound structure | Analytical data |
|---|---|---|
| 124 | 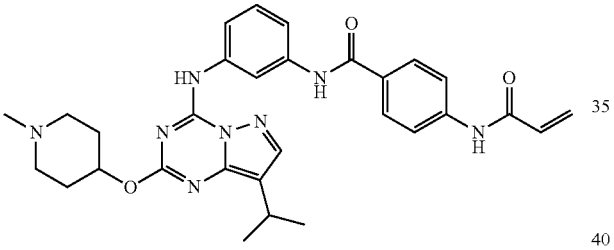 | $^1$H NMR (DMSO-$d_6$, 400 MHz): δ 9.80 (s, 1H), 9.56 (s, 2H), 9.372-9.32 (m, 1H), 8.18-8.16 (d, 1H), 7.93 (s, 1H), 7.73-7.71 (d, 1H), 7.17-7.08 (m, 2H), 6.53-6.47 (m, 1H), 6.34-6.30 (d, 1H), 5.18 (m, 1H), 4.99 (m, 1H), 4.58-4.55 (t, 3H), 3.91-3.85 (m, 3H), 3.46-3.43 (m, 1H), 3.30-3.27 (m, 1H), 3.12-3.10 (m, 3H), 2.95-2.93 (m, 1H), 2.78-2.73 (m, 5H), 2.45 (m, 1H), 2.24-2.20 (m, 1H), 2.14-2.11 (m, 1H), 1.96 (m, 1H), 1.72-1.64 (m, 4H), 1.57-1.54 (m, 4H), 1.22-1.21 (d, 6H); LCMS: m/z = 650.35 (M + H)$^+$. |

Example-23: Synthesis of 4-acrylamido-N-(3-((8-isopropyl-2-((1-methylpiperidin-4-yl)oxy)pyrazolo[1,5-a][1,3,5]triazin-4-yl)amino)phenyl)benzamide (Compound-125)

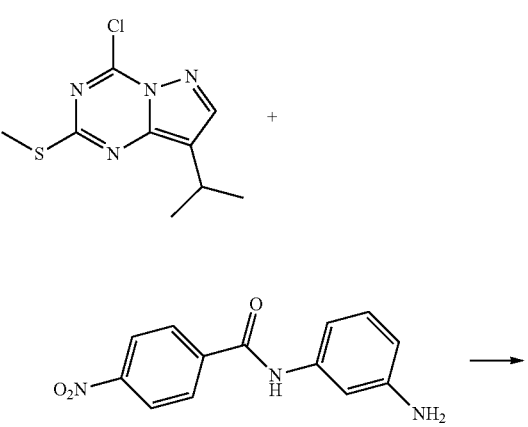

Step-1: Synthesis of N-(3-((8-isopropyl-2-(methylthio)pyrazolo[1,5-a][1,3,5]triazin-4-yl)amino)phenyl)-4-nitrobenzamide

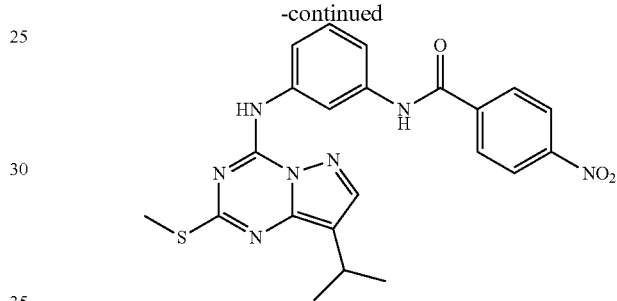

DIPEA (0.7 mL, 4.13 mmol) was added to a stirred solution of 4-chloro-8-isopropyl-2-(methylthio)pyrazolo[1,5-a][1,3,5]triazine, (0.2 g, 0.82 mmol; Intermediate-4) (Synthesized according to procedure described in WO2013/128028) and N-(3-aminophenyl)-4-nitrobenzamide (0.21 g, 0.82 mmol, Intermediate-15) in acetonitrile (5 mL) at 0° C. The resulting reaction mixture was stirred at ambient temperature for 4 h. After completion of the reaction, the reaction mixture was concentrated under vacuum and purified the residue in 100-200 mesh silica column by eluting with 15% ethyl acetate-hexane to afford the title compound (0.15 g, 40%). LCMS: m/z=464.05 (M+H)$^+$.

Step-2: Synthesis of N-(3-((8-isopropyl-2-(methylsulfonyl)pyrazolo[1,5-a][1,3,5]triazin-4-yl)amino)phenyl)-4-nitrobenzamide

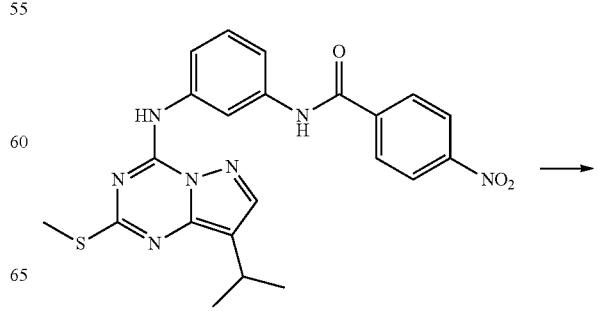

185

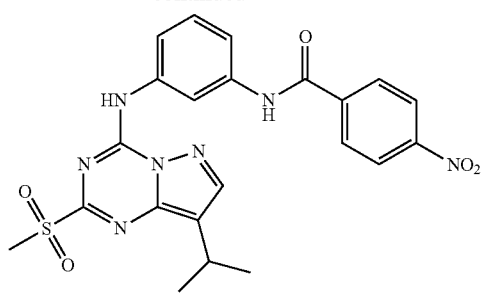

The process of this step was adopted from step-2 of example-19 (0.15 g, 93%). LCMS: m/z=496.1 (M+H)+.

Step-3: Synthesis of N-(3-((8-isopropyl-2-((1-methylpiperidin-4-yl)oxy)pyrazolo[1,5-a][1,3,5]triazin-4-yl)amino)phenyl)-4-nitrobenzamide

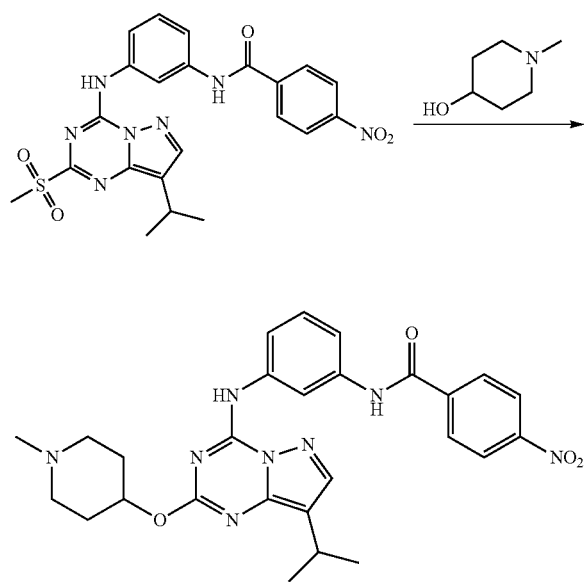

The process of this step was adopted from step-3 of example-19 (0.1 g, 66%). LCMS: m/z=531.15 (M+H)+.

Step-4: Synthesis of 4-Amino-N-(3-((8-isopropyl-2-((1-methylpiperidin-4-yl)oxy)pyrazolo [1,5-a][1,3,5]triazin-4-yl)amino)phenyl)benzamide

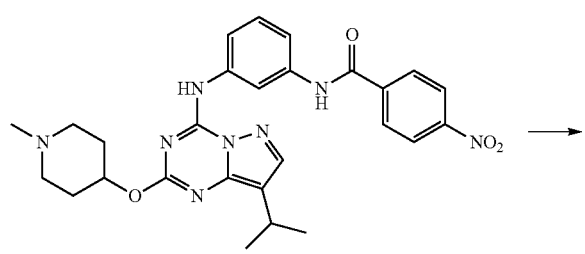

186

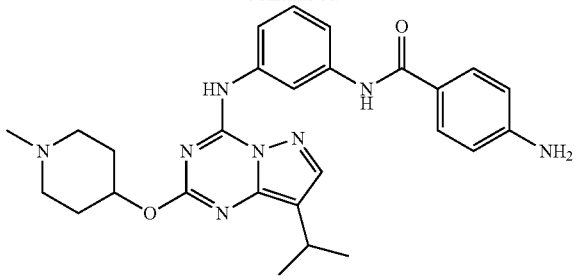

10% Pd/C (0.02 g) was added to a solution of N-(3-((8-isopropyl-2-((1-methylpiperidin-4-yl)oxy)pyrazolo[1,5-a][1,3,5]triazin-4-yl)amino)phenyl)-4-nitrobenzamide (0.1 g, 0.18 mmol) in methanol (5 mL). The reaction mixture was stirred under hydrogen balloon pressure for 4 h at room temperature. The reaction mixture was filtered over celite bed, celite bed washed with methanol. The filtrate was concentrated to obtain title compound (0.08 g crude). LCMS: m/z=501.15 (M+H)+.

Step-5: Synthesis of 4-acrylamido-N-(3-((8-isopropyl-2-((1-methylpiperidin-4-yl)oxy) pyrazolo[1,5-a][1,3,5] triazin-4-yl)amino)phenyl)benzamide

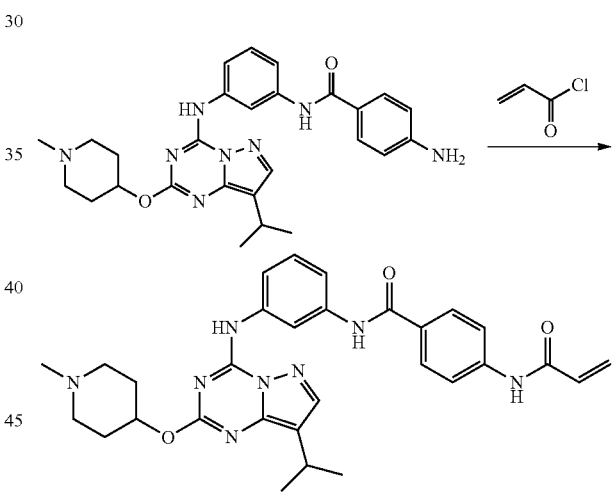

The process of this step was adopted from step-3 of example-18. The obtained crude compound was purified by prep. HPLC (Method: A: 10 mm ammonium acetate in water, B: Acetonitrile-Methanol, Column: XDB-C-18 (250 mm*21.2 mm, 5 μm)) to afford desired title compound as acetate salt (0.008 g, 10%). $^1$HNMR (DMSO-$d_6$, 400 MHz): δ 10.5 (s, 1H), 10.2 (s, 1H), 8.25 (s, 1H), 8.03 (s, 1H), 7.98 (d, 2H), 7.81 (d, 2H), 7.53-7.54 (m, 1H), 7.41 (d, 1H), 7.37 (d, 1H), 6.44-6.52 (m, 2H), 6.30 (dd, 1H), 5.81 (dd, 1H), 4.9-4.92 (m, 1H), 3.16 (s, 3H), 2.94-3.05 (m, 4H), 2.59-2.60 (m, 3H), 1.62-1.65 (m, 2H), 1.28 (d, 6H). LCMS: m/z=555.45 (M+H)+.

The below compounds were prepared by procedure similar to the one described in Example-23 with appropriate variations in reactants, quantities of reagents at suitable reaction conditions. The physicochemical characteristics of the compounds are summarized herein below table.

| Compd. No. | Compound structure | Analytical data |
|---|---|---|
| 126 | 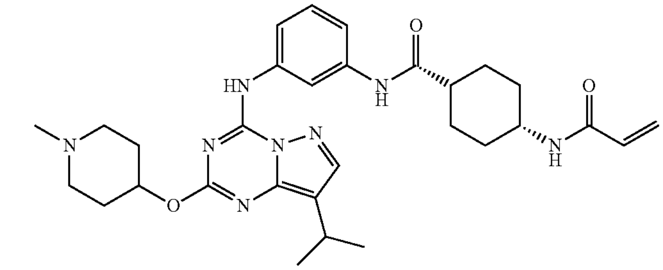 | ¹H NMR (DMSO-d₆, 400 MHz): δ 10.52 (s, 1H), 9.95 (s, 1H), 8.18 (s, 2H), 8.06-8.04 (m, 1H), 8.02 (m, 1H), 7.94 (s, 2H), 7.50-7.48 (d, 1H), 7.34-7.30 (m, 2H), 6.36-6.33 (m, 1H), 6.09-6.04 (d, 1H), 5.56-5.53 (d, 1H), 4.91 (m, 1H), 3.91 (m, 1H), 3.03-2.99 (m, 3H), 2.67-2.50 (m, 3H), 2.18-2.01 (m, 3H), 1.99-1.84 (m, 2H), 1.81-1.57 (m, 7H), 1.29-1.27 (d, 6H); LCMS: m/z = 561.40 (M + H)⁺. |
| 127 | 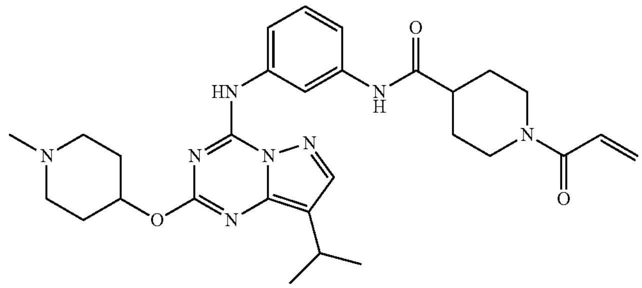 [SMILES: C=CC(=O)N1CCC(C(=O)Nc2cccc(Nc3nc(OC4CCN(C)CC4)nc4c(C(C)C)cnn34)c2)CC1] | ¹H NMR (DMSO-d₆, 400 MHz): δ 10.52 (s, 1H), 10.05 (s, 1H), 8.01-7.99 (d, 1H), 7.45-7.43 (d, 1H), 7.37-7.35 (d, 1H), 7.32-7.28 (t, 1H), 6.86-6.79 (m, 1H), 6.12-6.07 (dd, 1H), 5.68-5.65 (dd, 1H), 4.89 (m, 1H), 4.5 (d, 1H), 4.1 (m, 1H), 3.38-3.36 (m, 2H), 3.10-3.02 (m, 1H), 3.0-2.98 (m, 1H), 2.7-2.62 (m, 4H), 2.15-2.11 (m, 2H), 2.11-2.06 (m, 2H), 1.99-1.97 (m, 2H), 1.86-1.83 (m, 2H), 1.66-1.64 (m, 2H), 1.53 (m, 2H), 1.29-1.27 (d, 6H); LCMS: m/z = 546.8 (M + H)⁺. |

Example-24: Synthesis of N-(1-acryloylpiperidin-4-yl)-3-((8-isopropyl-2-((1-methylpiperidin-4-yl)oxy)pyrazolo[1,5-a][1,3,5]triazin-4-yl)amino)benzamide (Compound-128)

Step-1: Synthesis of tert-butyl-4-(3-((8-isopropyl-2-(methylthio)pyrazolo[1,5-a][1,3,5]triazin-4-yl)amino)benzamido)piperidine-1-carboxylate Step-2: Synthesis of tert-butyl 4-(3-((8-isopropyl-2-(methylsulfonyl)pyrazolo[1,5-a][1,3,5]triazin-4-yl)amino)benzamido)piperidine-1-carboxylate

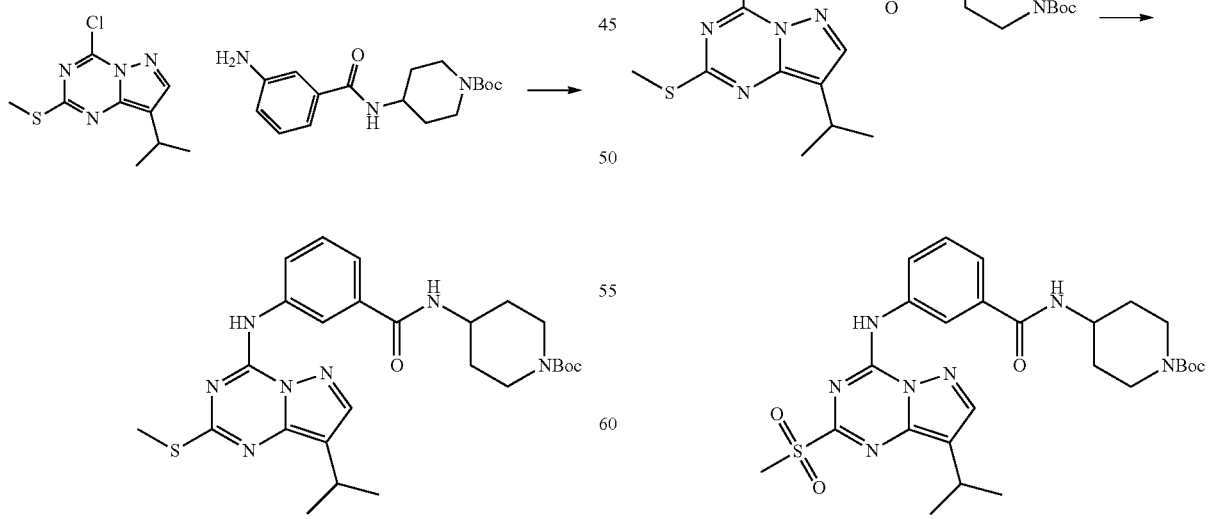

The process of this step was adopted from step-1 of example-23 (0.5 g crude); LCMS: m/z=526.40 (M+H)⁺.

The process of this step was adopted from step-2 of example-19 (0.4 g, 75%). LCMS: m/z=556.26 (M−H)⁺.

Step-3: Synthesis of tert-butyl 4-(3-((8-isopropyl-2-((1-methylpiperidin-4-yl)oxy)pyrazolo[1,5-a][1,3,5]triazin-4-yl)amino)benzamido)piperidine-1-carboxylate

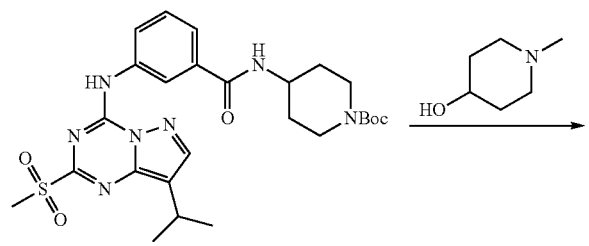

The process of this step was adopted from step-3 of example-19 (0.2 g, 47%). LCMS: m/z=593.90 (M+1)$^+$.

Step-4: Synthesis of 3-((8-isopropyl-2-((1-methylpiperidin-4-yl)oxy)pyrazolo[1,5-a][1,3,5]triazin-4-yl)amino)-N-(piperidin-4-yl)benzamide

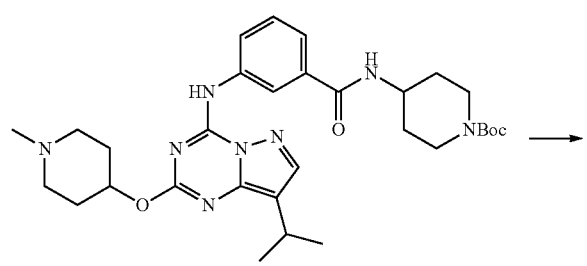

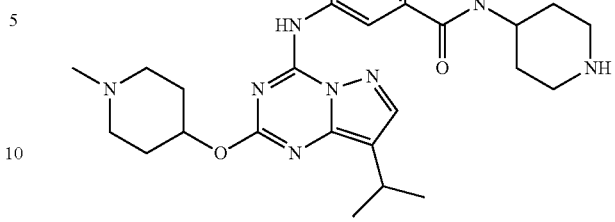

The process of this step was adopted from step-2 of example-18 (0.15 g crude). LCMS: m/z=493.40 (M+H)$^+$.

Step-5: Synthesis of N-(1-acryloylpiperidin-4-yl)-3-((8-isopropyl-2-((1-methylpiperidin-4-yl)oxy)pyrazolo[1,5-a][1,3, 5]triazin-4-yl)amino)benzamide

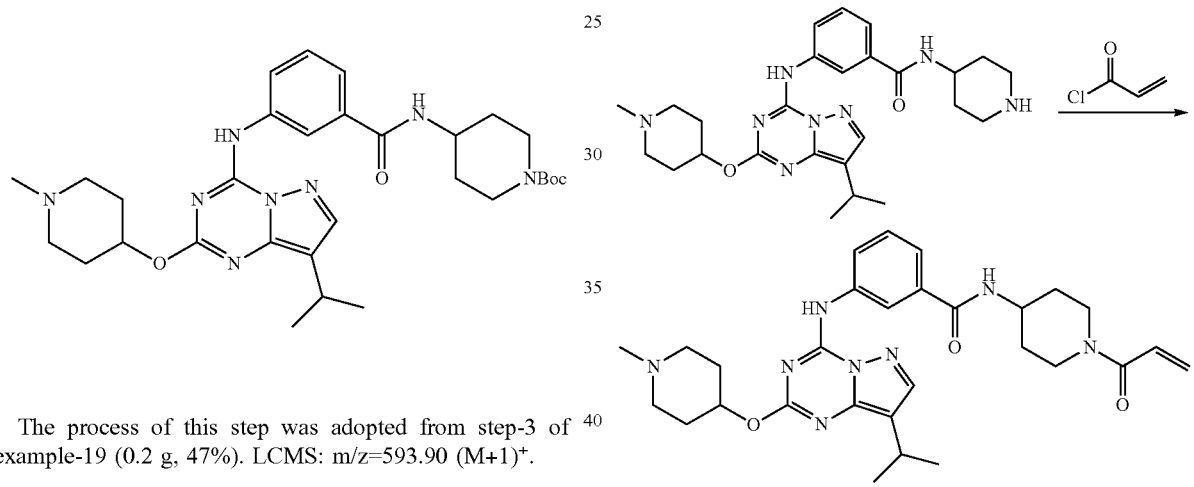

The process of this step was adopted from step-3 of example-19. The obtained crude compound was purified by preparative HPLC (Method: A: 0.01% NH$_4$OH in water, B: Acetonitrile, Column: Kinetex EVO C-18 (21.2 mm*150 mm, 5 μm)) to afford desired title compound (0.010 g, 9%). $^1$HNMR (DMSO-d$_6$, 400 MHz): δ 8.35-8.33 (d, 1H), 8.21 (s, 1H), 8.02 (s, 1H), 7.86-7.84 (d, 1H), 7.65-7.63 (d, 1H), 7.50-7.46 (t, 1H), 6.85-6.78 (m, 1H), 6.11-6.07 (m, 1H), 5.69-5.66 (m, 1H), 4.87-4.84 (m, 1H), 4.39-4.36 (m, 1H), 4.07-3.98 (m, 2H), 3.22-3.14 (m, 2H), 3.04-2.97 (m, 1H), 2.83-2.80 (m, 2H), 2.67-2.61 (m, 2H), 2.15-2.10 (m, 4H), 2.08-1.98 (m, 2H), 1.88 (m, 2H), 1.87-1.68 (m, 2H), 1.66-1.45 (m, 2H), 1.28-1.27 (d, 6H); LCMS: m/z=547.40 (M+H)$^+$.

The below compound was prepared by procedure similar to the one described in Example-24 with appropriate variations in reactants, quantities of reagents, in presence of suitable solvents at suitable reaction conditions. The physicochemical characteristics of the compounds are summarized herein below table.

| Compd. No. | Compound structure | Analytical data |
|---|---|---|
| 129 | 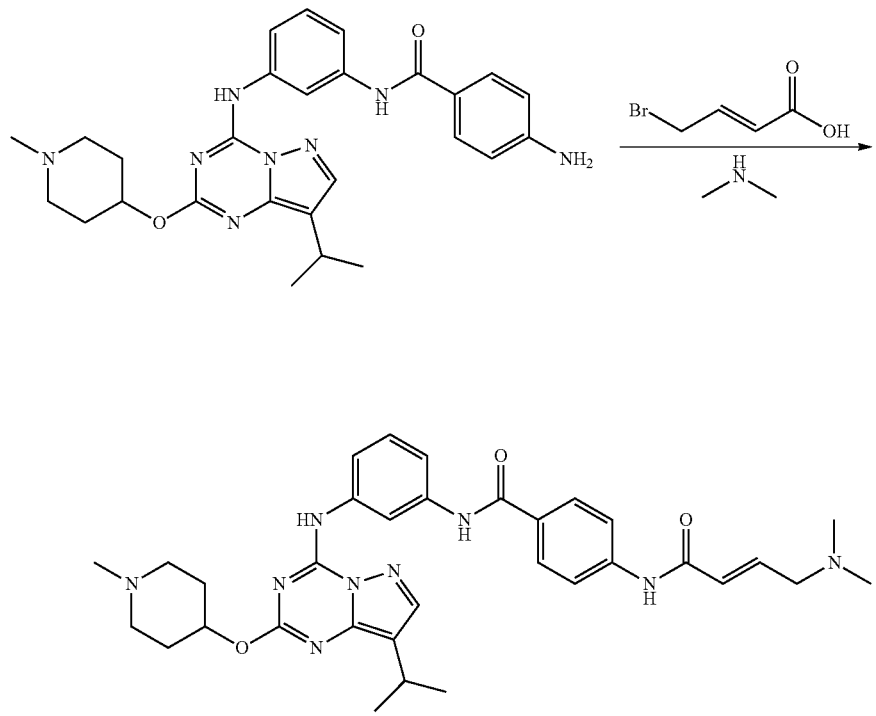 | ¹H NMR (DMSO-d$_6$, 400 MHz): δ 10.65 (s, 1H), 8.31-8.30 (d, 1H), 8.13 (s, 1H), 7.94 (s, 1H), 7.78 (s, 1H), 7.56 (s, 1H), 7.42 (m, 1H), 6.81-6.50 (m, 1H), 6.06-6.02 (m, 1H), 5.64-5.61 (d, 1H), 4.81 (m, 1H), 3.99-3.90 (m, 3H), 3.75 (m, 1H), 2.99-2.92 (m, 3H), 2.69-2.59 (m, 2H), 2.07-2.04 (m, 2H), 2.03-1.95 (m, 2H), 1.95-1.92 (m, 2H), 1.73 (m, 2H), 1.63-1.61 (m, 2H), 1.39 (m, 2H), 1.25-1.23 (d, 6H); LCMS: m/z = 547.2 (M + H)⁺. |

Example-25: Synthesis of (E)-4-(4-(dimethylamino)but-2-enamido)-N-(3-((8-isopropyl-2-((1-methylpiperidin-4-yl)oxy)pyrazolo[1,5-a][1,3,5]triazin-4-yl)amino)phenyl)benzamide (Compound-130)

Oxalyl chloride (0.025 g, 0.2 mmol) was added to a solution of bromocrotonoic acid (0.033 g, 0.2 mmol) in dry DCM (2 mL) was added followed by one drop of DMF was added. The reaction mixture was stirred for 2 h at room temperature and evaporated under reduced pressure to obtain (E)-4-bromobut-2-enoyl chloride. This was dissolved in dry DCM (5 mL) and added to a solution of 4-amino-N-(3-((8-isopropyl-2-((1-methylpiperidin-4-yl)oxy)pyrazolo[1,5-a][1,3,5]triazin-4-yl)amino)phenyl)benzamide (0.05 g, 0.1 mmol; step-5 product of example-23) in acetonitrile (2 mL) at 0° C. The resulting mixture was stirred for 1 h at same temperature and dimethyl amine (1 mL, 20 mmol) was added and continued stirring for 4 h at room temperature. The reaction mixture was quenched with ice-water and diluted with ethyl acetate. The aqueous layer was separated and extracted with ethyl acetate (2×25 mL). The combined organic phase was washed with brine, dried over Na$_2$SO$_4$, filtered and concentrated. The residue was purified by prep. HPLC (Method: A: Ammonium acetate, B: Acetonitrile-Water (1:1), Column: Gemini-NX to afford desired title compound (0.05 g, 20%). ¹HNMR (DMSO-d$_6$, 400 MHz): δ 10.68-10.65 (d, 2H), 10.32-10.29 (d, 1H), 9.91 (s, 1H), 8.25-8.19 (d, 1H), 8.08 (s, 1H), 8.00-7.98 (d, 2H), 7.84-7.82 (d, 2H), 7.55-7.52 (t, 1H), 7.47-7.37 (m, 2H), 6.82-6.75 (m, 1H), 6.51-6.48 (d, 1H), 5.33 (s, 1H), 5.11 (s, 1H), 3.96 (s, 3H), 3.51-3.48 (d, 2H), 3.35-3.32 (m, 2H), 3.17-3.02 (m, 4H), 2.82 (s, 7H), 2.72-2.71 (m, 2H), 2.33 (s, 1H), 2.24-2.21 (d, 1H), 2.05-1.98 (t, 1H), 1.81-1.78 (m, 1H), 1.31-1.29 (d, 6H); LCMS: m/z=612.4 (M+H)⁺.

Example-26: Synthesis of (1s,4s)-4-((E)-4-(dimethylamino)but-2-enamido)-N-(3-((8-isopropyl-2-((1-methylpiperidin-4-yl)oxy)pyrazolo[1,5-a][1,3,5]triazin-4-yl)amino)phenyl)cyclohexane-1-carboxamide (Compound-131)

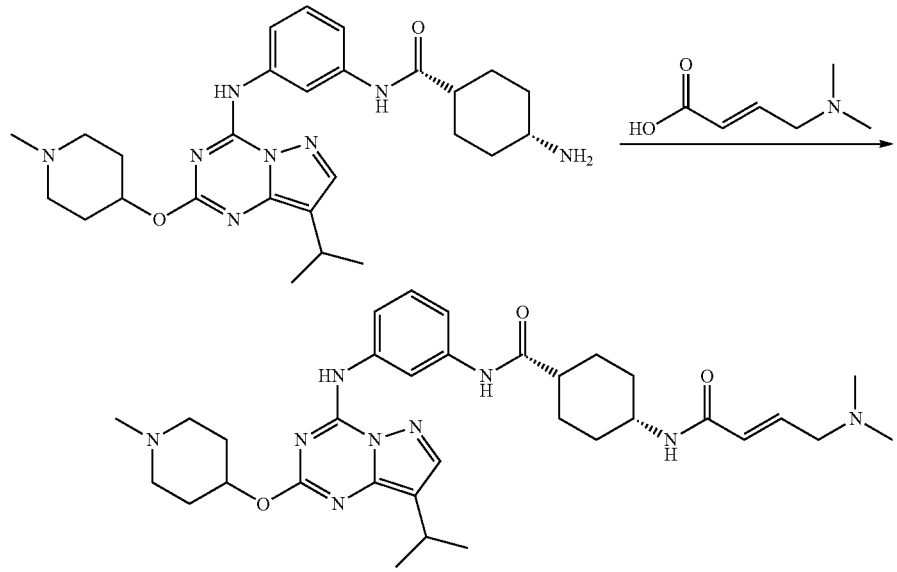

To a cooled solution of (E)-4-(dimethylamino)but-2-enoic acid hydrochloride (0.025 g, 0.15 mmol) in DMF (2 mL) at 0° C. was added HATU (0.068 g, 0.18 mmol) followed by DIPEA (0.52 mL, 0.30 mmol) and added (1,4-cis)-4-amino-N-(3-((8-isopropyl-2-((1-methylpiperidin-4-yl)oxy)pyrazolo[1,5-a][1,3,5]triazin-4-yl)amino)phenyl)cyclohexane-1-carboxamide (0.076 g, 0.15 mmol). The reaction mixture was stirred for 2 h at room temperature. The reaction mixture was quenched with ice-water and diluted with ethyl acetate. The aqueous layer was separated and extracted with ethyl acetate (2×25 mL). The combined organic phase was washed with brine, dried over Na$_2$SO$_4$, filtered and concentrated (0.025 g, 26%). $^1$HNMR (DMSO-d$_6$, 400 MHz): δ 10.52 (s, 1H), 9.94 (s, 1H), 8.02 (s, 1H), 7.98-7.94 (m, 2H), 7.50-7.48 (d, 1H), 7.36-7.28 (m, 2H), 6.56-6.49 (m, 1H), 6.21-6.17 (d, 1H), 4.91-4.86 (m, 1H), 3.89 (m, 1H), 3.41-3.40 (m, 2H), 3.17 (d, 1H), 2.99-2.66 (m, 2H), 2.66-2.51 (m, 2H), 2.50-2.49 (m, 1H), 2.44-2.32 (m, 2H), 2.09-2.00 (m, 7H), 1.98-1.97 (m, 2H), 1.86-1.81 (m, 2H), 1.73-1.55 (m, 6H), 1.25-1.23 (d, 6H), 1.10-1.07 (m, 2H); LCMS: m/z=618.50 (M+H)$^+$.

The below compounds were prepared by procedure similar to the one described in Example-26 with appropriate variations in reactants, quantities of reagents, in presence of suitable solvents at suitable reaction conditions. The physicochemical characteristics of the compounds are summarized herein below table.

| Compd. No. | Compound structure | Analytical data |
|---|---|---|
| 132 | 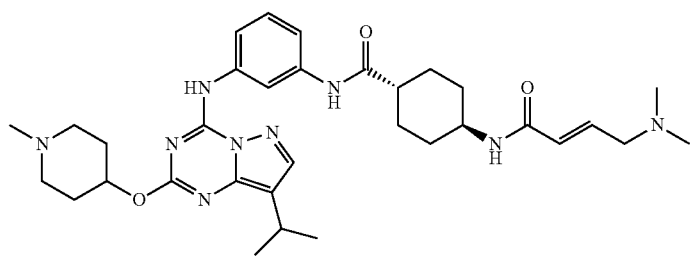 | $^1$H NMR (DMSO-d$_6$, 400 MHz): δ 10.5 (s, 1H), 9.95 (s, 1H), 8.02-7.99 (d, 2H), 7.91 (d, 1H), 7.46 (d, 1H), 7.36-7.28 (m, 2H), 6.57-6.50 (m, 1H), 6.01 (d, 1H), 4.93 (m, 1H), 3.58 (m, 1H), 3.04-2.91 (m, 4H), 2.67-2.63 (m, 2H), 2.32-2.29 (m, 2H), 2.13-2.10 (m, 3H), 2.07-2.00 (m, 7H), 1.97-1.89 (m, 2H), 1.89-1.87 (m, 4H), 1.69-1.64 (m, 2H), 1.55-1.46 (m, 3H), 1.33-1.27 (d, 6H). LCMS: m/z = 618.45 (M + H)$^+$. |

| Compd. No. | Compound structure | Analytical data |
|---|---|---|
| 133 | 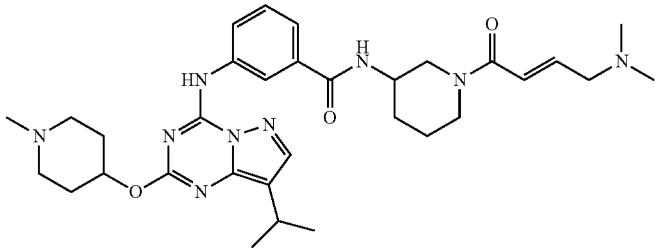 | ¹H NMR (DMSO-d₆, 400 MHz): δ 10.76-10.74 (d, 1H), 10.02-9.55 (m, 2H), 8.40 (m, 1H), 8.18 (s, 1H), 8.05 (s, 1H), 7.88-7.83 (t, 1H), 7.66-7.64 (d, 1H), 7.50-7.46 (t, 1H), 7.22 (s, 2H), 7.09 (s, 3H), 6.96 (s, 1H), 6.88-6.83 (dd, 1H), 6.58-6.52 (m, 1H), 5.18 (m, 1H), 4.43-4.40 (m, 1H), 3.94-3.90 (d, 1H), 3.85-3.77 (m, 2H), 3.47 (m, 1H), 3.16 (m, 2H), 3.01-2.94 (m, 1H), 2.91 (m, 2H), 2.77-2.74 (m, 2H), 2.68 (s, 1H), 2.59 (m, 1H), 2.19 (m, 1H), 2.04-2.00 (m, 1H), 1.91 (m, 1H), 1.79-1.77 (m, 2H), 1.61 (m, 1H), 1.41 (m, 1H), 1.27-1.25 (d, 6H); LCMS: m/z = 604.2 (M + H)⁺. |
| 134 | 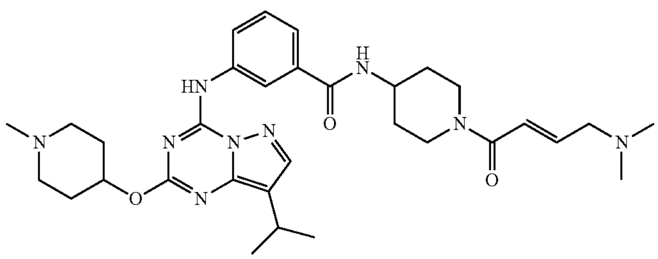 | ¹H NMR (DMSO-d₆, 400 MHz): δ 10.69 (s, 1H), 8.32-8.30 (d, 1H), 8.25 (s, 1H), 8.04 (s, 1H), 7.87-7.85 (d, 1H), 7.66-7.64 (d, 1H), 7.52-7.46 (t, 1H), 6.66-6.56 (m, 1H), 4.91-4.90 (m, 1H), 4.39-4.36 (m, 1H), 4.06-4.03 (m, 3H), 3.20-3.15 (m, 2H), 3.06-3.00 (m, 3H), 2.79-2.66 (m, 3H), 2.32-2.08 (m, 9H) 2.00-1.99 (m, 2H), 1.86 (m, 2H), 1.72-1.70 (m, 2H), 1.43-1.41 (m, 2H), 1.29-1.27 (d, 6H), 1.19-1.06 (m, 1H); LCMS: m/z = 604.40 (M + H)⁺. |

Example-27: Synthesis of (1s,4s)-4-(((E)-4-(dimethylamino)-4-oxobut-2-en-1-yl)amino)-N-(3-(((8-isopropyl-2-((1-methylpiperidin-4-yl)oxy)pyrazolo[1,5-a][1,3,5]triazin-4-yl)amino)methyl)phenyl)cyclohexane-1-carboxamide (Compound-135)

Step-1: Synthesis of tert-butyl ((1s,4s)-4-((3-(((8-isopropyl-2-((1-methylpiperidin-4-yl)oxy)pyrazolo[1,5-a][1,3,5]triazin-4-yl)amino)methyl)phenyl)carbamoyl)cyclohexyl) carbamate

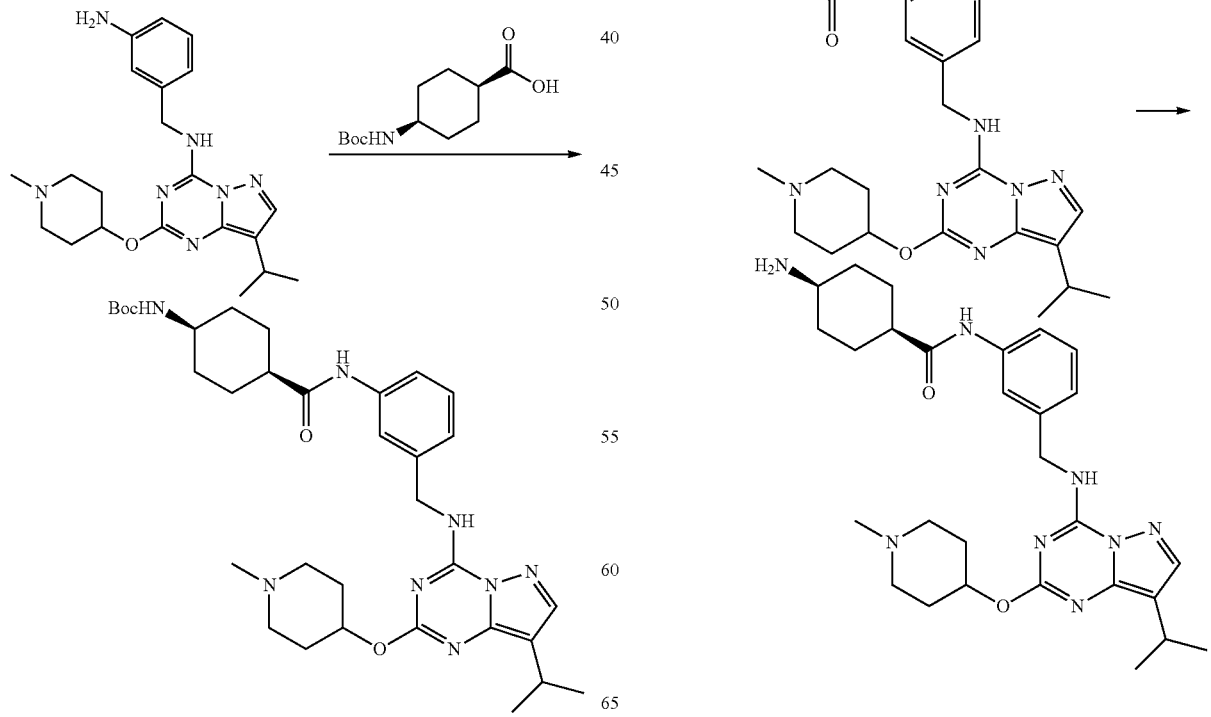

The process of this step was adopted from step-1 of example-18 (0.3 g, 95%). LCMS: m/z=621.85 (M+H)⁺.

Step-2: Synthesis of (1 s,4s)-4-amino-N-(3-(((8-isopropyl-2-((1-methylpiperidin-4-yl)oxy)pyrazolo[1,5-a][1,3,5]triazin-4-yl)amino)methyl)phenyl)cyclohexane-1-carboxamide The process of this step was adopted from step-2 of example-18 (0.2 g, 94.7). LCMS: m/z=521.45 (M+H)⁺.

Step-3: Synthesis of (1s,4s)-4-(((E)-4-(dimethylamino)-4-oxobut-2-en-1-yl)amino)-N-(3-(((8-isopropyl-2-((1-methylpiperidin-4-yl)oxy)pyrazolo[1,5-a][1,3, 5]triazin-4-yl)amino)methyl) phenyl) cyclohexane-1-carboxamide Example-28: Synthesis of Synthesis of 1-acryloyl-N-(3-(((8-isopropyl-2-methoxypyrazolo[1,5-a][1,3, 5]triazin-4-yl)amino)methyl)phenyl)piperidine-4-carboxamide (Compound-136)

Step-1: Synthesis of 8-isopropyl-2-methoxy-N-(3-nitrobenzyl)pyrazolo[1,5-a][1,3,5]triazin-4-amine

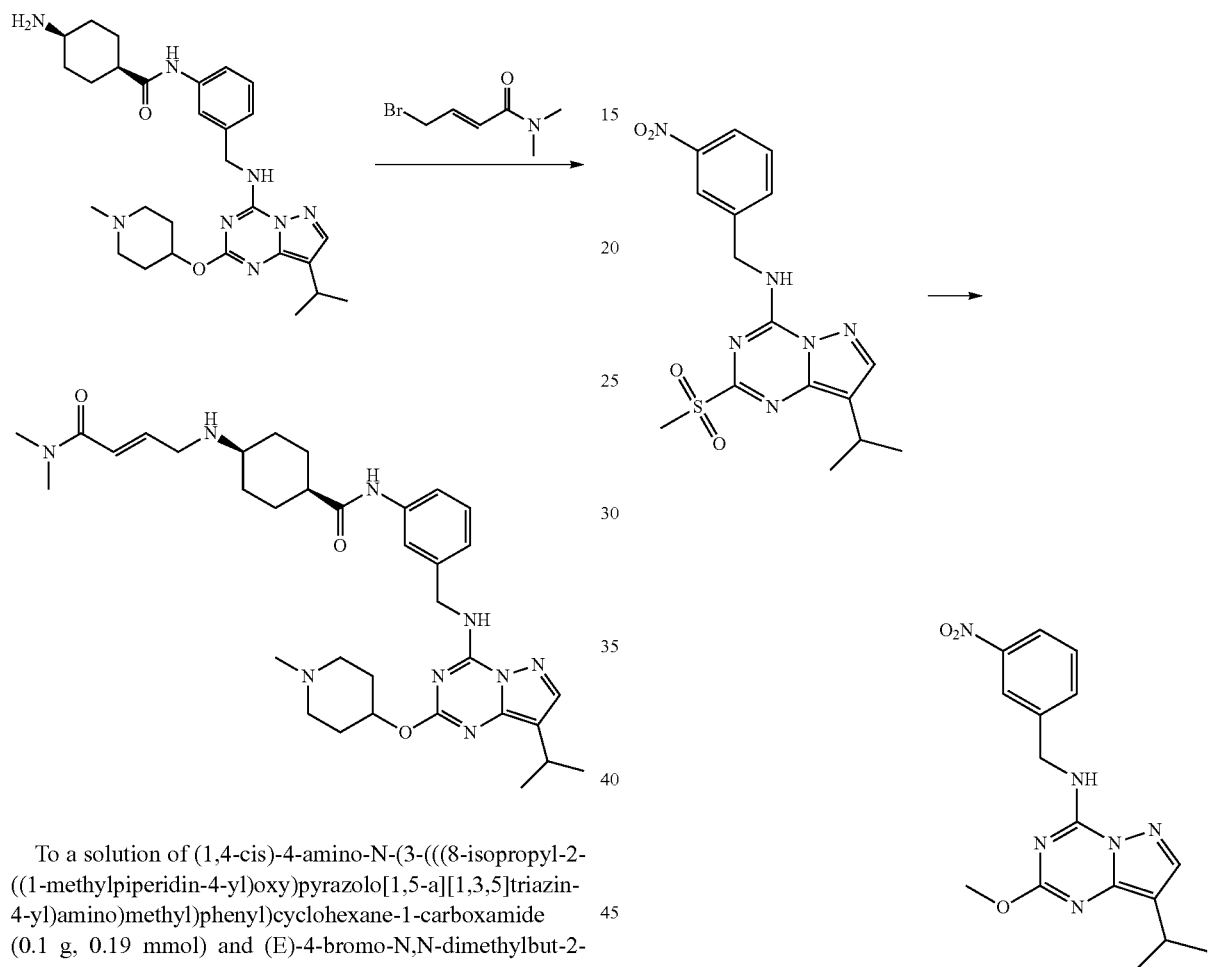

To a solution of (1,4-cis)-4-amino-N-(3-(((8-isopropyl-2-((1-methylpiperidin-4-yl)oxy)pyrazolo[1,5-a][1,3,5]triazin-4-yl)amino)methyl)phenyl)cyclohexane-1-carboxamide (0.1 g, 0.19 mmol) and (E)-4-bromo-N,N-dimethylbut-2-enamide (0.044 g, 0.23 mmol) in ACN (3 mL) was added DIPEA (0.06 mL, 0.384 mmol) at RT, then stirred for 12 hr, After reaction completion, quenched with water and diluted with ethyl acetate. The aqueous layer was separated and extracted with ethyl acetate (2×15 mL). The combined organic phase was washed with brine, dried over $Na_2SO_4$, filtered and concentrated. The residue was purified by preparative HPLC (Method: A: 0.1% TFA in Water, B: ACN, Column: EVO C18 (21.2 mm×150 mm particle size 5 μm)) to afford desired title compound (0.030 g, 20%). $^1$H NMR (DMSO-$d_6$, 400 MHz): δ 9.84 (s, 1H), 7.97 (s, 1H), 7.85 (m, 1H), 7.55-7.53 (d, 1H), 7.48 (s, 1H), 7.25-7.21 (t, 1H), 7.05-6.96 (m, 2H), 6.70-6.66 (m, 1H), 5.12 (s, 1H), 4.62 (s, 2H), 4.25-4.19 (m, 3H), 3.44-3.43 (d, 5H), 3.09-2.89 (m, 4H), 2.80-2.77 (m, 3H), 2.66 (s, 1H), 2.32-2.35 (m, 3H), 2.11-2.10 (m, 2H), 1.86-1.84 (d, 2H), 1.74-1.68 (m, 4H), 1.62-1.57 (m, 2H), 1.22 (s, 6H); LCMS: m/z=632.80 (M+H)$^+$.

NaH (0.08 g, 2.05 mmol) was added to DMSO (4 mL) under inert atmosphere and stirred for 15 min. tert-butyl (4-hydroxybutyl)carbamate (0.38 g, 2.05 mmol) was added to the reaction mixture and continued stirring for 10 min. 8-isopropyl-2-(methylsulfonyl)-N-(3-nitrobenzyl)pyrazolo [1,5-a][1,3,5]triazin-4-amine (0.2 g, 0.51 mmol) was added and stirred for 10 min. Then the reaction mixture allowed to heat at 60° C. for 1 h. After completion of the reaction, cooled to room temperature and was quenched with ice-water and diluted with ethyl acetate. The aqueous layer was separated and extracted with ethyl acetate (2×25 mL). The combined organic phase was washed with brine, dried over $Na_2SO_4$, filtered and concentrated. The residue was purified by 100-200 silica gel column chromatography to afford desired title compound (0.1 g, 57%). LCMS: m/z=343.2 (M+H)$^+$.

Step-2: Synthesis of N-(3-aminobenzyl)-8-isopropyl-2-methoxypyrazolo[1,5-a][1,3,5]triazin-4-amine

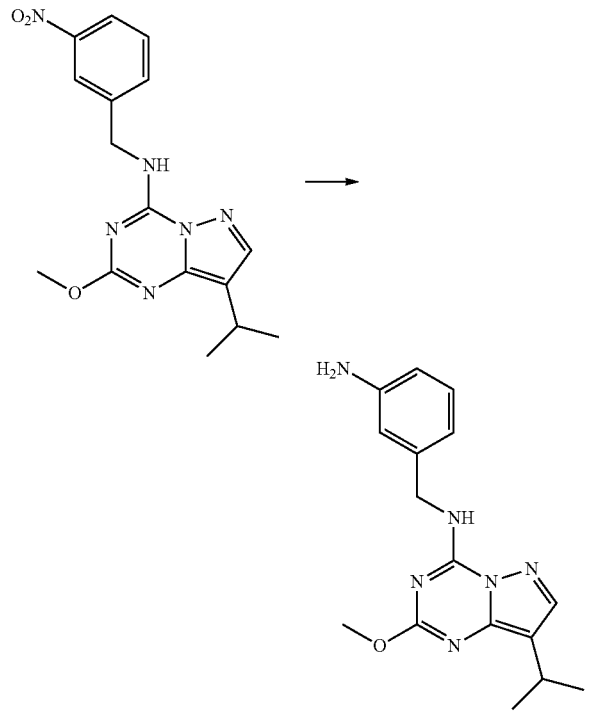

To a solution of 8-isopropyl-2-methoxy-N-(3-nitrobenzyl)pyrazolo[1,5-a][1,3,5]triazin-4-amine (0.1 g, 0.29 mmol) in THF:MeOH:Water (3:2:1) were added zinc (0.08 g, 1.46 mmol) and ammonium chloride (0.078 g, 1.46 mmol). The reaction mixture was stirred at room temperature for 4 h. After completion of reaction the reaction mixture filtered through celite and diluted with ethyl acetate. The aqueous layer was separated and extracted with ethyl acetate (2×25 mL). The combined organic phase was washed with brine, dried over $Na_2SO_4$, filtered and concentrated. The residue was purified by 100-200 silica gel column chromatography to afford desired title compound (0.06 g, Crude). LCMS: m/z=313.25 (M+H)$^+$.

Step-3: Synthesis of 1-acryloyl-N-(3-(((8-isopropyl-2-methoxypyrazolo[1,5-a][1,3,5]triazin-4-yl)amino)methyl)phenyl)piperidine-4-carboxamide

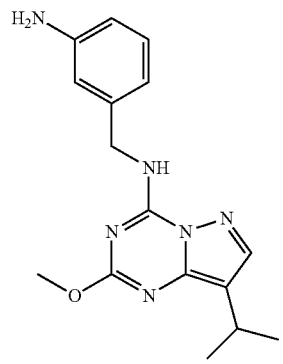

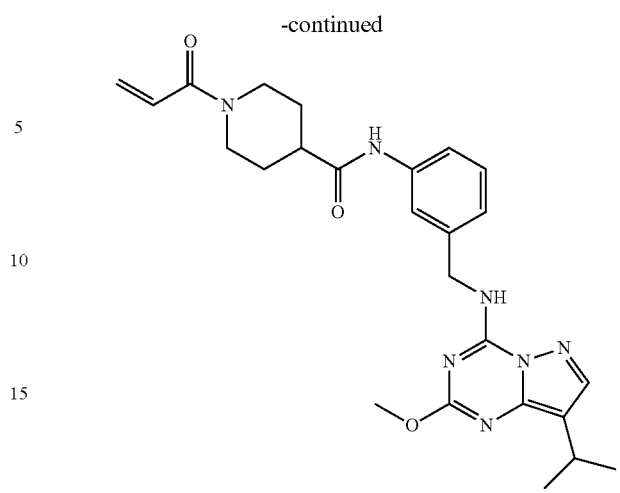

The process of this step was adopted from example-16. The obtained crude compound was purified by combiflash to afford the title compound (0.05 g, 65.7%). 1HNMR (DMSO-$d_6$, 400 MHz): δ 9.92 (s, 1H), 9.30-9.27 (t, 1H), 7.95 (s, 1H), 7.55-7.51 (m, 2H), 7.25-7.21 (t, 1H), 7.02-7.01 (d, 1H), 6.84-6.77 (m, 1H), 6.11-6.06 (d, 1H), 5.67-5.64 (d, 1H), 4.60-4.59 (d, 2H), 4.44-4.41 (d, 1H), 4.10-4.07 (d, 1H), 3.83 (s, 3H), 3.59 (s, 1H), 3.07-2.98 (m, 2H), 2.67-2.57 (m, 4H), 1.81-1.75 (t, 2H), 1.49-1.46 (m, 3H), 1.27-1.25 (d, 6H); LCMS: m/z=478.3 (M+H)$^+$.

Example-29: Synthesis of (E)-4-(dimethylamino)-1-(4-(2-(((8-isopropyl-2-((tetrahydro-2H-pyran-4-yl)amino)pyrazolo[1,5-a][1,3,5]triazin-4-yl)amino)methyl)phenyl)piperazin-1-yl)but-2-en-1-one (Compound-137)

Step-1: Synthesis of tert-butyl 4-(2-(((8-isopropyl-2-(methylthio)pyrazolo[1,5-a][1,3,5]triazin-4-yl)amino)methyl)phenyl)piperazine-1-carboxylate

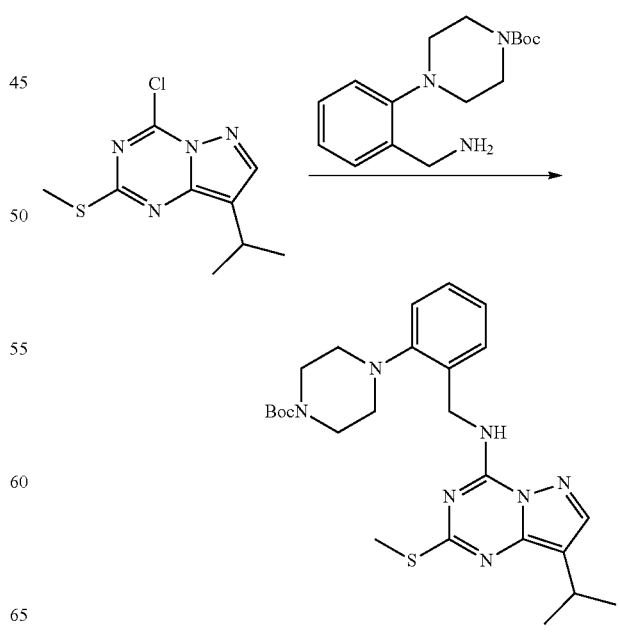

The process of this step was adopted from step-1 of example-4 (0.8 g, 80%). LCMS: m/z=498.2 (M+H)⁺.

Step-2: Synthesis of 4-(tert-butoxycarbonyl)-1-(2-(((8-isopropyl-2-(methylsulfonyl)pyrazolo [1,5-a][1,3,5]triazin-4-yl)amino)methyl)phenyl)piperazine 1-oxide

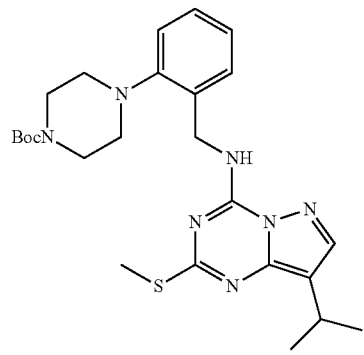

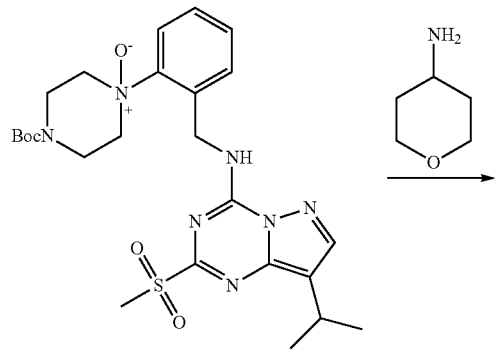

The process of this step was adopted from step-2 of example-4 (0.7 g, crude). LCMS: m/z=546.3 (M+H)⁺.

Step-3: Synthesis of 4-(tert-butoxycarbonyl)-1-(2-(((8-isopropyl-2-((tetrahydro-2H-pyran-4-yl)amino)pyrazolo[1,5-a][1,3,5]triazin-4-yl)amino)methyl)phenyl)piperazine 1-oxide

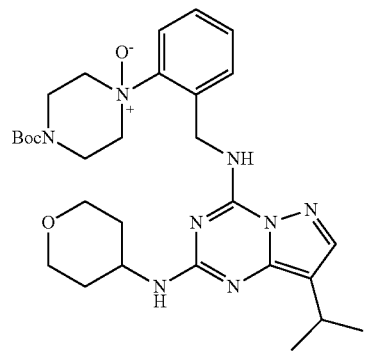

The process of this step was adopted from step-3 of example-4 (0.6 g, crude). LCMS: m/z=567.7 (M+H)⁺.

Step-4: Synthesis of 8-isopropyl-N4-(2-(piperazin-1-yl)benzyl)-N2-(tetrahydro-2H-pyran-4-yl)pyrazolo [1,5-a][1,3,5]triazine-2,4-diamine

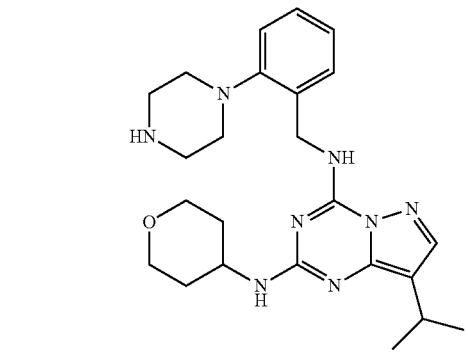

The process of this step was adopted from step-4 of example-4 (0.40 g, crude). LCMS: m/z=451.3 (M+H)⁺.

Step-6: Synthesis of (E)-4-(dimethylamino)-1-(4-(2-(((8-isopropyl-2-((tetrahydro-2H-pyran-4-yl)amino)pyrazolo[1,5-a][1,3,5]triazin-4-yl)amino)methyl)phenyl)piperazin-1-yl)but-2-en-1-one

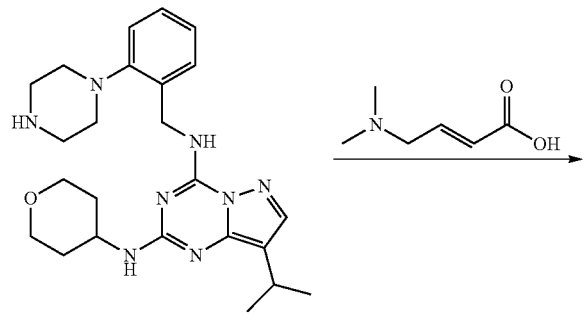

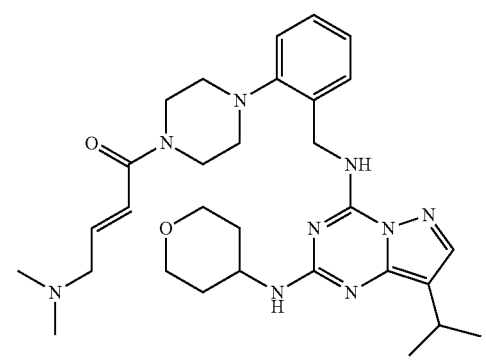

To a cooled solution of (E)-4-(dimethylamino)but-2-enoic acid (0.073 g, 0.44 mmol) in DMF (5 mL) at 0° C. was added HATU (0.25 g, 0.666 mmol) followed by DIPEA (0.32 mL, 1.77 mmol) and finally added 8-isopropyl-N4-(2-(piperazin-1-yl)benzyl)-N2-(tetrahydro-2H-pyran-4-yl)pyrazolo[1,5-a][1,3,5]triazine-2,4-diamine (0.2 g, 0.444 mmol). The reaction mixture was stirred for 1 h at room temperature. The reaction mixture was quenched with ice-water and diluted with ethyl acetate. The aqueous layer was separated and extracted with ethyl acetate (2×25 mL). The combined organic phase was washed with brine, dried over Na$_2$SO$_4$, filtered and concentrated the crude residue was purified by preparative HPLC (Method: A: 0.01% TFA in water, B: ACN: MeOH, Column: Kinetex Evo C18: (150 mm*21.2 mm) to afford desired title compound as TFA salt. To removal TFA passed the compound through vari pure basic resin column using MeOH as eluent to afford the title compound as free base (0.07 g, 38%). $^1$H NMR (DMSO-d$_6$, 400 MHz): δ 8.80-8.50 (d, 1H), 7.72 (s, 1H), 7.23-7.16 (m, 3H), 7.06 (t, 1H), 6.80 (s, 1H), 6.64-6.63 (m, 2H), 4.76-4.74 (d, 2H), 3.82-3.73 (m, 8H), 3.04-3.03 (d, 2H), 2.92-2.86 (m, 5H), 2.67 (s, 1H), 2.45 (s, 1H), 2.15 (s, 6H); 1.82 (s, 1H), 1.46 (s, 2H), 1.24-1.22 (d, 7H); LCMS: m/z=562.45 (M+H)$^+$.

Example-30: Synthesis of (E)-1-(4-(((8-isopropyl-2-((tetrahydro-2H-pyran-4-yl)amino)pyrazolo[1,5-a][1,3,5]triazin-4-yl)amino)methyl)piperidin-1-yl)-4-(pyrrolidin-1-yl)but-2-en-1-one (Compound-138)

Step-1: Synthesis of tert-butyl 4-(((8-isopropyl-2-(methylthio)pyrazolo[1,5-a][1,3,5]triazin-4-yl)amino)methyl)piperidine-1-carboxylate

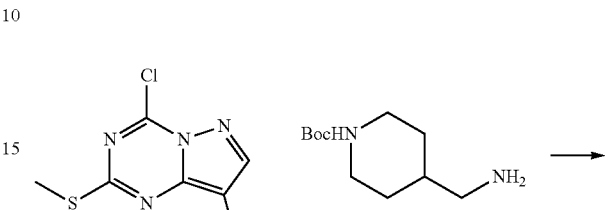

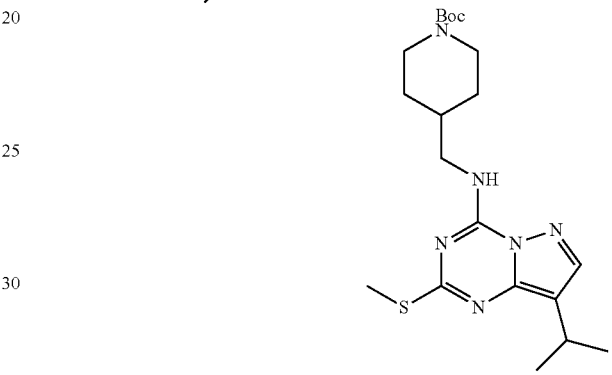

tert-Butyl 4-(aminomethyl)piperidine-1-carboxylate (0.619 g, 2.89 mmol) was added to a solution of 4-chloro-8-isopropyl-2-(methylthio)pyrazolo[1,5-a][1,3,5]triazine (0.7 g, 2.89 mmol) in acetonitrile (50 mL) at 0° C. The resulting reaction mixture was stirred at ambient temperature for 15 h. After completion of the reaction, the reaction mixture was concentrated under vacuum and purified the residue in 100-200 mesh silica column by eluting with 5% ethyl acetate-hexane to afford the title compound (0.9 g, 74%). LCMS: m/z=421.4 (M+H)$^+$.

Step-2: Synthesis of tert-butyl 4-(((8-isopropyl-2-(methyl sulfonyl)pyrazolo[1,5-a][1,3,5]triazin-4-yl)amino)methyl)piperidine-1-carboxylate

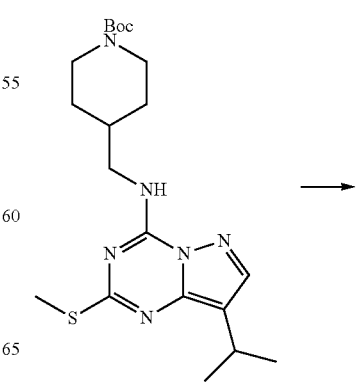

205 -continued

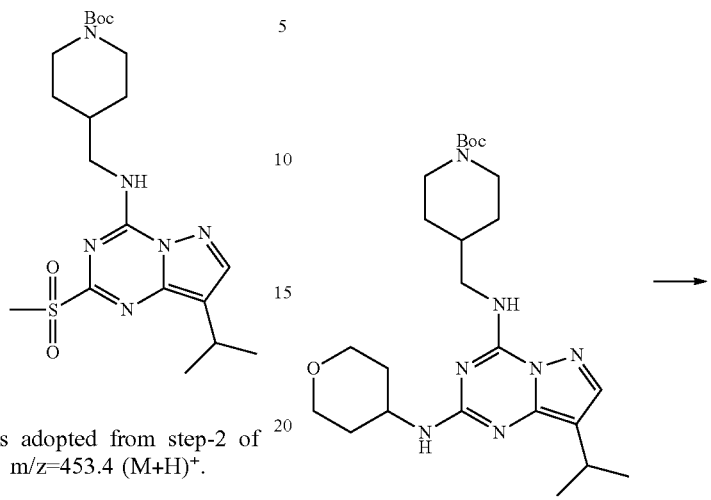

The process of this step was adopted from step-2 of example-4 (0.5 g, 58%). LCMS: m/z=453.4 (M+H)⁺.

Step-3: Synthesis of tert-butyl 4-(((8-isopropyl-2-((tetrahydro-2H-pyran-4-yl)amino)pyrazolo[1,5-a][1,3,5]triazin-4-yl)amino)methyl)piperidine-1-carboxylate

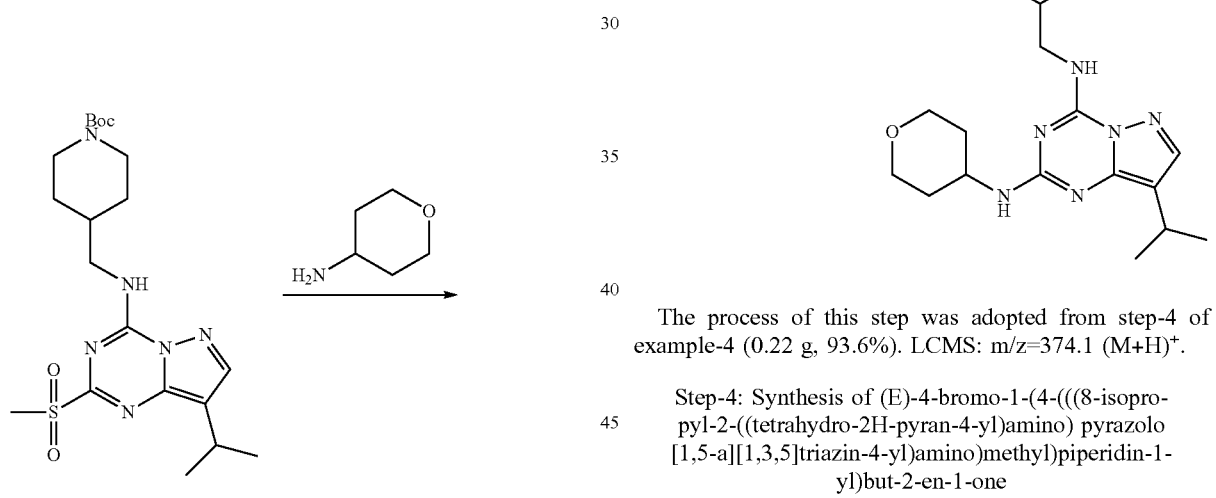

The process of this step was adopted from step-3 of example-4 (0.32 g, 67.6%). LCMS: m/z=474.5 (M+H)⁺.

206

Step-4: Synthesis of 8-isopropyl-N4-(piperidin-4-ylmethyl)-N2-(tetrahydro-2H-pyran-4-yl)pyrazolo[1,5-a][1,3,5]triazine-2,4-diamine The process of this step was adopted from step-4 of example-4 (0.22 g, 93.6%). LCMS: m/z=374.1 (M+H)⁺.

Step-4: Synthesis of (E)-4-bromo-1-(4-(((8-isopropyl-2-((tetrahydro-2H-pyran-4-yl)amino) pyrazolo[1,5-a][1,3,5]triazin-4-yl)amino)methyl)piperidin-1-yl)but-2-en-1-one

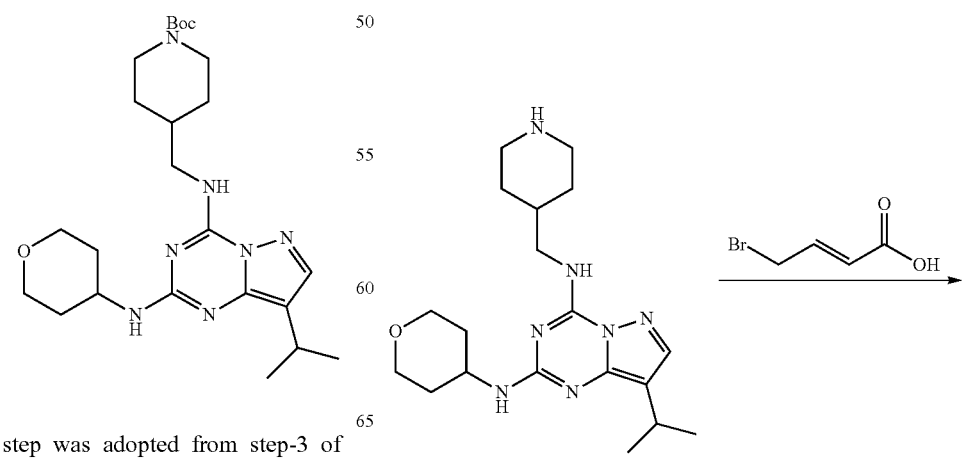

-continued

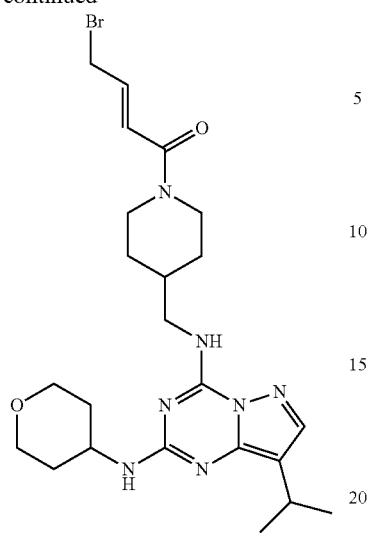

-continued

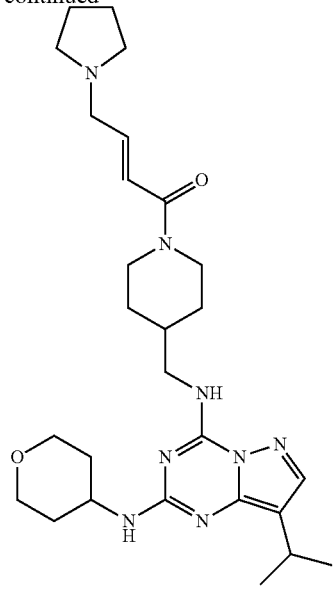

To a cooled solution of (E)-4-bromobut-2-enoic acid (0.66 g, 0.8 mmol) in DMF (10 mL) at 0° C. was added HATU (0.3 g, 0.8 mmol) followed by DIPEA (0.139 mL, 0.8 mmol) and finally added 8-isopropyl-N4-(piperidin-4-ylmethyl)-N2-(tetrahydro-2H-pyran-4-yl) pyrazolo[1,5-a][1,3,5]triazine-2,4-diamine (0.15 g, 0.4 mmol). The reaction mixture was stirred for 1 h at room temperature. The reaction mixture was quenched with ice-water and diluted with ethyl acetate. The aqueous layer was separated and extracted with ethyl acetate (2×25 mL). The combined organic phase was washed with brine, dried over Na$_2$SO$_4$, filtered and concentrated. The residue was purified by 100-200 silica gel column chromatography to afford desired title compound (0.135 g, 86.5%). LCMS: m/z=522.0 (M+H)$^+$.

Step-5: Synthesis of (E)-1-(4-(((8-isopropyl-2-((tetrahydro-2H-pyran-4-yl)amino)pyrazolo [1,5-a][1,3,5]triazin-4-yl)amino)methyl)piperidin-1-yl)-4-(pyrrolidin-1-yl)but-2-en-1-one

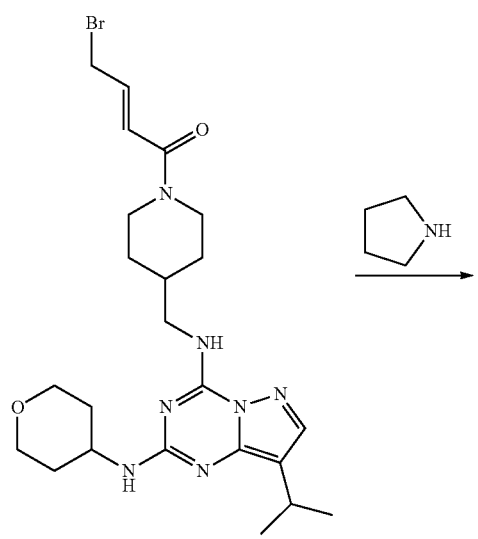

K$_2$CO$_3$ (0.09 g, 0.65 mmol) and pyrrolidine (0.028 g, 0.39 mmol) was sequentially added to a solution of (E)-4-bromo-1-(4-(((8-isopropyl-2-((tetrahydro-2H-pyran-4-yl)amino) pyrazolo[1,5-a][1,3,5]triazin-4-yl)amino)methyl)piperidin-1-yl)but-2-en-1-one (0.17 g, 0.33 mmol) in ACN (10 mL) and the resulting mix was allowed to stir for 4 h at 60° C. The reaction mixture was quenched with water and diluted with ethyl acetate. The aqueous layer was separated and extracted with ethyl acetate (2×25 mL). The combined organic phase was washed with brine, dried over Na$_2$SO$_4$, filtered and concentrated. The residue was purified by prep. HPLC (Method-A: 0.1% formic acid in water, B: Acetonitrile-Methanol, Column: KINETEX C18 (21.2 mm*150 mm, 5 μm)) to afford desired title compound (0.02 g, 11.9%). $^1$HNMR (DMSO-d$_6$, 400 MHz): δ 8.30 (d, 1H), 7.68 (s, 1H), 6.89 (d, 1H), 6.54-6.64 (m, 2H), 4.38-4.35 (d, 1H), 4.02-3.99 (d, 1H), 4.87-4.84 (d, 2H), 3.40-3.29 (m, 2H), 3.16 (d, 2H), 3.04-2.86 (m, 2H), 2.58-2.41 (m, 8H), 2.02-1.97 (m, 2H), 1.88-1.78 (m, 2H), 1.68-1.67 (m, 5H), 1.53-1.45 (m, 2H), 1.23-1.2 (m, 6H), 1.06-1.04 (m, 2H); LCMS: m/z=511.80 (M+H)$^+$.

Example-31: Synthesis of 1-acryloyl-N-(3-(((3-isopropyl-5-((tetrahydro-2H-pyran-4-yl)amino)pyrazolo [1,5-a]pyrimidin-7-yl)amino)methyl)phenyl)azetidine-2-carboxamide (Compound-139)

Step-1: Synthesis of 5-chloro-3-isopropyl-N-(3-nitrobenzyl)pyrazolo[1,5-a]pyrimidin-7-amine

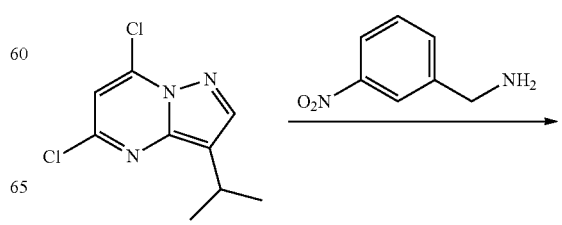

-continued

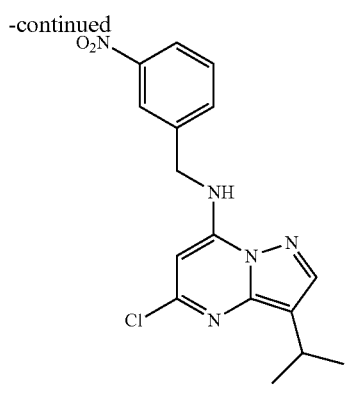

The process of this step was adopted from step-1 of example-4 (0.8 g, 99%). LCMS: m/z=346 (M+H)⁺.

Step-2: Synthesis of tert-butyl (5-chloro-3-isopropylpyrazolo [1,5-a]pyrimidin-7-yl)(3-nitrobenzyl)carbamate To a solution of 5-chloro-3-isopropyl-N-(3-nitrobenzyl) pyrazolo[1,5-a]pyrimidin-7-amine (0.8 g, 2.31 mmol) in CCl₄ (20 mL) was added (BOC)₂O (0.6 g, 2.78 mmol), followed by DMAP (0.028 g, 0.23 mmol) and reaction mixture was stirred at room temperature for 1 h. After completion of the reaction, the reaction mixture was concentrated to afford the title compound (1 g, 86%). LCMS: m/z=446 (M+H)⁺.

Step-3: Synthesis of tert-butyl (3-isopropyl-5-((tetrahydro-2H-pyran-4-yl)amino) pyrazolo[1,5-a]pyrimidin-7-yl)(3-nitrobenzyl)carbamate

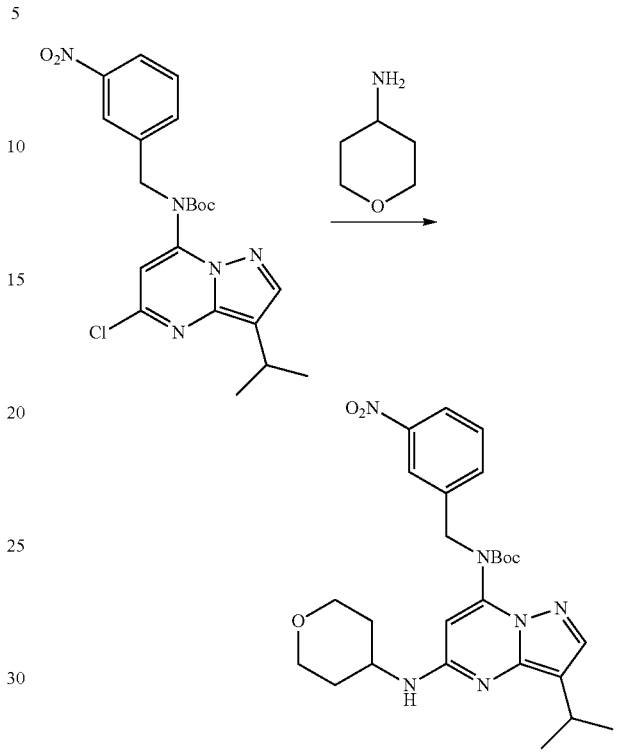

To a solution of tert-butyl (5-chloro-3-isopropylpyrazolo [1,5-a]pyrimidin-7-yl)(3-nitrobenzyl)carbamate (1 g, 2.24 mmol) and tetrahydro-2H-pyran-4-amine (0.68 g, 6.74 mmol) in toluene (20 mL) was added NaO^tBu (0.31 g, 3.28 mmol) and degassed with N₂ gas for 10 min. Then added BINAP (0.2 g, 0.33 mmol) followed by Pd₂(dba)₃ (0.1 g, 0.1 mmol), then reaction mixture was heated to 100° C. for 12 h. After completion of the reaction, the reaction mixture was cooled to room temperature and filtered through celite bed and washed with ethyl acetate (2×20 mL). The filtrate was concentrated under vacuum and purified by column chromatography using 100-200 silica gel to afford the title compound (0.8 g, 70%). LCMS: m/z=511 (M+H)⁺.

Step-4: Synthesis of tert-butyl (3-aminobenzyl)(3-isopropyl-5-((tetrahydro-2H-pyran-4-yl)amino)pyrazolo[1,5-a]pyrimidin-7-yl)carbamate

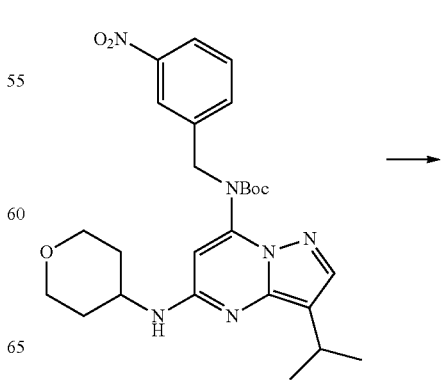

-continued

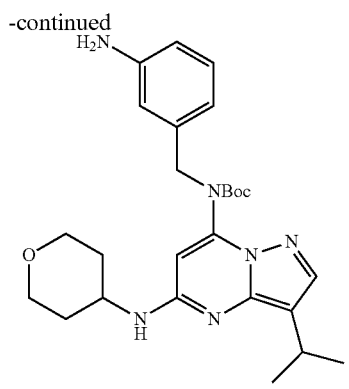

To a solution of tert-butyl (3-isopropyl-5-((tetrahydro-2H-pyran-4-yl)amino)pyrazolo[1,5-a]pyrimidin-7-yl)(3-nitrobenzyl)carbamate (0.8 g, 1.56 mmol) in THF:MeOH:Water (3:2:1 ratio, 20 mL) were added zinc (1.02 g, 15.68 mmol) and ammonium chloride (1.7 g, 31.36 mmol). The reaction mixture was stirred at room temperature for 4 h. After completion of reaction, the reaction mixture was filtered through celite and diluted with ethyl acetate. The aqueous layer was separated and extracted with ethyl acetate (2×25 mL). The combined organic phase was washed with brine, dried over $Na_2SO_4$, filtered and concentrated. The residue was purified by 100-200 silica gel column chromatography to afford desired title compound (0.6 g, 87%). LCMS: m/z=480.8 (M+H)$^+$.

Step-5: Synthesis of tert-butyl (3-(1-acryloylazetidine-2-carboxamido)benzyl)(3-isopropyl-5-((tetrahydro-2H-pyran-4-yl)amino)pyrazolo[1,5-a]pyrimidin-7-yl)carbamate

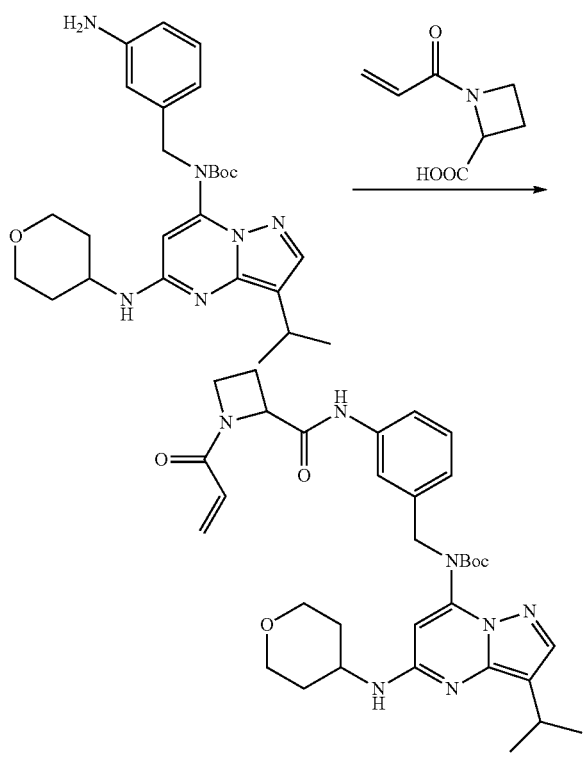

The process of this step was adopted from example-1 (0.3 g, crude). LCMS: m/z=617.9 (M+H)$^+$.

Step-6: Synthesis of 1-acryloyl-N-(3-(((3-isopropyl-5-((tetrahydro-2H-pyran-4-yl)amino) pyrazolo[1,5-a]pyrimidin-7-yl)amino)methyl)phenyl)azetidine-2-carboxamide

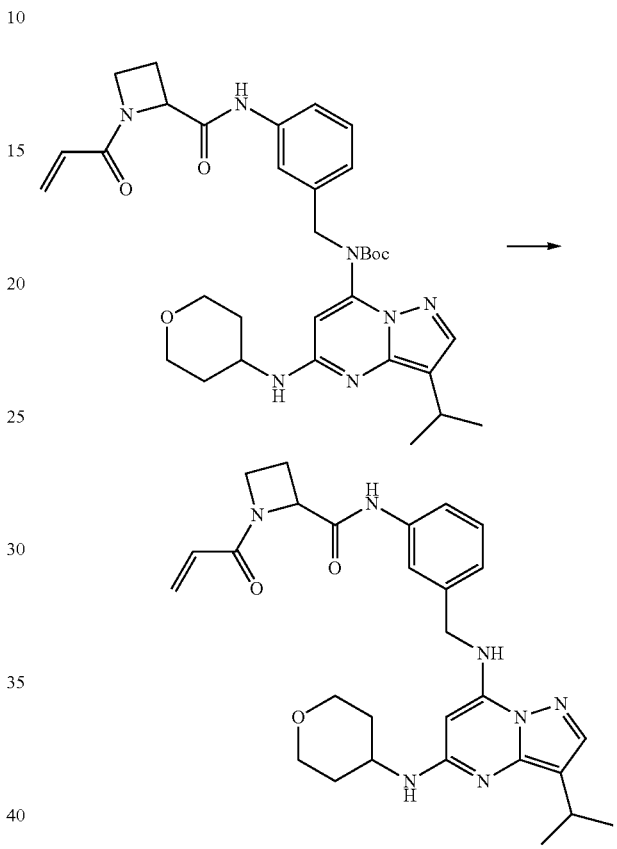

The process of this step was adopted from step-2 of example-2. The obtained crude compound was purified by preparative HPLC (Method: A: 0.02% Ammonia in water, B: ACN:MeOH (1:1) Column: X bridge C18: (150 mm*21.2 mm) to afford desired title compound as free base (0.1 g, 10%). $^1$HNMR (DMSO-d$_6$, 400 MHz): δ 10.17 (s, 1H), 7.83-7.81 (m, 1H), 7.61 (s, 1H), 7.58-7.52 (m, 2H), 7.29-7.25 (m, 1H), 7.05-7.02 (t, 1H), 6.57-6.55 (m, 2H), 6.36-6.29 (m, 1H), 6.13-6.05 (m, 2H), 5.72-5.69 (m, 1H), 5.58-5.57 (m, 1H), 5.01 (s, 2H), 4.43-4.42 (d, 2H), 4.21-4.15 (m, 1H), 3.88-3.79 (m, 2H), 3.37-3.34 (m, 2H), 2.95-2.92 (m, 1H), 2.20 (m, 1H), 1.84-1.81 (d, 2H), 1.38-1.33 (m, 2H), 1.24-1.22 (d, 6H); LCMS: m/z=518.8 (M+H)$^+$.

Although the present application has been illustrated by certain of the preceding examples, it is not to be construed as being limited thereby; but rather, the present application encompasses the generic area as hereinbefore disclosed. Various modifications and embodiments can be made without departing from the spirit and scope thereof. For example, the following compounds which can be prepared by following similar procedure as described above with suitable modifications known to the one ordinary skilled in the art are also included in the scope of the present application

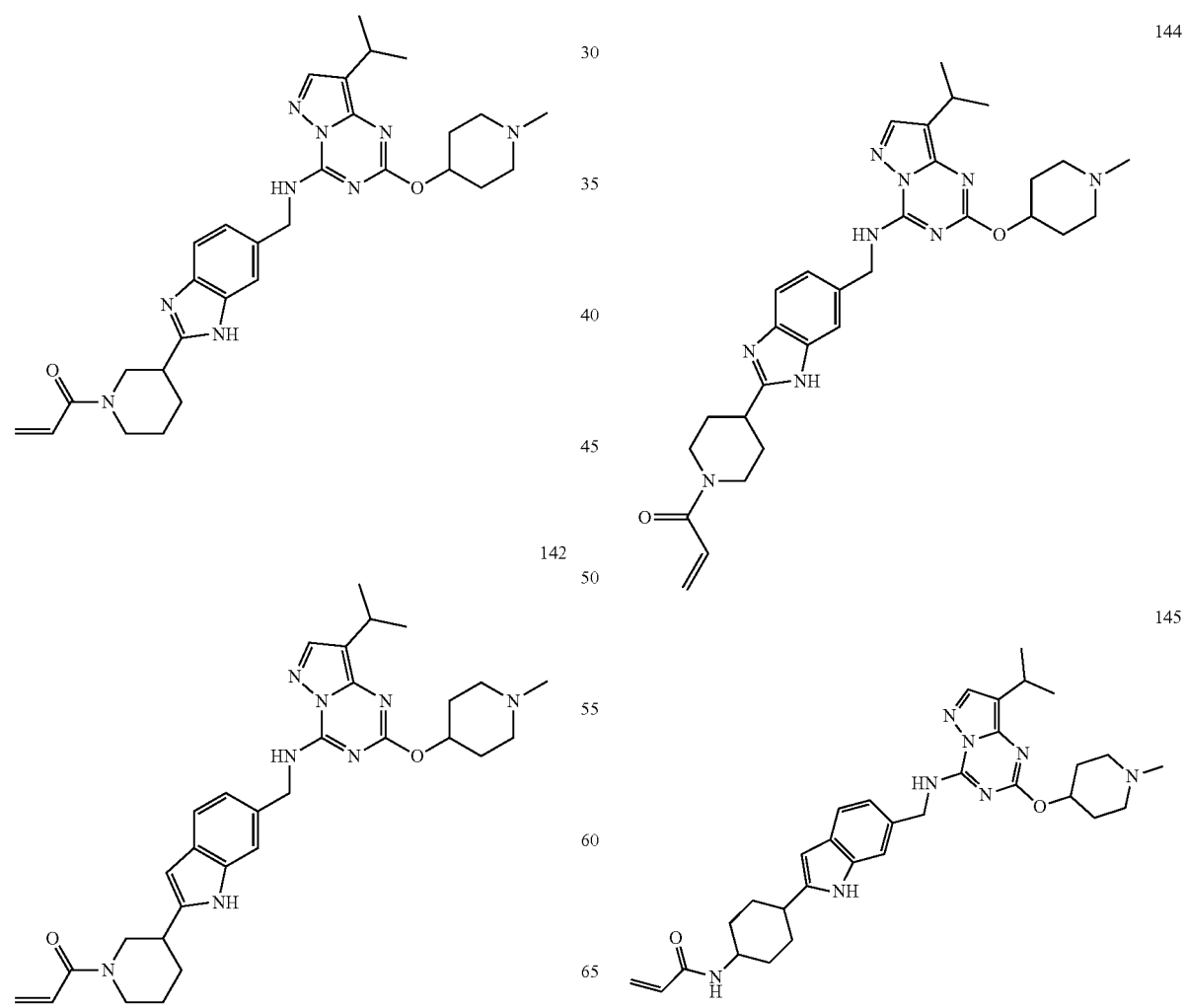

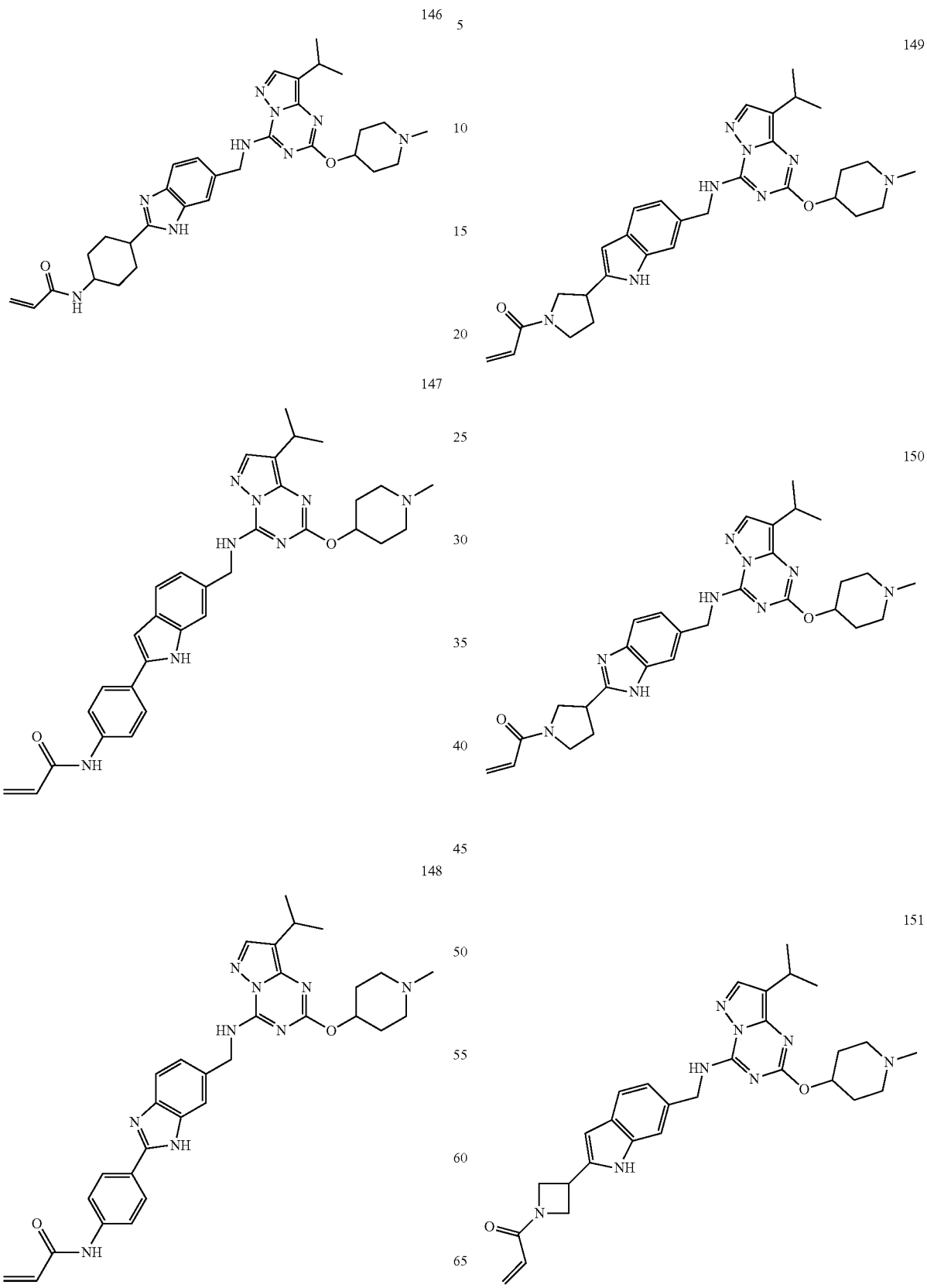

217
-continued
152
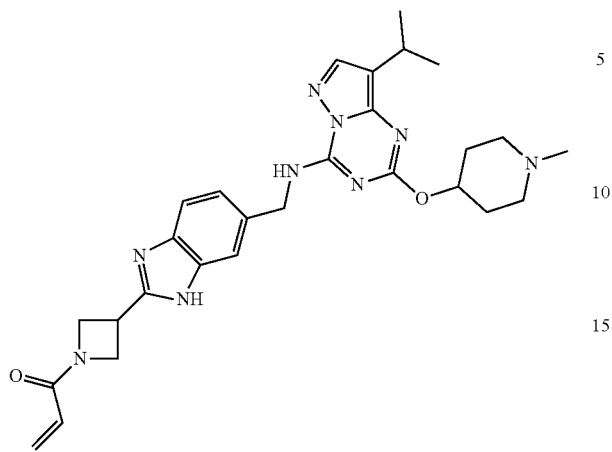
153
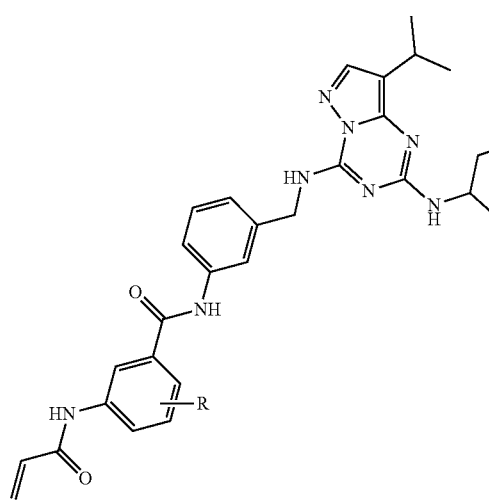
R = F, Me, OMe, Cl
154
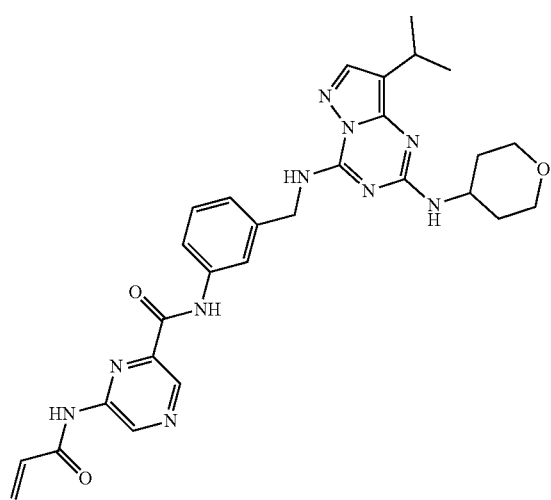
218
-continued
155
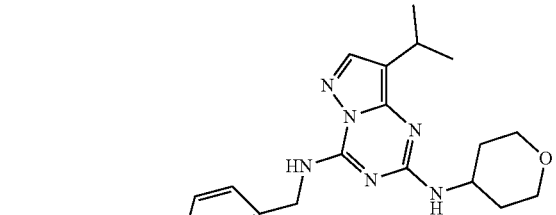
156
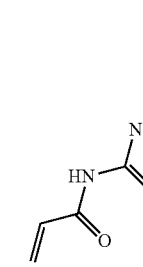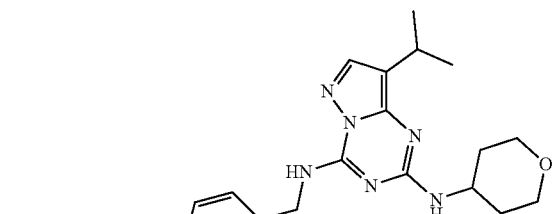
157
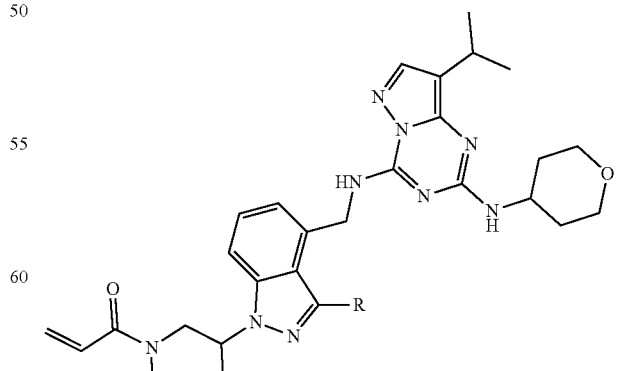
R = H, Me, Et, I-Pr, cPr -continued

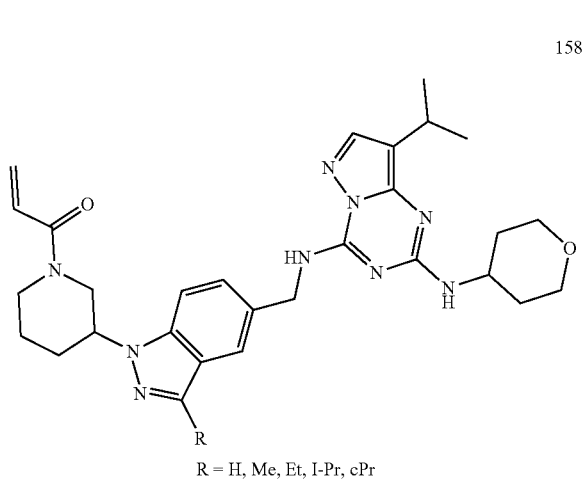

158

R = H, Me, Et, I-Pr, cPr

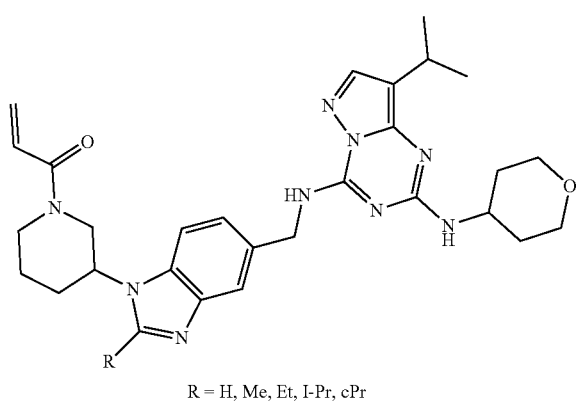

159

R = H, Me, Et, I-Pr, cPr

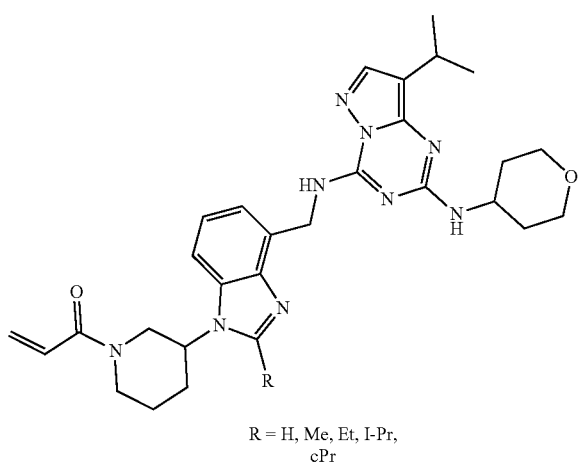

160

R = H, Me, Et, I-Pr, cPr

-continued

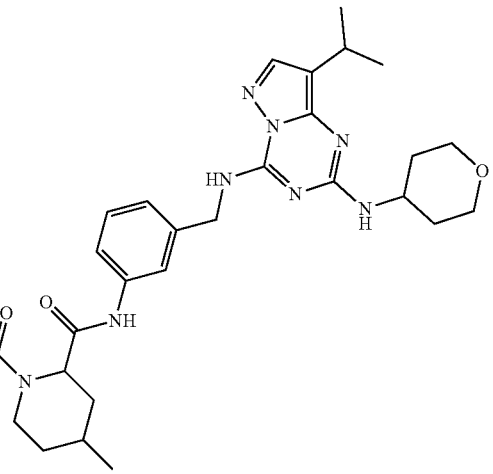

161

Example-32: Biochemical Assay for CDK7

The ability of compounds to inhibit CDK7 kinase activity was tested in a TR-FRET assay using 5 nM of CDK7/CycH/ MNAT1 obtained from Invitrogen, USA. Test compounds were pre-incubated with the kinase at room temperature for 60 min. After incubation, substrate mix [100 nM Ultra-light MBP (Perkin Elmer, USA) and 1 mM ATP (Sigma)] was added. The above reaction was stopped by the addition of 40 mM EDTA after 60 minutes of kinase reaction. 1 nM Eu-labelled antiphospho-MBP antibody [Perkin Elmer, USA] was added, mixed well and the fluorescence emission at 615 nm and 665 nm [excitation at 340 nm] was measured. The final DMSO concentration in the assay was 1%. For $IC_{50}$ determination, appropriate concentrations were made by $\frac{1}{3}^{rd}$ serial dilutions of 10 mM DMSO stock solution of test compound. All the fluorescence measurements were made in a Victor 3 Multilabel Counter [Perkin Elmer, USA]. The $IC_{50}$ was determined by fitting the dose response data to sigmoidal curve fitting equation using GraphPad Prism software V5. To identify compounds that inhibit CDK7 irreversibly, time depended inhibition studies were carried by pre-incubating compound with the enzyme at three time points (20, 60 and 180 min) and carrying out assay as described above.

Selected compounds were screened in the above mentioned assay procedure. The % inhibition of the selected compounds and the $IC_{50}$ values are summarised in the below table; wherein group "A" refers to an $IC_{50}$ value of less than or equal to 300 nM, group "B" refers to $IC_{50}$ value in range of 300.01 to 1000 nM and group "C" refers to $IC_{50}$ value of greater than 1000 nM.

| Compound No. | % inhibition @ 10 µM | $IC_{50}$ | Compound No. | % inhibition @ 10 µM | $IC_{50}$ |
|---|---|---|---|---|---|
| 1. | 88 | B | 2. | 98 | A |
| 3. | 96 | A | 4. | 93 | A |
| 5. | 94 | A | 6. | 91 | A |
| 7. | 91 | C | 8. | 96 | A |
| 9. | 85 | C | 10. | 89 | B |
| 11. | 89 | B | 12. | 92 | B |
| 13. | 93 | B | 14. | 97 | A |
| 15. | 98 | A | 16. | — | A |

-continued

| Compound No. | % inhibition @ 10 μM | $IC_{50}$ | Compound No. | % inhibition @ 10 μM | $IC_{50}$ |
|---|---|---|---|---|---|
| 17. | 84 | C | 18. | 101 | A |
| 19. | 100 | A | 20. | 100 | A |
| 21. | 96 | A | 22. | 98 | A |
| 23. | 98 | A | 24. | 98 | A |
| 25. | 99 | A | 26. | 95 | B |
| 27. | 100 | A | 28. | 99 | A |
| 29. | 98 | A | 30. | 98 | A |
| 31. | 100 | A | 32. | 91 | A |
| 33. | 86 | B | 34. | 73 | C |
| 35. | 99 | A | 36. | 91 | B |
| 37. | 91 | A | 38. | 95 | A |
| 39. | 76 | C | 40. | 99 | A |
| 41. | 92 | B | 42. | 99 | A |
| 43. | 79 | B | 44. | 94 | A |
| 45. | 73 | C | 46. | 98 | A |
| 47. | 100 | A | 48. | 98 | A |
| 49. | 84 | C | 50. | 97 | A |
| 51. | 91 | B | 52. | 96 | — |
| 53. | 99 | A | 54. | 98 | A |
| 55. | 99 | A | 56. | 97 | A |
| 57. | 84 | C | 58. | 96 | B |
| 59. | 98 | A | 60. | 98 | A |
| 61. | 76 | C | 62. | 97 | A |
| 63. | 94 | B | 64. | 91 | B |
| 65. | 86 | C | 66. | 98 | A |
| 67. | 91 | B | 68. | 92 | B |
| 69. | 98 | A | 70. | 85 | B |
| 71. | 92 | B | 72. | 84 | B |
| 73. | 101 | A | 74. | 99 | A |
| 75. | 97 | A | 76. | 81 | C |
| 77. | 99 | A | 78. | 100 | A |
| 79. | 96 | A | 80. | 94 | B |
| 81. | 98 | A | 82. | 93 | B |
| 83. | 96 | A | 84. | 97 | A |
| 85. | 99 | A | 86. | 99 | A |
| 87. | 32 | — | 88. | 97 | A |
| 89. | 38 | — | 90. | 95 | A |
| 91. | 94 | A | 92. | 97 | A |
| 93. | 96 | A | 94. | 99 | A |
| 95. | 93 | A | 96. | 87 | B |
| 97. | 87 | B | 98. | 88 | B |
| 99. | 82 | C | 100. | 82 | B |
| 101. | 96 | A | 102. | 82 | B |
| 103. | 80 | C | 104. | 78 | C |
| 105. | 92 | A | 106. | 91 | C |
| 107. | 95 | A | 108. | 99 | A |
| 109. | 98 | A | 110. | 99 | A |
| 111. | 95 | A | 112. | 99 | A |
| 113. | — | A | 114. | 97 | A |
| 115. | 94 | A | 116. | 92 | A |
| 117. | 95 | A | 118. | 93 | B |
| 119. | 99 | A | 120. | 93 | A |
| 121. | 93 | A | 122. | — | A |
| 123. | 96 | A | 124. | 94 | A |
| 125. | 86 | A | 126. | 80 | C |
| 127. | 95 | A | 128. | 93 | A |
| 129. | 94 | A | 130. | 97 | A |
| 131. | 86 | B | 132. | 90 | A |
| 133. | 97 | A | 134. | 97 | A |
| 135. | 97 | A | 136. | 73 | C |
| 137. | 99 | A | 138. | 64 | C |
| 139. | 98 | A | 40A. | — | A |
| 40B. | — | A | 40C. | — | A |
| 40D. | — | B | 48A. | — | A |

Example-33: In Vivo Efficacy of CDK7 Inhibitor in the MV4-11 Human Acute Myeloid Leukemia (AML) Cancer Xenograft Model The effect of the CDK7 inhibitor to inhibit the growth of MV4-11 xenograft tumors implanted in mice was evaluated. Briefly, MV4-11 cells were grown in Iscove's Modified Dulbecco's Medium (Sigma Aldrich) medium supplemented with 10% FBS (Invitrogen) and 1% penicillin streptomycin (Invitorgen). To establish tumors, $15 \times 10^6$ MV4-11 cells were injected subcutaneously in 200 μl of 1:1 HBSS (Sigma: H4641) and ECM gel (Corning) into the right hind flank of male atthymic nude mice (Envigo). Tumor volume was measured thrice a week and body weight was monitored daily. To estimate tumor volumes, the length (D) and width (d), of the xenograft tumors were measured manually with calipers and the tumor volume was calculated using the formula: Tumor volume=$(D \times d^2)/2$. Treatment was initiated when the average tumor size had reached approximately 250 mm3. The animals were randomized based on tumor volumes into two groups of seven animals each. To evaluate efficacy, compound-115 was administered intraperitoneally once per day (q24 h/qd schedule). The treatment period was for 14 days after which the overall efficacy was evaluated based on tumor volume changes observed during the treatment period. Tumor volumes were analyzed using one-way ANOVA with Dunnett's multiple comparisons test for comparison of treatment versus control group. Results are shown in graph (FIG. 1).

Example-34: Inhibition of RNA Polymerase II CTD Phosphorylation in Cell Western Assay 25000 cells (MDA-MB-231/NCI-H358) were seeded in 96 well black clear bottom plate incubated for overnight before addition of selected compound. 3 fold dilutions of selected compound diluted in DMSO starting from 10 μM, added to cells and incubated for 4 hours at 37° C., 5% $CO_2$ incubator. Cells were washed once with 100 μl of phosphate buffered saline (sigma #P3813), then fixed with 100 μl/well of 4% Para formaldehyde for 60 min at room temperature, in dark. The cells were washed 3 times with 100 μl of wash buffer (PBS with 0.1% Triton-X-100), later blocked for 2 hours at room temperature in blocking buffer (5% BSA in PBST). Cells were stained overnight at 4° C. with Phospho RNA Pol II (S5) (Millipore #04-1572, Abcam #5131) or Phospho RNA Pol II (Ser-2), antibody (Bethyl labs #A300-654-A) in blocking buffer. Post incubation cells were washed with Delifia wash buffer (Perkin Elmer #4010-0010). Cells were treated with LANCE secondary antibodies (LANCE® Eu-W1024 perkin elmer #AD-0076 for phospho Ser-5 CTD RNA pol-II and Delfia Eu-N1 anti rabbit IgG Perkin elmer #AD0106 for phospho Ser-2 CTD RNA pol-II) for 2 hours in assay buffer (Perkin Elmer #1244-111), Cells were washed 3 times with Delfia wash buffer post incubation, Enhancement solution (Perkin Elmer #1244-105) added and incubated for 20 mins. Europium readings were taken in Victor-3 instrument. Cell normalization was done using Hoechst dye (0.5 μg/ml).

The inhibition ($EC_{50}$ in μM) of RNA polymerase II CTD phosphosphorylation for selected compounds was evaluated in below table:

Selected compounds were screened in the above mentioned assay procedure. The $EC_{50}$ values are summarised in the below table; wherein group "A" refers to an $EC_{50}$ value of less than or equal to 1 μM, group "B" refers to $EC_{50}$ value in range of 1 to 10 μM and group "C" refers to $EC_{50}$ value of greater than 10 μM.

| Compound No. | $EC_{50}$ | Compound No. | $EC_{50}$ |
|---|---|---|---|
| 1 | A | 2 | A |
| 3 | A | 4 | A |
| 5 | B | 6 | B |

-continued

| Compound No. | EC$_{50}$ | Compound No. | EC$_{50}$ |
|---|---|---|---|
| 8 | A | 13 | B |
| 14 | B | 15 | C |
| 18 | A | 20 | A |
| 21 | A | 24 | A |
| 32 | B | 38 | B |
| 69 | B | 78 | A |
| 83 | A | 85 | B |
| 88 | B | 90 | B |
| 91 | C | 92 | B |
| 93 | B | 94 | A |
| 95 | A | 96 | B |
| 97 | B | 101 | B |
| 105 | C | 106 | B |
| 107 | B | 108 | B |
| 109 | B | 110 | B |
| 111 | B | 114 | B |
| 115 | A | 116 | B |
| 117 | B | 119 | C |
| 122 | C | 124 | C |
| 125 | A | 128 | B |
| 129 | B | 131 | C |
| 132 | C | 134 | B |

We claim:

1. A compound of formula (I):

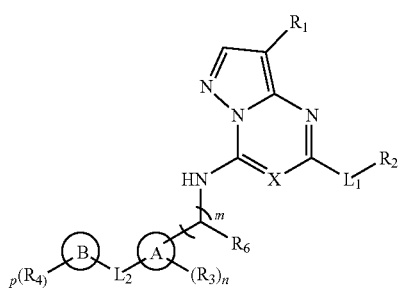

or a pharmaceutically acceptable salt or a stereoisomer thereof;

wherein,

X is CH or N;

Ring A is 1,3-phenylene, pyridyl or pyridine-N-oxide;

Ring B is cycloalkyl, heterocycloalkyl or heteroaryl;

$R_1$ is hydrogen, alkyl or cycloalkyl;

$R_2$ is an optionally substituted alkyl, cycloalkyl or heterocycloalkyl; wherein the optional substituents are amino, halo, hydroxy, alkyl, alkoxy, alkoxyalkoxy, alkylamino, or haloalkyl;

$R_3$ at each occurrence independently is halo, alkyl, hydroxy, or haloalkyl;

$R_4$ at each occurrence independently is —(NH)$_q$—S(O)$_2$—CH=CH$_2$, —(NH)$_q$—CH$_2$—CH=CH—

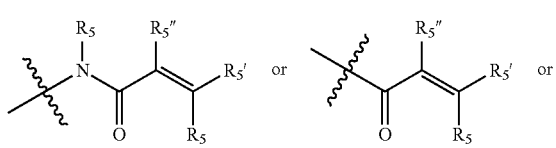

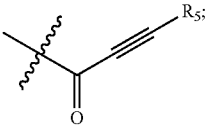

C(O)—NR$_a$R$_b$, wherein R$_5$ and R$_5$" at each occurrence independently are hydrogen or alkyl; R$_5$' is hydrogen, halo, alkyl, alkoxyalkyl or —CH$_2$—NR$_a$R$_b$;

$R_6$ is hydrogen or alkyl;

$R_a$ and $R_b$ are independently hydrogen or alkyl; or $R_a$ and $R_b$ along with the nitrogen atom to which they are attached form an optionally substituted heterocyclic ring having 0-2 additional heteroatoms selected from O, S and N; wherein the optional substituent is one or more alkyl or halo;

$L_1$ is —O—, or —NH—;

$L_2$ is absent or optionally substituted C$_1$-C$_6$ alkylene, wherein one or more methylene units of the alkylene is optionally and independently replaced with —C(O)—, —O—, —N(R$_7$)—or cycloalkylene; wherein R$_7$ is hydrogen or alkyl;

m is 0 to 1;

n is 0, 1 or 2;

p is 1; and q is 0 to 1.

2. The compound of claim 1, wherein the compound of formula (I) is a compound of formula (IB):

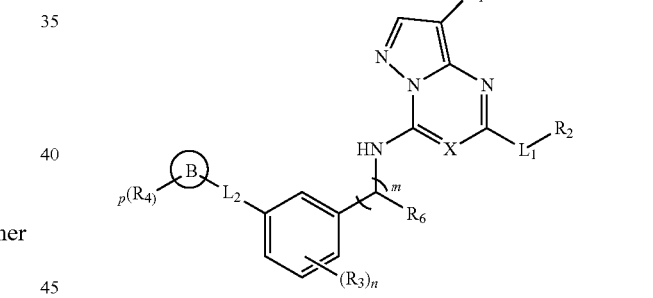

or a pharmaceutically acceptable salt thereof or a stereoisomer thereof.

3. The compound of claim 1, wherein the compound of formula (I) is a compound of formula (IC):

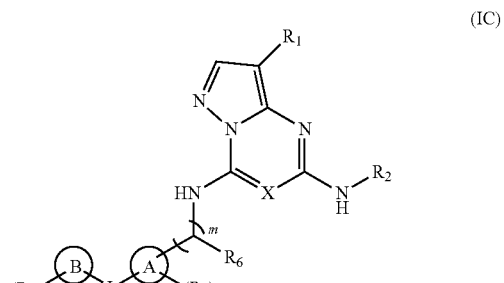

or a pharmaceutically acceptable salt thereof or a stereoisomer thereof;

wherein,
R₂ is optionally substituted cycloalkyl or optionally substituted heterocycloalkyl.

4. The compound of claim 1, wherein the compound of formula (I) is a compound of formula (IE):

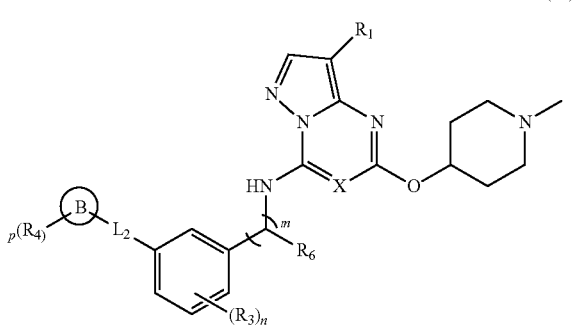

(IE)

or a pharmaceutically acceptable salt thereof or a stereoisomer thereof.

5. The compound of claim 1, wherein ring A is 1,3-phenylene or pyridyl.

6. The compound of claim 1, wherein $R_2$ is cyclohexyl or other optionally substituted cycloalkyl, or $R_2$ is N-methyl-4-piperidinyl, tetrahydro-4-pyranyl or other optionally substituted heterocycloalkyl.

7. The compound of claim 1, wherein $R_1$ is hydrogen, isopropyl or other alkyl.

8. The compound of claim 1, wherein $R_4$ is

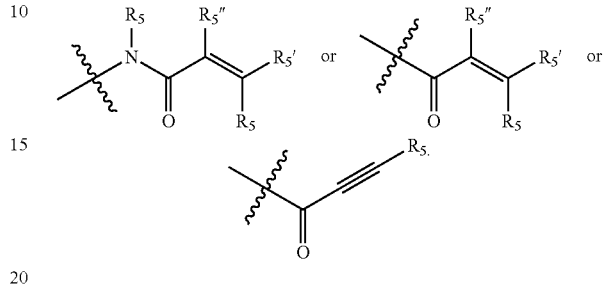

9. The compound of claim 8, wherein $R_5'$ is —CH₂—$NR_aR_b$; wherein $R_a$ and $R_b$ are independently hydrogen or alkyl.

10. The compound of claim 1, wherein the compound is selected from:

| Compound No: | IUPAC name |
|---|---|
| 1. | 1-acryloyl-N-(3-(((8-isopropyl-2-((tetrahydro-2H-pyran-4-yl)amino)pyrazolo[1,5-a][1,3,5]triazin-4-yl)amino)methyl)phenyl)piperidine-3-carboxamide; |
| 2. | 1-acryloyl-N-(3-(((8-isopropyl-2-((tetrahydro-2H-pyran-4-yl)amino)pyrazolo[1,5-a][1,3,5]triazin-4-yl)amino)methyl)phenyl)azetidine-2-carboxamide; |
| 3. | 1-acryloyl-N-(3-(((8-isopropyl-2-((tetrahydro-2H-pyran-4-yl)amino)pyrazolo[1,5-a][1,3,5]triazin-4-yl)amino)methyl)phenyl)pyrrolidine-2-carboxamide; |
| 4. | 1-acryloyl-N-(3-(((8-isopropyl-2-((tetrahydro-2H-pyran-4-yl)amino)pyrazolo[1,5-a][1,3,5]triazin-4-yl)amino)methyl)phenyl)pyrrolidine-3-carboxamide; |
| 7. | (1,4-cis)-4-acrylamido-N-(3-(((8-isopropyl-2-((tetrahydro-2H-pyran-4-yl)amino)pyrazolo[1,5-a][1,3,5]triazin-4-yl)amino)methyl)phenyl)cyclohexane-1-carboxamide; |
| 8. | 1-acryloyl-N-(3-(((8-isopropyl-2-((1-methylpiperidin-4-yl)amino)pyrazolo[1,5-a][1,3,5]triazin-4-yl)amino)methyl)phenyl)piperidine-3-carboxamide; |
| 9. | (1,4-cis)-4-acrylamido-N-(3-(((2-(((1r,4r)-4-hydroxycyclohexyl)amino)-8-isopropylpyrazolo[1,5-a][1,3,5]triazin-4-yl)amino)methyl)phenyl)cyclohexane-1-carboxamide; |
| 10. | Isomer-1: 4-acrylamido-N-(3-(((2-((3-hydroxycyclohexyl)amino)-8-isopropyl pyrazolo[1,5-a][1,3,5]triazin-4-yl)amino)methyl)phenyl)cyclohexane-1-carboxamide; |
| 12. | Isomer-1: 1-acryloyl-N-(3-(((2-((3-hydroxycyclohexyl)amino)-8-isopropyl pyrazolo[1,5-a][1,3,5]triazin-4-yl)amino)methyl)phenyl)pyrrolidine-3-carboxamide; |
| 14. | 1-acryloyl-N-(3-(((2-(((3S,4S)-3-fluoropiperidin-4-yl)amino)-8-isopropyl pyrazolo[1,5-a][1,3,5]triazin-4-yl)amino)methyl)phenyl)pyrrolidine-3-carboxamide; |
| 15. | 1-acryloyl-N-(3-(((2-((3-aminocyclohexyl)amino)-8-isopropylpyrazolo[1,5-a][1,3,5]triazin-4-yl)amino)methyl)phenyl)pyrrolidine-3-carboxamide; |
| 16. | 1-acryloyl-N-(3-(((8-isopropyl-2-((tetrahydro-2H-pyran-3-yl)amino)pyrazolo[1,5-a][1,3,5]triazin-4-yl)amino)methyl)phenyl)piperidine-2-carboxamide; |
| 17. | N-(3-(((8-isopropyl-2-((tetrahydro-2H-pyran-4-yl)amino)pyrazolo[1,5-a][1,3,5]triazin-4-yl)amino)methyl)phenyl)-1-(3-methylbut-2-enoyl)azetidine-2-carboxamide; |
| 18. | 1-acryloyl-N-(3-(((8-isopropyl-2-((tetrahydro-2H-pyran-4-yl)amino)pyrazolo[1,5-a][1,3,5]triazin-4-yl)amino)methyl)phenyl)azetidine-3-carboxamide; |
| 19. | (R)-1-acryloyl-N-(3-(((8-isopropyl-2-((tetrahydro-2H-pyran-4-yl)amino)pyrazolo[1,5-a][1,3,5]triazin-4-yl)amino)methyl)phenyl)azetidine-2-carboxamide; |

| Compound No: | IUPAC name |
| --- | --- |
| 20. | (S)-1-acryloyl-N-(3-(((8-isopropyl-2-((tetrahydro-2H-pyran-4-yl)amino) pyrazolo[1,5-a][1,3,5]triazin-4-yl)amino)methyl)phenyl)azetidine-2-carboxamide; |
| 21. | 1-acryloyl-N-(3-(((8-isopropyl-2-((tetrahydro-2H-pyran-4-yl)amino)pyrazolo[1,5-a][1,3,5]triazin-4-yl)amino)methyl)phenyl)piperidine-2-carboxamide; |
| 22. | 3-acrylamido-N-(3-(((8-isopropyl-2-((tetrahydro-2H-pyran-4-yl)amino)pyrazolo[1,5-a][1,3,5]triazin-4-yl)amino)methyl)phenyl)cyclohexane-1-carboxamide; |
| 23. | 4-acryloyl-N-(3-(((8-isopropyl-2-((tetrahydro-2H-pyran-4-yl)amino)pyrazolo[1,5-a][1,3,5]triazin-4-yl)amino)methyl)phenyl)morpholine-2-carboxamide; |
| 24. | 4-acryloyl-N-(3-(((8-isopropyl-2-((tetrahydro-2H-pyran-4-yl)amino)pyrazolo[1,5-a][1,3,5]triazin-4-yl)amino)methyl)phenyl)morpholine-3-carboxamide; |
| 25. | N-(3-(((8-isopropyl-2-((tetrahydro-2H-pyran-4-yl)amino)pyrazolo[1,5-a][1,3,5]triazin-4-yl)amino)methyl)phenyl)-4-propioloylmorpholine-3-carboxamide; |
| 26. | 4-acryloyl-N-(4-ethyl-3-(((8-isopropyl-2-((tetrahydro-2H-pyran-4-yl)amino) pyrazolo[1,5-a][1,3,5]triazin-4-yl)amino)methyl)phenyl)morpholine-3-carboxamide; |
| 27. | 1-acryloyl-N-(3-(((8-isopropyl-2-((tetrahydro-2H-pyran-4-yl)amino)pyrazolo[1,5-a][1,3,5]triazin-4-yl)amino)methyl)-4-methylphenyl)azetidine-2-carboxamide; |
| 28. | 1-acryloyl-N-(5-(((8-isopropyl-2-((tetrahydro-2H-pyran-4-yl)amino)pyrazolo[1,5-a][1,3,5]triazin-4-yl)amino)methyl)-2-methylphenyl)azetidine-2-carboxamide; |
| 29. | 1-acryloyl-N-(4-fluoro-3-(((8-isopropyl-2-((tetrahydro-2H-pyran-4-yl)amino) pyrazolo[1,5-a][1,3,5]triazin-4-yl)amino)methyl)phenyl)azetidine-2-carboxamide; |
| 30. | 1-acryloyl-N-(2-fluoro-3-(((8-isopropyl-2-((tetrahydro-2H-pyran-4-yl)amino) pyrazolo[1,5-a][1,3,5]triazin-4-yl)amino)methyl)phenyl)azetidine-2-carboxamide; |
| 31. | 1-acryloyl-N-(3-fluoro-5-(((8-isopropyl-2-((tetrahydro-2H-pyran-4-yl)amino) pyrazolo[1,5-a][1,3,5]triazin-4-yl)amino)methyl)phenyl)azetidine-2-carboxamide; |
| 32. | 1-acryloyl-N-(4-fluoro-3-(((8-isopropyl-2-((tetrahydro-2H-pyran-4-yl)amino) pyrazolo[1,5-a][1,3,5]triazin-4-yl)amino)methyl)phenyl)pyrrolidine-3-carboxamide; |
| 33. | 1-acryloyl-N-(3-fluoro-5-(((8-isopropyl-2-((tetrahydro-2H-pyran-4-yl)amino) pyrazolo[1,5-a][1,3,5]triazin-4-yl)amino)methyl)phenyl)pyrrolidine-3-carboxamide; |
| 34. | 1-acryloyl-N-(3-(((8-isopropyl-2-((tetrahydro-2H-pyran-4-yl)amino)pyrazolo[1,5-a][1,3,5]triazin-4-yl)amino)methyl)-4-methylphenyl)piperidine-2-carboxamide; |
| 35. | 1-acryloyl-N-(2-fluoro-3-(((8-isopropyl-2-((tetrahydro-2H-pyran-4-yl)amino) pyrazolo[1,5-a][1,3,5]triazin-4-yl)amino)methyl)phenyl)piperidine-2-carboxamide; |
| 36. | 1-acryloyl-N-(3-fluoro-5-(((8-isopropyl-2-((tetrahydro-2H-pyran-4-yl)amino) pyrazolo[1,5-a][1,3,5]triazin-4-yl)amino)methyl)phenyl)piperidine-2-carboxamide; |
| 37. | 1-acryloyl-N-(4-fluoro-3-(((8-isopropyl-2-((tetrahydro-2H-pyran-4-yl)amino) pyrazolo[1,5-a][1,3,5]triazin-4-yl)amino)methyl)phenyl)piperidine-2-carboxamide; |
| 38. | (1,4-cis)-4-acrylamido-N-(2-fluoro-3-(((8-isopropyl-2-((tetrahydro-2H-pyran-4-yl)amino)pyrazolo[1,5-a][1,3,5]triazin-4-yl)amino)methyl)phenyl)cyclohexane-1-carboxamide; |
| 39. | (1,4-cis)-4-acrylamido-N-(4-fluoro-3-(((8-isopropyl-2-((tetrahydro-2H-pyran-4-yl)amino)pyrazolo[1,5-a][1,3,5]triazin-4-yl)amino)methyl)phenyl)cyclohexane-1-carboxamide; |
| 40. | 4-acryloyl-N-(5-(((8-isopropyl-2-((tetrahydro-2H-pyran-4-yl)amino)pyrazolo[1,5-a][1,3,5]triazin-4-yl)amino)methyl)pyridin-3-yl)morpholine-3-carboxamide; |
| 40D. | 1-acryloyl-N-(3-(((8-isopropyl-2-(((S)-tetrahydro-2H-pyran-3-yl)amino) pyrazolo[1,5-a][1,3,5]triazin-4-yl)amino)methyl)phenyl)piperidine-2-carboxamide; |
| 40E. | 1-acryloyl-N-(3-(((8-isopropyl-2-(((R)-tetrahydro-2H-pyran-3-yl)amino) pyrazolo[1,5-a][1,3,5]triazin-4-yl)amino)methyl)phenyl)piperidine-2-carboxamide; |
| 41. | (S)-N-(1-acryloylpiperidin-3-yl)-3-(((8-isopropyl-2-((tetrahydro-2H-pyran-4-yl)amino)pyrazolo[1,5-a][1,3,5]triazin-4-yl)amino)methyl)benzamide; |
| 42. | 1-acryloyl-N-(4-fluoro-3-(((8-isopropyl-2-((tetrahydro-2H-pyran-4-yl)amino)pyrazolo[1,5-a][1,3,5]triazin-4-yl)amino)methyl)phenyl)azetidine-2-carboxamide; |
| 43. | 1-acryloyl-N-(2-fluoro-5-(((8-isopropyl-2-((tetrahydro-2H-pyran-4-yl)amino) pyrazolo[1,5-a][1,3,5]triazin-4- |

-continued

| Compound No: | IUPAC name |
|---|---|
| | yl)amino)methyl)phenyl)pyrrolidine-3-carboxamide; pyran-4-yl)amino)pyrazolo[1,5-a][1,3,5]triazin-4-yl)amino)methyl)phenyl)but-2-enamide; |
| 44. | 1-acryloyl-N-(2-fluoro-5-(((8-isopropyl-2-((tetrahydro-2H-pyran-4-yl)amino)pyrazolo[1,5-a][1,3,5]triazin-4-yl)amino)methyl)phenyl)piperidine-2-carboxamide; |
| 45. | 1-acryloyl-N-(3-(1-((8-isopropyl-2-((tetrahydro-2H-pyran-4-yl)amino)pyrazolo[1,5-a][1,3,5]triazin-4-yl)amino)ethyl)phenyl)piperidine-3-carboxamide; |
| 46. | 3-(((8-isopropyl-2-((tetrahydro-2H-pyran-4-yl)amino)pyrazolo[1,5-a][1,3,5]triazin-4-yl)amino)methyl)phenyl 4-acryloylpiperazine-1-carboxylate; |
| 64. | (E)-1-(4-(dimethylamino)but-2-enoyl)-N-(2-fluoro-5-(((8-isopropyl-2-((tetrahydro-2H-pyran-4-yl)amino)pyrazolo[1,5-a][1,3,5]triazin-4-yl)amino)methyl)phenyl)pyrrolidine-3-carboxamide; |
| 65. | (E)-1-(but-2-enoyl)-N-(3-(((8-isopropyl-2-((tetrahydro-2H-pyran-4-yl)amino) pyrazolo[1,5-a][1,3,5]triazin-4-yl)amino)methyl)phenyl)azetidine-2-carboxamide; |
| 66. | N-(3-(((8-isopropyl-2-((tetrahydro-2H-pyran-4-yl)amino)pyrazolo[1,5-a][1,3,5] triazin-4-yl)amino)methyl)phenyl)-1-propioloylazetidine-2-carboxamide; |
| 67. | N-(3-(((8-isopropyl-2-((tetrahydro-2H-pyran-4-yl)amino)pyrazolo[1,5-a][1,3,5]triazin-4-yl)amino)methyl)phenyl)-1-methacryloylazetidine-2-carboxamide; |
| 68. | (E)-N-(3-(((8-isopropyl-2-((tetrahydro-2H-pyran-4-yl)amino)pyrazolo[1,5-a] [1,3,5]triazin-4-yl)amino)methyl)phenyl)-1-(4-methoxybut-2-enoyl)pyrrolidine-3-carboxamide; |
| 69. | (E)-1-(4-(dimethylamino)but-2-enoyl)-N-(3-(((8-isopropyl-2-((tetrahydro-2H-pyran-4-yl)amino)pyrazolo[1,5-a][1,3,5]triazin-4-yl)amino)methyl)phenyl)pyrrolidine-3-carboxamide; |
| 70. | (E)-1-(4-(dimethylamino)but-2-enoyl)-N-(4-fluoro-3-(((8-isopropyl-2-((tetrahydro-2H-pyran-4-yl)amino)pyrazolo[1,5-a][1,3,5]triazin-4-yl)amino) methyl)phenyl)pyrrolidine-3-carboxamide; |
| 71. | (E)-1-(4-(dimethylamino)but-2-enoyl)-N-(3-fluoro-5-(((8-isopropyl-2-((tetrahydro-2H-pyran-4-yl)amino)pyrazolo[1,5-a][1,3,5]triazin-4-yl)amino) methyl)phenyl)pyrrolidine-3-carboxamide; |
| 72. | (E)-1-(4-(dimethylamino)but-2-enoyl)-N-(3-(1-((8-isopropyl-2-((tetrahydro-2H-pyran-4-yl)amino)pyrazolo[1,5-a][1,3,5]triazin-4-yl)amino)ethyl)phenyl)piperidine-3-carboxamide; |
| 73. | (E)-4-(4-(dimethylamino)but-2-enoyl)-N-(3-(((8-isopropyl-2-((tetrahydro-2H-pyran-4-yl)amino)pyrazolo[1,5-a][1,3,5]triazin-4-yl)amino)methyl)phenyl)morpholine-3-carboxamide; |
| 74. | (E)-1-(4-(dimethylamino)but-2-enoyl)-N-(3-(((8-isopropyl-2-((tetrahydro-2H-pyran-4-yl)amino)pyrazolo[1,5-a][1,3,5]triazin-4-yl)amino)methyl)phenyl) piperidine-2-carboxamide; |
| 75. | 3-(((8-isopropyl-2-((tetrahydro-2H-pyran-4-yl)amino)pyrazolo[1,5-a][1,3,5] triazin-4-yl)amino)methyl)phenyl(E)-4-(4-(dimethylamino)but-2-enoyl) piperazine-1-carboxylate; |
| 76. | (E)-1-(4-(dimethylamino)-4-oxobut-2-en-1-yl)-N-(3-(((8-isopropyl-2-((tetrahydro-2H-pyran-4-yl)amino)pyrazolo[1,5-a][1,3,5]triazin-4-yl)amino)methyl) phenyl)azetidine-2-carboxamide; |
| 77. | (E)-N-(3-(((8-isopropyl-2-((tetrahydro-2H-pyran-4-yl)amino)pyrazolo[1,5-a][1,3,5]triazin-4-yl)amino)methyl)phenyl)-1-(4-(pyrrolidin-1-yl)but-2-enoyl)piperidine-2-carboxamide; |
| 78. | N-(3-(((8-isopropyl-2-((tetrahydro-2H-pyran-4-yl)amino)pyrazolo[1,5-a][1,3,5]triazin-4-yl)amino)methyl)phenyl)-1-(vinylsulfonyl)piperidine-2-carboxamide; |
| 83. | 1-acrylamido-N-(3-(((8-isopropyl-2-((tetrahydro-2H-pyran-4-yl)amino)pyrazolo [1,5-a][1,3,5]triazin-4-yl)amino)methyl)phenyl)cyclopropane-1-carboxamide; |
| 84. | N-(3-(((8-isopropyl-2-((tetrahydro-2H-pyran-4-yl)amino)pyrazolo[1,5-a] [1,3,5]triazin-4-yl)amino)methyl)phenyl)-1-(N-methylacrylamido)cyclopropane-1-carboxamide; |
| 85. | 4-acrylamido-N-(3-(((8-isopropyl-2-((tetrahydro-2H-pyran-4-yl)amino)pyrazolo [1,5-a][1,3,5]triazin-4-yl)amino)methyl)phenyl)-1-methyl-1H-pyrazole-3-carboxamide; |
| 86. | 1-acryloyl-N-(3-((8-isopropyl-2-((tetrahydro-2H-pyran-4-yl)amino)pyrazolo[1,5-a][1,3,5]triazin-4-yl)amino)phenyl)azetidine-2-carboxamide; |
| 87. | (1,4-cis)-4-acrylamido-N-(3-((8-isopropyl-2-((tetrahydro-2H-pyran-4-yl)amino) pyrazolo[1,5-a][1,3,5]triazin-4-yl)amino)phenyl)cyclohexane-1-carboxamide; |
| 88. | 1-acryloyl-N-(3-(((8-ethyl-2-((1-methylpiperidin-4-yl)oxy)pyrazolo[1,5-a][1,3,5] triazin-4-yl)amino)methyl)phenyl)piperidine-4-carboxamide; |
| 89. | 1-acryloyl-N-(3-(((2-((1-methylpiperidin-4-yl)oxy)pyrazolo[1,5-a][1,3,5]triazin-4-yl)amino)methyl)phenyl)piperidine-3-carboxamide; |

| Compound No: | IUPAC name |
|---|---|
| 90. | (1,4-cis)-4-acrylamido-N-(3-(((8-ethyl-2-((1-methylpiperidin-4-yl)oxy)pyrazolo[1,5-a][1,3,5]triazin-4-yl)amino)methyl)phenyl)cyclohexane-1-carboxamide; |
| 91. | (1,4-trans)-4-acrylamido-N-(3-(((8-isoproprayl-2-((1-methylpiperidin-4-yl)oxy) pyrazolo[1,5-a][1,3,5]triazin-4-yl)amino)methyl)phenyl)cyclohexane-1-carboxamide; |
| 92. | 4-acrylamido-N-(3-(((2-((3-fluoro-1-methylpiperidin-4-yl)amino)-8-isopropylpyrazolo[1,5-a][1,3,5]triazin-4-yl)amino)methyl)phenyl)cyclohexane-1-carboxamide; |
| 94. | 1-acryloyl-N-(3-(((8-isopropyl-2-((1-methylpiperidin-4-yl)oxy)pyrazolo[1,5-a][1,3,5]triazin-4-yl)amino)methyl)phenyl)azetidine-2-carboxamide; |
| 95. | 1-acryloyl-N-(3-(((8-isopropyl-2-((tetrahydro-2H-pyran-4-yl)oxy)pyrazolo[1,5-a][1,3,5]triazin-4-yl)amino)methyl)phenyl)pyrrolidine-3-carboxamide; |
| 96. | 1-acryloyl-N-(3-(((8-isopropyl-2-((tetrahydro-2H-pyran-4-yl)oxy)pyrazolo[1,5-a][1,3,5]triazin-4-yl)amino)methyl)phenyl)piperidine-3-carboxamide; |
| 97. | (1,4-cis)-4-acrylamido-N-(3-(((8-isopropyl-2-((tetrahydro-2H-pyran-4-yl)oxy) pyrazolo[1,5-a][1,3,5]triazin-4-yl)amino)methyl)phenyl)cyclohexane-1-carboxamide; |
| 98. | 4-acrylamido-N-(3-(((2-((3-fluorotetrahydro-2H-pyran-4-yl)oxy)-8-isopropylpyrazolo[1,5-a][1,3,5]triazin-4-yl)amino)methyl)phenyl)cyclohexane-1-carboxamide; |
| 100. | (1,4-cis)-4-acrylamido-N-(3-(((8-isopropyl-2-((tetrahydrofuran-3-yl)oxy)pyrazolo [1,5-a][1,3,5]triazin-4-yl)amino)methyl)phenyl)cyclohexane-1-carboxamide; |
| 101. | (1,4-cis)-4-acrylamido-N-(3-(((8-isopropyl-2-((1-methylpyrrolidin-3-yl)oxy) pyrazolo[1,5-a][1,3,5]triazin-4-yl)amino)methyl)phenyl)cyclohexane-1-carboxamide; |
| 102. | 1-acryloyl-N-(3-(((2-isobutoxy-8-isopropylpyrazolo[1,5-a][1,3,5]triazin-4-yl)amino)methyl)phenyl)pyrrolidine-3-carboxamide; |
| 103. | 1-acryloyl-N-(3-(((8-isopropyl-2-(2-methoxyethoxy)pyrazolo[1,5-a][1,3,5]triazin-4-yl)amino)methyl)phenyl)pyrrolidine-3-carboxamide; |
| 104. | 1-acryloyl-N-(3-(((8-isopropyl-2-(2-(2-methoxyethoxy)ethoxy)pyrazolo[1,5-a][1,3,5]triazin-4-yl)amino)methyl)phenyl)pyrrolidine-3-carboxamide; |
| 105. | (1,4-cis)-4-acrylamido-N-(3-(((8-cyclopropyl-2-((1-methylpiperidin-4-yl)oxy) pyrazolo[1,5-a][1,3,5]triazin-4-yl)amino)methyl)phenyl)cyclohexane-1-carboxamide; |
| 106. | (1,4-cis)-4-acrylamido-N-(3-(((8-isopropyl-2-((tetrahydro-2H-pyran-4-yl)amino) pyrazolo[1,5-a][1,3,5]triazin-4-yl)amino)methyl)phenyl)cyclohexane-1-carboxamide; |
| 107. | 1-acryloyl-N-(3-(((2-(4-aminobutoxy)-8-isopropylpyrazolo[1,5-a][1,3,5]triazin-4-yl)amino)methyl)phenyl)piperidine-4-carboxamide; |
| 108. | 1-acryloyl-N-(3-(((8-isopropyl-2-((1-methylpiperidin-4-yl)oxy)pyrazolo[1,5-a][1,3,5]triazin-4-yl)amino)methyl)phenyl)pyrrolidine-3-carboxamide; |
| 111. | 1-acryloyl-N-(3-(((8-isopropyl-2-((1-methylpiperidin-4-yl)oxy)pyrazolo[1,5-a][1,3,5]triazin-4-yl)amino)methyl)phenyl)piperidine-4-carboxamide; |
| 112. | 4-acryloyl-N-(3-(((8-isopropyl-2-((1-methylpiperidin-4-yl)oxy)pyrazolo[1,5-a][1,3,5]triazin-4-yl)amino)methyl)phenyl)morpholine-2-carboxamide; |
| 113. | 4-acryloyl-N-(3-(((8-isopropyl-2-((1-methylpiperidin-4-yl)oxy)pyrazolo[1,5-a][1,3,5]triazin-4-yl)amino)methyl)phenyl)morpholine-3-carboxamide; |
| 114. | 3-acrylamido-N-(3-(((8-isopropyl-2-((1-methylpiperidin-4-yl)oxy)pyrazolo[1,5-a][1,3,5]triazin-4-yl)amino)methyl)phenyl)cyclohexane-1-carboxamide; |
| 115. | (1,4-cis)-4-acrylamido-N-(3-(((8-isopropyl-2-((1-methylpiperidin-4-yl)oxy) pyrazolo[1,5-a][1,3,5]triazin-4-yl)amino)methyl)phenyl)cyclohexane-1-carboxamide; |
| 116. | 1-acryloyl-N-(3-(((8-isopropyl-2-((1-methylpiperidin-4-yl)oxy)pyrazolo[1,5-a][1,3,5]triazin-4-yl)amino)methyl)phenyl)piperidine-3-carboxamide; |
| 117. | 1-acryloyl-N-(2-fluoro-5-(((8-isopropyl-2-((1-methylpiperidin-4-yl)oxy)pyrazolo[1,5-a][1,3,5]triazin-4-yl)amino)methyl)phenyl)piperidine-3-carboxamide; |
| 118. | (1,4-cis)-4-acrylamido-N-(2-fluoro-5-(((8-isopropyl-2-((1-methylpiperidin-4-yl)oxy)pyrazolo[1,5-a][1,3,5]triazin-4-yl)amino)methyl)phenyl)cyclohexane-1-carboxamide; |
| 119. | 1-acryloyl-N-(3-(1-((8-isopropyl-2-((1-methylpiperidin-4-yl)oxy)pyrazolo[1,5-a][1,3,5]triazin-4-yl)amino)ethyl)phenyl)piperidine-3-carboxamide; |
| 120. | 2-(1-acryloylpiperidine-3-carboxamido)-5-(((8-isopropyl-2-((1-methylpiperidin-4-yl)oxy)pyrazolo[1,5-a][1,3,5]triazin-4-yl)amino)methyl)pyridine 1-oxide; |
| 121. | 3-(((8-isopropyl-2-((1-methylpiperidin-4-yl)oxy)pyrazolo[1,5-a][1,3,5]triazin-4-yl)amino)methyl)phenyl 4-acryloylpiperazine-1-carboxylate; |

| Compound No: | IUPAC name |
|---|---|
| 122. | (E)-1-(4-(dimethylamino)but-2-enoyl)-N-(3-(((8-isopropyl-2-((1-methylpiperidin-4-yl)oxy)pyrazolo[1,5-a][1,3,5]triazin-4-yl)amino)methyl)phenyl)piperidine-3-carboxamide; |
| 123. | (E)-1-(4-(dimethylamino)but-2-enoyl)-N-(2-fluoro-5-(((8-isopropyl-2-((1-methylpiperidin-4-yl)oxy)pyrazolo[1,5-a][1,3,5]triazin-4-yl)amino)methyl) phenyl)piperidine-3-carboxamide; |
| 124. | (1,4-cis)-4-((E)-4-(dimethylamino)but-2-enamido)-N-(2-fluoro-5-(((8-isopropyl-2-((1-methylpiperidin-4-yl)oxy)pyrazolo[1,5-a][1,3,5]triazin-4-yl)amino)methyl) phenyl)cyclohexane-1-carboxamide; |
| 126. | (1,4-cis)-4-acrylamido-N-(3-((8-isopropyl-2-((1-methylpiperidin-4-yl)oxy)pyrazolo[1,5-a][1,3,5]triazin-4-yl)amino)phenyl)cyclohexane-1-carboxamide; |
| 127. | 1-acryloyl-N-(3-((8-isopropyl-2-((1-methylpiperidin-4-yl)oxy)pyrazolo[1,5-a][1,3,5]triazin-4-yl)amino)phenyl)piperidine-4-carboxamide; |
| 128. | N-(1-acryloylpiperidin-4-yl)-3-((8-isopropyl-2-((1-methylpiperidin-4-yl)oxy)pyrazolo[1,5-a][1,3,5]triazin-4-yl)amino)benzamide; |
| 129. | N-(1-acryloylpiperidin-3-yl)-3-((8-isopropyl-2-((1-methylpiperidin-4-yl)oxy)pyrazolo[1,5-a][1,3,5]triazin-4-yl)amino)benzamide; |
| 131. | (1,4-cis)-4-((E)-4-(dimethylamino)but-2-enamido)-N-(3-((8-isopropyl-2-((1-methylpiperidin-4-yl)oxy)pyrazolo[1,5-a][1,3,5]triazin-4-yl)amino)phenyl) cyclohexane-1-carboxamide; |
| 132. | (1,4-Trans)-4-((E)-4-(dimethylamino)but-2-enamido)-N-(3-((8-isopropyl-2-((1-methylpiperidin-4-yl)oxy)pyrazolo[1,5-a][1,3,5]triazin-4-yl)amino)phenyl) cyclohexane-1-carboxamide; |
| 133. | (E)-N-(1-(4-(dimethylamino)but-2-enoyl)piperidin-3-yl)-3-((8-isopropyl-2-((1-methylpiperidin-4-yl)oxy)pyrazolo[1,5-a][1,3,5]triazin-4-yl)amino)benzamide; |
| 134. | (E)-N-(1-(4-(dimethylamino)but-2-enoyl)piperidin-4-yl)-3-((8-isopropyl-2-((1-methylpiperidin-4-yl)oxy)pyrazolo[1,5-a][1,3,5]triazin-4-yl)amino)benzamide; |
| 135. | (1,4-cis)-4-(((E)-4-(dimethylamino)-4-oxobut-2-en-1-yl)amino)-N-(3-(((8-isopropyl-2-((1-methylpiperidin-4-yl)oxy)pyrazolo[1,5-a][1,3,5]triazin-4-yl)amino)methyl)phenyl)cyclohexane-1-carboxamide; |
| 136. | 1-acryloyl-N-(3-(((8-isopropyl-2-methoxypyrazolo[1,5-a][1,3,5]triazin-4-yl)amino)methyl)phenyl)piperidine-4-carboxamide; or |
| 139. | 1-acryloyl-N-(3-(((3-isopropyl-5-((tetrahydro-2H-pyran-4-yl)amino)pyrazolo[1,5-a]pyrimidin-7-yl)amino)methyl)phenyl)azetidine-2-carboxamide, | or a pharmaceutically acceptable salt or a stereoisomer thereof.

11. A pharmaceutical composition comprising a compound of claim 1, or a pharmaceutically acceptable salt or a stereoisomer thereof and at least one pharmaceutically acceptable carrier or excipient.

12. A method of treating a subject suffering from a hematopoietic cancer with aberrant activity of selective transcriptional CDKs comprising administering a therapeutically effective amount of the pharmaceutical composition of claim 11.

13. A method of treating a hematopoietic cancer mediated by selective transcriptional CDKs in a subject comprising administering a therapeutically effective amount of the compound of claim 1.

14. A method of inhibiting selective transcriptional CDKs in a subject, comprising administering to the subject a compound of claim 1.

15. The method of claim 13, wherein the hematopoietic cancer is leukemia, acute lymphoblastic leukemia, acute lymphocytic leukemia, Hodgkins lymphoma, non-Hodgkins lymphoma, B-cell lymphoma, T-cell lymphoma, hairy cell lymphoma, myeloma, mantle cell lymphoma, Burkett's lymphoma, chronic myelogenous leukemia, or promyelocytic leukemia.

16. The method of claim 13, wherein the hematopoietic cancer is acute myeloid leukemia.

17. The method of claim 13, further comprising a step of administering to the subject in need thereof one or more chemotherapeutic agents independently selected from anti-proliferative agents, anti-cancer agents, immunosuppressant agents and pain-relieving agents.

18. The method of claim 13, wherein the selective transcriptional CDKs are CDK7, CDK9, CDK12, CDK13 or CDK 18.

19. The compound of claim 10, wherein compound 119 has the structure:

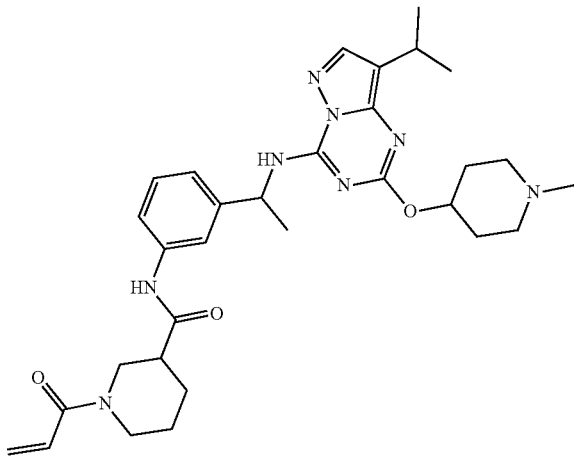 [SMILES: C=CC(=O)N1CCCC(C(=O)Nc2cccc(C(C)Nc3nc(OC4CCN(C)CC4)nc4c(C(C)C)cnn34)c2)C1]

or a pharmaceutically acceptable salt or a stereoisomer thereof.

20. The compound of claim 10, wherein compound 94 has the structure:

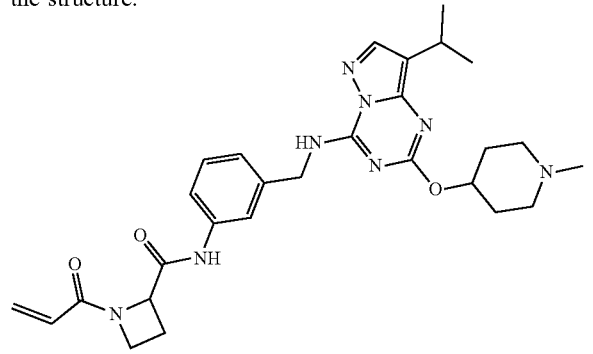

or a pharmaceutically acceptable salt or a stereoisomer thereof.

21. The compound of claim 10, wherein compound 46 has the structure:

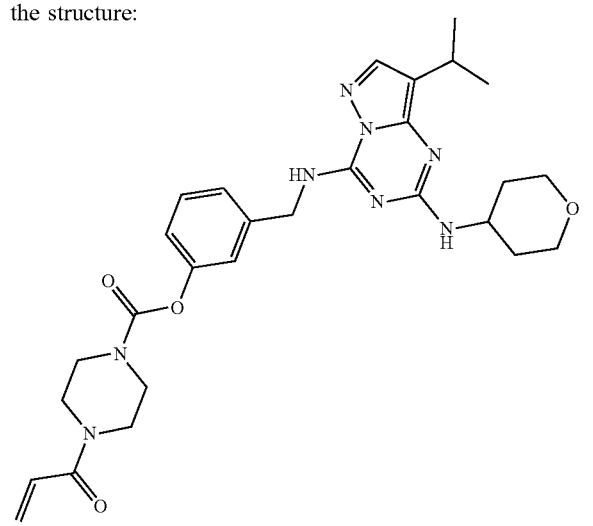

or a pharmaceutically acceptable salt or a stereoisomer thereof.

22. The compound of claim 10, wherein compound 115 has the structure:

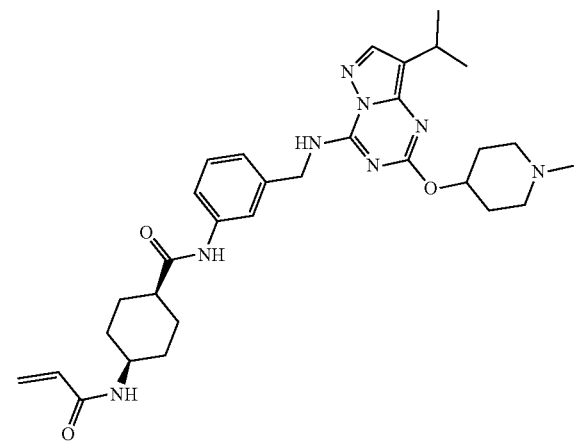 [SMILES: C=CC(=O)N[C@H]1CC[C@@H](C(=O)Nc2cccc(CNc3nc(OC4CCN(C)CC4)nc4c(C(C)C)cnn34)c2)CC1]

or a pharmaceutically acceptable salt or a stereoisomer thereof.

* * * * *